(12) United States Patent
Kolb et al.

(10) Patent No.: US 10,976,325 B2
(45) Date of Patent: *Apr. 13, 2021

(54) ASSAYS TO DETECT NEURODEGENERATION

(71) Applicant: JANSSEN PHARMACEUTICA NV, New Brunswick, NJ (US)

(72) Inventors: Hartmuth Christian Kolb, San Diego, CA (US); Gallen Triana-Baltzer, San Diego, CA (US); John Randall Slemmon, West Windsor, NJ (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 16/751,886

(22) Filed: Jan. 24, 2020

(65) Prior Publication Data

US 2020/0182888 A1 Jun. 11, 2020

Related U.S. Application Data

(63) Continuation of application No. 16/291,264, filed on Mar. 4, 2019, now Pat. No. 10,591,492.

(60) Provisional application No. 62/638,524, filed on Mar. 5, 2018.

(51) Int. Cl.
| | | |
|---|---|---|
| G01N 33/68 | (2006.01) | |
| C12Q 1/48 | (2006.01) | |
| G01N 33/573 | (2006.01) | |

(52) U.S. Cl.
CPC ......... *G01N 33/6896* (2013.01); *C12Q 1/485* (2013.01); *G01N 33/573* (2013.01); *G01N 2440/14* (2013.01); *G01N 2800/2821* (2013.01); *G01N 2800/2828* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,492,812 A | 2/1996 | Vooheis |
| 6,008,024 A | 12/1999 | Vandermeeren |
| 6,121,003 A | 9/2000 | Vanmechelen |
| 6,670,137 B2 | 12/2003 | Vanmechelen |
| 7,442,516 B2 | 10/2008 | Ohno |
| 7,888,050 B2 | 2/2011 | Reagan |
| 8,114,617 B2 | 2/2012 | Reagan |
| 8,778,343 B2 | 7/2014 | Kayed |
| 9,733,260 B2 | 8/2017 | Michaelsen |
| 2010/0316564 A1 | 12/2010 | Sigurdsson |
| 2014/0161875 A1 | 6/2014 | Winderickx |
| 2014/0302046 A1 | 10/2014 | Sigurdsson |
| 2015/0307600 A1 | 10/2015 | Alderfer et al. |
| 2016/0376351 A1 | 12/2016 | Adolfsson |
| 2017/0152307 A1 | 6/2017 | Wadia |
| 2018/0186855 A1 | 7/2018 | Rosenthal |

FOREIGN PATENT DOCUMENTS

| | | |
|---|---|---|
| WO | 011972 A1 | 1/2014 |
| WO | 2015/122922 A1 | 8/2015 |

OTHER PUBLICATIONS

Abhinandan, et al., Analysis and improvements to Kabat and Structurally Correct Numbering of antibody Variable domains., Molelcular Immunology, Jul. 9, 2008, pp. 3832-3839, vol. 45.
Barthelemy, et al., Differential Mass Spectrometry Profiles of Tau Protein in the Cerebrospinal Fluid of Patients with Alzheimer's Disease, Progressive Supranuclear Palsy, and Dementia with Lewy Bodies, Journal of Alzheimer's Disease, Jan. 4, 2016, pp. 1033-1043, vol. 51.
Butner, et al., Tau Protein Binds to Microtubules through a Flexible Array of Distributed Weak Sites., The Journal of Cell Biology, Nov. 1, 1991, pp. 717-730, vol. 115 Issue.
Chen, et al., Enhancement and destruction of antibody function by somatic mutation: unequal occurrence is controlled by V gene combinatorial associations, The EMBO Journal, 1995, pp. 2784-2794, vol. 14 Issue 12.
Chothia, et al, Canonical Structures for the Hypervariable Regions of Immunoglobulins, J. Mol. Biol.., Apr. 23, 1987, pp. 901-917, vol. 196.
Chothia, et al., Structural Repertoire of the Human VH Segments, J. Mol. Biol, Jun. 2, 1992, pp. 799-817, vol. 227.
Clavaguera, et al., Transmission and spreading of tauopathy in transgenic mouse brain, Nature Cellbiology, Jun. 7, 2009, pp. 909-913, vol. 11 Issue 7.
D'Abramo, et al., Detecting tau in serum of transgenic animal models after tau immunotherapy treatment, Neurobiology of Aging, 2016, pp. 58-65, vol. 37.
Fishwild, et al., High-avidity human IgGK monoclonal antibodies from a novel strain of rninilocus transgenic mice, Nature Biotechnology, May 1, 1996, pp. 845-851, vol. 14.

(Continued)

*Primary Examiner* — Adam Weidner
(74) *Attorney, Agent, or Firm* — Grimes & Yvon LLP

(57) ABSTRACT

Methods of measuring the amount of singly- or multiply-phosphorylated p217+ tau protein in a sample are provided. Methods of detecting or diagnosing tauopathies, methods of determining the effectiveness of a treatment of a tauopathy, and methods of determining whether a subject is suitable for anti-p217+ tau antibody therapy are also provided. Also described are antibodies for use in the methods and kits comprising the antibodies.

6 Claims, 73 Drawing Sheets

Specification includes a Sequence Listing.

(56) References Cited

OTHER PUBLICATIONS

Frost, et al., Propagation of Tau Misfolding from the Outside to the Inside of a Cell, The Journal of Biological Chemistry, May 8, 2009, pp. 12845-12652, vol. 284 Issue 19.

Hanger, et al., Novel Phosphorylation Sites in Tau from Alzheimer Brain Support a Role for Casein Kinase 1 in Disease Pathogenesis, The Journal of Biological Chemistry, Aug. 10, 2007, pp. 23645-23654, vol. 282 Issue 32.

Hanger, et al., Tau phosphorylation: the therapeutic challenge for neurodegenerative disease, Cell Press, Feb. 24, 2009, pp. 112-119, vol. 15 Issue 3.

Iqbal, et al., Tau in Alzheimer Disease and Related Tauopathies, Current Alzheimer Research, Jan. 2, 2010, pp. 656-664, vol. 7 Issue 8.

Juan C. Almagro., Identification of differences in the specificity-determining residues of antibodies that recognize antigens of different size: implications for the rational design of antibody repertoires, Journal of Yiolecular Recognition, Dec. 17, 2003, pp. 132-143, vol. 17.

Knappik, et al., Fully Synthetic Human Combinatorial Antibody Libraries (HuCAL) Based on Modular Consensus Frameworks and CDRs Randomized with Trinucleotides, J. Mol, Biol., 2000, pp. 57-86, vol. 296.

Kohler, et al., Continuous cultures of fused cells secreting antibody of predefined specificity, Nature, Aug. 7, 1975, pp. 495-497, vol. 256.

Krebs, et al., High-throughput generation and engineering of recombinant human antibodies, Journal of Immunological Methods, Apr. 6, 2001, pp. 67-84, vol. 254.

Kussie, et al., A Single Engineered Amino Acid Substitution Changes Antibody Fine Specificity, Journal of Immunology, 1994, pp. 146-152, vol. 152 Issue 1.

Lefranc, et al., IMGT unique numbering for immunoglobulin and T cell receptor variable domains and Ig superfamily V-like domains, Developmental and Comparative Immunology, May 29, 2002, pp. 55-77, vol. 27.

Lonberg, et al., Antigen-specific human antibodies from mice comprising four distinct genetic modifications, Nature, Apr. 28, 1994, pp. 856-859, vol. 368.

Mendez, et al., Functional transplant of megabase human immunoglobulin loci recapitulates human antibody response in mice, nature genetics, 1997, pp. 146-156, vol. 15.

Meredith, et al., Characterization of Novel CSF Tau and ptau Biomarkers for Alzheimer's Disease, PLOS ONE, Oct. 7, 2013, pp. 1-14, vol. 8 Issue 10.

Morris, et al., The Many Faces of Tau, Neuron, May 12, 2011, pp. 410-426, vol. 70.

Russell, et al., Comprehensive Quantitative Profiling of Tau and Phosphorylated Tau Peptides in Cerebrospinal Fluid by Mass Spectrometry Provides New Biomarker Candidates, Journal of Alzheimer's Disease, 2017, pp. 303-313, vol. 55.

Shi, et al., De Novo Selection of High-Affinity Antibodies from Synthetic Fab Libraries Displayed on Phage as pIX Fusion Proteins, J, Mol. Biol., Jan. 28, 2010, pp. 385-396, vol. 397 Issue 2.

Tramontano, et al., Framework Residue 71 is a Major Determinant of the Position and Conformation of the Second Hypervariable Region in the V H Domains of Immunoglobulins, J. Mol. Biol, May 18, 1990, pp. 175-182, vol. 215.

Wu, et al., An Analysis of the Sequences of the Variable Regions of Bence Jones Proteins and Myeloma Light Chains and Their Implications for Antibody Complementarity., Bence Jones Proteins and Myeloma Light Chains, Aug. 1, 1970, pp. 211-250, Page number.

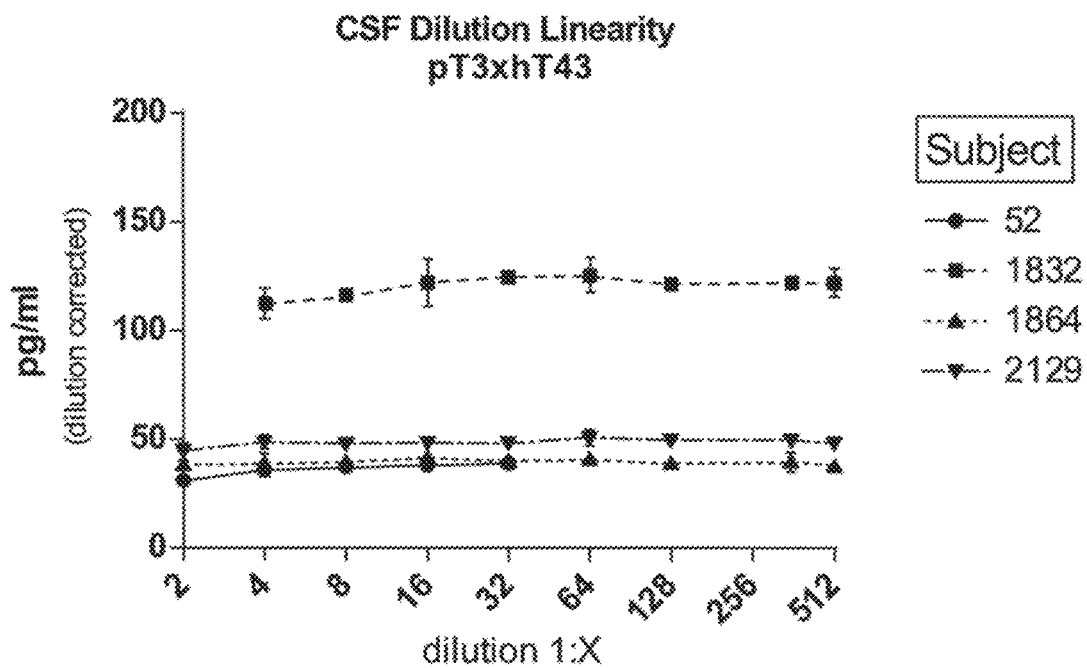
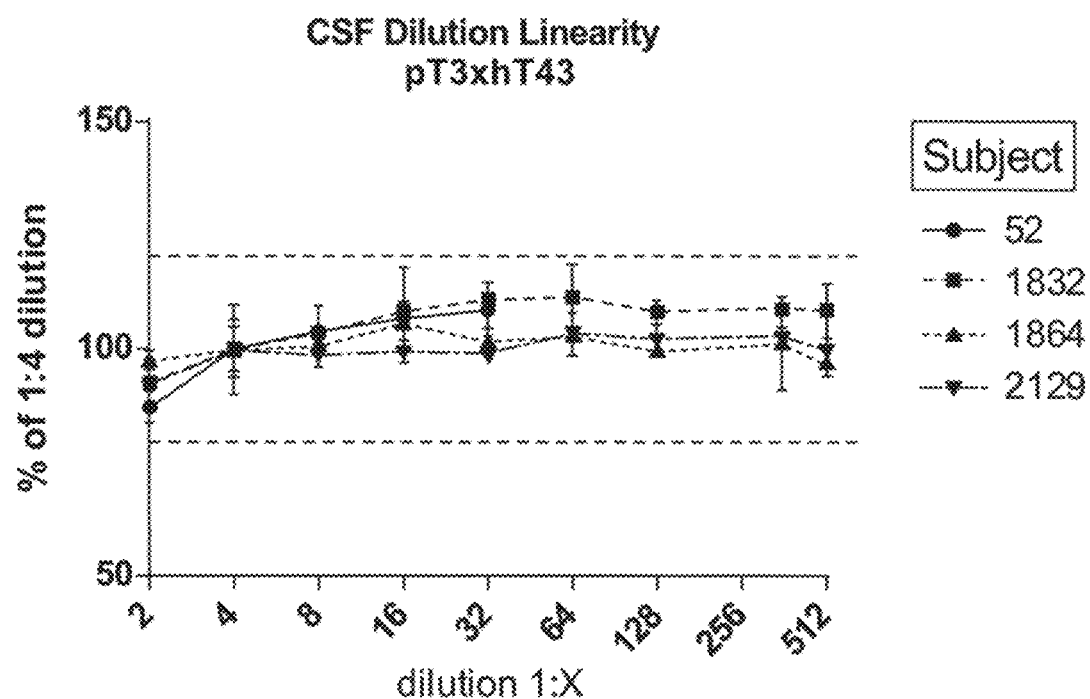

impact of soluble p217+ Tau mAbs on pT3xhT43 signal in CSF impact of soluble p217+ Tau mAbs on pT3xpT82 signal in CSF Alkaline phosphatase treatment of CSF p217+ tau fragment profile

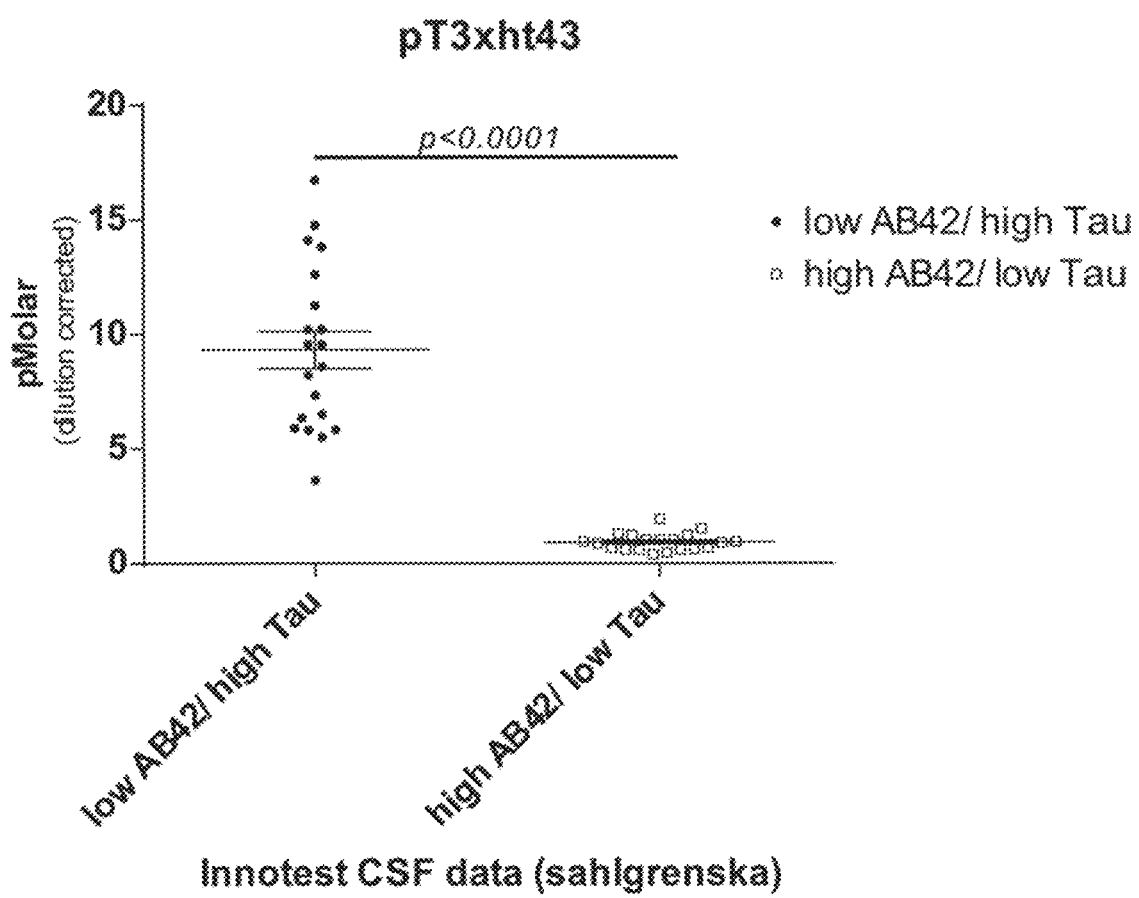

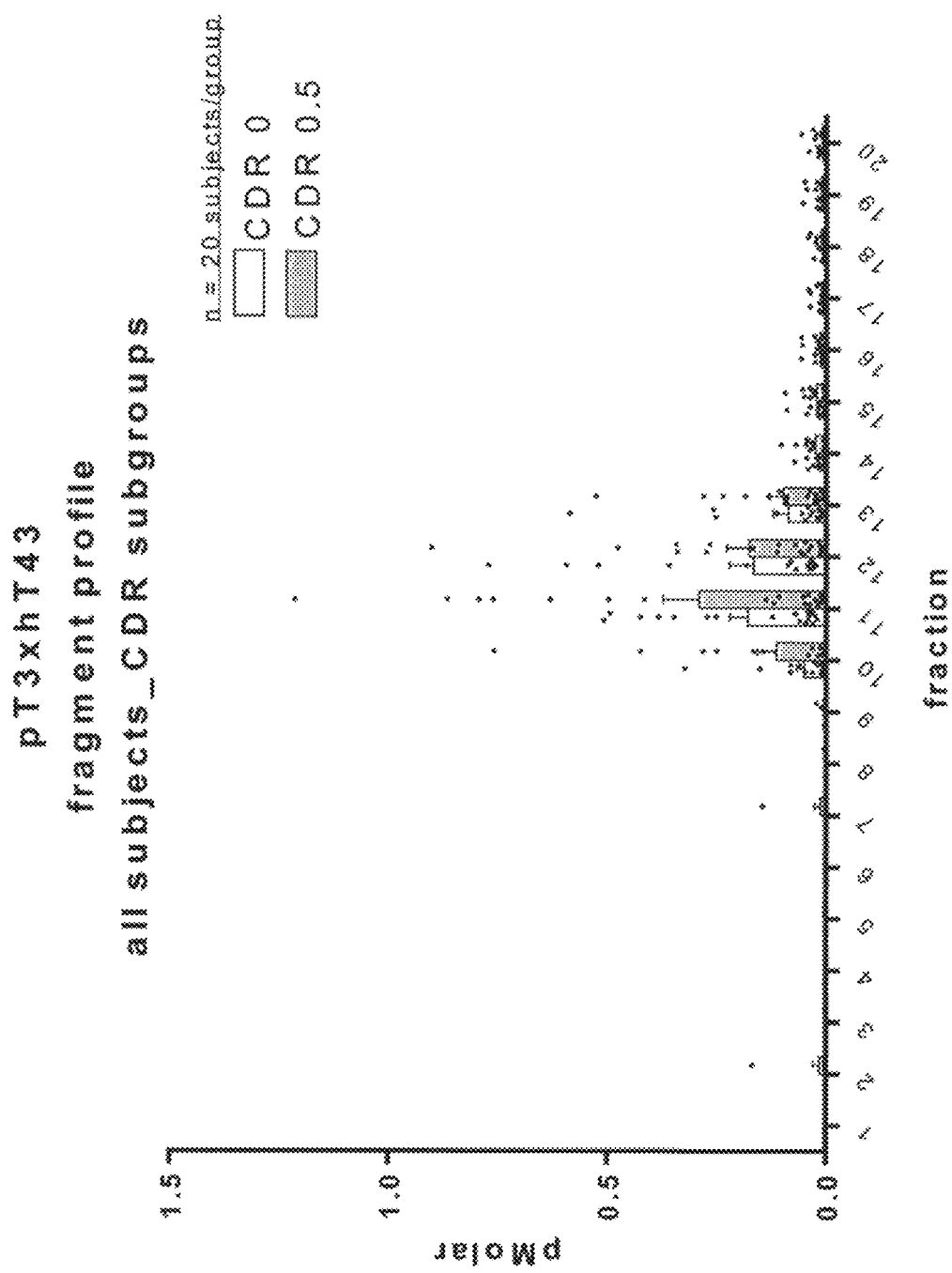

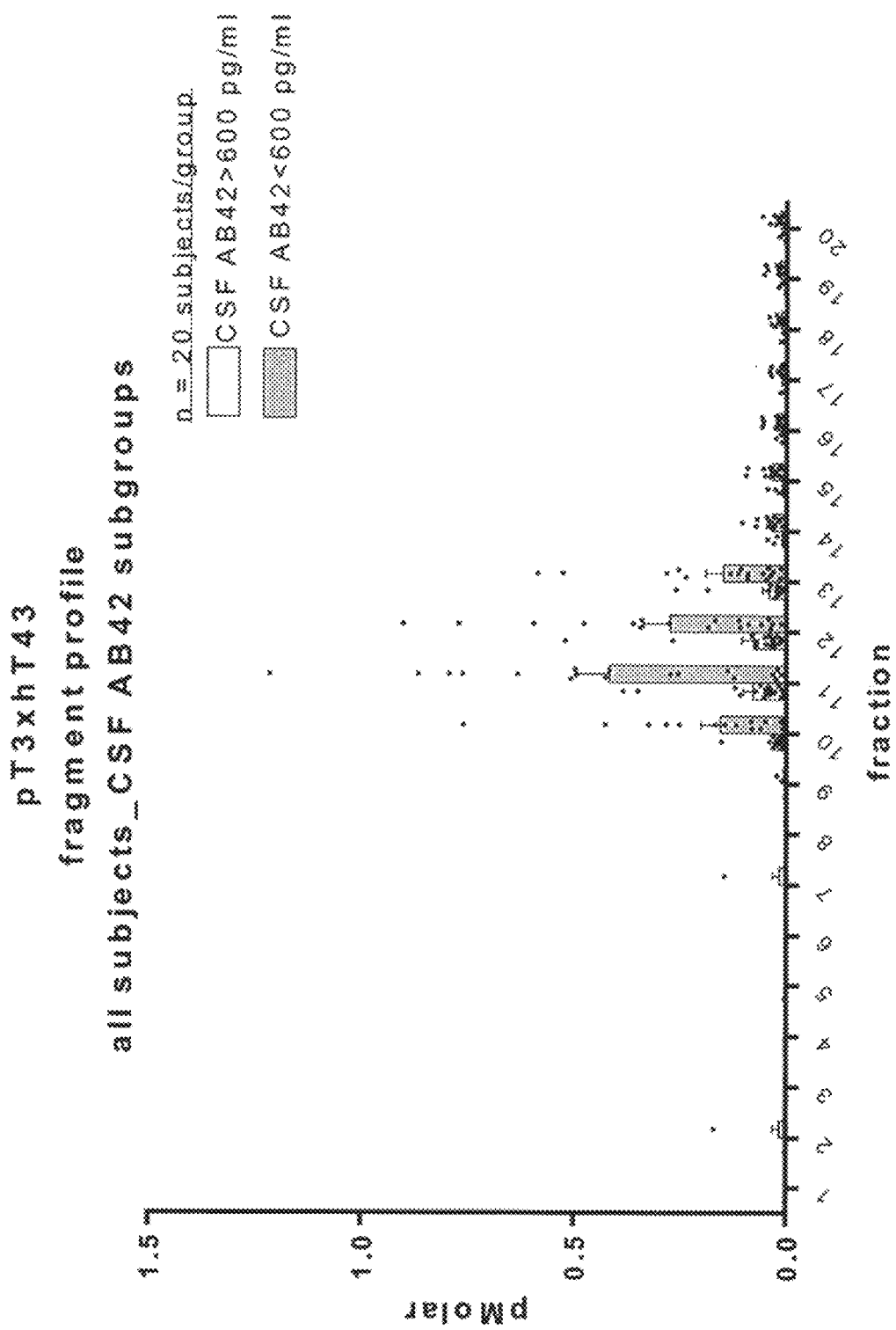

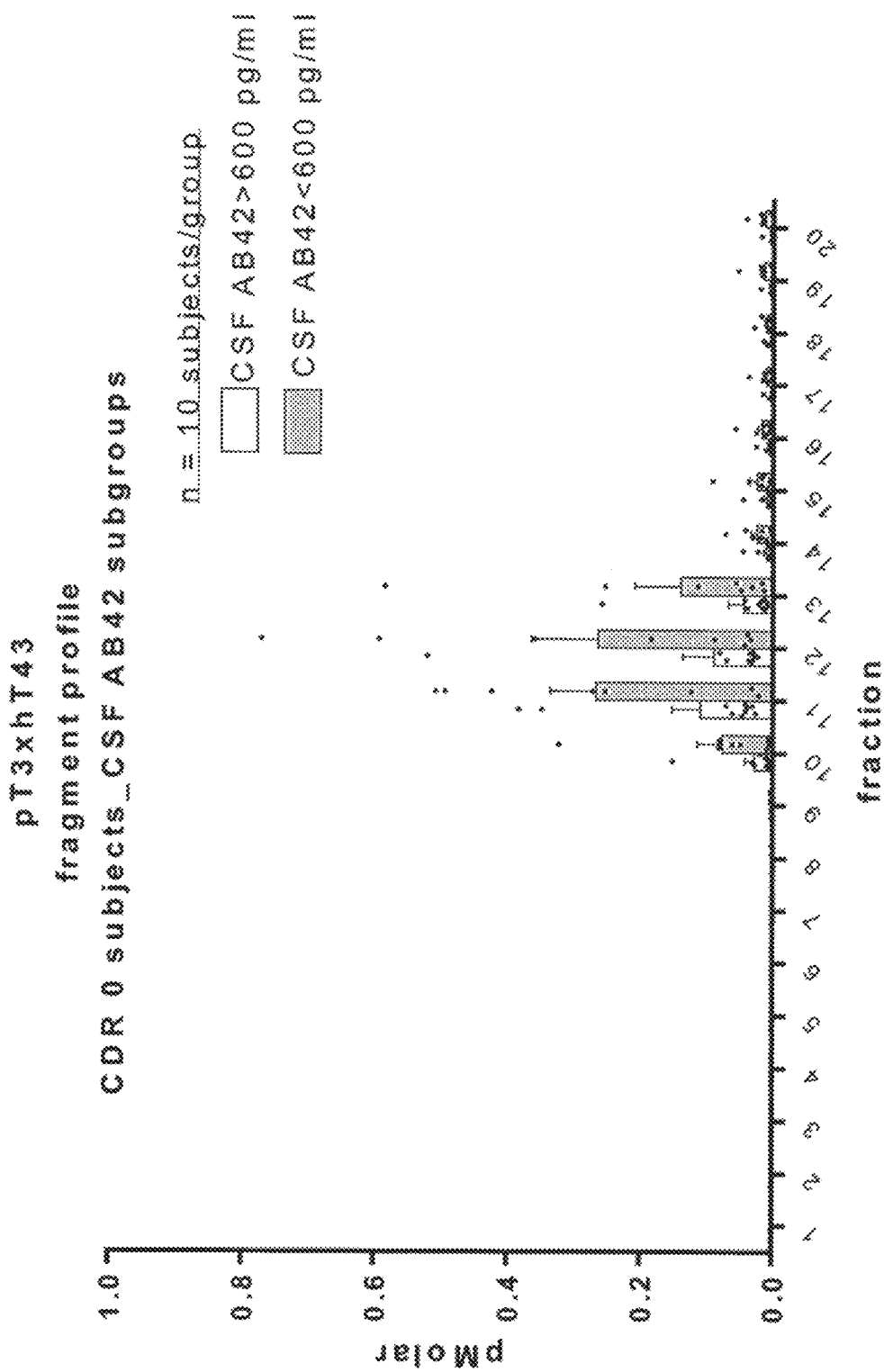

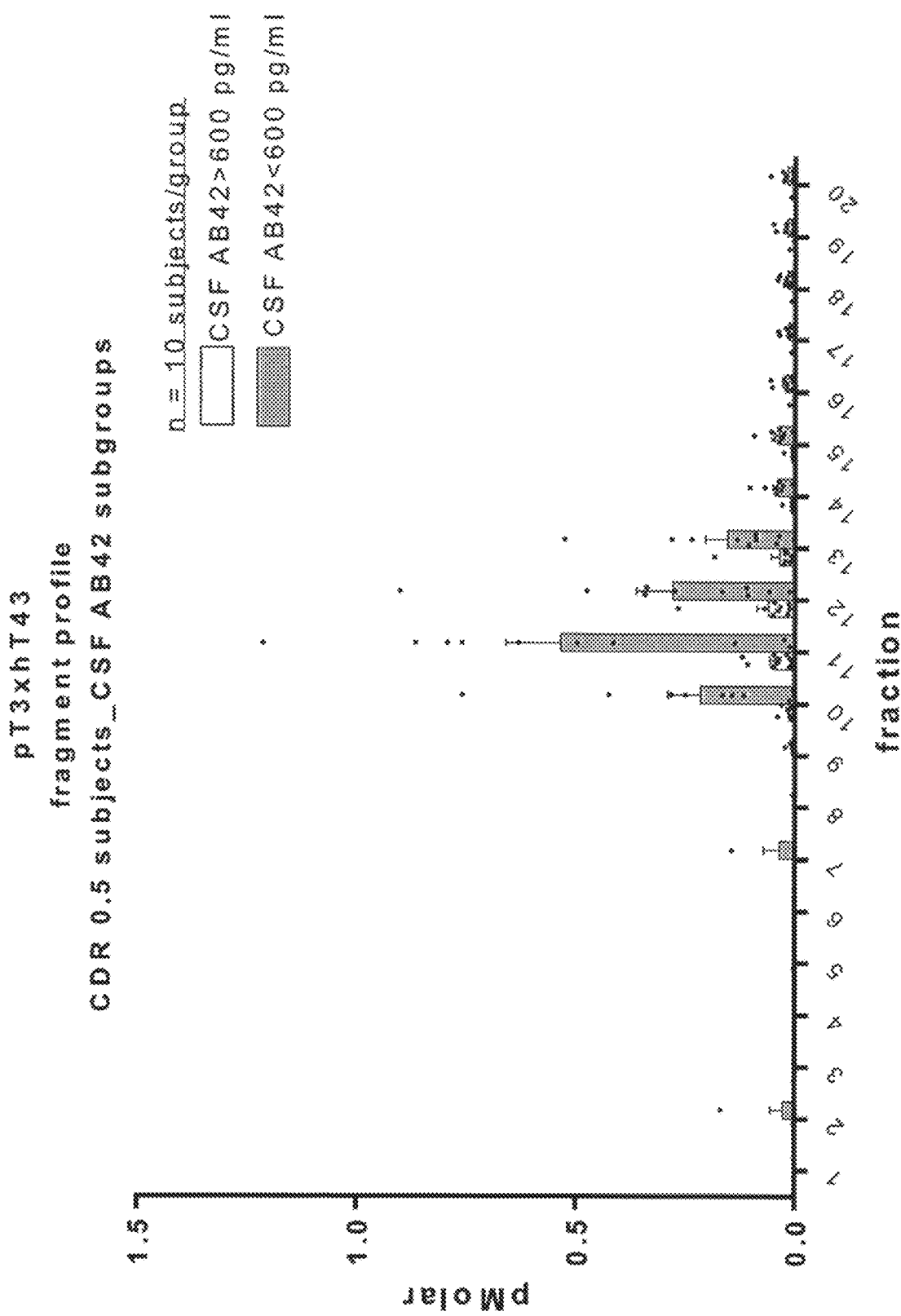

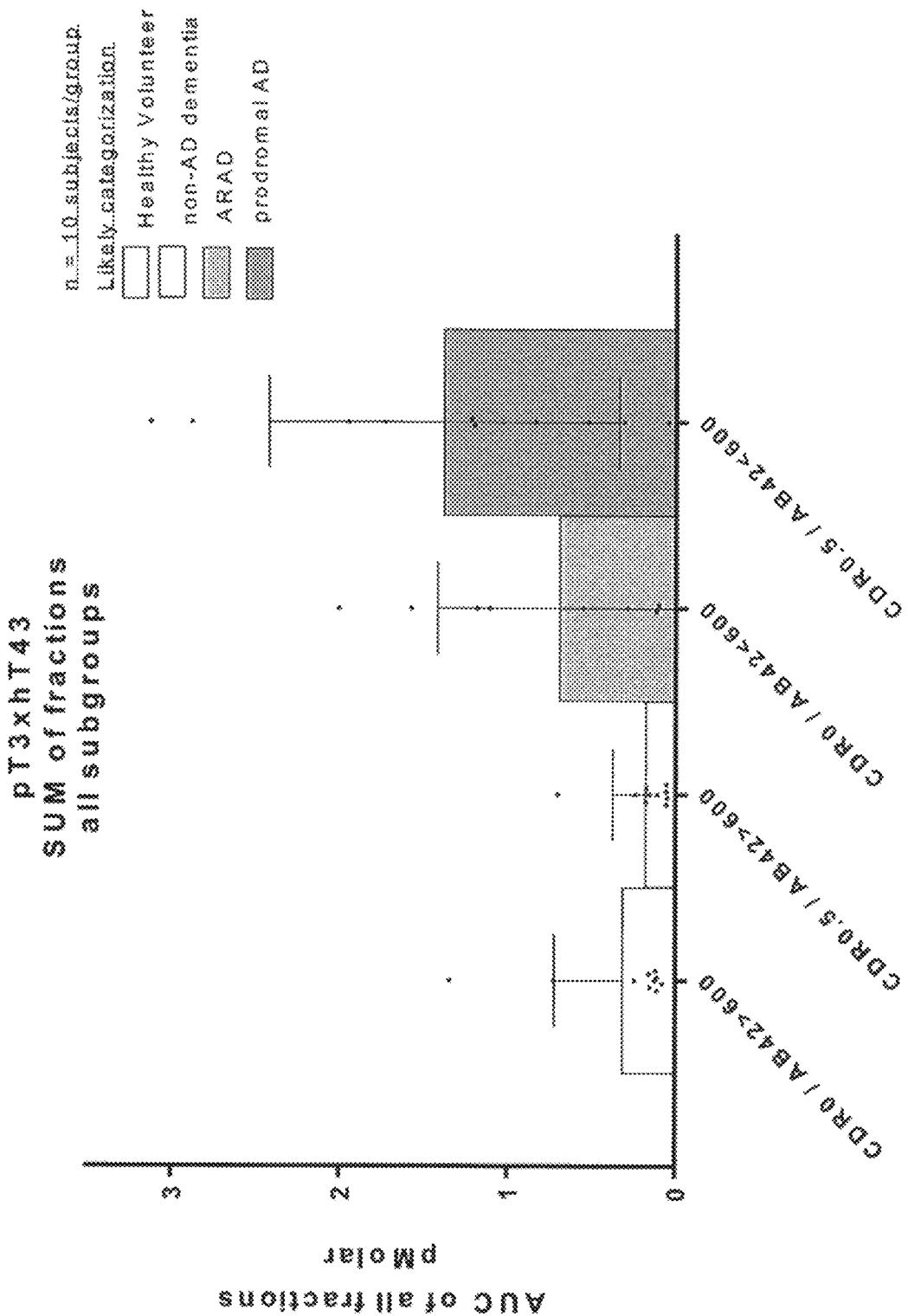

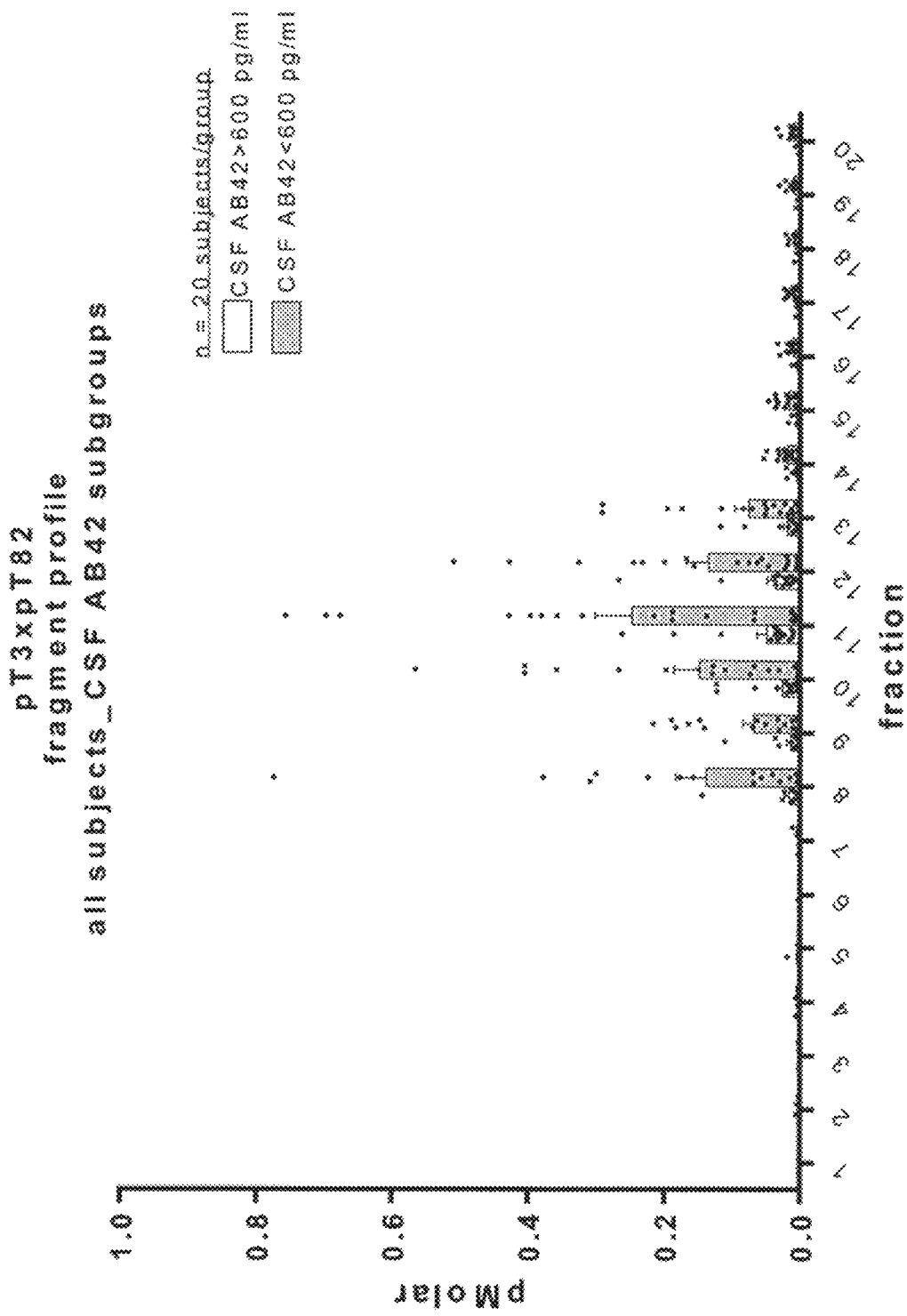

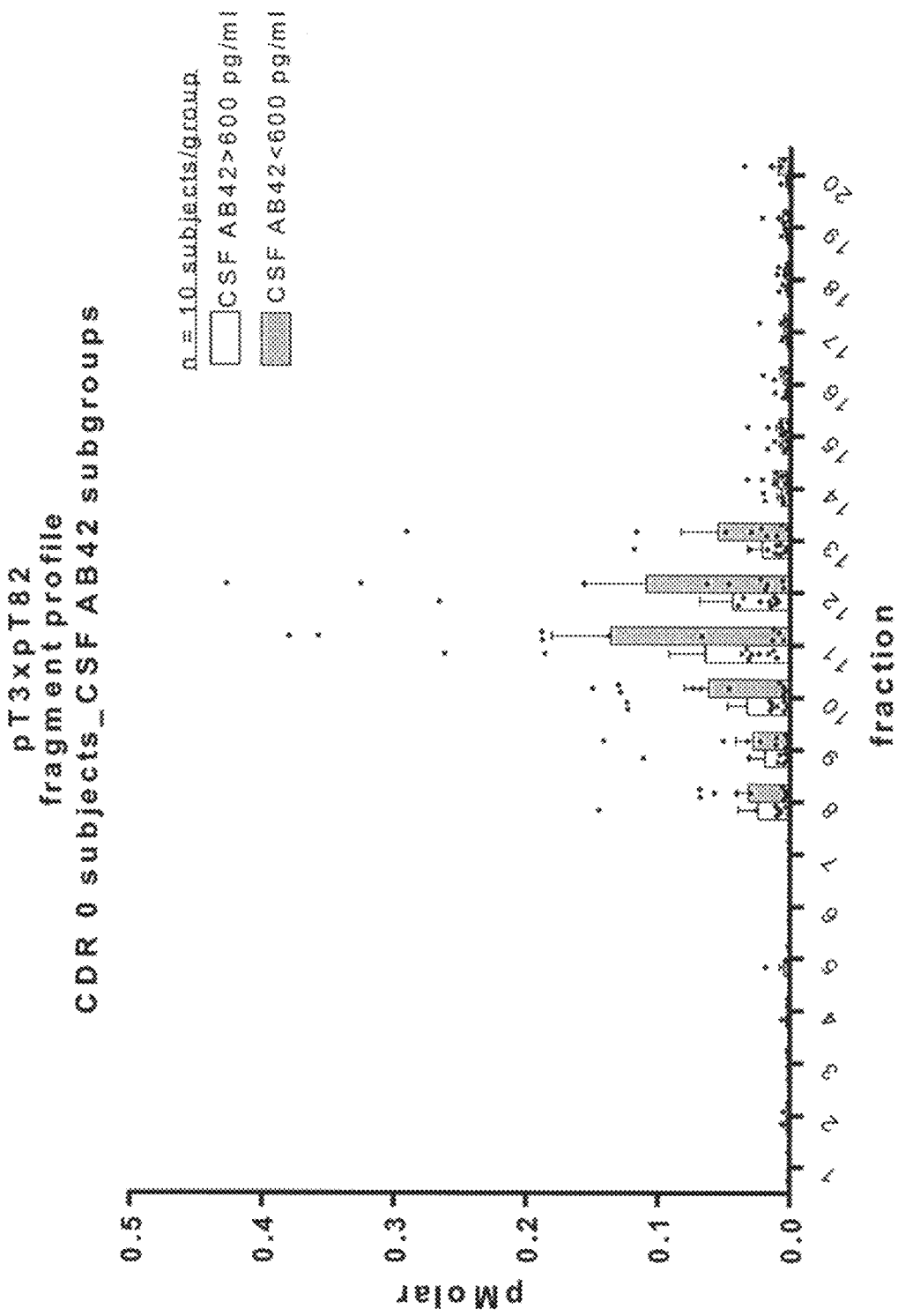

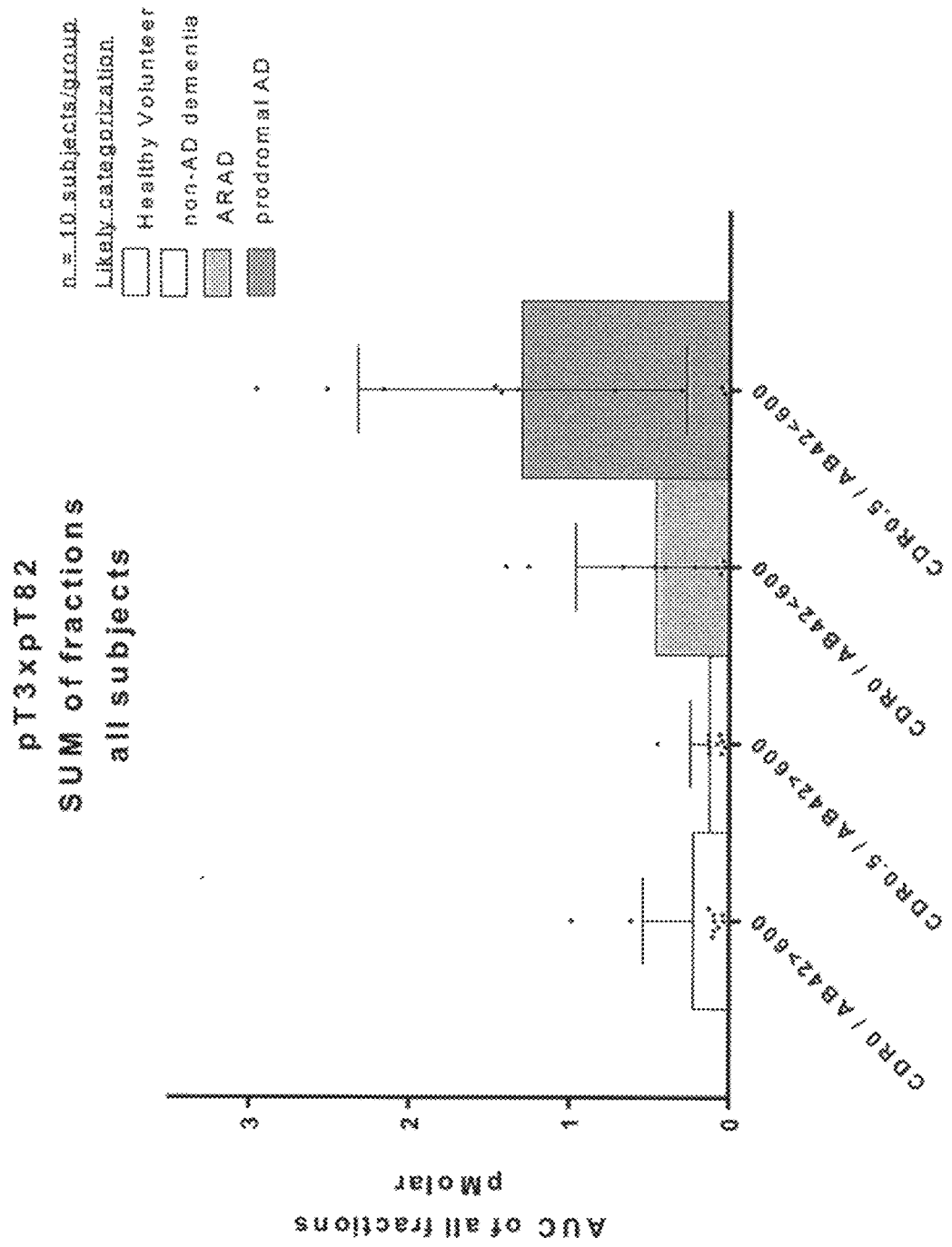

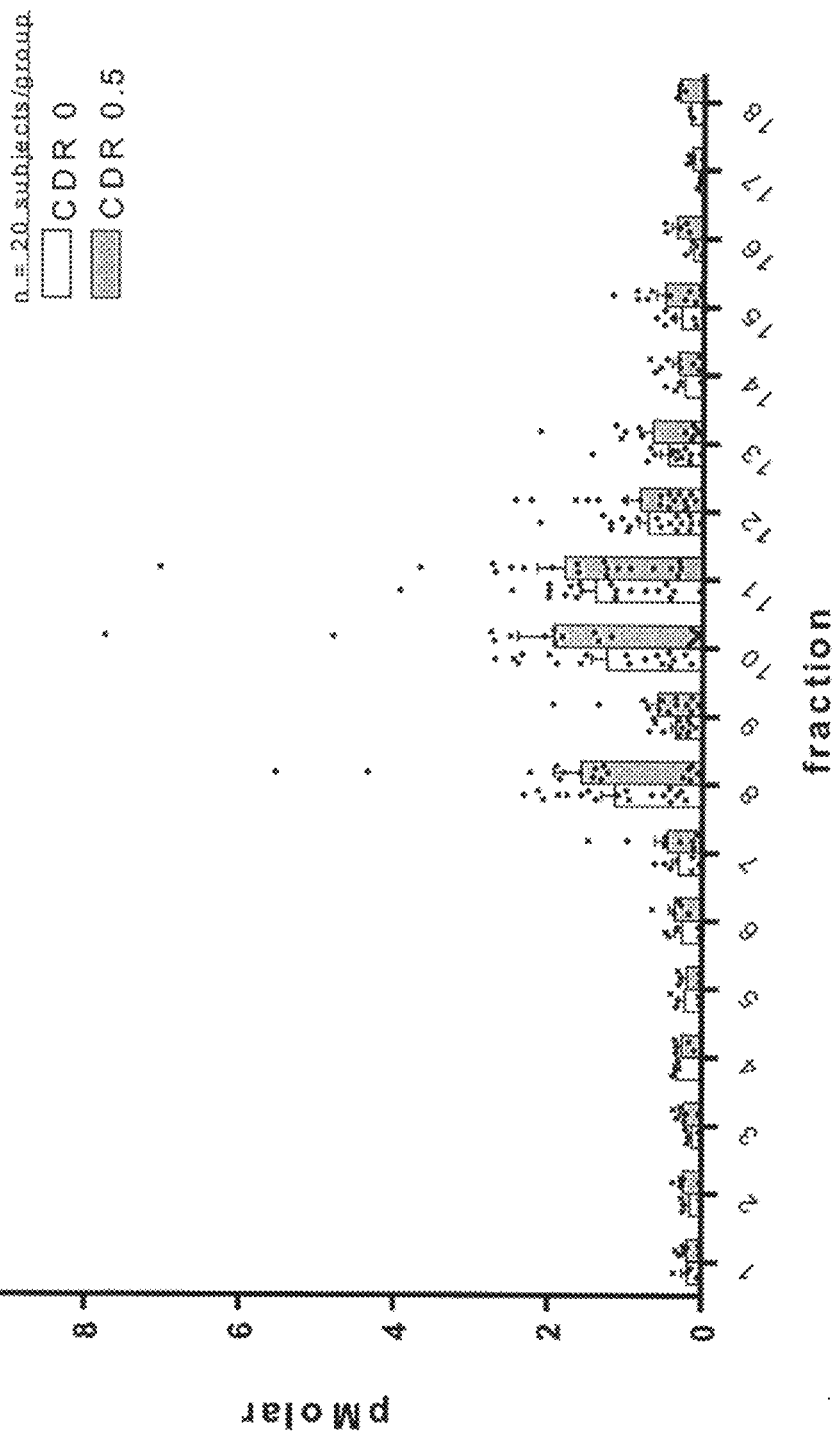

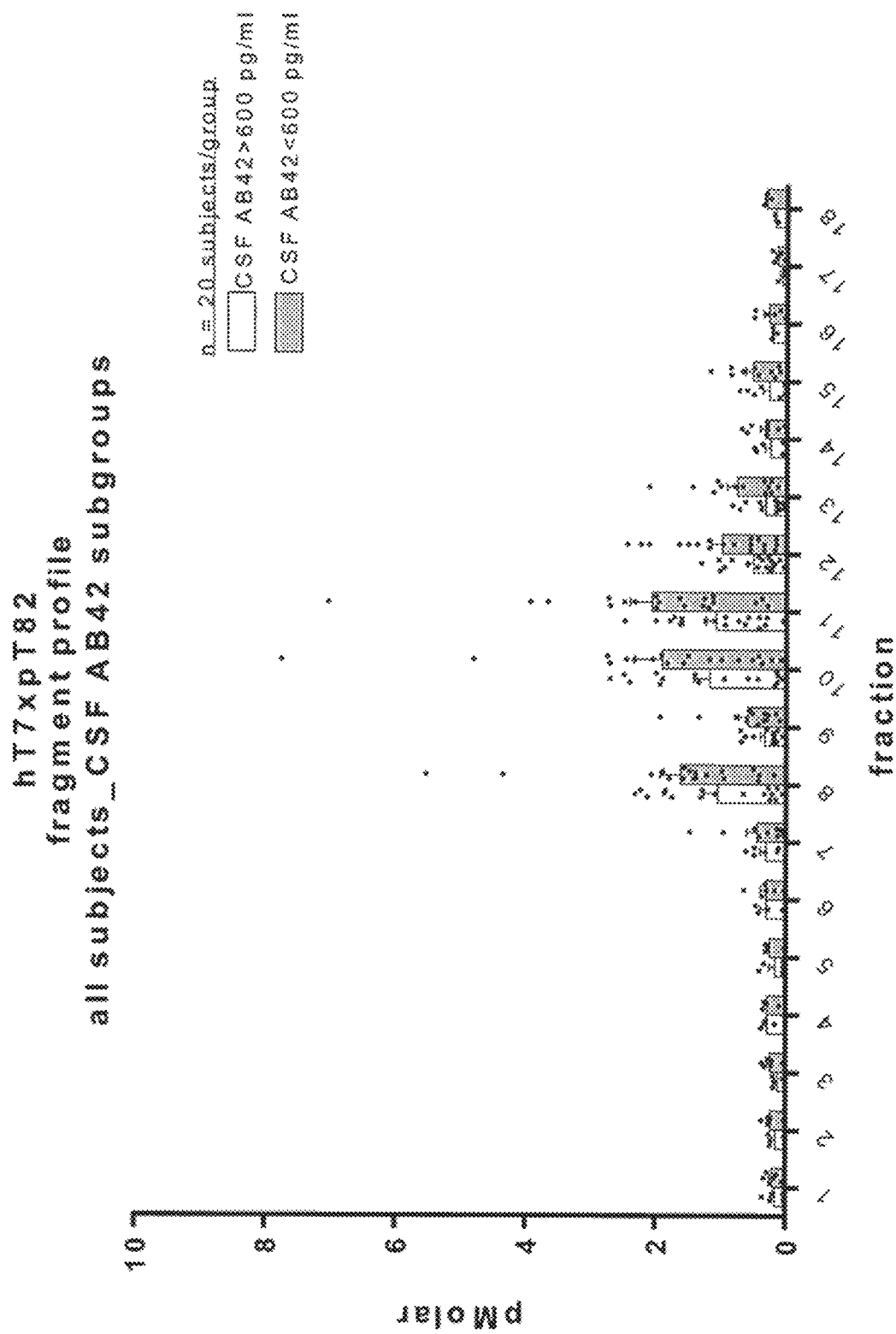

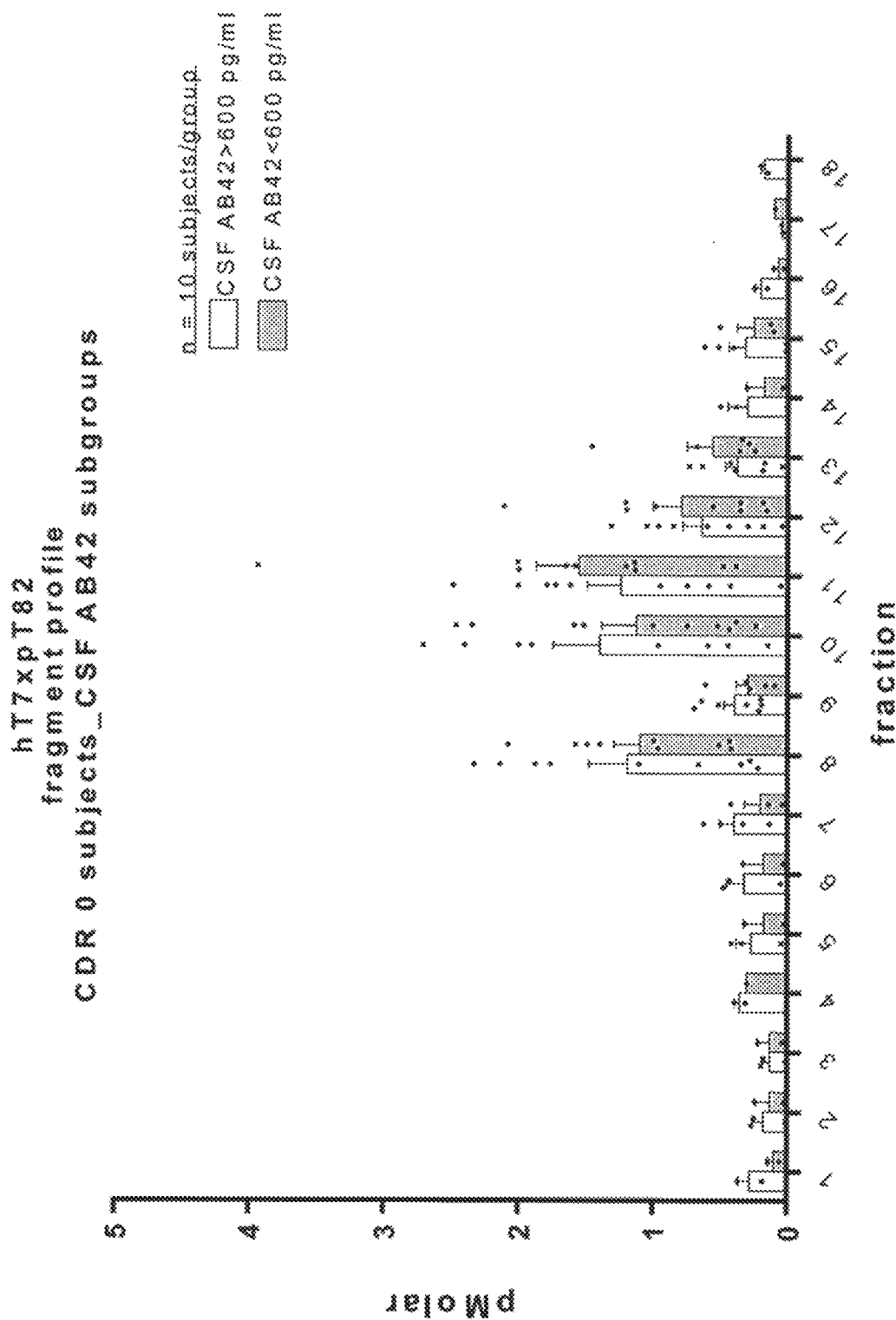

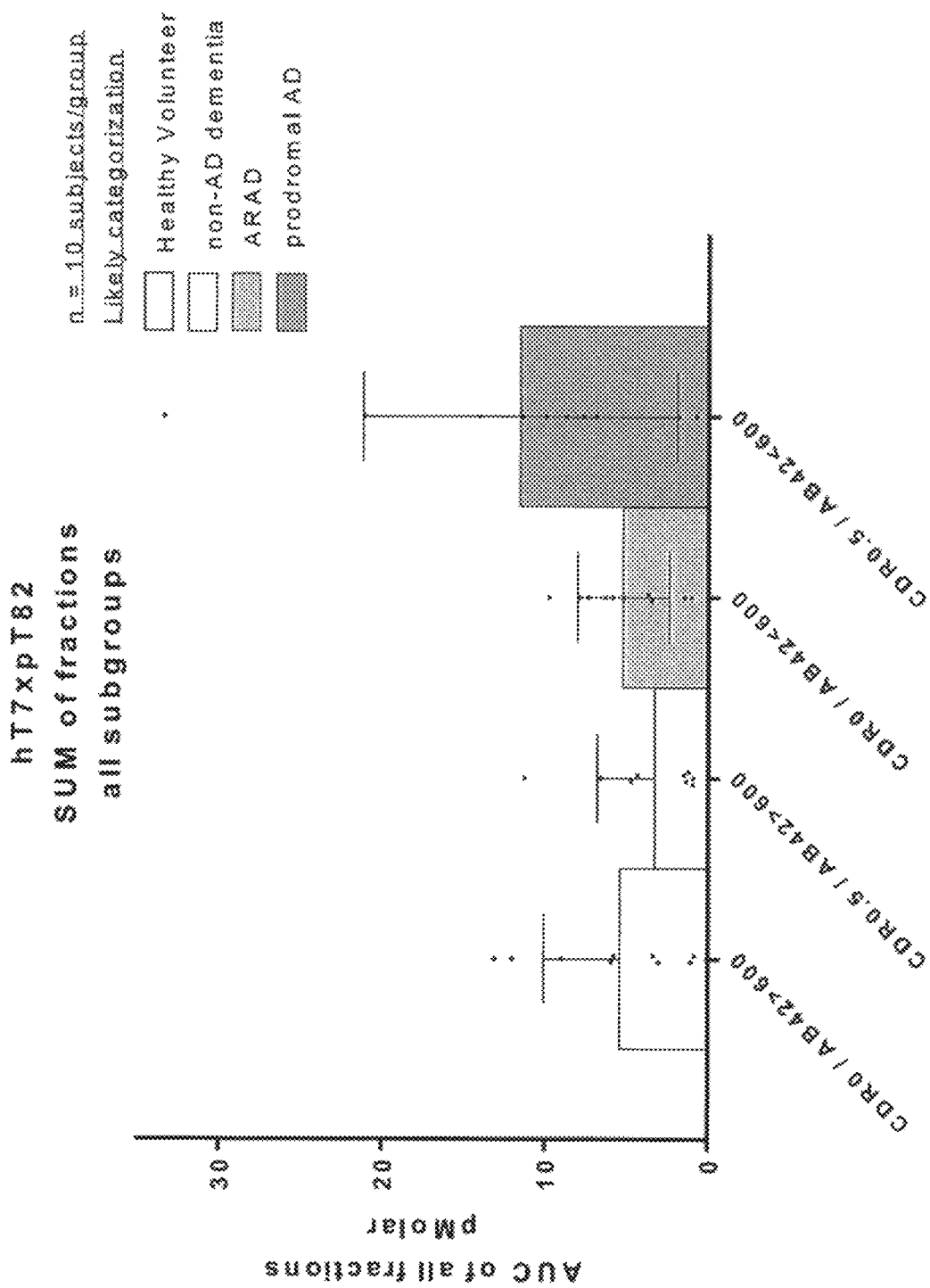

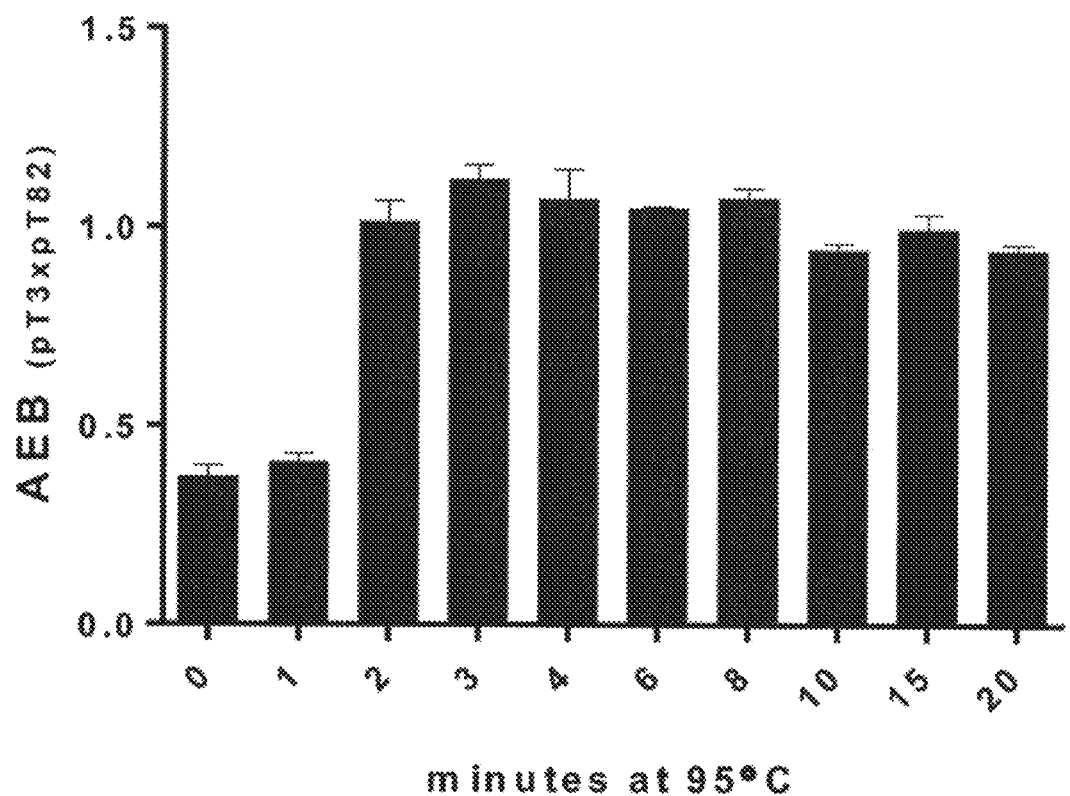

ASSAYS TO DETECT NEURODEGENERATION

CROSS REFERENCE TO RELATED APPLICATIONS

This application is a continuation application of U.S. application Ser. No. 16/291,264 with a filing date of Mar. 4, 2019, which claims priority to U.S. Provisional Application No. 62/638,524 with a filing date of Mar. 5, 2018. The provisional application is incorporated by reference in its entirety.

FIELD OF THE INVENTION

The invention relates to compositions and methods for detecting neurodegeneration. In particular, the invention relates to methods of measuring the amount of singly- or multiply-phosphorylated p217+ tau protein species in a biological sample and uses thereof, as well as antibodies and kits for use in the methods.

BACKGROUND OF THE INVENTION

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in ethnic groups worldwide and presents a major present and future public health problem.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles of paired helical filaments, are generally found in several areas of the human brain important for memory and cognitive function in patients with AD.

Neurofibrillary tangles are primarily composed of aggregates of hyper-phosphorylated tau protein. The main physiological function of tau is microtubule polymerization and stabilization. The binding of tau to microtubules takes place by ionic interactions between positive charges in the microtubule binding region of tau and negative charges on the microtubule lattice (Butner and Kirschner, *J Cell Biol.* 115(3):717-30, 1991). Tau protein contains 85 possible phosphorylation sites, and phosphorylation at many of these sites interferes with the primary function of tau. Tau that is bound to the axonal microtubule lattice is in a hypo-phosphorylation state, while aggregated tau in AD is hyper-phosphorylated, providing unique epitopes that are distinct from the physiologically active pool of tau (Iqbal et al., *Curr Alzheimer Res.* 7(8): 656-664, 2010).

The progression of tauopathy in an AD brain follows distinct spreading patterns. A tauopathy transmission and spreading hypothesis has been described based on the Braak stages of tauopathy progression in the human brain and tauopathy spreading after tau aggregate injections in pre-clinical tau models (Frost et al., *J Biol Chem.* 284:12845-52, 2009; Clavaguera et al., *Nat Cell Biol.* 11:909-13, 2009). It is believed that tauopathy can spread in a prion-like fashion from one brain region to the next. This spreading process would involve an externalization of tau seeds that can be taken up by nearby neurons and induce further tauopathy.

Fragments of tau protein in the neurofibrillary tangles move to the cerebrospinal fluid (CSF) where they can be harvested by lumbar puncture and measured by sensitive assays. The presence of neurological disease can thus be detected using assays that recognize tau protein-derived fragments in CSF. Such tau assays require the ability to recognize tau species characteristic of a neurodegenerative condition. Multiply-phosphorylated tau is the leading example of AD-associated tau protein. Therefore, assays that detect multiply-phosphorylated tau protein in CSF may be most effective in detecting the presence of AD.

Phosphorylation is not the only posttranslational modification to consider in measuring tau. Recent studies have demonstrated that in CSF, tau protein exists primarily as fragments rather than as full-length protein (Meredith et al. *PLoS One.* 8(10):e76523, 2013). Further, the tau fragmentation pattern may be influenced by disease, as proteolysis is frequently aberrant in pathological conditions. Consequently, tau-based assays for neurodegeneration need to provide information not only on the phosphorylation status (e.g. phosphorylation site), but also on the nature of the tau fragments (e.g. length of tau fragment, polarity) that are being measured. However, translation of this idea is hampered by the low endogenous levels of phosphorylated tau, especially in samples from healthy subjects.

In summary, there remains a need for sensitive, precise and accurate methods for detecting multiply-phosphorylated tau in biological fluids. Such methods would be useful to effectively detect, diagnose, stage and track disease progression of neurodegenerative diseases, such as AD and other tauopathies. The methods would also be useful as pharmacodynamics markers for measuring levels of total, free, and therapeutic antibody-bound multiply-phosphorylated tau. The ability to detect and measure multiply-phosphorylated tau fragments is of further importance to the field, as the transmissible tau species may be one or more tau fragments.

BRIEF SUMMARY OF THE INVENTION

The invention satisfies the need to detect forms of tau in CSF that are linked to neurodegenerative diseases. The invention enables detection of singly- or multiply-phosphorylated tau as well as detection of tau fragments.

High sensitivity Enzyme Linked Immunoassays (ELISAs) according to embodiment the invention were developed and qualified for measuring a p217+ tau comprising a phosphorylated tau epitope ("p217+ tau epitope" or "pT3 epitope") comprising phosphorylated residues T212 and/or T217 having the sequence of (212) R(pT)PSLPTPPTR (SEQ ID NO: 25), (217) RTPSLP(pT)PPTR (SEQ ID NO: 26) or (212&217) R(pT)PSLP(pT)PPTR (SEQ ID NO: 27).

Assays according to embodiments of the invention are capable of measuring p217+ tau species in various fluid matrices including but not limited to CSF, interstitial fluid (ISF), brain homogenate, serum, plasma and denatured or enriched versions thereof. Assays according to embodiments of the invention use a first monoclonal antibody directed to a pT3 epitope of tau as a capture antibody, and a second monoclonal antibody directed to a second epitope of tau as a detection antibody. The assays are highly sensitive, precise, accurate, transferable between labs, dilution linear, and applicable to many sample types. In addition to measurement of p217+ tau species in raw biological fluid, the assays can be used to measure samples with or without denaturing, or after immunoprecipitation, two complementary techniques to quantify the amount of free p217+ tau or p217+ tau bound to an endogenous or therapeutically-administered antibody. The assays can be used in tandem with reverse phase High Performance Liquid Chromatography (rpHPLC) to measure fractionated CSF, allowing for analysis of the fragment profile of p217+ tau.

In one general aspect, the invention relates to a method of measuring the amount of p217+ tau peptides in a sample. The method comprises: (i) contacting the sample with a capture antibody directed against a p217+ tau epitope to capture p217+ tau peptides in the sample, and (ii) contacting the captured p217+ tau peptides with a detection antibody directed against an epitope comprising amino acid residues 119 to 126, such as amino acid residues 116-127, of tau protein, or an epitope containing amino acid residues 7 to 20 of tau protein to thereby measure an amount of p217+ tau peptides or an amount of long p217+ tau peptides, respectively, wherein the numbering of the amino acid is with reference to the amino acid sequence set forth in SEQ ID NO: 1.

In one particular aspect, the invention relates to a method of determining a relative amount of long p217+ tau peptides or short p217 tau peptide fragments in a sample. The method comprises (i) contacting the sample with a capture antibody directed against a p217+ tau epitope to capture p217+ tau peptides in the sample, (ii) contacting the captured p217+ tau peptides with a first detection antibody directed against an epitope comprising amino acid residues 119 to 126 of tau protein to thereby measure an amount of p217+ tau peptides, (iii) contacting the captured p217+ tau peptides with a second detection antibody directed against an epitope comprising amino acid residues 7 to 20 of tau protein to thereby measure an amount of long p217+ tau peptides, and (iv) determining a relative amount of long p217+ tau peptides or short p217+ tau peptides based on the amount of p217+ tau peptides and the amount of long p217+ tau peptides, wherein the numbering of the amino acid is with reference to the amino acid sequence set forth in SEQ ID NO: 1.

In one embodiment of the invention, an amount of short p217+ tau peptides in a sample is calculated based on the amount of p217+ tau peptides and the amount of long p217+ tau peptides in the sample, e.g., by subtracting the amount of long p217+ tau peptides from the amount of p217+ tau peptides. In another embodiment, a ratio between the amount of short p217+ tau peptides to the amount of p217+ tau peptides, a ratio between the amount of long p217+ tau peptides to the amount of p217+ tau peptides, or a ratio between the amount of long p217+ tau peptides to the amount of short p217+ tau peptides is determined based on the amount of p217+ tau peptides and the amount of long p217+ tau peptides in the sample. According to embodiments of the invention, the amount of p217+ tau peptides and/or the amount of long p217+ tau peptides in a sample, as well as information based on the measure amounts, such as the calculated amount of the short p217+ tau peptides and one or more of the ratios described above, can be used for one or more diagnostic purposes.

Accordingly, in one particular aspect, the invention relates to a method of determining a ratio of p217+ tau peptides to total tau peptides in a sample. The method comprises (i) contacting the sample with a capture antibody directed against a p217+ tau epitope to capture p217+ tau peptides in the sample, and contacting the sample with a phosphorylation-independent capture antibody directed against an epitope between amino acids 150 and 250 of tau protein, preferably an epitope comprising amino acids 159-163 of tau protein, to capture total tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and contacting the capture total tau peptides with the first detection antibody to thereby measure an amount of total tau peptides; and (b) contacting the captured p217+ tau peptides with a second detection antibody directed against an epitope comprising amino acid residues 7 to 20 of tau protein to thereby measure an amount of long p217+ tau peptides, and contacting the capture total tau peptides with the second detection antibody to thereby measure an amount of total long tau peptides, and (iii) determining a ratio of the amount of the p217+ tau peptides to the amount of the total tau peptides, or a ratio of the amount of the long p217+ tau peptides to the amount of the total long tau peptides, wherein the numbering of the amino acid is with reference to the amino acid sequence set forth in SEQ ID NO: 1. In one embodiment, an amount of short p217+ tau peptides is calculated by subtracting the amount of long p217+ tau peptides from the amount of p217+ tau peptides, an amount of total short tau peptides is calculated by subtracting the amount of total long tau peptides from the amount of total tau peptides, and a ratio of the amount of short p217+ tau peptides to the amount of the total short tau peptides is determined.

According to a particular aspect, a method of the invention comprises (i) contacting a biological sample, preferably a CSF sample, from a subject, with a capture antibody directed against a p217+ tau epitope to capture p217+ tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and (b) contacting the captured p217+ tau peptides with a second detection antibody directed against an epitope comprising amino acid residues 7 to 20 of tau protein to thereby measure an amount of long p217+ tau peptides, and (iii) determining whether or not the subject suffers from a tauopathy or is at risk of developing a tauopathy based on at least one of the amount of p217+ tau peptides, the amount of long p217+ tau peptides, an amount of short p217+ tau peptides obtained by subtracting the amount of long p217+ tau peptides from the amount of p217+ tau peptides, and ratios thereof, wherein the numbering of the amino acid is with reference to the amino acid sequence set forth in SEQ ID NO: 1. In one embodiment, the method further comprises administering to the subject a therapeutic agent for treating or preventing the tauopathy.

According to a particular aspect, a method of the invention comprises (i) contacting a biological sample, preferably a CSF sample, from a subject, with a capture antibody directed against a p217+ tau epitope to capture p217+ tau peptides in the sample, and contacting the sample with a phosphorylation-independent capture antibody directed against an epitope between amino acids 150 and 250 of tau protein, preferably an epitope comprising amino acids 159-163 of tau protein, to capture total tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and contacting the capture total tau peptides with the first detection antibody to thereby measure an amount of total tau peptides; and (b) contacting the captured p217+ tau peptides with a second detection antibody directed against an epitope comprising amino acid residues 7 to 20 of tau protein to thereby measure an amount of long p217+ tau peptides, and contacting the capture total tau peptides with the second detection antibody to thereby measure an amount of total long tau peptides, and (iii) determining whether or not the subject suffers from a tauopathy or is at risk of developing a tauopathy based on at least one of (a) a ratio of the amount of p217+ tau peptides to the amount of total tau peptides, (b) a ratio of the amount of long p217+ tau peptides to the amount of total long tau peptides, and (c) a ratio of an amount of short p217+ tau peptides to the amount of total short p217+ tau peptides, wherein the amount of short p217+ tau peptides is obtained by subtracting the amount of long p217+ tau peptides from the amount of p217+ tau peptides, and the amount of total short tau peptides is obtained by subtracting the amount of total short tau peptides from the amount of total tau peptides, wherein the numbering of the amino acid is with reference to the amino acid sequence set forth in SEQ ID NO: 1. In one embodiment, the method further comprises administering to the subject a therapeutic agent for treating or preventing the tauopathy.

According to another particular aspect, a method of the invention comprises (i) contacting a biological sample, preferably a CSF sample, from a subject under a treatment, with a capture antibody directed against a p217+ tau epitope to capture p217+ tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and (b) contacting the captured p217+ tau peptides with a second detection antibody directed against an epitope comprising amino acid residues 7 to 20 of tau protein to thereby measure an amount of long p217+ tau peptides, and (iii) determining the effectiveness of the treatment in the subject based on at least one of the amount of p217+ tau peptides, the amount of long p217+ tau peptides, an amount of short p217+ tau peptides obtained by subtracting the amount of long p217+ tau peptides from the amount of p217+ tau peptides, and ratios thereof, wherein the numbering of the amino acid is with reference to the amino acid sequence set forth in SEQ ID NO: 1. In one embodiment, the method further comprises administering to the subject a therapeutic agent for treating or preventing the tauopathy.

According to another particular aspect, a method of the invention comprises (i) contacting a biological sample, preferably a CSF sample, from a subject under a treatment, with a capture antibody directed against a p217+ tau epitope to capture p217+ tau peptides in the sample, and contacting the sample with a phosphorylation-independent capture antibody directed against an epitope between amino acids 150 and 250 of tau protein, preferably an epitope comprising amino acids 159-163 of tau protein, to capture total tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and contacting the capture total tau peptides with the first detection antibody to thereby measure an amount of total tau peptides; and (b) contacting the captured p217+ tau peptides with a second detection antibody directed against an epitope comprising amino acid residues 7 to 20 of tau protein to thereby measure an amount of long p217+ tau peptides, and contacting the capture total tau peptides with the second detection antibody to thereby measure an amount of total long tau peptides, and (iii) determining the effectiveness of the treatment in the subject based on at least one of (a) a ratio of the amount of p217+ tau peptides to the amount of total tau peptides, (b) a ratio of the amount of long p217+ tau peptides to the amount of total long tau peptides, and (c) a ratio of an amount of short p217+ tau peptides to the amount of total short tau peptides, wherein the amount of short p217+ tau peptides is obtained by subtracting the amount of long p217+ tau peptides from the amount of p217+ tau peptides, and the amount of total short tau peptides is obtained by subtracting the amount of total short tau peptides from the amount of total tau peptides, wherein the numbering of the amino acid is with reference to the amino acid sequence set forth in SEQ ID NO: 1. In one embodiment, the method further comprises administering to the subject a therapeutic agent for treating or preventing the tauopathy.

According to another particular aspect, a method of the invention comprises (i) contacting a biological sample, preferably a CSF sample, from a subject, with a capture antibody directed against a p217+ tau epitope to capture p217+ tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and (b) contacting the captured p217+ tau peptides with a second detection antibody directed against an epitope comprising amino acid residues 7 to 20 of tau protein to thereby measure an amount of long p217+ tau peptides, and (iii) determining whether or not the subject is suitable for an anti-p217+ tau antibody based on at least one of the amount of p217+ tau peptides, the amount of long p217+ tau peptides, an amount of short p217+ tau peptides obtained by subtracting the amount of long p217+ tau peptides from the amount of p217+ tau peptides, and ratios thereof, wherein the numbering of the amino acid is with reference to the amino acid sequence set forth in SEQ ID NO: 1. In one embodiment, the method further comprises administering to the subject an anti-p217+ tau antibody for treating or preventing the tauopathy.

According to another particular aspect, a method of the invention comprises (i) contacting a biological sample, preferably a CSF sample, from a subject, with a capture antibody directed against a p217+ tau epitope to capture p217+ tau peptides in the sample, and contacting the sample with a phosphorylation-independent capture antibody directed against an epitope between amino acids 150 and 250 of tau protein, preferably an epitope comprising amino acids 159-163 of tau protein, to capture total tau peptides in the sample, (ii) conducting at least one of (a) contacting the captured p217+ tau peptides with a first detection antibody directed against an epitope comprising amino acid residues 119 to 126 of tau protein to thereby measure an amount of p217+ tau peptides, and contacting the capture total tau peptides with the first detection antibody to thereby measure an amount of total tau peptides; and (b) contacting the captured p217+ tau peptides with a second detection antibody directed against an epitope comprising amino acid residues 7 to 20 of tau protein to thereby measure an amount of long p217+ tau peptides, and contacting the capture total tau peptides with the second detection antibody to thereby measure an amount of total long tau peptides, and (iii) determining whether or not the subject is suitable for an anti-p217+ tau antibody therapy based on at least one of (a) a ratio of the amount of p217+ tau peptides to the amount of total tau peptides, (b) a ratio of the amount of long p217+ tau peptides to the amount of total long tau peptides, and (c) a ratio of an amount of short p217+ tau peptides to the amount of total short tau peptides, wherein the amount of short p217+ tau peptides is obtained by subtracting the amount of long p217+ tau peptides from the amount of p217+ tau peptides, and the amount of total short tau peptides is obtained by subtracting the amount of total short tau peptides from the amount of total tau peptides, wherein the numbering of the amino acid is with reference to the amino acid sequence set forth in SEQ ID NO: 1. In one embodiment, the method further comprises administering to the subject an anti-p217+ tau antibody for treating or preventing the tauopathy.

In another particular aspect, the invention relates to a method of monitoring a treatment with an anti-p217+ tau antibody in a subject, the method comprising: (i) obtaining a biological sample from the subject, (ii) separating the biological sample into a first sample containing p217+ tau free of the anti-p217+ tau antibody, preferably from of IgG, and a second sample containing p217+ tau peptides bound to the anti-p217+ tau antibody, (iii) obtaining a third sample containing p217+ tau free of anti-p217+ tau antibody from the second sample, preferably via rpHPLC, (iv) contacting each of the first sample and the third sample with a capture antibody directed against a p217+ tau epitope to capture p217+ tau peptides in each of the samples, (v) conducting at least one of (a) contacting the captured p217+ tau peptides with a first detection antibody directed against an epitope comprising amino acid residues 119 to 126 of tau protein to thereby measure an amount of p217+ tau peptides in each of the samples, and (b) contacting the captured p217+ tau peptides with a second detection antibody directed against an epitope comprising amino acid residues 7 to 20 of tau protein to thereby measure an amount of long p217+ tau peptides in each of the samples, (vi) monitoring the treatment with the anti-p217+ tau antibody based on at least one of the amount of the p217+ tau peptides and the amount of the long p217+ tau peptides in each of the samples, wherein the numbering of the amino acid is with reference to the amino acid sequence set forth in SEQ ID NO: 1. For example, the treatment with the anti-p217+ tau antibody can be monitored based on a ratio of the amount of long p217+ tau peptides in the first sample to that in the third sample, a ratio of the amount of the p217+ tau peptides in the first sample to that in the third sample, or a ratio of the amount of short p217+ tau peptides (which can be calculated by subtracting the amount of the long p217+ tau peptides from the amount of the p217+ tau peptides) in the first sample to that in the third sample. In one embodiment, the method further comprises administering to the subject an anti-p217+ tau antibody for treating or preventing the tauopathy.

In another general aspect, the invention relates to a method of monitoring a treatment with an anti-p217+ tau antibody in a subject, the method comprising: (i) obtaining a biological sample from the subject, (ii) obtaining a semi-denatured sample from the biological sample containing total p217+ tau, wherein the semi-denatured sample is heated to denature the antibodies in the sample, and obtaining a non-denatured sample from the biological sample containing p217+ tau free of the anti-p217+ tau antibody, (iii) contacting each of the semi-denatured sample and the non-denatured sample with a capture antibody directed against a p217+ tau epitope to capture p217+ tau peptides in each of the samples, (v) conducting at least one of (a) contacting the captured p217+ tau peptides with a first detection antibody directed against an epitope comprising amino acid residues 119 to 126 of tau protein to thereby measure an amount of p217+ tau peptides in each of the samples, and (b) contacting the captured p217+ tau peptides with a second detection antibody directed against an epitope comprising amino acid residues 7 to 20 of tau protein to thereby measure an amount of long p217+ tau peptides in each of the samples, and vi) monitoring the treatment with the anti-p217+ tau antibody based on at least one of the amount of the p217+ tau peptides and the amount of the long p217+ tau peptides in each of the samples, wherein the numbering of the amino acid is with reference to the amino acid sequence set forth in SEQ ID NO: 1. For example, the treatment with the anti-p217+ tau antibody can be monitored based on a ratio of the amount of the long p217+ tau peptides in the semi-denatured sample to that in the non-denatured sample, a ratio of the amount of the p217+ tau peptides in the semi-denatured sample to that in the non-denatured sample, or a ratio of the amount of the short p217+ tau peptides (which can be calculated by subtracting the amount of the long p217+ tau peptides from the amount of the p217+ tau peptides) in the semi-denatured sample to that in the non-denatured sample. In one embodiment, the method further comprises administering to the subject an anti-p217+ tau antibody for treating or preventing the tauopathy.

According to a particular aspect, the tauopathy includes, but is not limited to, one or more selected from the group consisting of Alzheimer's disease (including familial Alzheimer's disease and sporadic Alzheimer's disease), frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Preferably, the tauopathy is Alzheimer's disease (including familial Alzheimer's disease and sporadic Alzheimer's disease), FTDP-17 or progressive supranuclear palsy.

Most preferably, the tauopathy is Alzheimer's disease (including familial Alzheimer's disease and sporadic Alzheimer's disease).

According to a particular aspect, the lower limit of quantification of a method of the invention is about 40 fg/ml p217+ tau peptides and the lower limit of detection of a method of the invention is about 2 fg/ml p217+ tau peptides.

According to a particular aspect, the sample is a biological sample, such as a blood, brain homogenate, or cerebral spinal fluid (CSF) sample, from a subject in need thereof. Preferably, the biological sample is a CSF sample from a subject in need of a diagnosis of tauopathy, monitoring the effectiveness of a tauopathy treatment, or determination on the suitability for an anti-p217+ tau antibody therapy.

According to a particular aspect, a capture antibody useful for methods of the invention is directed against a p217+ tau epitope, preferably a p217+ tau epitope containing the amino acid sequence of SEQ ID NO: 25, 26 or 27. In one embodiment, a capture antibody useful for methods of the invention comprises immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively. Preferably, the capture antibody has a heavy chain variable region comprising polypeptide sequence of SEQ ID NO: 28 or 30 and a light chain variable region having the polypeptide sequence of SEQ ID NO: 29 or 31.

According to a particular aspect, a detection antibody useful for methods of the invention is directed against an epitope comprising amino acid residues 119 to 126 of tau protein, preferably an epitope comprising the amino acid sequence of SEQ ID NO: 10, such as the amino acid sequence of SEQ ID NO:11. In one embodiment, a detection antibody useful for methods of the invention comprises immunoglobulin heavy chain HCDR1, HCDR2 and HCDR3 having the polypeptide sequences of SEQ ID NOs: 2, 3 and 4, respectively; and immunoglobulin light chain LCDR1, LCDR2 and LCDR3 having the polypeptide sequences of SEQ ID NOs: 5, 6 and 7, respectively. Preferably, the detection antibody is a pT82 antibody comprising a heavy chain variable region having the polypeptide sequence of SEQ ID NO: 8 and a light chain variable region having the polypeptide sequence of SEQ ID NO: 9.

According to another particular aspect, a detection antibody useful for methods of the invention is directed against an epitope containing amino acid residues 7 to 20 of tau protein, preferably an epitope having the amino acid sequence of SEQ ID NO: 20. In one embodiment, a detection antibody useful for methods of the invention comprises immunoglobulin heavy chain HCDR1, HCDR2 and HCDR3 having the polypeptide sequences of SEQ ID NOs: 12, 13 and 14, respectively; and immunoglobulin light chain LCDR1, LCDR2 and LCDR3 having the polypeptide sequences of SEQ ID NOs: 15, 16 and 17, respectively. Preferably, the detection antibody is a hT43 antibody comprising a heavy chain variable region having the polypeptide sequence of SEQ ID NO: 18 and a light chain variable region having the polypeptide sequence of SEQ ID NO: 19.

According to another particular aspect, a phosphorylation-independent capture antibody useful for the invention is directed against an epitope between amino acids 150 and 250 of tau protein, preferably an epitope comprising amino acids 211 to 221 of tau protein, or an epitope comprising amino acids 159 to 163 of tau protein, more preferably an epitope having the amino acid sequence of SEQ ID NO:21. In one embodiment, a phosphorylation-independent capture antibody useful for the invention is a hT7 antibody.

According to another particular aspect, the sample used in methods of the invention is obtained after fractionating a biological sample using reverse phase high-performance liquid chromatography (rpHPLC).

In another general aspect, the invention relates to an isolated detection antibody or antigen-binding fragment thereof that binds to a tau protein at an epitope comprising amino acid residues 7 to 20 of tau protein, comprising (a) immunoglobulin heavy chain HCDR1, HCDR2 and HCDR3 having the polypeptide sequences of SEQ ID NOs: 12, 13 and 14, respectively; and (b) immunoglobulin light chain LCDR1, LCDR2 and LCDR3 having the polypeptide sequences of SEQ ID NOs: 15, 16 and 17, respectively. According to a particular aspect, the isolated detection antibody or antigen-binding fragment thereof comprises a heavy chain variable region having a polypeptide sequence of SEQ ID NO: 18, and a light chain variable region having a polypeptide sequence of SEQ ID NO: 19. Preferably, the isolated detection antibody or antigen-binding fragment thereof that binds to a tau protein at an epitope comprising amino acid residues 7 to 20 of tau protein is a hT43 antibody.

In another general aspect, the invention relates to a kit comprising (a) a capture antibody directed against a p217+ tau epitope, and (b) a detection antibody directed against a tau protein epitope comprising amino acid residues 7 to 20 or 116 to 127 of tau protein. Optionally, the kit further comprises a phosphorylation-independent capture antibody directed against a tau epitope between amino acids 150 and 250 of tau protein. The kit can be used, for example, to measure the amount of p217+ tau peptides, the amount of long p217+ tau peptides, the amount of short p217+ tau peptides, the ratio of the amount of short p217+ tau peptides to the amount of long p217+ tau peptides, the ratio of the amount of short p217+ tau peptides to the amount of total short tau peptides in a sample, etc. The kit can also be for various diagnostic or monitoring purposes, e.g., to determine whether or not a subject suffers from a tauopathy or is at risk of developing a tauopathy, monitoring the efficacy of a treatment against a tauopathy, such as a treatment with an anti-p217+ tau antibody, to determine whether or not the subject is suitable for an anti-p217+ tau antibody, etc.

According to a particular aspect, a kit of the invention comprises a capture antibody, which has immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively. Preferably, the capture antibody has a heavy chain variable region comprising polypeptide sequence of SEQ ID NO: 28 and a light chain variable region having the polypeptide sequence of SEQ ID NO: 29.

According to another particular aspect, a kit of the invention comprises a detection antibody, which comprises immunoglobulin heavy chain HCDR1, HCDR2 and HCDR3 having the polypeptide sequences of SEQ ID NOs: 2, 3 and 4, respectively; and immunoglobulin light chain LCDR1, LCDR2 and LCDR3 having the polypeptide sequences of SEQ ID NOs: 5, 6 and 7, respectively. Preferably, the detection antibody is a pT82 antibody comprising a heavy chain variable region having the polypeptide sequence of SEQ ID NO: 8 and a light chain variable region having the polypeptide sequence of SEQ ID NO: 9.

According to another particular aspect, a kit of the invention comprises a detection antibody, which comprises immunoglobulin heavy chain HCDR1, HCDR2 and HCDR3 having the polypeptide sequences of SEQ ID NOs: 12, 13 and 14, respectively; and immunoglobulin light chain LCDR1, LCDR2 and LCDR3 having the polypeptide sequences of SEQ ID NOs: 15, 16 and 17, respectively. Preferably, the detection antibody is a hT43 antibody comprising a heavy chain variable region having the polypeptide sequence of SEQ ID NO: 18 and a light chain variable region having the polypeptide sequence of SEQ ID NO: 19.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIGS. 2A-2E show the dilution linearity of pT3xhT43 and pT3xpT82 assays in CSF samples with measurements shown (A, C and E) in dilution corrected pg/ml or (B and D) as dilution corrected % of 1:4 measurement, with dashed lines indicating +/−20% of 1:4 measurements.

FIGS. 12A-12D show the results of (A) pT3xhT43, (B) pT3xpT82, (C) hT7xpT82, and (D) ratio of pT3xpT82 vs. hT7xpT82 analysis of crude CSF from AD and HV patients.

FIGS. 21A-21C show the differential kinetics of antibody vs. p217+ tau damage either (A, C) with or (B) without heat-mediated denaturation. (A) humanized PT3 mAb/CSF mix; (B) untreated CSF; (C) humanized PT3 mAb.

DETAILED DESCRIPTION OF THE INVENTION

Figure 1:
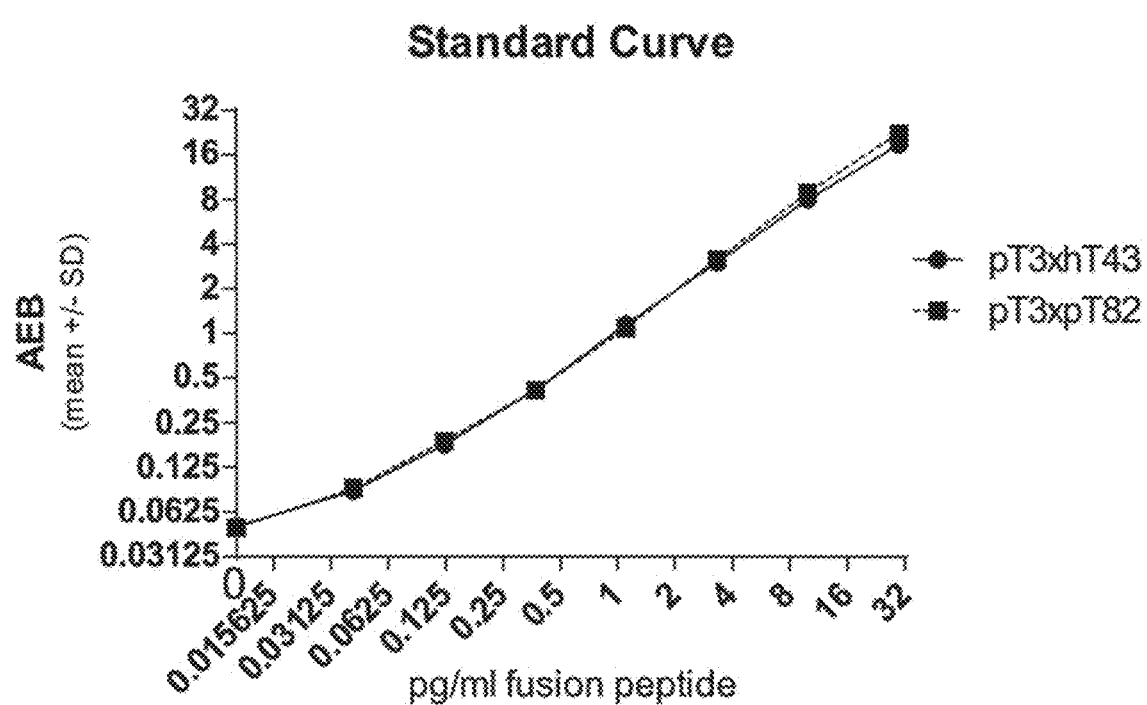
FIG. 1 shows a representative standard curve for the pT3xhT43 and pT3xpT82 assays generated using calibrant peptides with mean+/−SD of duplicate measurements shown at each point.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Definitions

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the term "antibody" or "immunoglobulin" is used in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Antibody structures are well known. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of any vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from mouse antibodies or human antibodies.

In addition to the heavy and light constant domains, antibodies contain light and heavy chain variable regions. An immunoglobulin light or heavy chain variable region consists of a "framework" region interrupted by "antigen-binding sites." The antigen-binding sites are defined using various terms and numbering schemes as follows:

(i) Kabat: "Complementarity Determining Regions" or "CDRs" are based on sequence variability (Wu and Kabat, *J Exp Med.* 132:211-50, 1970). Generally, the antigen-binding site has three CDRs in each variable region (e.g., HCDR1, HCDR2 and HCDR3 in the heavy chain variable region (VH) and LCDR1, LCDR2 and LCDR3 in the light chain variable region (VL));

(ii) Chothia: The term "hypervariable region," "HVR" refers to the regions of an antibody variable domain which are hypervariable in structure as defined by Chothia and Lesk (Chothia and Lesk, *J Mol Biol.* 196:901-17, 1987). Generally, the antigen-binding site has three hypervariable regions in each VH (H1, H2, H3) and VL (L1, L2, L3). Numbering systems as well as annotation of CDRs and HVRs have been revised by Abhinandan and Martin (Abhinandan and Martin, *Mol Immunol.* 45:3832-9, 2008);

(iii) IMGT: Another definition of the regions that form the antigen-binding site has been proposed by Lefranc (Lefranc et al., *Dev Comp Immunol.* 27:55-77, 2003) based on the comparison of V domains from immunoglobulins and T-cell receptors. The International ImMunoGeneTics (IMGT) database (http://www_imgt_org) provides a standardized numbering and definition of these regions. The correspondence between CDRs, HVRs and IMGT delineations is described in Lefranc et al., 2003, Id.;

(iv) The antigen-binding site can also be delineated based on "Specificity Determining Residue Usage" (SDRU) (Almagro, *Mol Recognit.* 17:132-43, 2004), where SDR, refers to amino acid residues of an immunoglobulin that are directly involved in antigen contact.

"Framework" or "framework sequence" is the remaining sequences within the variable region of an antibody other than those defined to be antigen-binding site sequences. Because the exact definition of an antigen-binding site can be determined by various delineations as described above, the exact framework sequence depends on the definition of the antigen-binding site. The framework regions (FRs) are the more highly conserved portions of variable domains. The variable domains of native heavy and light chains each comprise four FRs (FR1, FR2, FR3 and FR4, respectively) which generally adopt a beta-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., *J. Mol. Biol.* 227: 799-817, 1992; Tramontano et al., *J. Mol. Biol.* 215:175-182, 1990). Despite their high sequence variability, five of the six loops adopt just a small repertoire of main-chain conformations, called "canonical structures." These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the constant region of the heavy chain. According to other particular embodiments, the antigen-binding fragment comprises Fab and F(ab').

As used herein, the term "epitope" refers to a site on an antigen to which an immunoglobulin, antibody, or antigen-binding fragment thereof, specifically binds. Epitopes can be formed both from contiguous amino acids or from noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, G. E. Morris, Ed. (1996).

As used herein, the term "tau" or "tau protein" refers to an abundant central and peripheral nervous system protein having multiple isoforms. In the human central nervous system (CNS), six major tau isoforms ranging in size from 352 to 441 amino acids in length exist due to alternative splicing (Hanger et al., *Trends Mol Med.* 15:112-9, 2009). The isoforms differ from each other by the regulated inclusion of 0-2 N-terminal inserts, and 3 or 4 tandemly arranged microtubule-binding repeats, and are referred to as 0N3R, 1N3R, 2N3R, 0N4R, 1N4R and 2N4R. As used herein, the term "control tau" refers to the tau isoform of SEQ ID NO: 1 that is devoid of phosphorylation and other post-translational modifications. As used herein, the term "tau" includes proteins comprising mutations, e.g., point mutations, fragments, insertions, deletions and splice variants of full length wild type tau. The term "tau" also encompasses post-translational modifications of the tau amino acid sequence. Post-translational modifications include, but are not limited to, phosphorylation.

Unless otherwise indicated, as used herein, the numbering of the amino acid in a tau protein or fragment thereof is with reference to the amino acid sequence set forth in SEQ ID NO: 1.

As used herein, the term "p217+ tau peptides," "p217+ tau," or "p217+ tau protein" means a human tau protein or tau fragment that is phosphorylated at one or both of residue 217 (pT217) and residue 212 (pT212) of tau protein, wherein the numbering of the positions is according to the numbering in SEQ ID NO: 1.

As used herein, the term "p217+ tau epitope" refers to a tau epitope containing at least one of phosphorylated T217 and phosphorylated T212, wherein the numbering of the positions is according to the numbering in SEQ ID NO: 1. Examples of p217+ tau epitope include, e.g., a pT3 epitope. As used herein, the term "pT3 epitope" refers to an epitope containing amino acids 210-220 of human tau protein that is phosphorylated at least one reside of T217 and T212 of human tau, wherein the numbering of the positions is according to the numbering in SEQ ID NO: 1. Examples of pT3 epitope include, e.g., SEQ ID NO: 25, 26 and 27.

As used herein, each of the terms "long p217+ tau peptides," "long p217+ tau," "long form of p217+ tau peptides," or "long p217+ tau peptides fragment" has the same meaning, referring to a p217+ tau peptides that comprises the p217+ tau epitope and an epitope comprising amino acid residues 7 to 20 of tau protein. The "long p217+ tau peptides" according to embodiments of the invention can have different lengths. For example, the amino-terminus of a "long p217+ tau peptides fragment" can be the amino acid residue 1, 2, 4, 5, 6, or 7 of tau protein.

As used herein, each of the terms "short p217+ tau peptides," "short p217+ tau," "short form of p217+ tau peptides," or "short p217+ tau peptides fragment" has the same meaning, referring to a p217+ tau peptides that comprises the p217+ tau epitope and an epitope comprising amino acid residues 119 to 126 of tau protein, but does not contain an epitope comprising amino acid residues 7 to 20 of tau protein. The "short p217+ tau peptides" according to embodiments of the invention can have different lengths. For example, the amino-terminus of a "short p217+ tau peptides" can be any of the amino acid residues between the epitope comprising amino acid residues 7 to 20 of tau protein and the epitope comprising amino acid residues 119 to 126 of tau protein.

As used herein, each of the terms "long tau peptide," "long tau," "long form of tau peptide," or "long tau peptide fragment" has the same meaning, referring to a tau peptide that comprises the tau epitope recognized by a phosphorylation-independent capture antibody and an epitope comprising amino acid residues 7 to 20 of tau protein. The "long tau peptide fragments" according to embodiments of the invention can have different lengths. For example, the amino-terminus of a "long tau peptide fragment" can be the amino acid residue 1, 2, 4, 5, 6, or 7 of tau protein.

As used herein, each of the terms "short tau peptide," "short tau," "short form of tau peptide," or "short tau peptide fragment" has the same meaning, referring to a tau peptide that comprises the tau epitope recognized by a phosphorylation-independent capture antibody and an epitope comprising amino acid residues 119 to 126 of tau protein, but does not contain an epitope comprising amino acid residues 7 to 20 of tau protein. The "short tau peptide fragments" according to embodiments of the invention can have different lengths. For example, the amino-terminus of a "short tau peptide" can be any of the amino acid residues between the epitope comprising amino acid residues 7 to 20 of tau protein and the epitope comprising amino acid residues 119 to 126 of tau protein.

As used herein, the term "capture antibody" refers to an antibody that binds to an antigen of interest and is directly or indirectly linked to a solid support. Examples of solid supports include, but are not limited to, microparticles or beads, such as a magnetic beads. Examples of capture antibodies include, but are not limited to, a monoclonal antibody that binds to a p217+ tau epitope. According to embodiments of the invention, the capture antibody can be a monoclonal antibody comprising immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37. In a particular embodiment, the capture antibody is pT3. As used herein, the term "pT3" refers to an antibody that binds to p217+ tau peptides and has a heavy chain variable region amino acid sequence of SEQ ID NO: 28 and a light chain variable region amino acid sequence of SEQ ID NO: 29. In one embodiment, the pT3 monoclonal antibody is expressed by a mouse-hybridoma. In another embodiment, the capture antibody is a humanized antibody having a heavy chain variable region amino acid sequence of SEQ ID NO: 30 and a light chain variable region amino acid sequence of SEQ ID NO: 31.

According to other embodiments of the invention, the capture antibody can be a monoclonal antibody that binds to an epitope between amino acids 150 and 250 of tau protein, preferably amino acids 211-221 or amino acids 159-163 of human tau protein, in a phosphorylation-independent manner, and the numbering of the positions is according to the numbering in SEQ ID NO: 1. In a particular embodiment, the capture antibody is hT7. As used herein, the term "hT7" refers to a publicly available monoclonal antibody that binds to an epitope comprising amino acids 159-163 of human tau protein, wherein the numbering of the positions is according to the numbering in SEQ ID NO: 1. A hT7 monoclonal antibody is commercially available, e.g., from ThermoFisher (e.g., Catalog #: MN1000).

As used herein, the term "detection antibody" refers to an antibody that binds to an antigen of interest and has a detectible label or is linked to a secondary detection system. Examples of detectable labels include, but are not limited to, various enzymes, prosthetic groups, fluorescent materials, luminescent materials, bioluminescent materials, and radioactive materials. Examples of detection antibodies include, but are not limited to, a monoclonal antibody that binds to tau protein, preferably an epitope comprising amino acids 7-20 or 116-127 of human tau protein, wherein the numbering of the positions is according to the numbering in SEQ ID NO: 1. When a monoclonal antibody that binds to a tau protein at an epitope comprising amino acids 7-20 is used as a detection antibody for captured p217+ tau peptides, long tau fragments are detected. When a monoclonal antibody that binds to a tau protein at an epitope comprising amino acids 116-127 is used as a detection antibody for captured p217+ tau peptides, both short and long tau fragments are detected.

In a particular embodiment, the detection antibody is hT43. As used herein, the term "hT43" refers to a monoclonal antibody that binds to an epitope comprising amino acids 7-20 of human tau protein, wherein the numbering of the positions is according to the numbering in SEQ ID NO: 1, and the antibody has a heavy chain variable region amino acid sequence of SEQ ID NO: 8 and a light chain variable region amino acid sequence of SEQ ID NO: 9. In another particular embodiment, the detection antibody is pT82. As used herein, the term "pT82" refers to a monoclonal antibody that binds to an epitope comprising amino acids 119-126, preferably 116-127, of human tau protein, wherein the numbering of the positions is according to the numbering in SEQ ID NO: 1, and the antibody has a heavy chain variable region amino acid sequence of SEQ ID NO: 18 and a light chain variable region amino acid sequence of SEQ ID NO: 19.

As used herein, the term "pT3-based assay" refers to an assay according to an embodiment of the invention wherein the pT3 antibody is used as the capture antibody. As used herein, the term "pT3xhT43" refers to an assay according to an embodiment of the invention wherein the pT3 antibody is used as the capture antibody and the hT43 antibody is used as the detection antibody. As used herein, the term "pT3xpT82" refers to an assay according to an embodiment of the invention wherein the pT3 antibody is used as the capture antibody and the pT82 antibody is used as the detection antibody.

As used herein, the term "hT7-based assay" refers to assays according to embodiments of the invention wherein the hT7 antibody is used as the capture antibody. As used herein, the term "hT7xpT82" refers to assays according to embodiments of the invention wherein the hT7 antibody is used as the capture antibody and the pT82 antibody is used as the detection antibody.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig, marmoset or mouse) or a primate (e.g., a monkey, chimpanzee, or human). In particular embodiments, the subject is a human.

As used herein a "tauopathy" encompasses any neurodegenerative disease that involves the pathological aggregation of tau within the brain. In addition to familial and sporadic AD, other exemplary tauopathies are frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, and chronic traumatic encephalopathy, such as dementia pugulistica (boxing disease) (Morris et al., *Neuron,* 70:410-26, 2011).

As used herein, the terms "determining," "measuring," "assessing," and "assaying" are used interchangeably and include both quantitative and qualitative determinations. These terms refer to any form of measurement, and include determining if a characteristic, trait, or feature is present or not. Assessing may be relative or absolute. "Assessing the presence of" includes determining the amount of something present, as well as determining whether it is present or absent.

As used herein, the term "diagnosis" means detecting a disease or disorder or determining the stage or degree of a disease or disorder, such as a tauopathy. Usually, a diagnosis of a disease or disorder is based on the evaluation of one or more factors and/or symptoms that are indicative of the disease. A diagnosis can be made based on the presence, absence or amount of a factor which is indicative of presence or absence of the disease or condition, e.g. p217+ tau. Each factor or symptom that is considered to be indicative for the diagnosis of a particular disease does not need be exclusively related to the particular disease, i.e. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, e.g. an anti-p217+ tau antibody therapy, or predicting the pattern of response to a drug therapy, e.g. an anti-p217+ tau antibody therapy. The diagnostic methods may be used independently, or in combination with other diagnosing and/or staging methods known in the medical arts for a particular disease or disorder, e.g., Alzheimer's disease.

As used herein, the terms "increase" and "decrease" refer to differences in the quantity of a particular biomarker in a sample as compared to a control or reference level. For example, the quantity of particular peptide, may be present at an elevated amount or at a decreased amount in samples of patients with a disease compared to a reference level. In one embodiment, an "increase of a level" or "decrease of a level" may be a difference between the level of biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, an "increase of a level" or "decrease of a level" may be a statistically significant difference between the level of the biomarker present in a sample as compared to a control. For example, a difference may be statistically significant if the measured level of the biomarker falls outside of about 1.0 standard deviation, about 1.5 standard deviations, about 2.0 standard deviations, or about 2.5 stand deviations of the mean of any control or reference group. The reference or control can be, for example, a sample from a healthy individual, or a sample taken from the same individual at an earlier time point, such as a time point prior to administration of a therapeutic or an earlier time point during a therapeutic regimen.

As used herein, the term "isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

An "isolated antibody that binds to a tau protein" or an "isolated anti-tau antibody", as used herein, is intended to refer to an antibody that specifically binds tau protein and which is substantially free of other antibodies having different antigenic specificities (for instance, an isolated anti-tau detection antibody is substantially free of antibodies that specifically bind antigens other than tau). An isolated anti-tau detection antibody can, however, have cross-reactivity to other related antigens, for instance from other species (such as tau species homologs).

As used herein, the term "specifically binds" or "specific binding" refers to the ability of an anti-tau antibody of the invention to bind to a predetermined target with a dissociation constant ($K_D$) of about $1\times10^{-6}$ M or tighter, for example, about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. The KD is obtained from the ratio of Kd to Ka (i.e., Kd/Ka) and is expressed as a molar concentration (M). KD values for antibodies can be determined using methods in the art in view of the present disclosure. For example, the KD value of an anti-tau antibody can be determined by using surface plasmon resonance, such as by using a biosensor system, e.g., a Biacore® system, a Proteon instrument (BioRad), a KinExA instrument (Sapidyne), ELISA or competitive binding assays known to those skilled in the art. Typically, an anti-tau antibody binds to a predetermined target (i.e. tau) with a $K_D$ that is at least ten fold less than its $K_D$ for a nonspecific target as measured by surface plasmon resonance using, for example, a Proteon Instrument (BioRad). The anti-tau antibodies that specifically bind to tau can, however, have cross-reactivity to other related targets, for example, to the same predetermined target from other species (homologs), such as from mouse, rat, marmoset, dog or pig.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector" is a replicon in which another nucleic acid segment can be operably inserted so as to bring about the replication or expression of the segment.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected with a nucleic acid molecule of the invention. In another embodiment, a "host cell" is a progeny or potential progeny of such a transfected cell. A progeny of a cell may or may not be identical to the parent cell, e.g., due to mutations or environmental influences that can occur in succeeding generations or integration of the nucleic acid molecule into the host cell genome.

The term "expression" as used herein refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed detection antibody or antigen-binding fragment thereof that binds tau can be within the cytoplasm of a host cell, into the extracellular milieu such as the growth medium of a cell culture, or anchored to the cell membrane.

Anti-Tau Antibodies

In one general aspect, the invention relates to isolated detection antibodies or antigen-binding fragments thereof that bind tau protein that has been immobilized by a capture antibody. Such anti-tau antibodies can have the properties of binding a phosphorylated epitope on tau or binding to a non-phosphorylated epitope on tau. Anti-tau detection antibodies can be useful as research or diagnostic reagents to detect tau in biological samples.

According to a particular aspect, the invention relates to an isolated detection antibody or antigen-binding fragment thereof that binds to a tau protein at an epitope comprising amino acid residues 119-126, preferably amino acid residues 116 to 127, of tau protein.

According to a particular aspect, the isolated detection antibody or antigen-binding fragment thereof that binds to tau protein at an epitope comprising amino acid residues 116 to 127 of tau protein comprises (a) immunoglobulin heavy chain HCDR1, HCDR2 and HCDR3 having the polypeptide sequences of SEQ ID NOs: 2, 3 and 4, respectively; and (b) immunoglobulin light chain LCDR1, LCDR2 and LCDR3 having the polypeptide sequences of SEQ ID NOs: 5, 6 and 7, respectively.

According to a particular aspect, the isolated detection antibody or antigen-binding fragment thereof that binds to tau protein at an epitope comprising amino acid residues 116 to 127 of tau protein comprises a heavy chain variable region having a polypeptide sequence at least 80%, preferably at least 85% or 90%, more preferably at least 95%, and most preferably 100%, identical to SEQ ID NO: 8 and a light chain variable region having a polypeptide sequence at least 80%, preferably at least 85% or 90%, more preferably at least 95%, and most preferably 100%, identical to SEQ ID NO: 9.

Preferably, the isolated detection antibody or antigen-binding fragment thereof that binds to tau protein at an epitope comprising amino acid residues 116 to 127 of tau protein is a pT82 antibody.

According to a particular aspect, the invention relates to an isolated detection antibody or antigen-binding fragment thereof that binds to a tau protein at an epitope comprising amino acid residues 7 to 20 of tau protein.

According to a particular aspect, the isolated detection antibody or antigen-binding fragment thereof that binds to tau protein at an epitope comprising amino acid residues 7 to 20 of tau protein comprises (a) immunoglobulin heavy chain HCDR1, HCDR2 and HCDR3 having the polypeptide sequences of SEQ ID NOs: 12, 13 and 14, respectively; and (b) immunoglobulin light chain LCDR1, LCDR2 and LCDR3 having the polypeptide sequences of SEQ ID NOs: 15, 16 and 17, respectively.

According to a particular aspect, the isolated detection antibody or antigen-binding fragment thereof that binds to tau protein at an epitope comprising amino acid residues 7 to 20 of tau protein comprises a heavy chain variable region having a polypeptide sequence at least 80%, preferably at least 85% or 90%, more preferably at least 95%, and most preferably 100%, identical to SEQ ID NO: 18 and a light chain variable region having a polypeptide sequence at least 80%, preferably at least 85% or 90%, more preferably at least 95%, and most preferably 100%, identical to SEQ ID NO: 19.

Preferably, the isolated detection antibody or antigen-binding fragment thereof that binds to tau protein at an epitope comprising amino acid residues 7 to 20 of tau protein is a hT43 antibody.

Antibodies of the present invention can be produced by a variety of techniques, for example by the hybridoma method (Kohler and Milstein, *Nature*. 256:495-7, 1975). Chimeric mAbs containing a light chain and heavy chain variable region derived from a donor antibody (typically murine) in association with light and heavy chain constant regions derived from an acceptor antibody (typically another mammalian species such as human) can be prepared by a method disclosed in U.S. Pat. No. 4,816,567. CDR-grafted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Fully human mAbs lacking any non-human sequences can be prepared from human immunoglobulin transgenic mice by techniques referenced in (Lonberg et al., *Nature*. 368:856-9, 1994; Fishwild et al., *Nat Biotechnol*. 14:845-51, 1996; Mendez et al., *Nat Genet*. 15:146-56, 1997). Human mAbs can also be prepared and optimized from phage display libraries (Knappik et al., *J Mol Biol*. 296:57-86, 2000; Krebs et al., *J Immunol Methods*. 254:67-84, 2001; Shi et al., *J Mol Biol*. 397:385-96, 2010).

The functional activity of detection antibodies and antigen-binding fragments thereof that bind tau can be characterized by methods known in the art. Methods for characterizing antibodies and antigen-binding fragments thereof that bind tau include, but are not limited to, affinity and specificity assays including Biacore, ELISA, and FACS analysis, immunohistochemistry analysis, etc.

Several well known methodologies can be employed to determine the binding epitope of the antibodies of the invention. For example, when the structures of both individual components are known, in silico protein-protein docking can be carried out to identify compatible sites of interaction. Hydrogen-deuterium (H/D) exchange can be carried out with the antigen and antibody complex to map regions on the antigen that are bound by the antibody. Segment and point mutagenesis of the antigen can be used to locate amino acids important for antibody binding. Co-crystal structure of antibody-antigen complex is used to identify residues contributing to the epitope and paratope.

In another general aspect, the invention relates to an isolated polynucleotide encoding a detection antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding detection antibodies or antigen-binding fragments thereof of the invention can be altered without changing the amino acid sequences of the proteins. Exemplary isolated polynucleotides are polynucleotides encoding polypeptides comprising immunoglobulin heavy chain CDRs HCDR1, HCDR2 and HCDR3 shown in SEQ ID NOs: 2, 3 and 4, respectively, or polypeptides comprising immunoglobulin light chain CDRs LCDR1, LCDR2 and LCDR3 shown in SEQ ID NOs: 5, 6 and 7, respectively. Other exemplary isolated polynucleotides are polynucleotides encoding polypeptides comprising immunoglobulin heavy chain CDRs HCDR1, HCDR2 and HCDR3 shown in SEQ ID NOs: 12, 13 and 14, respectively, or polypeptides comprising immunoglobulin light chain CDRs LCDR1, LCDR2 and LCDR3 shown in SEQ ID NOs: 15, 16 and 17, respectively. Other exemplary isolated polynucleotides are polynucleotides encoding antibody variable regions of the invention. Other polynucleotides which, given the degeneracy of the genetic code or codon preferences in a given expression system, encode the antibodies of the invention are also within the scope of the invention. The isolated nucleic acids of the present invention can be made using well known recombinant or synthetic techniques. DNA encoding the monoclonal antibodies is readily isolated and sequenced using methods known in the art. Where a hybridoma is produced, such cells can serve as a source of such DNA. Alternatively, display techniques wherein the coding sequence and the translation product are linked, such as phage or ribosomal display libraries, can be used.

In another general aspect, the invention relates to a vector comprising an isolated polynucleotide encoding a detection antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated polynucleotide encoding a detection antibody or antigen-binding fragment thereof of the invention. Any host cell known to those skilled in the art in view of the present disclosure can be used for recombinant expression of antibodies or antigen-binding fragments thereof of the invention. Such host cells can be eukaryotic cells, bacterial cells, plant cells or archaeal cells. Exemplary eukaryotic cells can be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1 SV (Lonza Biologics), CHO-K1 (ATCC CRL-61, Invitrogen) or DG44.

In another general aspect, the invention relates to a method of producing a detection antibody or antigen-binding fragment thereof of the invention, comprising culturing a cell comprising a polynucleotide encoding the detection antibody or antigen-binding fragment thereof under conditions to produce a detection antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art.

Diagnostic Methods

The invention relates to measurement of p217+ tau species that are enriched in AD, e.g., by using a capture antibody, such as a pT3, which selectively immobilizes the p217+ tau species, in combination with an anti-tau detection antibody, which is labeled with a reporter element that allows detection of the captured p217+ tau species. Methods of the invention can be used for various diagnostic purposes, e.g., for diagnosing AD or other tauopathies in a subject, monitoring the effectiveness of a treatment, identifying a subject suitable for an anti-p217+ tau treatment, etc.

According to an embodiment of the invention, p217+ tau peptides in a sample of interest are captured with a capture antibody directed against a p217+ tau epitope, such as an epitope having the amino acid sequence of SEQ ID NO: 25, 26 or 27. The captured p217+ tau peptides, while all contain the p217+ tau epitope, may have different length, which can be detected by detection antibodies binding to different epitopes. For example, a detection antibody directed against an epitope comprising amino acid residues 7 to 20 of tau protein can only detect captured p217+ tau peptides or fragments thereof that still contain amino acid residues 7 to 20 of tau protein ("long p217+ tau peptides"), while a detection antibody directed against an epitope comprising amino acid residues 119 to 126 of tau protein can detect not only the long p217+ tau peptides, but also the short p217+ tau peptides. The captured p217+ tau peptides can be contacted with a detection antibody directed against an epitope comprising amino acid residues 7 to 20 or 116 to 127 of tau protein to thereby detect and measure the amount of the long p217+ tau peptides or the p217+ tau peptides (long and short p217+ tau peptides) in the sample. An amount of short p217+ tau peptides in a sample is calculated by subtracting the amount of long p217+ tau peptides from the amount of p217+ tau peptides.

According to another embodiment of the invention, in addition to capturing and measuring the amount of p217+ tau peptides in a sample, total tau peptides in the sample are captured with a phosphorylation-independent capture antibody, such as an antibody directed against an epitope between amino acids 150 and 250 of tau protein, preferably an epitope comprising amino acids 159-163 of tau protein. The captured total tau peptides can be contacted with a detection antibody directed against an epitope comprising amino acid residues 7 to 20 or 116 to 127 of tau protein to thereby detect and measure the amount of the total long tau peptides or the total tau peptides (long and short tau peptide fragments) in the sample. An amount of short total tau peptides in a sample is calculated by subtracting the amount of long total tau peptides from the amount of total tau peptides.

According to embodiments of the invention, a value related to p217+ tau peptides in a sample, such as the amount of p217+ tau peptides and the amount of long p217+ tau peptides, optionally the amount of total tau peptides and the amount of total long tau fragments, in a sample, as well as information based on the measure amounts, such as the calculated short p217+ tau peptides and short total tau peptides, or a ratio related to p217+ tau peptides, such as a ratio of the amount of short tau peptide fragments to the amount of long tau peptide fragments, a ratio of the amount of short p217+ tau peptides to the total amount of short tau fragments, a ratio of amount of long p217+ tau peptides to the total amount of long tau fragments, etc., can be used for one or more diagnostic purposes.

Diagnosis is performed by comparing a value related to p217+ tau peptides in a sample from a subject to corresponding baseline values. The baseline values can represent the mean levels in a population of healthy individuals. Baseline values can also represent previous levels determined in the same subject. In one embodiment, it is determined that a subject is suffering from a tauopathy if a value related to p217+ tau peptides in the biological sample from the subject, such as the amount of the long or short p217 tau peptides, or a ratio related to p217+ tau peptides, e.g., a ratio of the amount of short p217+ tau peptides to the amount of long p217+ tau peptides, is significantly higher than a corresponding baseline value. As used herein, "significant higher" refers to a higher value that is statistically significant, not due to chance alone, which has a p-value of 0.05 or less. A "significant higher" can be at least about 1%, 2%, 5%, or 10% higher than that found in healthy volunteers, at a p-value of less than 0.05, 0.04, 0.03, 0.01, 0.005, 0.001, etc.

In one embodiment, a method of the invention comprises (i) contacting a biological sample, preferably a CSF sample, with a capture antibody directed against an epitope comprising phosphorylated p217+ tau to capture p217+ tau peptides in the sample, (ii) contacting the captured p217+ tau peptides with a detection antibody directed against an epitope comprising amino acid residues 7 to 20 to thereby measure the amount of long p217+ tau peptides, and/or with a detection antibody directed against an epitope comprising amino acid residues 119 to 126 of tau protein to thereby measure the amount of long and short p217+ tau peptides in the sample, and (iii) determining whether or not the subject suffers from a tauopathy or is at risk of developing a tauopathy based on the amount of the p217+ tau peptides or the ratio of the amount of short p217+ tau peptides to the amount of long p217+ tau peptides. Diagnosis can be performed by comparing the amount or concentration of p217+ tau peptides in a sample from the subject to corresponding baseline values. Diagnosis can also be performed by comparing the ratio of the amount of short p217+ tau peptides to the amount of long p217+ tau peptides in a sample from the subject to corresponding baseline values.

In another embodiment, a method of the invention comprises (i) contacting a biological sample, preferably a CSF sample, with a capture antibody directed against a p217+ tau epitope to capture p217+ tau peptides in the sample, or with a phosphorylation-independent capture antibody directed against a tau epitope between amino acids 150 and 250 of tau protein to capture total tau peptides in the sample, (ii) contacting the captured p217+ tau peptides, or the captured total tau peptides, with a detection antibody directed against an epitope comprising amino acid residues 116 to 127 of tau protein to thereby measure the amount of long and short p217+ tau peptides, or the amount of total short tau peptides, in the sample, and (iii) determining whether or not the subject suffers from a tauopathy or is at risk of developing a tauopathy based on the amount of the ratio of the amount of short p217+ tau peptides to the amount of total short tau peptides in the biological sample. Diagnosis can be performed by comparing the ratio of the amount of short p217+ tau peptides to the amount of total short tau peptides comprising the same region of tau protein as that recognized by the pT3 antibody, i.e. amino acids 211-221 of tau, in a sample from the subject to corresponding baseline values.

In another embodiment, a method of the invention comprises (i) contacting a biological sample, preferably a CSF sample, with a capture antibody directed against a p217+ tau epitope to capture p217+ tau peptides in the sample, (ii) contacting the captured p217+ tau peptides with a detection antibody directed against an epitope comprising amino acid residues 7 to 20 to thereby measure the amount of long p217+ tau peptides, and/or with a detection antibody directed against an epitope comprising amino acid residues 116 to 127 of tau protein to thereby measure the amount of long and short p217+ tau peptides in the sample, and (iii) determining the effectiveness of the treatment in the subject based on the amount of the p217+ tau peptides or the ratio of the amount of short p217+ tau peptides to the amount of long p217+ tau peptides.

In yet another embodiment, a method of the invention comprises (i) contacting a biological sample, preferably a CSF sample, with a capture antibody directed against a p217+ tau epitope to capture p217+ tau peptides in the sample, or with a phosphorylation-independent capture antibody directed against a tau epitope between amino acids 150 and 250 of tau protein to capture total tau peptides in the sample, (ii) contacting the captured p217+ tau peptides, or the captured total tau peptides, with a detection antibody directed against an epitope comprising amino acid residues 116 to 127 of tau protein to thereby measure the amount of long and short p217+ tau peptides, or the amount of total short tau peptides, in the sample, and (iii) determining the effectiveness of the treatment in the subject based on the amount of the ratio of the amount of short p217+ tau peptides to the amount of total short tau peptides in the biological sample.

In yet another embodiment, the effectiveness of the treatment in the subject is determined by monitoring the amount of the p217+ tau peptides, the ratio of the amount of short p217+ tau peptides to the amount of long p217+ tau peptides, or the ratio of the amount of short p217+ tau peptides to the amount of total short tau peptides, before, during, or after the treatment. A decrease in values relative to baseline signals a positive response to treatment. Values can also increase temporarily in biological fluids as pathological tau is being cleared from the brain.

According to a particular aspect, the tauopathy includes, but is not limited to, one or more selected from the group consisting of Alzheimer's disease (including familial Alzheimer's disease and sporadic Alzheimer's disease), frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Preferably, the tauopathy is Alzheimer's disease (including familial Alzheimer's disease and sporadic Alzheimer's disease), FTDP-17 or progressive supranuclear palsy.

Most preferably, the tauopathy is Alzheimer's disease (including familial Alzheimer's disease and sporadic Alzheimer's disease).

According to one embodiment, a method of the invention comprises (i) contacting a biological sample, preferably a CSF sample, with a capture antibody directed against a p217+ tau epitope to capture p217+ tau peptides in the sample, (ii) contacting the captured p217+ tau peptides with a detection antibody directed against an epitope comprising amino acid residues 7 to 20 to thereby measure the amount of long p217+ tau peptides, and/or with a detection antibody directed against an epitope comprising amino acid residues 116 to 127 of tau protein to thereby measure the amount of long and short p217+ tau peptides in the sample, and (iii) determining whether or not the subject is suitable for an anti-p217+ tau antibody therapy based on the amount of the p217+ tau peptides or the ratio of the amount of short p217+ tau peptides to the amount of long p217+ tau peptides.

According to a particular aspect, it is determined that a subject is suitable for an anti-p217+ tau antibody therapy if the amount of p217+ tau peptides in the biological sample, or the ratio of the amount of short p217+ tau peptides to the amount of long p217+ tau peptides in the biological sample is significantly higher than a corresponding baseline value.

According to another particular aspect, a method of the invention comprises (i) contacting a biological sample, preferably a CSF sample, with a capture antibody directed against a p217+ tau epitope to capture p217+ tau peptides in the sample, or with a phosphorylation-independent capture antibody directed against a tau epitope between amino acids 150 and 250 of tau protein to capture total tau peptides in the sample, (ii) contacting the captured p217+ tau peptides, or the captured total tau peptides, with a detection antibody directed against an epitope comprising amino acid residues 116 to 127 of tau protein to thereby measure the amount of long and short p217+ tau peptides, or the amount of total short tau peptides, in the sample, and (iii) determining whether or not the subject is suitable for an anti-p217+ tau antibody therapy based on the amount of the ratio of the amount of short p217+ tau peptides to the amount of total short tau peptides in the biological sample.

According to one embodiment, it is determined that a subject is suitable for an anti-p217+ tau antibody therapy if the ratio of the amount of short p217+ tau peptides to the amount of total short tau peptides is significantly higher than a corresponding baseline value.

The invention also relates to measuring p217+ tau that is in complex with antibody in a biological sample as well as free p217+ tau in the sample that is not antibody-bound. In one embodiment, total antibody is captured using affinity techniques, followed by denaturing conditions including chaotrophs, heat-inactivation, or other protein disruption techniques. The p217+ tau is separated from antibody using rpHPLC, and is measured using methods of the invention, allowing for quantification of antibody-bound p217+ tau.

According to a general aspect, the invention relates to a method of monitoring a treatment with an anti-p217+ tau antibody in a subject, the method comprising: (i) obtaining a biological sample from the subject, (ii) separating the biological sample into an IgG enriched sample containing antibody-bound p217+ tau, and an IgG depleted sample containing antibody-free p217+ tau, (iii) purifying the p217+ tau away from IgGs by rpHPLC to obtain an antibody-free p217+ tau sample, (iv) contacting each of the IgG enriched sample and the antibody-free p217+ tau sample with a capture antibody directed against a p217+ tau epitope to capture p217+ tau peptides in each of the samples, (v) contacting the captured p217+ tau peptides in each of the samples with a detection antibody directed against an epitope comprising amino acid residues 7 to 20 to thereby measure the amount of long p217+ tau peptides, or with a detection antibody directed against an epitope comprising amino acid residues 116 to 127 of tau protein to thereby measure the amount of long and short p217+ tau peptides in each of the samples, (vi) calculating the ratio of the amount of antibody-bound p217+ tau to the amount of antibody-free p217+ tau, and (vii) monitoring the treatment with the anti-p217+ tau antibody in the subject based on the calculated ratio.

According to another general aspect, the invention relates to a method of monitoring a treatment with an anti-p217+ tau antibody in a subject, the method comprising: (i) obtaining a biological sample from the subject, (ii) obtaining a semi-denatured sample from the biological sample containing total p217+ tau, and obtaining a non-denatured sample from the biological sample containing antibody-free p217+ tau, wherein the semi-denatured sample is heated to denature the antibodies in the sample, (iii) contacting each of the semi-denatured sample and the non-denatured sample with a capture antibody directed against a p217+ tau epitope to capture p217+ tau peptides in each of the samples, (iv) contacting the captured p217+ tau peptides in each of the samples with a detection antibody directed against an epitope comprising amino acid residues 7 to 20 to thereby measure the amount of long p217+ tau peptides, or with a detection antibody directed against an epitope comprising amino acid residues 116 to 127 of tau protein to thereby measure the amount of long and short p217+ tau peptides in each of the samples, (v) calculating the amount of the antibody-bound p217+ tau in the sample by subtracting the amount of the antibody-free p217+ tau from the amount of the total p217+ tau, (vi) calculating the ratio of the antibody-bound p217+ tau to the antibody-free p217+ tau, and (vii) monitoring the treatment with the anti-p217+ tau antibody in the subject based on the calculated ratio.

According to a particular aspect, the effectiveness of the treatment in the subject is determined by monitoring the amount of the antibody-bound and antibody-free p217+ tau peptides before, during, or after the treatment. A decrease in values of antibody-free p217+ tau relative to baseline, or an increase in values of antibody-bound p217+ tau relative to baseline, and therefore an increase in the ratio of the antibody-bound p217+ tau to the antibody-free p217+ tau relative to baseline, signals a positive response to treatment. Values of antibody-free p217+ tau can also increase temporarily in biological fluids as pathological tau is being cleared from the brain.

According to particular aspects, the capture antibody of methods of the invention is conjugated to a bead, such as a magnetic bead. According to other particular aspects, the detection antibody is biotinylated.

According to particular aspects, the amount of p217+ tau peptides measured in methods of the invention can be determined using any suitable techniques known in the art, including ELISA and single molecule array platform. According to particular aspects, methods of the invention use a high sensitivity array platform, such as Quanterix Simoa or MSD S-plex, to measure the amount of p217+ tau peptides in a sample. According to a particular aspect, the lower limit of quantification of methods of the invention is about 40 fg/ml and the lower limit of detection of the method is about 2 fg/ml.

According to a particular aspect, the sample used in methods of the invention is a biological sample, such as a blood, brain homogenate, or cerebral spinal fluid (CSF) sample. Preferably, the sample is a CSF sample. According to a particular aspect, the sample is a crude CSF sample. According to another particular aspect, the sample is obtained after fractionating a biological sample, such as CSF, using reverse phase high-performance liquid chromatography (rpHPLC), which separates full-length tau protein and differentially-sized tau fragments.

According to a particular aspect, the capture antibody of methods of the invention comprises immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively. Preferably, the capture antibody is a pT3 antibody comprising heavy chain variable region comprising polypeptide sequence of SEQ ID NO: 28 and a light chain variable region having the polypeptide sequence of SEQ ID NO: 29.

According to a particular aspect, the detection antibody of methods of the invention comprises immunoglobulin heavy chain HCDR1, HCDR2 and HCDR3 having the polypeptide sequences of SEQ ID NOs: 2, 3 and 4, respectively; and immunoglobulin light chain LCDR1, LCDR2 and LCDR3 having the polypeptide sequences of SEQ ID NOs: 5, 6 and 7, respectively. Preferably, the detection antibody is a pT82 antibody comprising a heavy chain variable region having the polypeptide sequence of SEQ ID NO: 8 and a light chain variable region having the polypeptide sequence of SEQ ID NO: 9.

According to another particular aspect, the detection antibody of methods of the invention comprises immunoglobulin heavy chain HCDR1, HCDR2 and HCDR3 having the polypeptide sequences of SEQ ID NOs: 12, 13 and 14, respectively; and immunoglobulin light chain LCDR1, LCDR2 and LCDR3 having the polypeptide sequences of SEQ ID NOs: 15, 16 and 17, respectively. Preferably, the detection antibody is a hT43 antibody comprising a heavy chain variable region having the polypeptide sequence of SEQ ID NO: 18 and a light chain variable region having the polypeptide sequence of SEQ ID NO: 19.

Kits

In another general aspect, the invention relates to a kit comprising (a) a capture antibody directed against a p217+ tau epitope, optionally a phosphorylation-independent capture antibody directed against a tau epitope between amino acids 150 and 250 of tau protein, and (b) at least one detection antibody directed against a tau protein epitope comprising amino acid residues 7 to 20 or 116 to 127 of tau protein. The kit is used to measure the amount of p217+ tau peptides, which is used the ratio of the amount of short p217+ tau peptides to the amount of long p217+ tau peptides, and/or the ratio of the amount of short p217+ tau peptides to the amount of total short tau peptides in a sample.

The detection antibody can contain any detectable label (e.g., fluorescent molecule, biotin, etc.) which is directly detectable or detectable via a secondary reaction (e.g., reaction with streptavidin). Alternatively, a second reagent containing the detectable label can be used, where the second reagent has binding specificity for the primary antibody. In a diagnostic kit suitable for measuring p217+ tau in a biological sample, the antibodies of the kit can be supplied pre-bound to a solid phase, such as to the wells of a microtiter dish or to beads.

According to a particular aspect, the capture antibody of a kit of the invention comprises immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively. Preferably, the capture antibody is a pT3 antibody comprising heavy chain variable region comprising polypeptide sequence of SEQ ID NO: 28 and a light chain variable region having the polypeptide sequence of SEQ ID NO: 29.

According to a particular aspect, the detection antibody of a kit of the invention comprises immunoglobulin heavy chain HCDR1, HCDR2 and HCDR3 having the polypeptide sequences of SEQ ID NOs: 2, 3 and 4, respectively; and immunoglobulin light chain LCDR1, LCDR2 and LCDR3 having the polypeptide sequences of SEQ ID NOs: 5, 6 and 7, respectively. Preferably, the detection antibody is a pT82 antibody comprising a heavy chain variable region having the polypeptide sequence of SEQ ID NO: 8 and a light chain variable region having the polypeptide sequence of SEQ ID NO: 9.

According to another particular aspect, the detection antibody of a kit of the invention comprises immunoglobulin heavy chain HCDR1, HCDR2 and HCDR3 having the polypeptide sequences of SEQ ID NOs: 12, 13 and 14, respectively; and immunoglobulin light chain LCDR1, LCDR2 and LCDR3 having the polypeptide sequences of SEQ ID NOs: 15, 16 and 17, respectively. Preferably, the detection antibody is a hT43 antibody comprising a heavy chain variable region having the polypeptide sequence of SEQ ID NO: 18 and a light chain variable region having the polypeptide sequence of SEQ ID NO: 19.

According to another particular aspect, a kit of the invention is used to measure the amount of p217+ tau peptides, the ratio of the amount of short p217+ tau peptides to the amount of long p217+ tau peptides, and/or the ratio of the amount of short p217+ tau peptides to the amount of total short tau peptides in a sample using a method of the invention.

The contents of all cited references (including literature references, issued patents, published patent applications, and co-pending patent applications) cited throughout this application are hereby expressly incorporated by reference.

Embodiments

The invention provides also the following non-limiting embodiments.

Embodiment 1 is a method of measuring the amount of p217+ tau peptides in a sample, comprising:
  (i) contacting the sample with a capture antibody directed against a p217+ tau epitope to capture p217+ tau peptides in the sample, and
  (ii) contacting the captured p217+ tau peptides with a detection antibody directed against an epitope comprising amino acid residues 119 to 126, such as amino acid residues 116-127, of tau protein, or an epitope containing amino acid residues 7 to 20 of tau protein to thereby measure an amount of p217+ tau peptides or an amount of long p217+ tau peptides, respectively.

Embodiment 2 is a method of determining a relative amount of long p217+ tau peptides or short p217 tau peptide fragments in a sample, comprises
  (i) contacting the sample with a capture antibody directed against a p217+ tau epitope to capture p217+ tau peptides in the sample,
  (ii) contacting the captured p217+ tau peptides with a first detection antibody directed against an epitope comprising amino acid residues 119 to 126 of tau protein to thereby measure an amount of p217+ tau peptides,
  (iii) contacting the captured p217+ tau peptides with a second detection antibody directed against an epitope comprising amino acid residues 7 to 20 of tau protein to thereby measure an amount of long p217+ tau peptides, and
  (iv) determining a relative amount of long p217+ tau peptides or short p217+ tau peptides based on the amount of p217+ tau peptides and the amount of long p217+ tau peptides.

Embodiment 3 is the method of Embodiment 1 or 2, wherein the capture antibody is conjugated to a bead, and wherein the detection antibody is biotinylated.

Embodiment 4 is the method of any of Embodiments 1-3, wherein the amount of p217+ tau peptides in the sample is measured using a high sensitivity platform.

Embodiment 5 is the method of any of Embodiments 1-4, wherein the lower limit of quantification of the method is about 40 fg/ml of the p217+ tau peptides and the lower limit of detection of the method is about 2 fg/ml of the p217+ tau peptides.

Embodiment 6 is the method of any of Embodiments 1-5, wherein the sample is a biological sample, preferably a CSF sample, from a subject, and the method further comprises determining whether or not the subject suffers from a tauopathy or is at risk of developing a tauopathy based on the amount of the p217+ tau peptides, the ratio of the amount of short p217+ tau peptides to the amount of long p217+ tau peptides, or the ratio of the amount of short p217+ tau peptides to the amount of total short tau peptides in the biological sample.

Embodiment 7 is the method of Embodiment 6, wherein the subject is determined to suffer from a tauopathy or to be at risk of developing a tauopathy if the amount of the p217+ tau peptides in the biological sample, the ratio of the amount of short p217+ tau peptides to the amount of long p217+ tau peptides, or the ratio of the amount of short p217+ tau peptides to the amount of total short tau peptides is significantly higher than a corresponding baseline values, such as the mean corresponding value of Healthy Volunteers.

Embodiment 8 is the method of any of Embodiments 1-5, wherein the sample is a biological sample, preferably a CSF sample, from a subject under a treatment of a tauopathy, and the method further comprises determining the effectiveness of the treatment in the subject based on the amount of the p217+ tau peptides, the ratio of the amount of short p217+ tau peptides to the amount of long p217+ tau peptides, or the ratio of the amount of short p217+ tau peptides to the amount of total short tau peptides in the biological sample.

Embodiment 9 is the method of Embodiment 8, wherein the treatment is determined to be effective if the amount of the p217+ tau peptides in the biological sample decreases over the course of treatment.

Embodiment 10 is the method of any of Embodiments 6-9, wherein the tauopathy is selected from the group consisting of Alzheimer's disease (including familial Alzheimer's disease and sporadic Alzheimer's disease), frontotemporal dementia with parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, Down syndrome, Gerstmann-Sträussler-Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, postencephalitic parkinsonism, chronic traumatic encephalopathy, and dementia pugulistica (boxing disease).

Embodiment 11 is the method of Embodiment 10, wherein the tauopathy is Alzheimer's disease.

Embodiment 12 is the method of any of Embodiments 1-5, wherein the sample is a biological sample, preferably a CSF sample, from a human subject, and the method further comprises determining whether or not the subject is suitable for an anti-p217+ tau antibody therapy based on the amount of the p217+ tau peptides, the ratio of the amount of short p217+ tau peptides to the amount of long p217+ tau peptides, or the ratio of the amount of short p217+ tau peptides to the amount of total short tau peptides in the biological sample.

Embodiment 13 is the method of Embodiment 12, wherein the subject is determined to be suitable for anti-p217+ tau antibody therapy if the amount of the p217+ tau peptides in the biological sample, the ratio of the amount of short p217+ tau peptides to the amount of long p217+ tau peptides, or the ratio of the amount of short p217+ tau peptides to the amount of total short tau peptides is significantly higher than a corresponding baseline values, such as the mean corresponding value of Healthy Volunteers.

Embodiment 14 is a method of monitoring a treatment with an anti-p217+ tau antibody in a subject, the method comprising:
i. obtaining a biological sample from the subject,
ii. separating the biological sample into an IgG enriched sample containing antibody-bound p217+ tau, and an IgG depleted sample containing antibody-free p217+ tau,
iii. contacting each of the IgG enriched sample and the IgG depleted sample with a capture antibody directed against an epitope comprising phosphorylated T212 and/or phosphorylated T217 of the tau protein to capture the p217+ tau peptides in each of the samples,
iv. contacting the captured p217+ tau peptides with a detection antibody directed against an epitope comprising amino acid residues 7 to 20 or 116 to 127 of tau protein to thereby measure the amount of the antibody-bound p217+ tau and the amount of the antibody-free p217+ tau in the biological sample,
v. calculating the ratio of the antibody-bound p217+ tau to the antibody-free p217+ tau, and
vi. monitoring the treatment with the anti-p217+ tau antibody in the subject based on the calculated ratio.

Embodiment 15 is a method of monitoring a treatment with an anti-p217+ tau antibody in a subject, the method comprising:
i. obtaining a biological sample from the subject,
ii. obtaining a semi-denatured sample from the biological sample containing total p217+ tau, and obtaining a non-denatured sample from the biological sample containing antibody-free p217+ tau, wherein the semi-denatured sample is heated to denature the antibodies in the sample,
iii. contacting each of the semi-denatured sample and the non-denatured sample with a capture antibody directed against an epitope comprising phosphorylated T212 and/or phosphorylated T217 of the tau protein to capture the p217+ tau peptides in each of the samples,
iv. contacting the captured p217+ tau peptides with a detection antibody directed against an epitope comprising amino acid residues 7 to 20 or 116 to 127 of tau protein to thereby measure the amount of the total p217+ tau and the amount of the antibody-free p217+ tau in the biological sample,
v. calculating the amount of the antibody-bound p217+ tau in the sample by subtracting the amount of the antibody-free p217+ tau from the amount of the total p217+ tau,
vi. calculating the ratio of the antibody-bound p217+ tau to the antibody-free p217+ tau, and
vii. monitoring the treatment with the anti-p217+ tau antibody in the subject based on the calculated ratio.

Embodiment 16 is the method of any one of Embodiments 1 to 15, wherein the capture antibody comprises immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively; preferably, the capture antibody has a heavy chain variable region comprising polypeptide sequence of SEQ ID NO: 28 and a light chain variable region having the polypeptide sequence of SEQ ID NO: 29.

Embodiment 17 is the method of any one of Embodiments 1 to 16, wherein the detection antibody comprises immunoglobulin heavy chain HCDR1, HCDR2 and HCDR3 having the polypeptide sequences of SEQ ID NOs: 2, 3 and 4, respectively; and immunoglobulin light chain LCDR1, LCDR2 and LCDR3 having the polypeptide sequences of SEQ ID NOs: 5, 6 and 7, respectively; preferably, the detection antibody comprises a heavy chain variable region having the polypeptide sequence of SEQ ID NO: 8 and a light chain variable region having the polypeptide sequence of SEQ ID NO: 9.

Embodiment 18 is the method of any one of Embodiments 1 to 16, wherein the detection antibody comprises immunoglobulin heavy chain HCDR1, HCDR2 and HCDR3 having the polypeptide sequences of SEQ ID NOs: 12, 13 and 14, respectively; and immunoglobulin light chain LCDR1, LCDR2 and LCDR3 having the polypeptide sequences of SEQ ID NOs: 15, 16 and 17, respectively; preferably, the detection antibody comprises a heavy chain variable region having the polypeptide sequence of SEQ ID NO: 18 and a light chain variable region having the polypeptide sequence of SEQ ID NO: 19.

Embodiment 19 is the method of any one of Embodiments 1 to 18, wherein the sample is a blood, brain homogenate, or cerebral spinal fluid (CSF) sample.

Embodiment 20 is the method of any one of Embodiments 1 to 19, wherein the sample is obtained after fractionating a biological sample using reverse phase high-performance liquid chromatography (rpHPLC).

Embodiment 21 is an isolated detection antibody or antigen-binding fragment thereof that binds to a tau protein at an epitope comprising amino acid residues 116 to 127 of tau protein, comprising:
  a. immunoglobulin heavy chain HCDR1, HCDR2 and HCDR3 having the polypeptide sequences of SEQ ID NOs: 2, 3 and 4, respectively; and
  b. immunoglobulin light chain LCDR1, LCDR2 and LCDR3 having the polypeptide sequences of SEQ ID NOs: 5, 6 and 7, respectively.

Embodiment 22 is the isolated detection antibody or antigen-binding fragment of Embodiment 21 comprising a heavy chain variable region having a polypeptide sequence of SEQ ID NO: 8, and a light chain variable region having a polypeptide sequence of SEQ ID NO: 9, preferably.

Embodiment 23 is an isolated detection antibody or antigen-binding fragment thereof that binds to a tau protein at an epitope comprising amino acid residues 7 to 20 of tau protein, comprising:
  a. immunoglobulin heavy chain HCDR1, HCDR2 and HCDR3 having the polypeptide sequences of SEQ ID NOs: 12, 13 and 14, respectively; and
  b. immunoglobulin light chain LCDR1, LCDR2 and LCDR3 having the polypeptide sequences of SEQ ID NOs: 15, 16 and 17, respectively.

Embodiment 24 is the isolated detection antibody or antigen-binding fragment of Embodiment 23 comprising a heavy chain variable region having a polypeptide sequence of SEQ ID NO: 18, and a light chain variable region having a polypeptide sequence of SEQ ID NO: 19, preferably.

Embodiment 25 is an isolated nucleic acid encoding the detection antibody or antigen-binding fragment thereof of any of Embodiments 21-24.

Embodiment 26 is a vector comprising the nucleic acid of Embodiment 25.

Embodiment 27 is a host cell comprising the nucleic acid of Embodiment 25.

Embodiment 28 is a method of producing the detection antibody or antigen-binding fragment thereof of any one of Embodiments 21-24, comprising culturing a cell comprising a nucleic acid encoding the antibody or antigen-binding fragment under conditions to produce the antibody or antigen-binding fragment, and recovering the antibody or antigen-binding fragment from the cell or cell culture.

Embodiment 29 is a kit comprising:
  a. a capture antibody directed against a singly- or multiply-phosphorylated tau protein epitope comprising phosphorylated T212 and/or phosphorylated T217 of the tau protein, and
  b. a detection antibody directed against a tau protein epitope comprising amino acid residues 7 to 20 or 116 to 127 of tau protein;

wherein the kit is used to measure the amount of p217+ tau peptides in a sample.

Embodiment 30 is the kit of Embodiment 29, wherein the capture antibody comprises immunoglobulin heavy chain HCDR1, HCDR2 and HCDR3 having the polypeptide sequences of SEQ ID NOs: 32, 33 and 34, respectively, and immunoglobulin light chain LCDR1, LCDR2 and LCDR3 having the polypeptide sequences of SEQ ID NOs: 35, 36 and 37, respectively; preferably, the capture antibody has a heavy chain variable region comprising polypeptide sequence of SEQ ID NO: 28 and a light chain variable region having the polypeptide sequence of SEQ ID NO: 29.

Embodiment 31 is the kit of Embodiment 29 or 30, wherein the detection antibody is the isolated detection antibody of any one of Embodiments 20-23.

EXAMPLES

The following examples of the invention are to further illustrate the nature of the invention. It should be understood that the following examples do not limit the invention and that the scope of the invention is to be determined by the appended claims.

Example 1. High Sensitivity Assay for Detecting p217+ Tau

Assay-specific reagents were as follows: Simoa Homebrew kit (Quanterix, cat #101351), Helper beads (Quanterix, cat #101732), pT3 mouse monoclonal antibody (mAb), hT43 mAb, pT82 mAb and hT7 mAb. pT3 is the parental antibody developed at Janssen that recognizes p217+ tau, and the humanized version thereof is referred to herein as humanized pT3 mAb.

The samples were diluted in 50 mM Tris, 50 mM NaCl, 5 mM EDTA, 2% Bovine Serum Albumin, 0.1% Tween 20, 0.05% ProClin 300, pH7.8.

Three custom peptides made by New England Peptide were used to calibrate the assay (calibrant peptides).

Peptide pT3xhT43 contains hT43, PT51 and pT3 epitopes connected by PEG4 linkers and has a molecular weight of 6893 g/mol. The amino acid sequence of peptide pT3xhT43 is PRQEFEVMEDHAGTYGLGDR(dPEG4)GKTKIATPR-GAAPPGQKG(dPEG4)GSRSR(pT)PS LP(pT)PP-TREPKKV-amide (SEQ ID NO: 22).

Peptide pT3xpT82 contains pT82 and pT3 epitopes connected by a PEG4 linker and has a molecular weight of 4551 g/mol. The amino acid sequence of peptide pT3xpT82 is Ac-SLEDEAAGHVTQARMVSK(dPEG4)GSRSR(pT) PSLP(pT)PPTREPKKV-amide (SEQ ID NO: 23).

Peptide hT7xpT82 contains pT82 and hT7 epitopes connected by a PEG4 linker and has a molecular weight of 3619 g/mol. The amino acid sequence of peptide hT7xpT82 is Ac-SLEDEAAGHVTQARMVSK(dPEG4)PR-GAAPPGQKGQANA-amide (SEQ ID NO: 24).

Reagent Prep

The capture beads were coated with 0.3 mg/ml capture Ab following the protocol provided in the Quanterix manual. The coated capture beads were diluted in Bead Diluent Buffer to 200,000 beads/ml, and 200,000 beads/ml Helper Beads were added so that the total concentration of beads was 400,000 beads/ml.

The detection antibodies were biotinylated at 60× following the protocol provided in the Quanterix manual and were diluted in Homebrew Detector/Sample Diluent to 1.8 ug/ml.

The calibrant peptides were reconstituted to 5 mg/ml in 0.1% phosphoric acid/water, aliquoted to 20 ul and frozen.

When ready for use, the calibrant peptide aliquots were thawed and diluted 1:1000 (e.g. 1.5 ul into 1498.5 ul), and the dilutions were diluted 1:1000 so that the final concentration of the peptides was 5000 pg/ml. A standard curve with 3× jumps was made, starting at 30 pg/ml.

CSF samples were diluted at least 1:4 in Sample Diluent. Healthy volunteer (HV) samples were diluted 1:5 or 1:10, and AD samples were diluted at least 1:20.

Simoa Assay

A custom Simoa assay was created comprising a two step protocol comprising 35 minutes with capture Ab, sample, and detection Ab, and washing, followed by 5 minutes with streptavidin β-galactosidase (SBG). Each reaction comprised 25 ul beads solution, 100 ul sample or calibrant, 20 ul detection solution, 100 ul SBG. The antibodies were assigned names, and up to five capture antibodies and five detection antibodies could be loaded at a time. The reactions were performed in the Simoa cuvettes by the instrument, washed one last time, and loaded into measurement discs with β-galactosidase substrate (RGP) before measurements were taken by the instrument.

Example 2. Separation of Native Tau Fragments on rpHPLC

Reagents were as follows: Trifluoracetic acid (HPLC grade), Water (HPLC grade), Acetonitrile (HPLC grade), Phosphoric acid (analytical grade), and HPLC binary gradient system, Immunoassay Buffer (100 mM TrisHCl, 100 mM NaCl, 0.05% Tween, & BSA, pH7.8).

The protocol was as follows: 500 ul of frozen CSF was thawed on ice for 30 min. The thawed CSF was added to 1.5 ml of 100 mM sodium phosphate pH 2.5 containing 100 mM sodium chloride and mixed. 1.8 ml of the resulting mixture was applied onto a C18 or similar reverse phase chromatography column equilibrated in 0.1% trifluoracetic acid in water. The HPLC column was then developed in an increasing gradient of acetonitrile. Fractions were collected across the elution. The fractions were adjusted to 10 mM in guanidine HCl and then dried in a vacuum concentrator. The dried fractions were resuspended in immunoassay buffer and subjected to measurement of the tau peptide in the fraction based on an anti-tau capture and detection antibody pair of the invention.

Example 3. Quantification of p217+ Tau that is Free or Bound by Antibodies

With additional upstream sample manipulation, the high sensitivity pT3-based assays can be used to measure the binding of p217+ tau by antibodies that are either produced within a patient or are administered exogenously, e.g. humanized pT3 mAb. This technique can be used as a pharmacodynamic assay to study therapeutic anti-p217+ tau antibodies such as humanized pT3 mAb. For example, the following methods can be used to measure p217+ tau that is antibody-free vs. antibody-bound.

Assay 1: Quantification of Free Vs. Bound p217+ Tau in Biological Fluids Using Immunocapture/Depletion Followed by rpHPLC Biological fluid (e.g. CSF) was incubated with protein A/G-coated magnetic beads (15 μl bead slurry per 0.5 mL CSF) for 2 hrs with rocking at room temperature to capture immunoglobulins in the sample. Beads were precipitated by magnet and the supernatant was transferred to second tube (sample="IgG depleted supernatant"). The beads were washed 4× with 1 mL cold Phosphate Buffered Saline (PBS). 0.5 mL of 6M GuHCl was then added to the tubes containing (a) washed beads and (b) IgG depleted supernatant, and the tubes were incubated for 20 minutes with rocking at room temperature. Beads were then precipitated by magnet, and the resulting supernatant was transferred to a third tube (sample="IgG concentrated supernatant"). Finally, 0.1 M phosphoric acid (pH 2) was added to the two solutions (1.0 mL phosphoric acid was added to the denatured IgG depleted supernatant, and 1.5 mL phosphoric acid was added to the IgG concentrated supernatant, to make samples up to a final volume of 2.0 mL) prior to separation by rpHPLC, carried out as in Example 2. The resulting rpHPLC fractions were reconstituted as described in Example 2 and measured using the Simoa p217+ tau assays of Example 1. Signal from the IgG depleted supernatant represents free p217+ tau (i.e., that which is not bound by antibodies), while signal from the IgG concentrated supernatant represents bound p217+ tau (i.e., that which is bound by antibodies, such as humanized pT3 mAb). rpHPLC separation and Simoa p217+ measurement of the same parental biological fluid (e.g. CSF) that was not subjected to the immunocapture/depletion process was analyzed simultaneously for assessment of total p217+ tau signal, as a control or as a normalizer for the free and bound measurements.

Assay 2: Quantification of Free Vs. Bound p217+ Tau in Biological Fluids Using Heat Denaturation of Antibodies An aliquot of biological fluid of interest (e.g. CSF) was heated at 95° C. for 4 minutes, followed by chilling on wet ice for 4 minutes (sample="semi-denatured fluid"). In parallel, a second aliquot of the same fluid was chilled on wet ice for 8 minutes (sample="non-denatured fluid"). Both samples were then measured using the Simoa p217+ tau assays of Example 1. Semi-denatured fluid signal represents total p217+ tau, while non-denatured fluid represents free p217+ tau. Subtracting the latter from the former yields measurement of bound tau. The precise heating time and temperature was determined to irreversibly modify any antibodies in the fluid such that they could no longer interfere with the Simoa p217+ tau assays, while the p217+ tau signal itself was spared any impact. This assay is not a direct measure of whether the antibodies are bound to p217+ tau, rather it demonstrates that assay-competing antibodies are present. However, the assay yielded similar results to those of the more laborious Assay 1.

Example 4. Biological Samples

Samples Used for Assay Development and Technical Qualification

The assays of Examples 1-3 were developed using CSF pooled from human subjects with high tau levels. Some experiments were also performed with CSF pooled from human subjects with low tau levels to ensure assay sensitivity that would be required for testing of healthy volunteers in Phase 1 trials. CSF from Cynomolgus Macaque (*Macaca fascicularis*) and Common Marmoset (*Callithrix jacchus*), obtained from Neu Encepharm GmbH (animal testing CRO), was also measured using the assays of Examples 1-3. Additionally, flash frozen brain samples from cognitively normal human subjects and Common Marmoset were homogenized and measured using the assays of Examples 1 and 3. Some experiments were performed with individual serums from clinically defined HV and AD subjects.

Samples Used for Preliminary Clinical Qualification
Cohort 1 ("Interassay Correlation Cohort"):
Ventricular fluid (VF) and lumbar fluid (LF) CSF samples were obtained from subjects with Normal Pressure Hydrocephalus (NPH) (n=11) (University of Kuopio, Professor Ville Lenoinen). These samples were separated by CSF Aβ42, total tau (tTau), and pTau181 measurements as determined by Innotest assays performed at the University of Sahlgrenska (Professor Kaj Blennow), and by brain biopsy amyloid and tau immunohistochemistry (IHC) measurements. rpHPLC and Simoa p217+ tau measurements were performed at Janssen Neuroscience Biomarkers, La Jolla.

Cohort 2 ("Clear HV Vs. Clear AD Cohort"):

LF CSF samples from biochemically defined Alzheimers Disease (AD) vs. Healthy Volunteer (HV) subjects (n=20 per group) were obtained from University of Sahlgrenska (Professor Kaj Blennow). CSF Aβ42, tTau, and pTau181 measurements by Innotest assays were performed at University of Sahlgrenska. Samples were selected from a large panel of samples based on segregation into predetermined AD vs. HV cutoff measures (AD=CSF Aβ42<400 pg/ml AND CSF tTau>600 pg/ml, HV=CSF Aβ42>400 pg/ml AND CSF tTau<600 pg/ml). rpHPLC and Simoa p217+ tau measurements were performed at Janssen Neuroscience Biomarkers, La Jolla.

Cohort 3 ("HV Vs. ARAD Vs. Early Stage AD Cohort"):

LF CSF samples from clinically defined normal (Clinical Dementia Rating 0; CDR 0) vs. mild memory complaint (CDR 0.5) subjects (n=20 per group) were obtained from Janssen study ALZ1005/1002. CSF Aβ42, tTau, and pTau181 measurements by Innotest assays were performed at University of Sahlgrenska. Based on the CDR and CSF Aβ42 scores, the subjects were classified into (a) HV=CDR 0 and Aβ42>600 pg/ml, (b) At Risk of AD (ARAD)=CDR 0 and Aβ42<600 pg/ml, (c) potentially non-AD dementia=CDR 0.5 and Aβ42>600 pg/ml, and (d) early stage AD=CDR 0.5 and Aβ42<600 pg/ml. rpHPLC and Simoa p217+ tau measurements were performed at Janssen Neuroscience Biomarkers, La Jolla.

Cohort 4 ("CDR 0 vs CDR1 Cohort"):

LF CSF samples from clinically defined normal (Clinical Dementia Rating 0; CDR 0) vs. mild memory complaint (CDR 1) subjects (n=5 per group) were obtained from Washington University. CDR & MMSE, as well as CSF Aβ42, tTau, and pTau181 measurements by Innotest assays were obtained at Washington University. Prior to shipment samples were coded so that Janssen was blind to sample identity or characterization. rpHPLC and Simoa tTau & p217+ tau measurements were performed at Janssen Neuroscience Biomarkers, La Jolla and sent to Washington University for analysis.

Cohort 5 ("HV Vs. MCI Vs. AD Cohort"):

LF CSF samples from clinically and biochemically (Innotest AB42>600 pg/ml) defined HV (n=7) were obtained from Precision Medicine, San Diego. LF CSF samples from clinically and biochemically (Innotest AB42<600 pg/ml) defined MCI (n=28) and AD (n=12) were obtained from University of Antwerp. rpHPLC and Simoa p217+ tau measurements were performed at Janssen Neuroscience Biomarkers, La Jolla.

Cohort 6 ("Disease Severity and Progression Cohort"):

LF CSF samples from clinically defined AD (Clinical Dementia Rating 1+) subjects (n=235) were obtained from Janssen study ELN115727301/302. These samples were baseline (pre-dose) samples from all subjects in the trial. In addition, CSF samples from 78 week follow up on the placebo subjects (n=90) was included to evaluate biomarkers of disease progression. Cognitive assessment (ADAS-COG, MMSE, NTB, CDR.SOB), ApoE genotype, gender, & age were obtained from the trial. Innotest AB42, Innotest AB40, Simoa NFL, pT3xpT82, pT3xhT43, and hT7xpT82 assays were performed at Janssen Neuroscience Biomarkers, La Jolla. Subjects were confirmed amyloid positive or negative based on the AB42/40 ratio cutoff of 0.09 (e.g. subjects with ratio <0.09=amyloid positive=AD, while those >0.09=amyloid negative=dementia from non-AD cause. 27 of the 235 subjects were determined to be amyloid negative, both groups were analyzed separately.

Samples Used for Evaluation of Target Engagement after Treatment with Anti-p217+ Agents LF CSF from HV subjects (n=40) treated with placebo or JNJ63733657 (single IV injection) were obtained from Janssen trial JNJ63733657EDI1001. pT3xpT82 assays were performed at Janssen Neuroscience Biomarkers, La Jolla. pT3xhT43 assays were performed at Quanterix Corporation, Lexington Mass.

Example 5. Screening of Capture and Detection Antibody Pairs Using the Simoa Platform Prior reports from Janssen Neuroscience Discovery and the literature (e.g., Meredith et al. *PLoS One.* 8(10):e76523, 2013; Barthelemy et al., *J Alzheimers Dis.* 51(4):1033-43, 2016; Russell et al., *J Alzheimers Dis.* 55(1):303-313, 2017; Hanger et al. *J Biol Chem.* 282(32):23645-54, 2007) have indicated that tau fragments containing amino acids 200-220, and especially some combination of phosphorylation at amino acids 212, 214, 217, are enriched in AD. Developing an assay to measure this particular tau species ("p217+ tau") could thus yield an improved biomarker for AD diagnosis and/or staging, as well as a potential predictive and/or pharmacodynamic assay for new drugs targeting this tau moiety. However, tau can be present at low levels (<200 pg/ml) in healthy volunteers, and p217+ tau is a minority component of total tau, so p217+ tau assays require optimal antibody pairs and high sensitivity.

To achieve this goal, a set of anti-tau mAbs discovered at Janssen, as well as some high-affinity commercial anti-tau mAbs, were evaluated for their ability to yield signal in a sandwich ELISA (sELISA) format when paired with pT3. Antibody pairs were screened on the Simoa HD-1 Analyzer platform (Quanterix Corporation) to provide the sensitivity required, using a serial dilution of a pool of CSF from AD subjects. Assay performance was based on Signal/Noise=average enzymes per bead (AEB) of sample diluted in sample diluent/AEB of assay diluent alone. Optimal detection antibodies to pair with pT3 were hT43, pT82, the Quanterix tau 2.0 detector reagent, and BT2 in that order of sensitivity (Table 1). hT43 and the Quanterix tau 2.0 detector reagent recognize the N-terminal region of tau, while pT82 and BT2 recognize sequences closer to the mid-region of tau. The best N-terminal (hT43) and mid-region (pT82) mAbs were selected for further optimization. Screening was performed in parallel at Janssen Neuroscience Biomarkers and at Quanterix Corporation, yielding similar results.

TABLE 1

Screening of specificity in AD CSF of tau detection antibodies paired with pT3.

| Detection Antibody | Epitope (tau aa) | S/N @ 1:2 dilution | S/N @ 1:4 dilution | S/N @ 1:8 dilution | S/N @ 1:16 dilution | S/N @ 1:32 dilution | S/N @ 1:64 dilution |
|---|---|---|---|---|---|---|---|
| hT43 | 7-20 | 955 | 587 | 313 | 183 | 102 | 55 |
| Quanterix tau 2.0 assay detector | 16-24 | 525 | 262 | 147 | 75 | 35 | 19 |
| pT82 | 116-127 | 733 | 400 | 211 | 105 | 48 | 23 |
| PT51 | 151-158 | 165 | 52 | 17 | 6 | 3 | 1 |
| PT98 | 159-163 | NT | NT | 17 | 7 | 3 | 2 |
| pT89 | 166-182 | 87 | 24 | 9 | 4 | 2 | 1 |
| BT2 | 193-198 | 732 | 245 | 78 | 28 | 10 | 4 |
| HT52 | 393-398 | NT | NT | 1 | 1 | 1 | 1 |
| HT60 | 423-440 | NT | NT | 1 | 1 | 1 | 1 |

Antibody epitope on tau and Signal/Noise (S/N) ratios in measuring pooled CSF from AD subjects is shown; NT = not tested.

Example 6. Optimization of pT3xhT43 and pT3xpT82 Assays

A series of optimization experiments were performed based on general Quanterix experience with optimizing assays on the Simoa platform. 10% mouse serum or 500 µg/ml mouse IgG were added to the detector diluents but did not improve assay sensitivity. Titrations of Detector mAb concentration (0.15, 0.3, 0.6, 1.2, and 1.8 µg/ml), SβG concentration (100, 200, or 300 pM), and Capture mAb bead concentrations (300K/well, 150K+200K helper beads) were evaluated. Protocol incubation times (65 minute vs. 35 minute), and sample volume (100 vs. 150 µl) were also evaluated. The ideal reagent concentrations for both assays were 150K capture beads +200K helper beads, 1.8 µg/ml detector, and 200 pM SBG, respectively. Sample volume and incubation time had minimal impact on the assay, so the lower conditions of 100 ul sample and 35 minute incubation were chosen.

Example 7. Technical Qualification of pT3xhT43 and pT3xpT82 Assays

Linear Range with Calibrant Material

Calibrant peptides described in Example 1 were produced. The calibrant peptides contained the core epitopes of pT3 and hT43, or pT3 and pT82 separated by PEG4 linkers, and they were used to generate standard curves. A representative standard curve is shown in FIG. 1. Calibrant peptides were titrated from 30 pg/ml to 0.041 pg/ml in 1:3 jumps in assay buffer and measured with the pT3xhT43 and pT3xpT82 assays. A 4-parameter curve fit data reduction method (4PL, 1/y2 weighted) was used to generate the calibration curve. The lower limit of detection (LLOD) was defined as the calculated calibrant level yielding an AEB equal to the average of the zero calibrator+2.5 standard deviations (SD), including 10% coefficient of variation (CV). With these criteria, the representative data yielded an LLOD of ~0.002 pg/ml. The Linear Range of the assay, lower limit of quantification (LLOQ) and upper limit of quantification (ULOQ), was defined as the lowest and highest standard curve points achieving CV<20% and recovery 80-120% of expected. With these criteria, the linear range for both the pT3xhT43 and pT3xpT82 assays was 0.041 to 30 pg/ml (FIG. 1, Table 2).

TABLE 2

Representative calibrant curve for optimized pT3xhT43 assay, with LLOD calculations

| pg/ml calibrant | Avg AEB | SD | CV (%) | S/B |
|---|---|---|---|---|
| 0 | .0185 | .0019 | 10 | |
| .034 | .1369 | .0260 | 19 | 7 |
| .103 | .1952 | .0039 | 2 | 11 |
| .309 | .5221 | .0626 | 12 | 28 |
| .926 | 1.4545 | .0145 | 1 | 78 |
| 2.78 | 5.4789 | .1096 | 2 | 295 |
| 8.33 | 11.4588 | 1.0313 | 9 | 617 |
| 25 | 24.0576 | .2406 | 1 | 1297 |

Figure 2C:
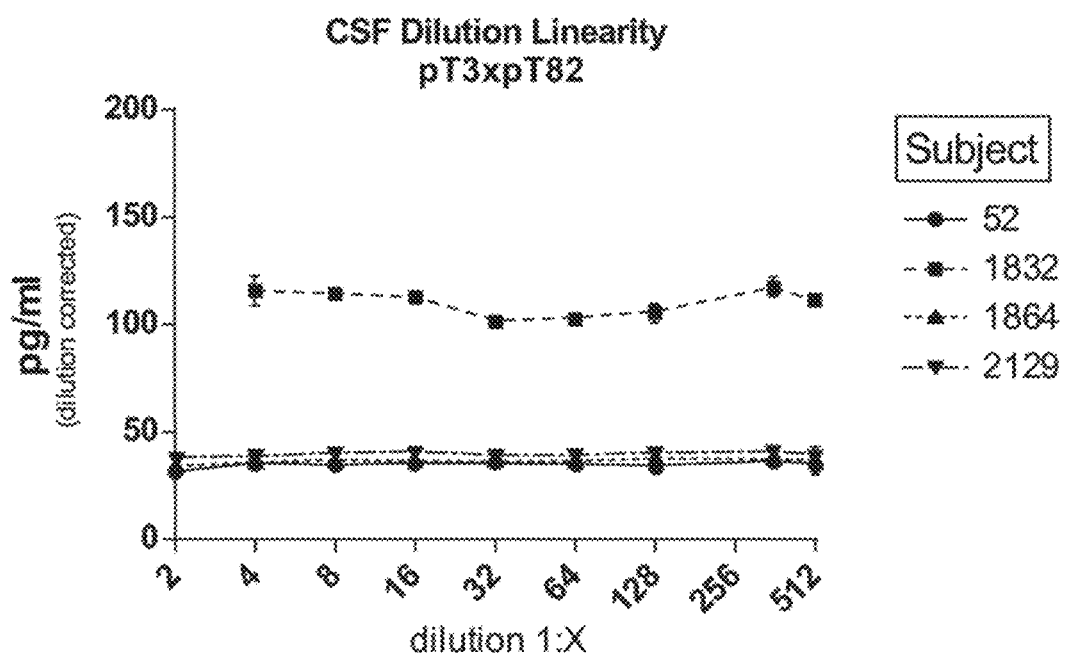
Figure 2D:
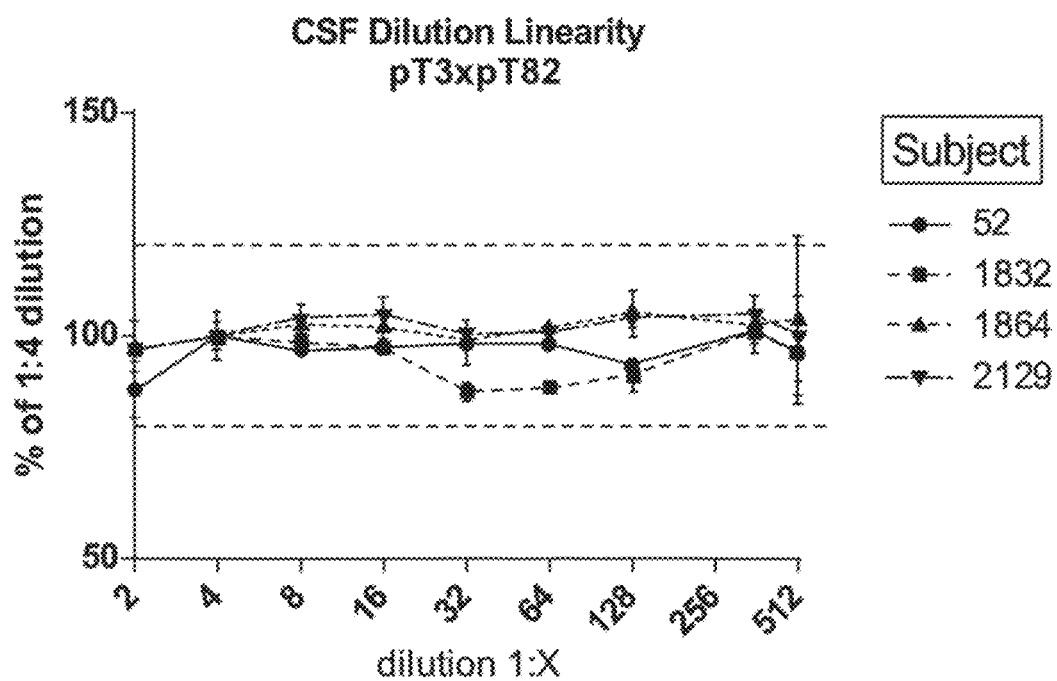
Figure 2E:
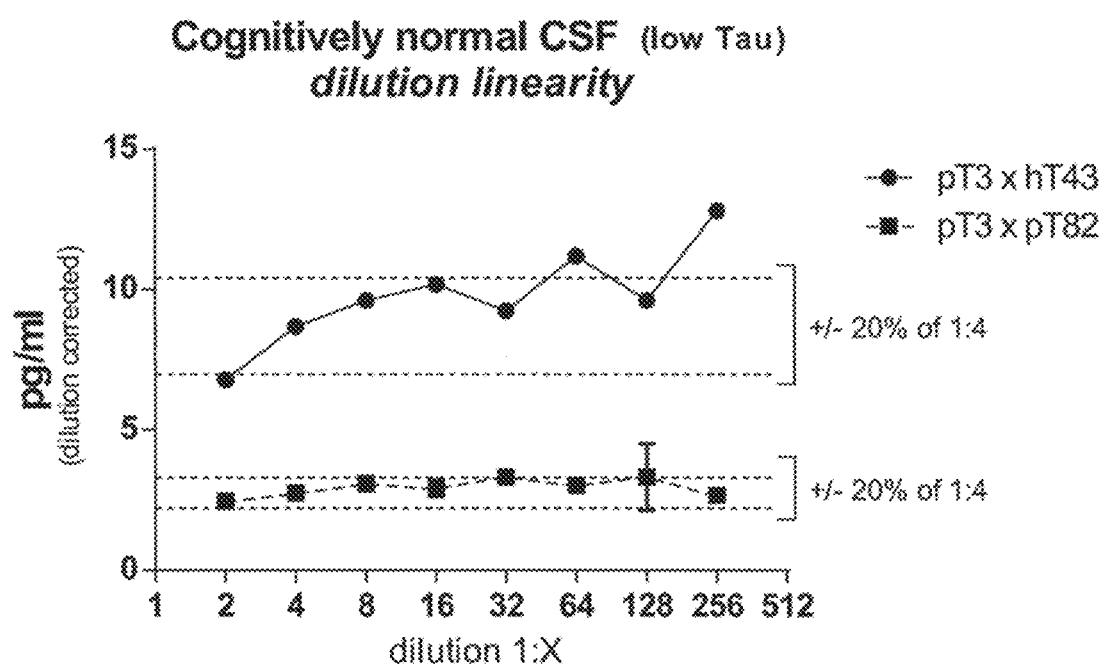

LLOD = .0185 + (2.5 × 0.0019) = .0231 AEB, which calculates to a theoretical concentration of 0.002 pg/ml Dilution Linearity with CSF To assess dilution linearity and determine ideal dilution for testing CSF samples, a panel of 4 CSF samples from AD subjects (high tau, low AB42) was titrated from 1:2 to 1:4096 dilution in assay buffer and measured in the p217+ tau assays. Samples diluted beyond 1:512 typically measured below LLOQ. Sample measurements from 1:4 through 1:512 were dilution linear, so that was the defined range for measuring CSF samples. To confirm in Cognitively Normal subjects, a pool of CSF from subjects with low tau and high AB42 was measured similarly. Dilution linearity was again observed for 1:4 through 1:256 dilution, and beyond this range the measurements fell below LLOQ (FIG. 2).

Precision

Figure 3:
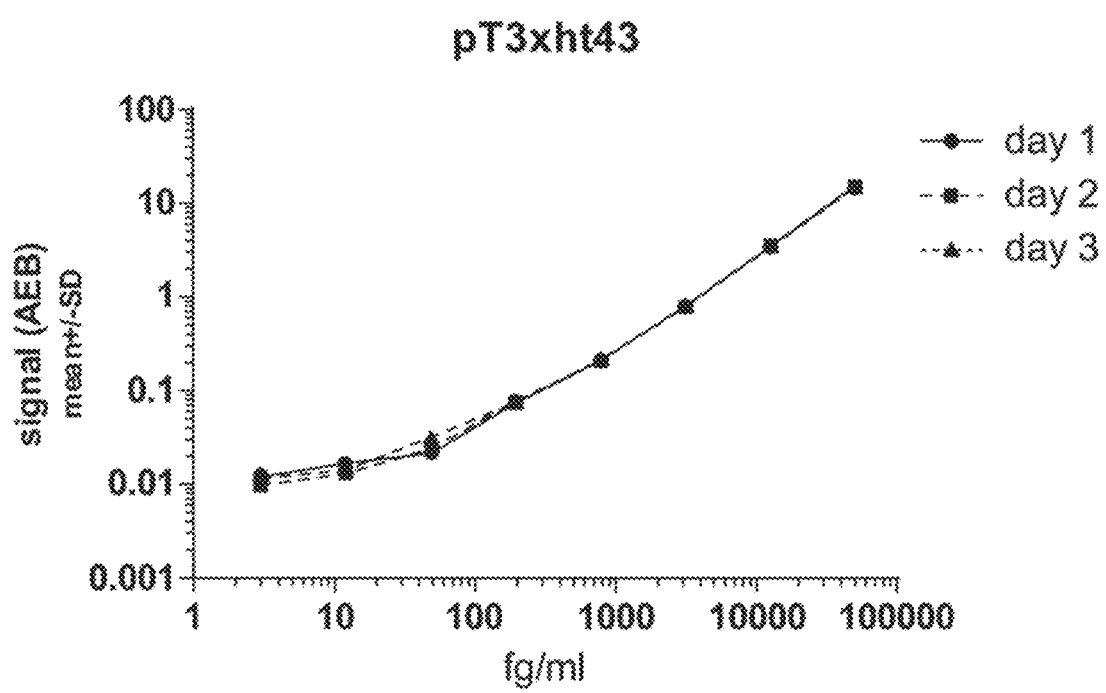
FIG. 3 shows the intra- and inter-test precision of the (A) pT3xhT43 and (B) pT3xpT82 assays.

To assess precision of the measurements, the standard curve for pT3xhT43 was prepared and measured on 3 separate days (FIG. 3 and Table 3). Calibrant peptide was diluted from 30 to 0.041 pg/ml in serial 1:3 jumps and measured in duplicate on the pT3xhT43 assay. The procedure was repeated over 3 successive days at the same site and by the same technician. Analysis of the 4 points in middle of the curve (where CSF samples are measured) indicated that the precision within a run (intra-test CV %) was always <10% and averaged from 2.46-5.18% CV, and the inter-test precision averaged 6.46% CV. These are well within the accepted limits of 20% CV for a research use only (RUO) assay and are in part attributed to the automated nature of all the ELISA steps in the Simoa HD-1 Analyzer.

TABLE 3

Intra-and inter-test precision of the pT3xhT43 assay

| fg/ml calibrant | Run1 Mean AEB | SD | CV % | Run2 Mean AEB | SD | CV % | Run3 Mean AEB | SD | CV % | Sum of runs Mean AEB | SD | CV % |
|---|---|---|---|---|---|---|---|---|---|---|---|---|
| 49 | .0228 | .0005 | 2.03 | .0248 | .0024 | 9.64 | .0319 | .0005 | 1.41 | .0265 | .0048 | 18.04 |
| 195 | .0762 | .0019 | 2.55 | .0777 | .0011 | 1.39 | .0785 | .0028 | 3.52 | .0775 | .0012 | 1.54 |
| 781 | .2130 | .0084 | 3.95 | .2161 | .0200 | 9.26 | .0210 | .0129 | 6.14 | .2130 | .0030 | 1.43 |
| 3125 | .8012 | .0105 | 1.31 | .8193 | .0036 | 0.44 | .7460 | .0289 | 3.88 | .7888 | .0382 | 4.84 |
| Mean | | | 2.46 | | | 5.18 | | | 3.74 | | | 6.46 |

Transferability Between Labs

Figure 4A:
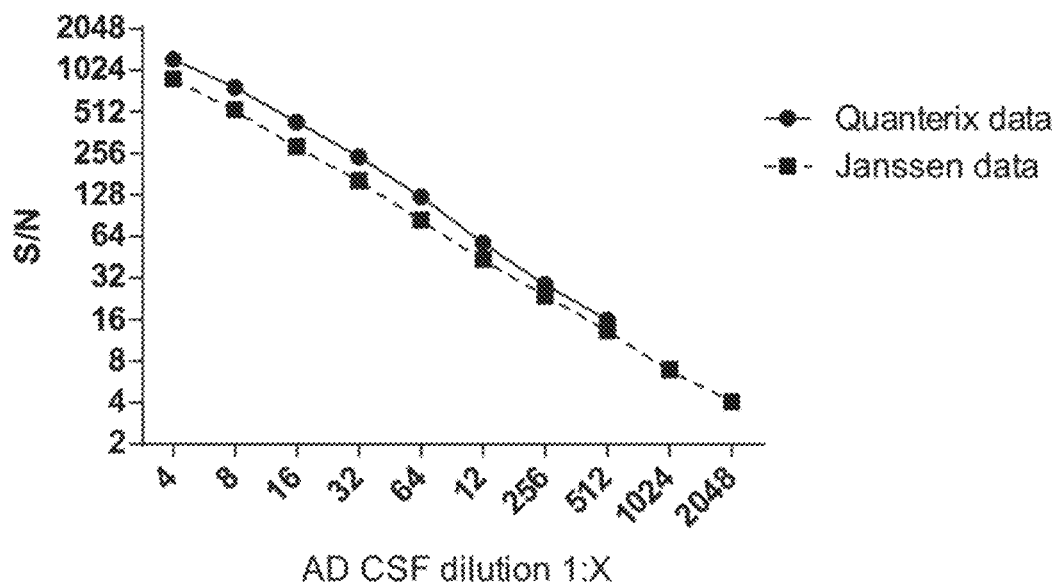
FIGS. 4A-4B show the precision between testing sites of the pT3xhT43 and pT3xpT82 assays with the data graphed as Signal/Noise (S/N).
Figure 4B:
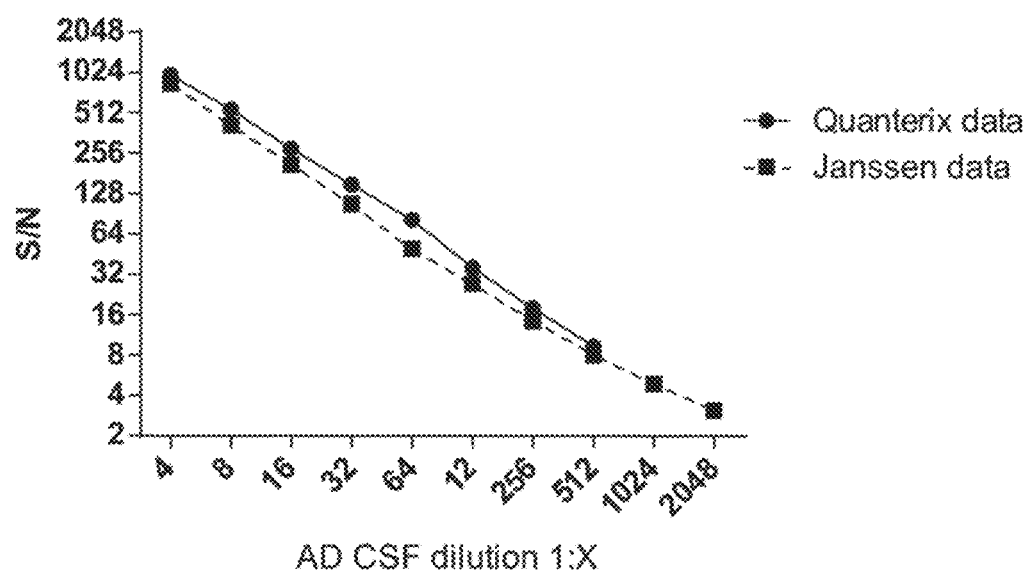

To evaluate precision of the p217+ tau assays between testing sites, the same AD CSF pool was measured, in titration, using the same lot of reagents at Janssen Neuroscience Biomarkers and at Quanterix Corporation. FIG. 4 shows that the measurements are very similar for the pT3xhT43 and pT3xpT82 assays at the two testing sites.

Accuracy

To assess accuracy of the assays, two different pools of HV CSF were spiked with known concentrations of the calibrant peptides (0, 2, or 20 pg/ml), diluted to the recommended 1:4 dilution, and then measured in the pT3xhT43 and pT3xpT82 assays. This is one measure of potential interference presented by components of the sample matrix. Levels of endogenous signal were subtracted from the 2 and 20 pg/ml spike measurements, and then observed concentration of the calibrant material was compared to expected concentration to calculate percent recovery. The measured concentrations were compared to the expected concentrations to calculate spike recovery, yielding average recovery of 114% (Table 4). This is well within the accepted limits of 80-120% recovery for an RUO assay, indicating no significant interference in CSF when tested at >1:4 dilution.

TABLE 4

Spike recovery of the pT3xhT43 assay

| CSF sample | Calibrant spike (pg/ml) | AEB | Calculated pg/ml | pg/ml CV % | Average pg/ml | Dilution corrected pg/ml | % recovery |
|---|---|---|---|---|---|---|---|
| 1 | 0 | 1.4863 | 0.945 | 3 | 0.924 | 3.69 | NA |
| | | 1.4209 | 0.902 | | | | |
| | 2 | 2.2451 | 1.44 | 2 | 1.42 | 5.69 | 100 |
| | | 2.1776 | 1.40 | | | | |
| | 20 | 8.9800 | 6.33 | 2 | 6.40 | 25.6 | 110 |
| | | 9.1679 | 6.48 | | | | |
| 2 | 0 | 1.9960 | 1.28 | 6 | 1.23 | 4.91 | NA |
| | | 1.8397 | 1.18 | | | | |
| | 2 | 2.8076 | 1.82 | 2 | 1.85 | 7.39 | 124 |
| | | 2.8886 | 1.88 | | | | |
| | 20 | 10.1636 | 7.28 | 1 | 7.34 | 29.4 | 122 |
| | | 10.3026 | 7.40 | | | | |
| | | AVERAGE RECOVERY | | | | | 114% |

Competition of Signal by p217+ Directed Antibodies in CSF

Figure 5A:
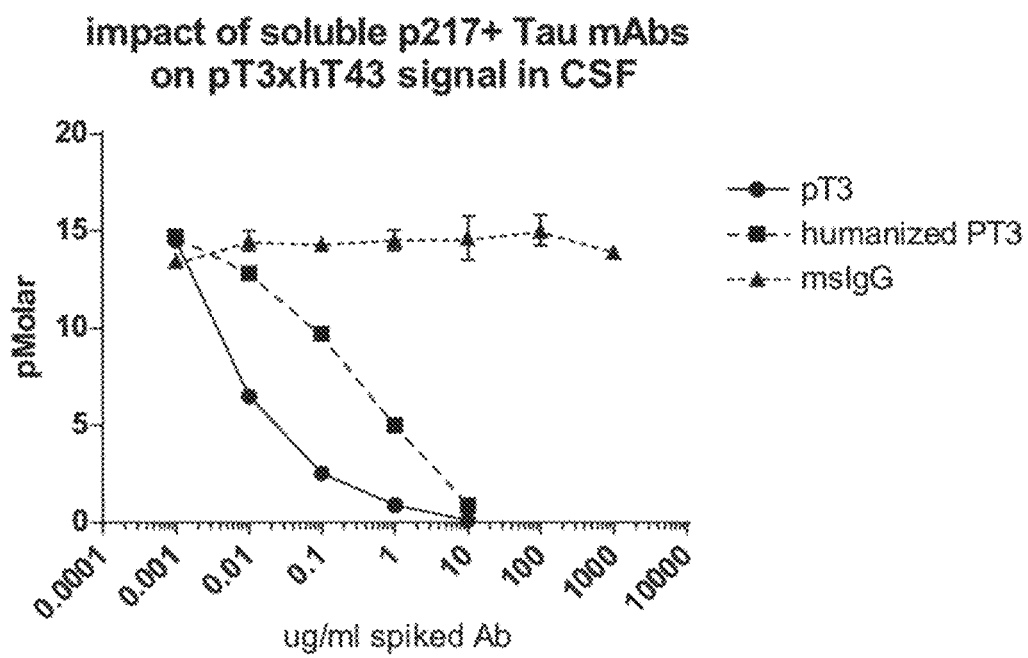
FIGS. 5A-5B show the competition of pT3-based assay signal by soluble p217+ tau-targeted antibodies on (A) pT3xhT43 and (B) pT3xpT82 assays.
Figure 5B:
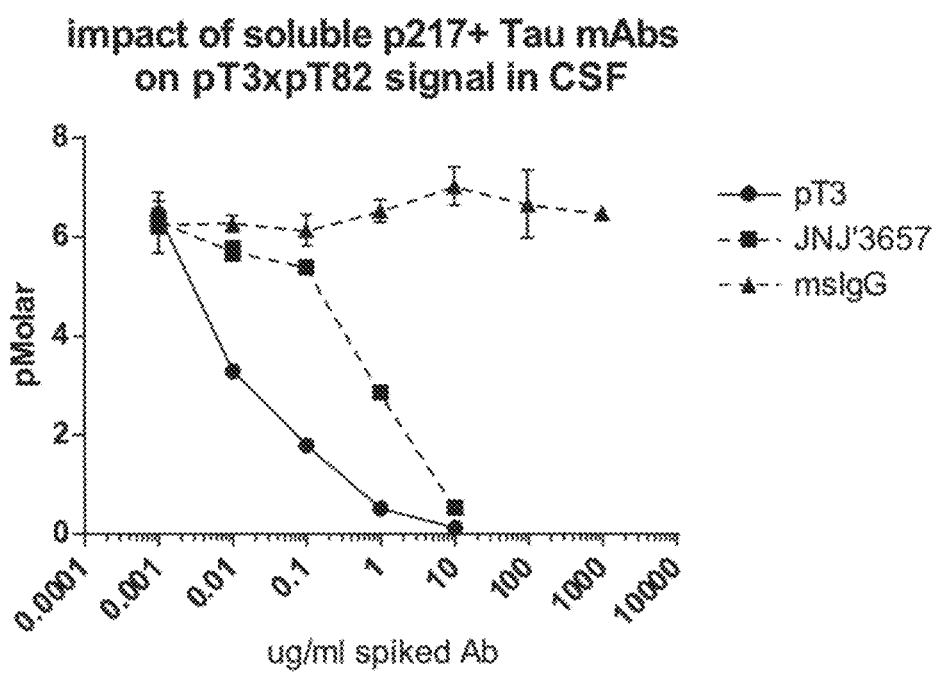

To confirm accuracy of the pT3xhT43 and pT3xpT82 assay signals in CSF, and to assess its potential utility as a pharmacodynamic assay in clinical studies of p217+ tau-directed antibodies, a pool of AD CSF was spiked with titrations of pT3 mAb or humanized pT3 mAb and measured in the pT3xhT43 and pT3xpT82 assays after a 2 hour incubation at room temperature (FIG. 5). Administration of the soluble pT3 and humanized pT3 antibodies reduced signal in the pT3-based assays in a dose dependent manner. Spiking msIgG (negative control) at comparable concentrations did not impact any of the measures. The lower competition ability of humanized pT3 mAb vs. pT3 can be attributed to the higher affinity of pT3 for p217+ tau.

Phosphorylation Dependency

To confirm the signal in CSF obtained with the pT3xhT43 and pT3xpT82 assays was indeed based on a phosphorylated epitope, AD CSF was treated with alkaline phosphatase to dephosphorylate all residues. The samples were then analyzed in the pT3 assays and in two hT7-based assays, hT7xpT82 or hT7xBT2. hT7 is known to be not dependent on phosphorylation, so it was used as a negative control.

Figure 6:
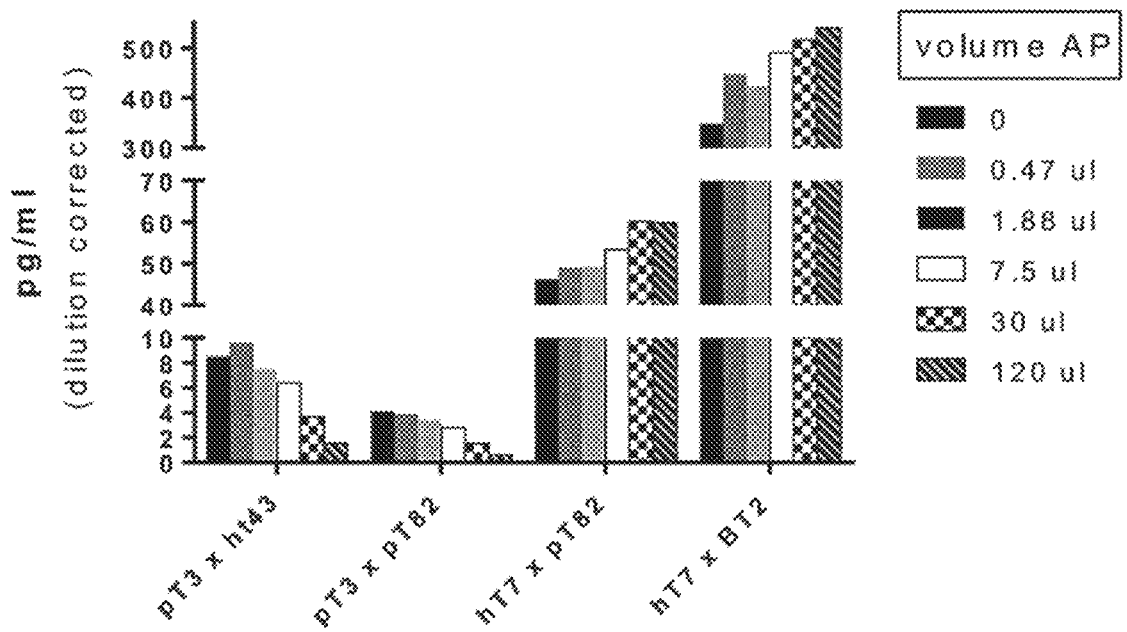
FIG. 6 shows the phosphorylation dependency of the pT3xhT43 and pT3xpT82 assays.

Pooled CSF from AD patients was treated with increasing amounts of alkaline phosphatase (AP) at 37° C. for 4 hrs in a zinc and magnesium chloride-containing buffer. The effect on the pT3-directed epitope was measured using the pT3xhT43 and pT3xpT82 assays. pT3xhT43 and pT3xpT82 signal was reduced by alkaline phosphatase treatment in a dose dependent manner. However, the non-phosphorylation dependent assays hT7xpT82 or hT7xBT2 did not show a signal decrease, they in fact showed an increase, as expected since pT7 binding is reduced by phosphorylation (FIG. 6).

p217+ Tau Fragment Profile

Figure 7:
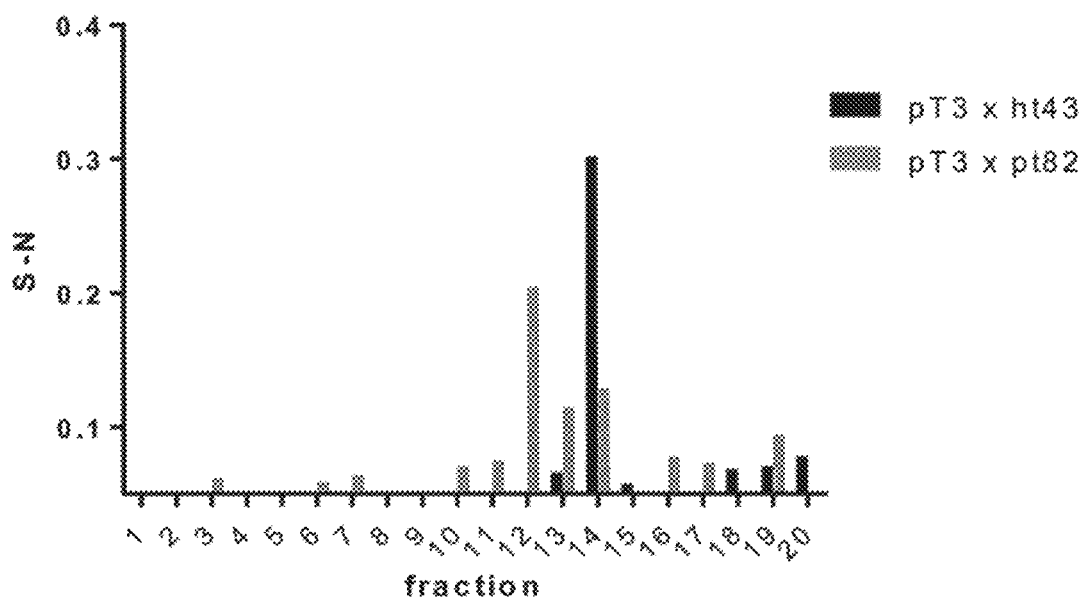
FIG. 7 shows a p217+ tau fragment profile of AD CSF, measured using the pT3xhT43 and pT3xpT82 assays, with data graphed as signal minus noise.

To explore the nature of the p217+ tau signal derived from measuring crude CSF, a sample of AD CSF was fractionated by rpHPLC via a method similar to that described in Meredith et al. *PLoS One.* 8(10):e76523, 2013. Fractions were collected and measured using the pT3xhT43 and pT3xpT82 assays (FIG. 7). In this chromatography format, smaller tau fractions elute sooner (smaller fraction number), while larger fractions elute later (larger fraction number). Full length tau elutes at fraction 19. The tau fragment profile indicated that there was very little full length tau detected by either of the assays, in line with prior reports (Meredith et al. *PLoS One.* 8(10):e76523, 2013, Barthelemy et al., *J Alzheimers Dis.* 51(4):1033-43, 2016). The pT3xpT82 assay detected two major peaks (tau species) that were smaller than full length tau (fractions 12 and 14), while pT3xhT43 assay detected only one of these major peaks (fraction 14). This indicated that p217+ tau in CSF exists in at least two fragments, a larger fragment encoding at least the region from hT43 to pT3 (aa 7-220 of tau) and a smaller fragment encoding at least the region from pT82 to pT3 (aa 116-220 of tau) but not reaching all the way to the hT43 epitope. That is, there is likely a proteolytic cleavage site between aa 20 and aa 116 that is only cleaved in a subset of tau molecules at any given time. The profile is not p217+ specific, as measurements with other tau assays that recognize a similar region of tau but are not phosphorylation-specific yield similar findings (data not shown).

Analyte Stability

Figure 8A:
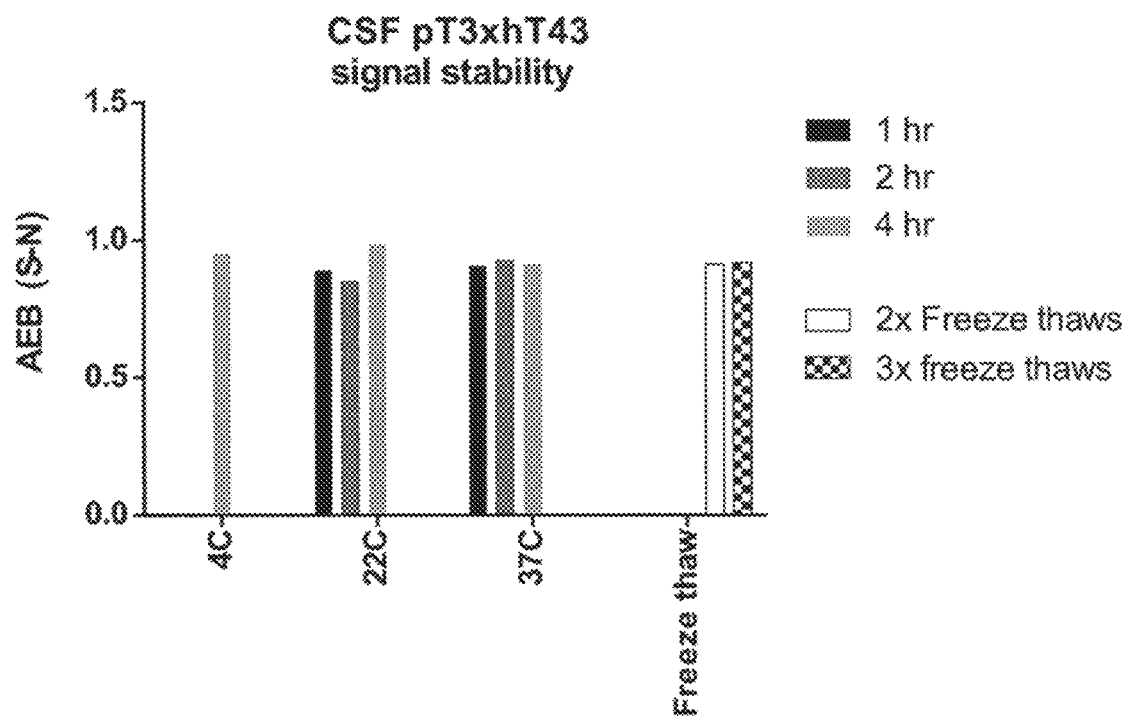
FIGS. 8A-8B show the temperature and freeze-thaw stability of p217+ tau signal in an AD CSF sample using the (A) pT3xhT43 and (B) hT7xpT82 assays.
Figure 8B:
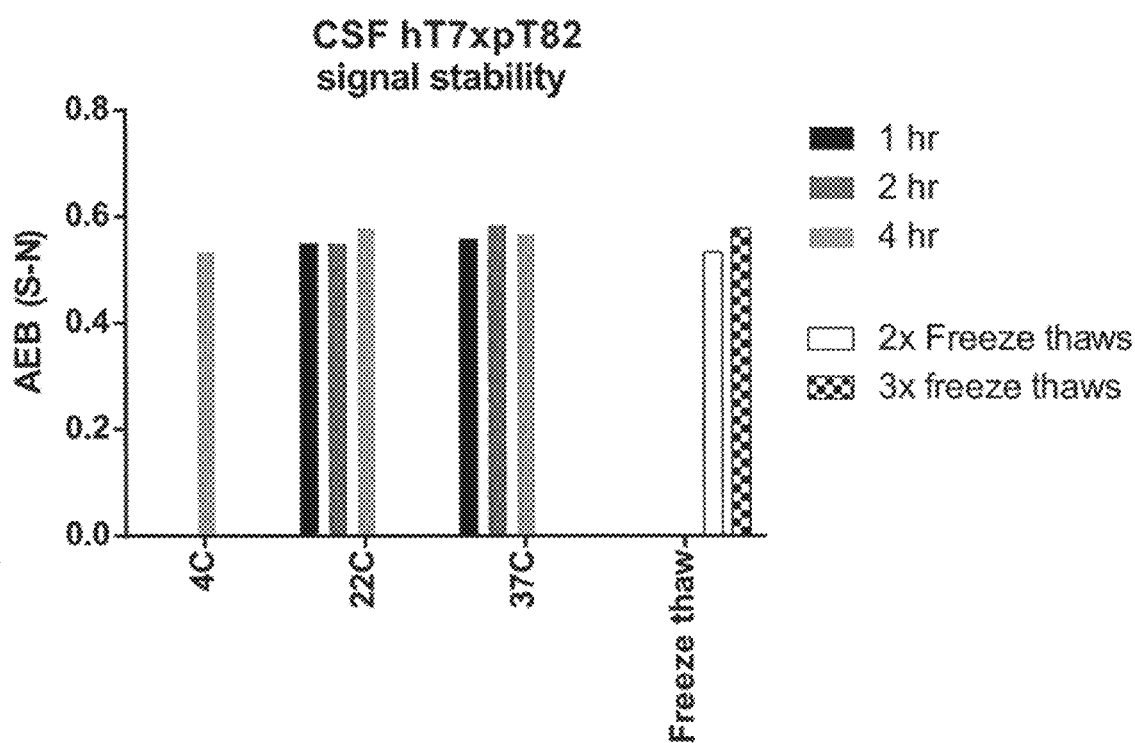
Figure 9:
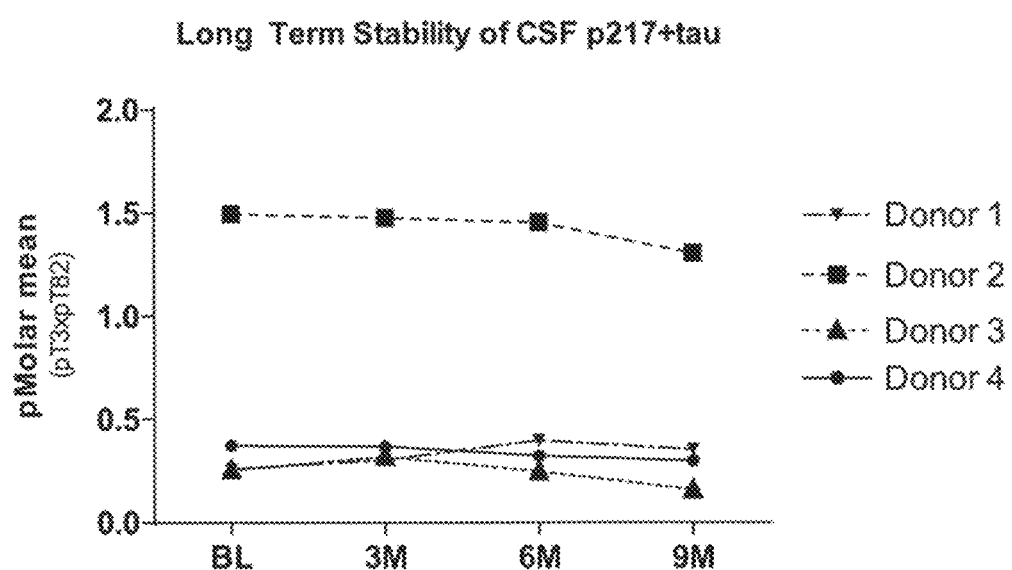
FIG. 9 shows the long term stability of p217+ tau signal in CSF samples after storage at −70° C. No change in signal was detected.
Figure 10A:
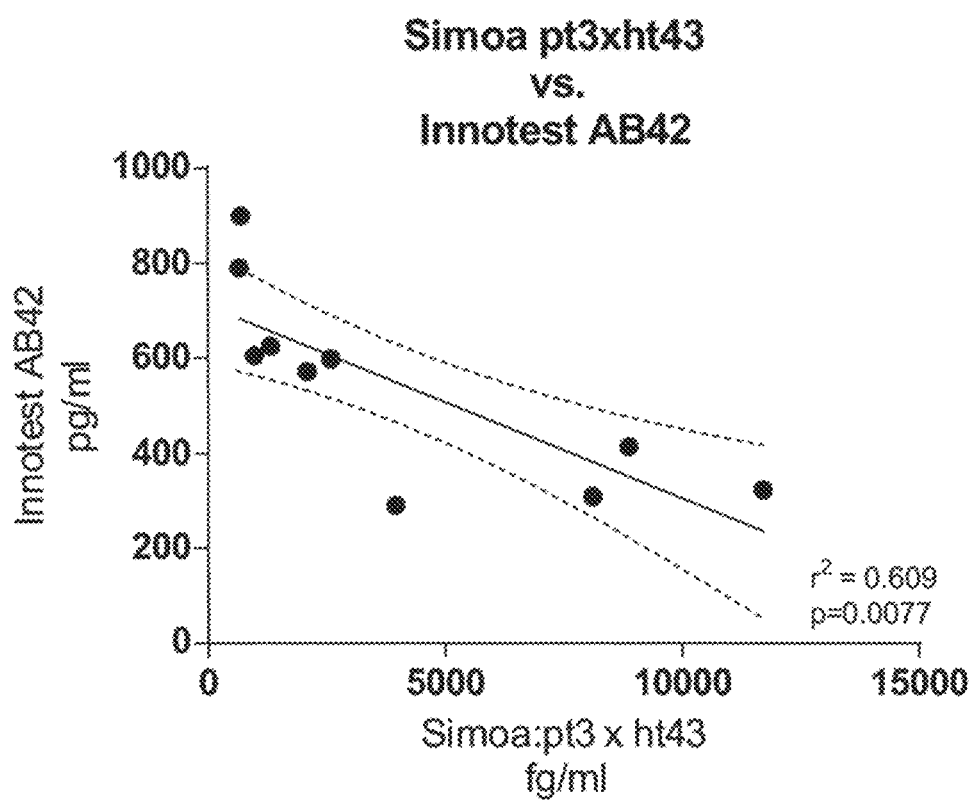
FIGS. 10A-10F show a correlation between p217+ tau and the classical AD biomarkers Aβ42, tTau (total Tau), and pTau181, as measured by (A-C) pT3xhT43 and (D-F) pT3xpT82 assay.
Figure 10B:
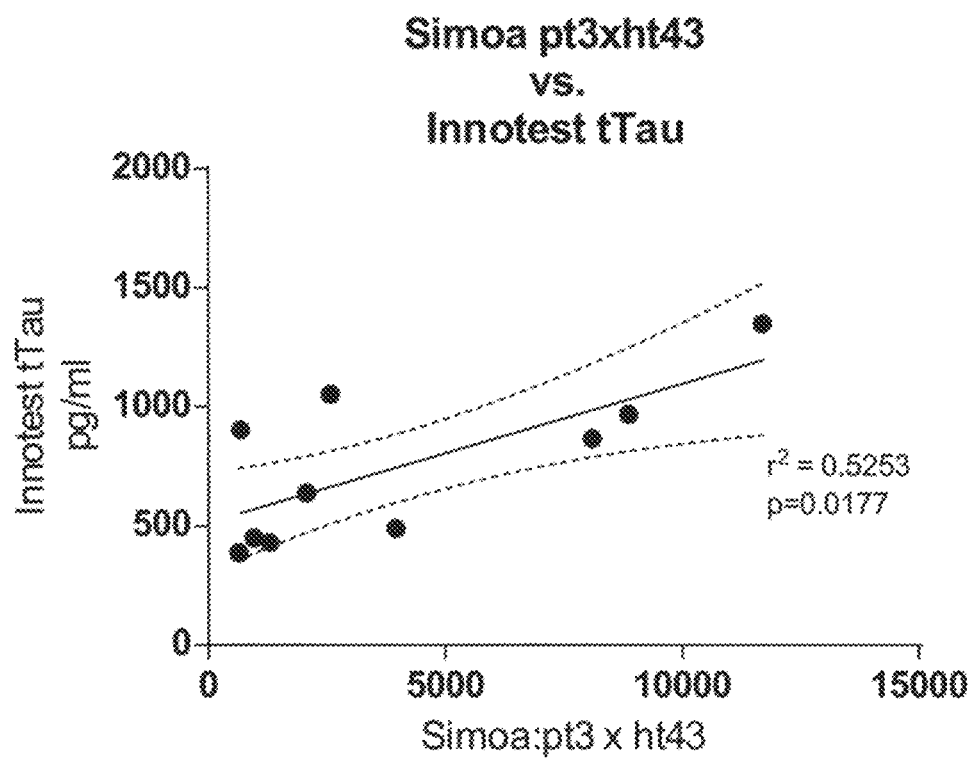
Figure 10C:
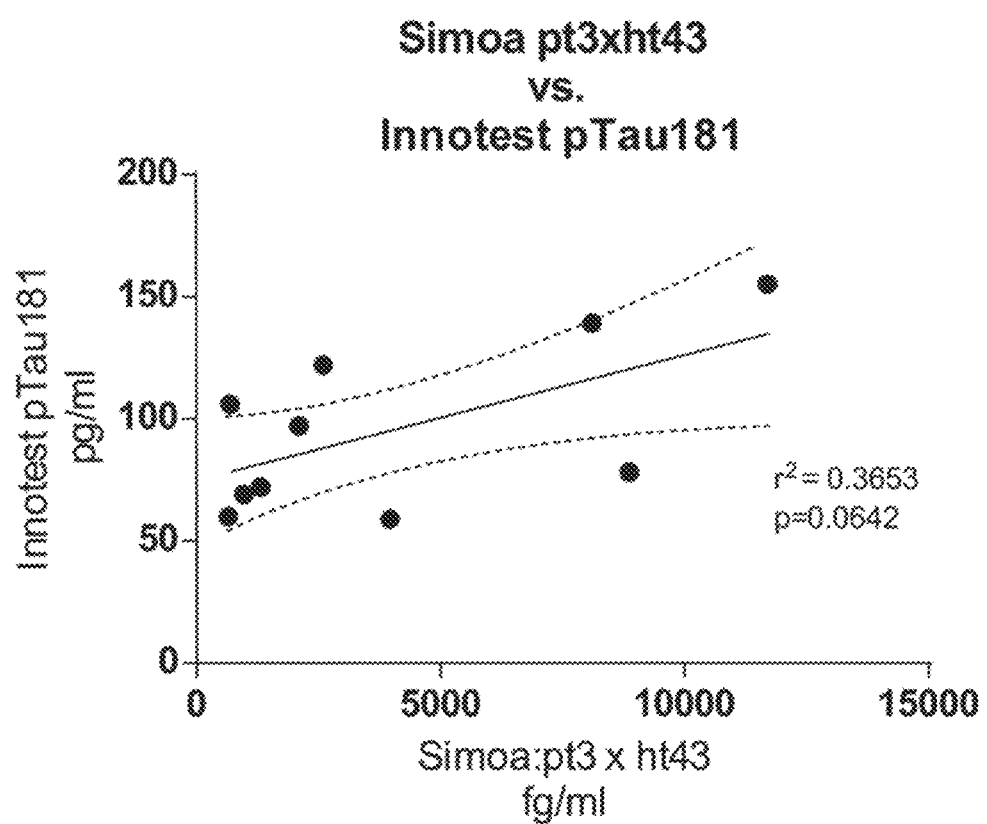
Figure 10D:
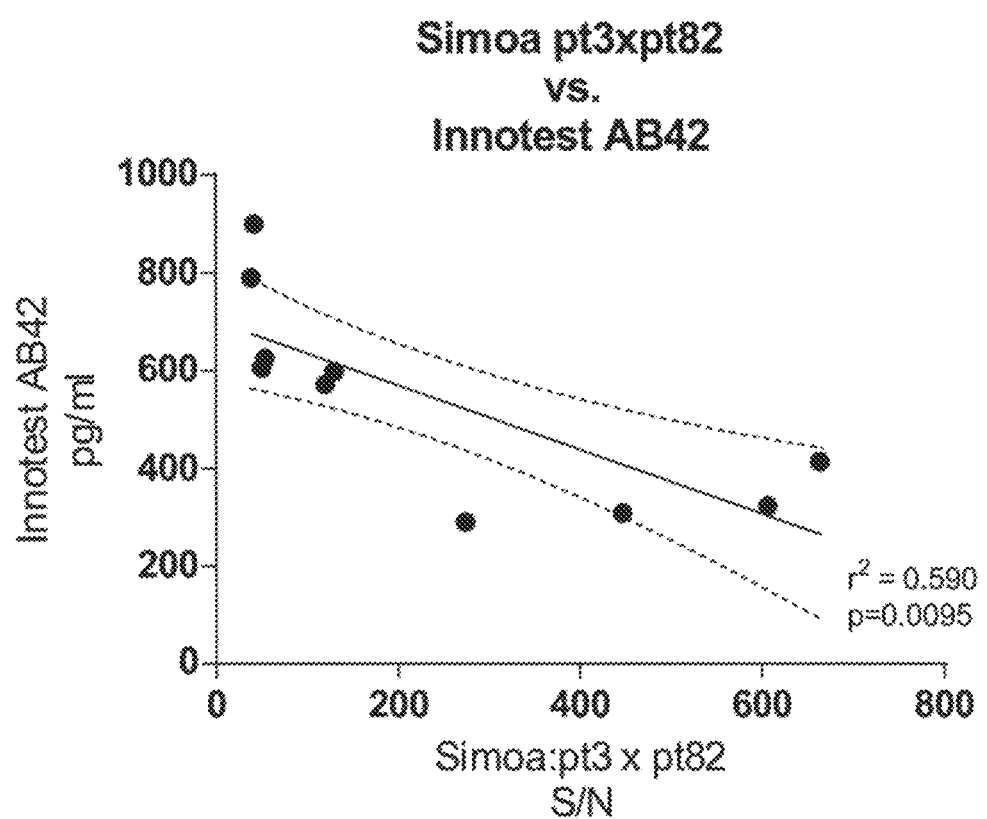
Figure 10E:
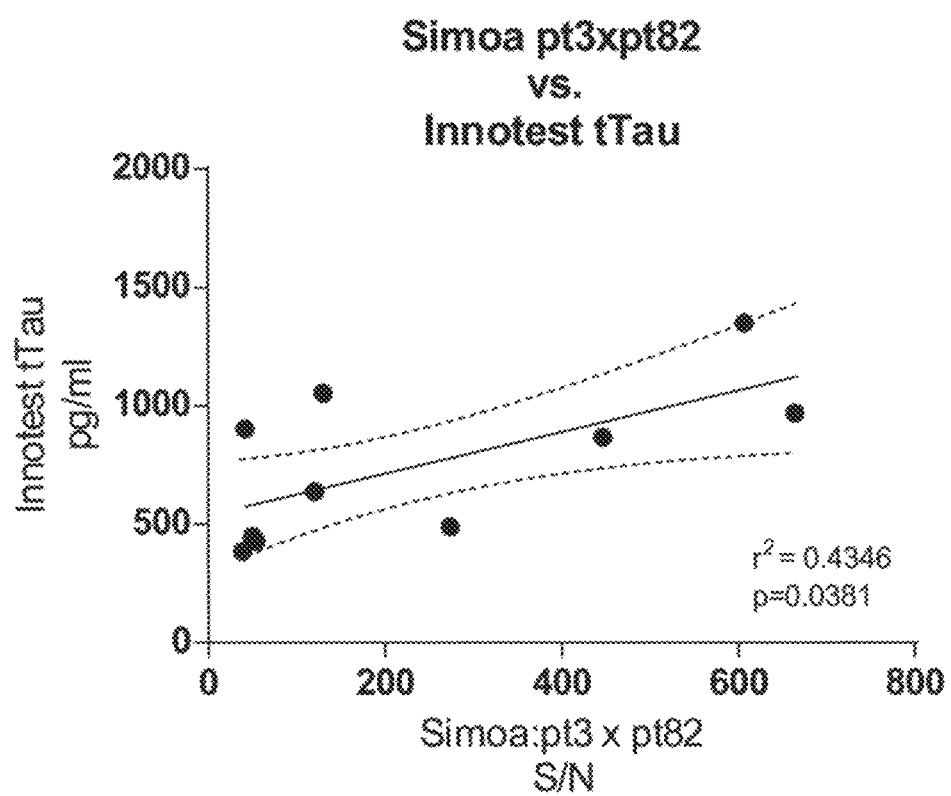
Figure 10F:
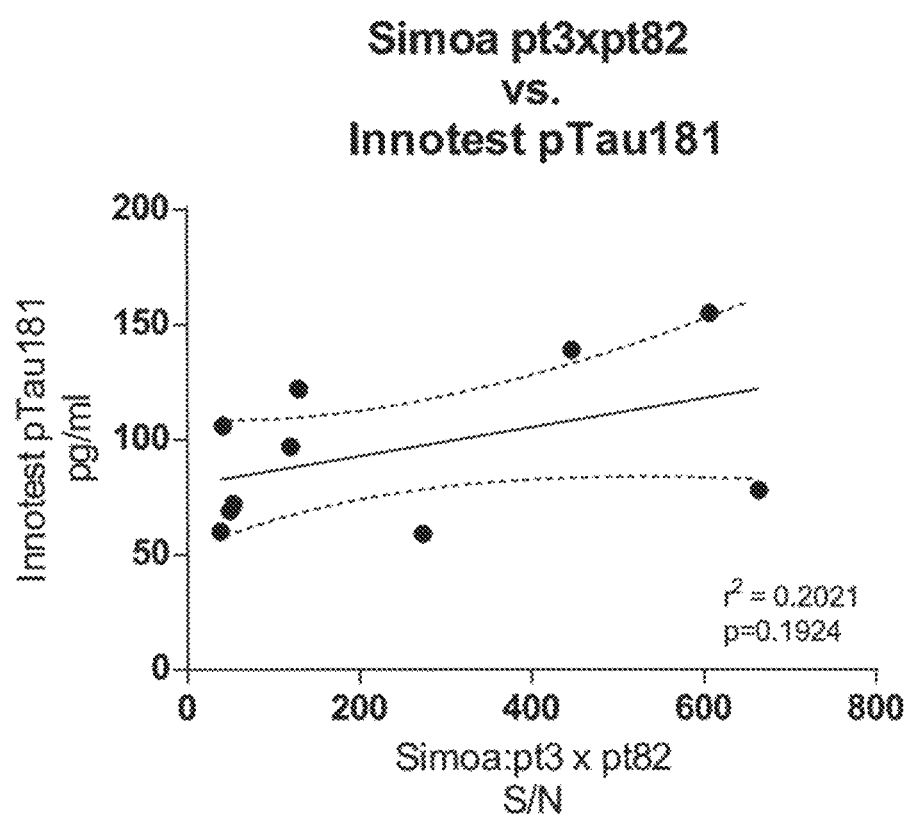

The stability of the endogenous p217+ tau epitope was assessed at various temperatures. A pool of AD CSF was aliquoted, and each aliquot subjected to storage at 4° C., 22° C., or 37° C. for 1, 2, or 4 hrs. Also, a subset of aliquots were freeze-thawed (–80° C. to 22° C.) 2 or 3 times. All samples were then diluted 1:20 and analyzed using pT3xhT43 and hT7xpT82 assays (FIG. 8). No significant change in signal was observed in any of the conditions tested, indicating that all 4 epitopes recognized by these assays are sufficiently stable to enable standard storage/testing procedures. Finally, CSF was collected prospectively from 4 donors then aliquoted and frozen at –70 C, samples were removed every 3 months for measurement with pT3xpT82 assay. No significant change in signal was observed at 3, 6, or 9 month timepoints (FIG. 9).

Example 8. Clinical Qualification of pT3xhT43 and pT3xpT82 Assays

To assess the utility of the pT3xhT43 and pT3xpT82 assays in diagnosis and staging of AD, three cohorts of CSF samples were obtained for p217+ tau measurement. Measurements were analyzed for correlation with cognition scores and with other classical AD biomarkers.

Cohort 1: "Interassay Correlation Cohort"

CSF samples, VF and LF, and brain biopsy (ventricle) were obtained from 10 subjects with the neurodegenerative disorder Normal Pressure Hydrocephalus (NPH), a condition characterized by excessive interstitial fluid production in the brain and presenting at a high incidence with AD. p217+ tau measurements were performed on crude CSF and analyzed for correlation with the traditional AD biomarkers.

Levels of Aβ42 (FIGS. 10A, 10D), tTau (FIGS. 10B, 10E), pTau181 (FIGS. 10C, 10F) in VF were determined by Innotest ELISA (classical measurement). The same samples were measured with the pT3xhT43 (FIGS. 10A, 10B, 10C) and pT3xpT82 (FIGS. 10D, 10E, 10F) assays, and correlations were evaluated. Both pT3xhT43 and pT3xpT82 assays revealed a negative correlation with CSF Aβ42 ($r^2$=0.609, p=0.0077 and $r^2$=0.590, p=0.0095, respectively), and a positive correlation with CSF tTau ($r^2$=0.525, p=0.0177 and $r^2$=0.435, p=0.0381, respectively), but they did not significantly correlate with CSF pTau181 (FIG. 10).

Figure 11A:
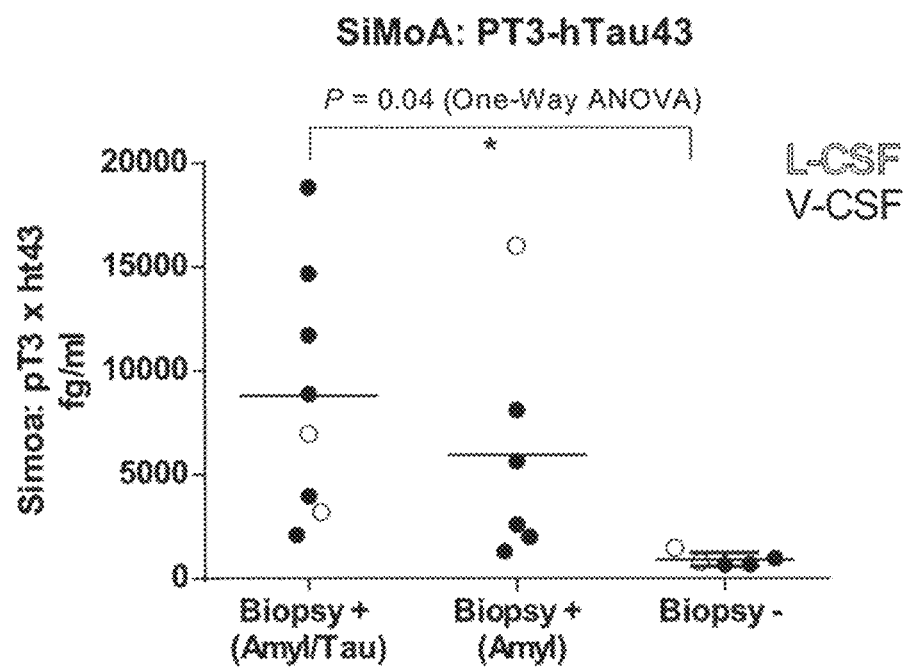
FIGS. 11A-11B show a correlation between brain biopsy IHC analysis and p217+ tau, as measured by (A) pT3xhT43 and (B) pT3xpT82 assays.
Figure 11B:
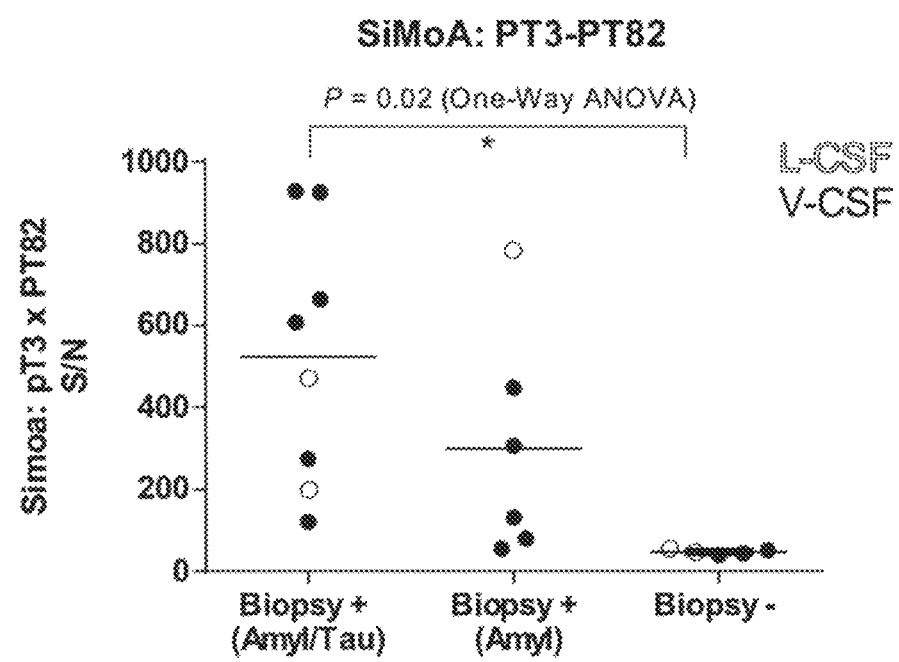

Brain biopsy from the same 10 NPH subjects was analyzed by IHC and pathologist-scored as amyloid positive/negative and tau positive/negative. When positive for both, the sample was designated "Biopsy+" and was a classical diagnosis for AD. When negative for both, the sample was designated "Biopsy–" and was a classical diagnosis for non-AD. Samples designated "Biopsy+(Amyl)" were positive for amyloid but negative for tau. CSF obtained from ventricular tap (VF=black dots) or lumbar tap (LF=red dots) was measured with the pT3xhT43 and pT3xpT82 assays, and correlations were evaluated (FIG. 11). Both pT3xhT43 and pT3xpT82 assays were able to separate brain biopsy negative (amyloid-/tau-) from positive samples (amyloid+/tau+) (p=0.04 and 0.02, respectively). Samples positive for amyloid, but not for tau, often measured between the biopsy+ and biopsy– samples. Amyloid plaques in the brain are believed to precede tau tangles, therefore amyloid+/tau– samples may represent early AD or another disease.

Cohort 2: "HV Vs. AD Cohort"

Figure 12B:
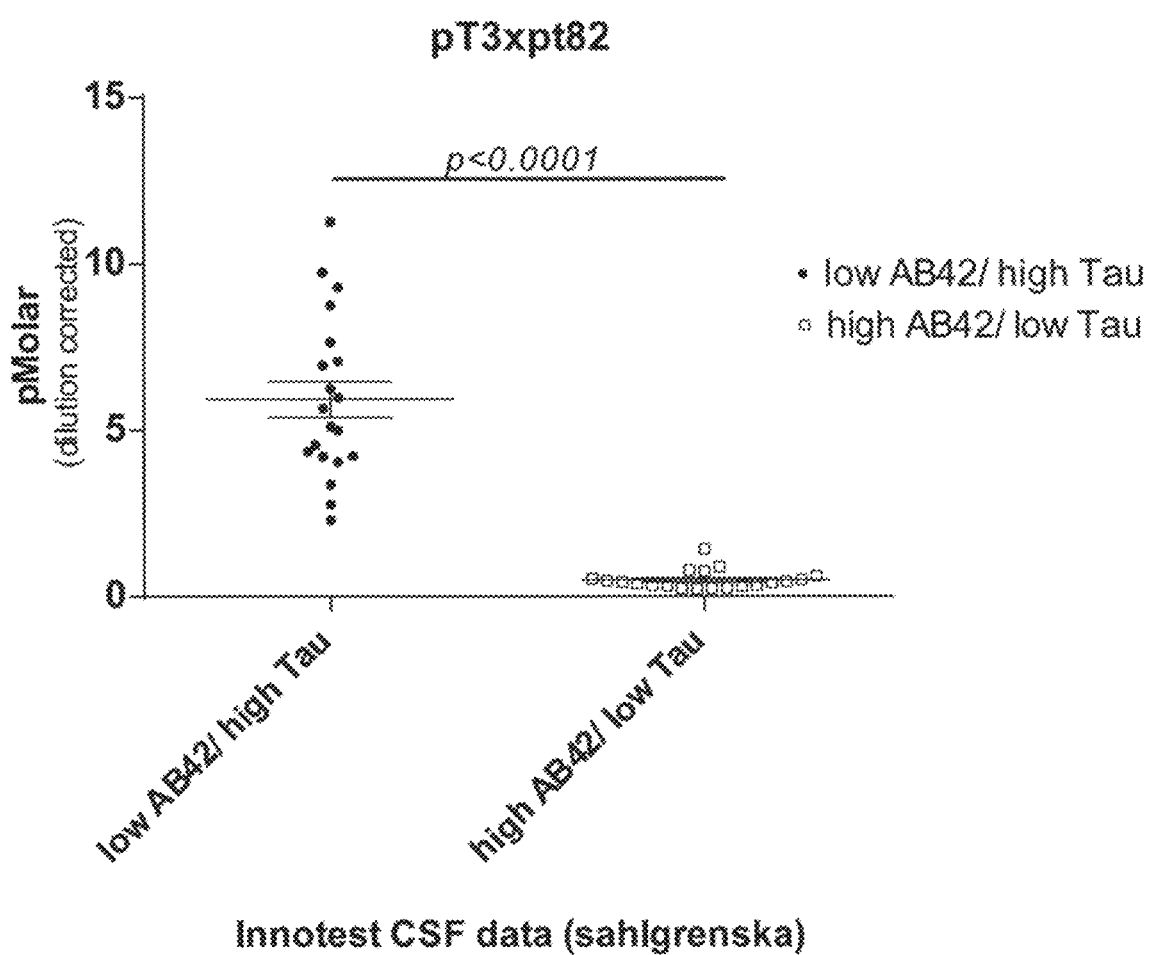
Figure 12C:
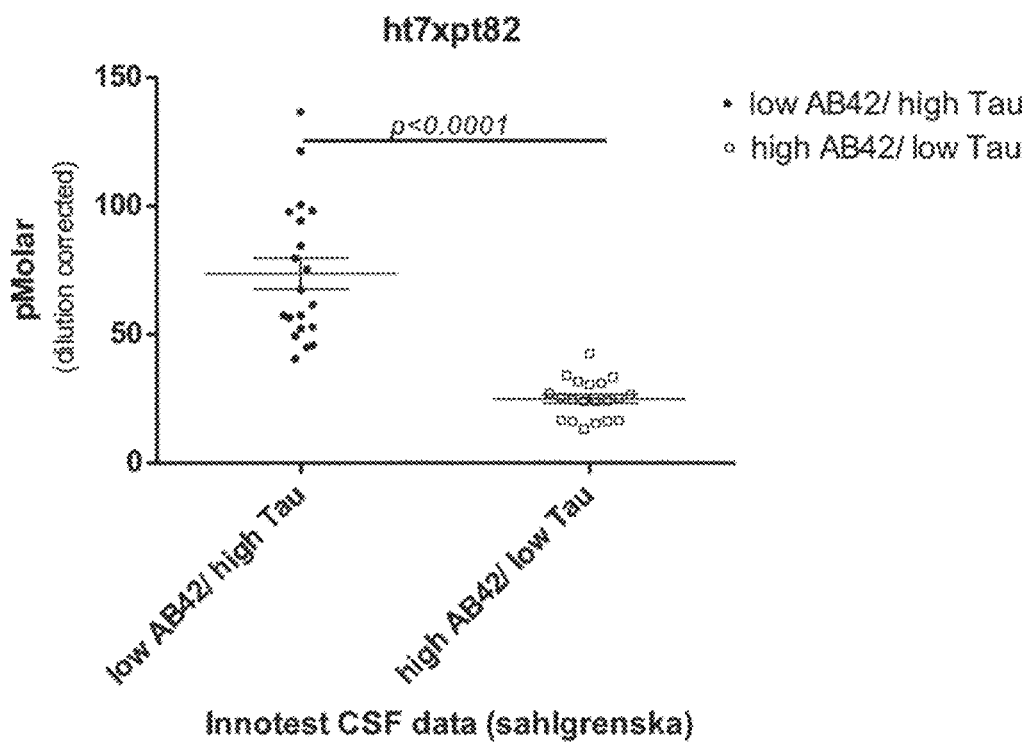
Figure 12D:
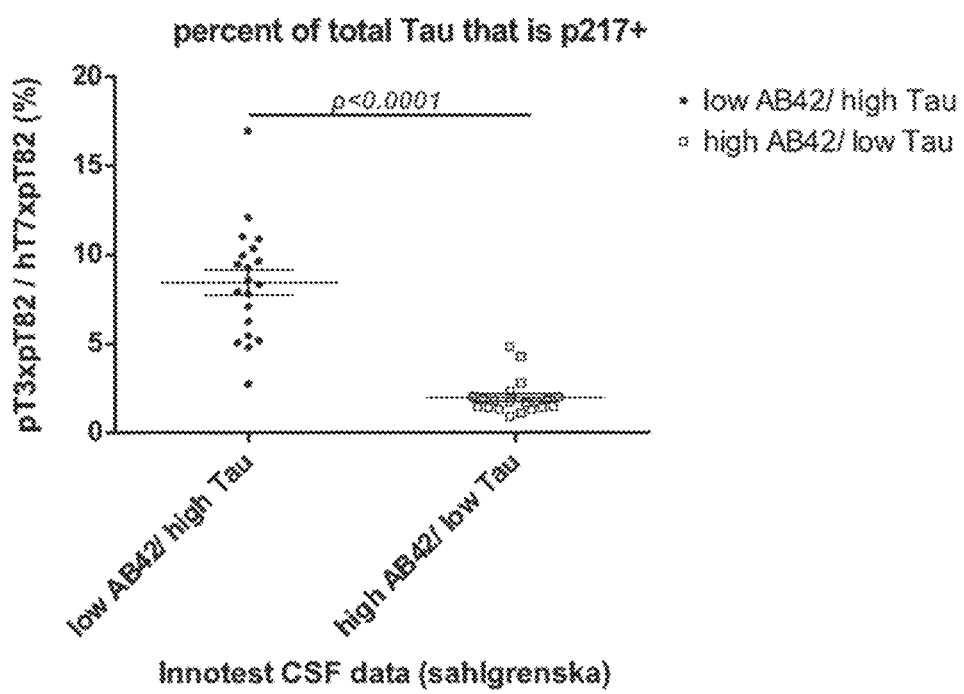

CSF samples (LF) from biochemically-defined AD vs. HV subjects (n=20 per group) were obtained from University of Sahlgrenska. Levels of Aβ42 and tTau were determined by Innotest ELISA (classical measurement) to subdivide the groups (AD=CSF Aβ42<400 pg/ml AND CSF tTau>600 pg/ml, HV=CSF Aβ42>400 pg/ml AND CSF tTau<600 pg/ml). Measurements were performed using pT3xhT43, pT3xpT82 and hT7xpT82 assays on crude CSF and a subset of rpHPLC-fractionated CSF. The results were analyzed for correlation with the traditional AD biomarkers (FIG. 12). The data in panels A and B of FIG. 12 demonstrated that the pT3 epitope is an indicator of patients at high risk of rapidly progressing to insipient AD. The pT3 epitope was highly elevated in patients demonstrating high total tau and low Aβ42. Conversely, the pT3 epitope was present at low levels in subjects with low total tau and high Aβ42. FIG. 11C confirmed that the elevated pT3 epitope-containing tau was driven at least in part by elevated levels of total tau, as demonstrated by the hT7xpT82 total tau assay, but not entirely (FIG. 12D). This indicates that both the amount of tau, and the extent to which it is phosphorylated at p217+ epitope, is elevated in AD.

Figure 13:
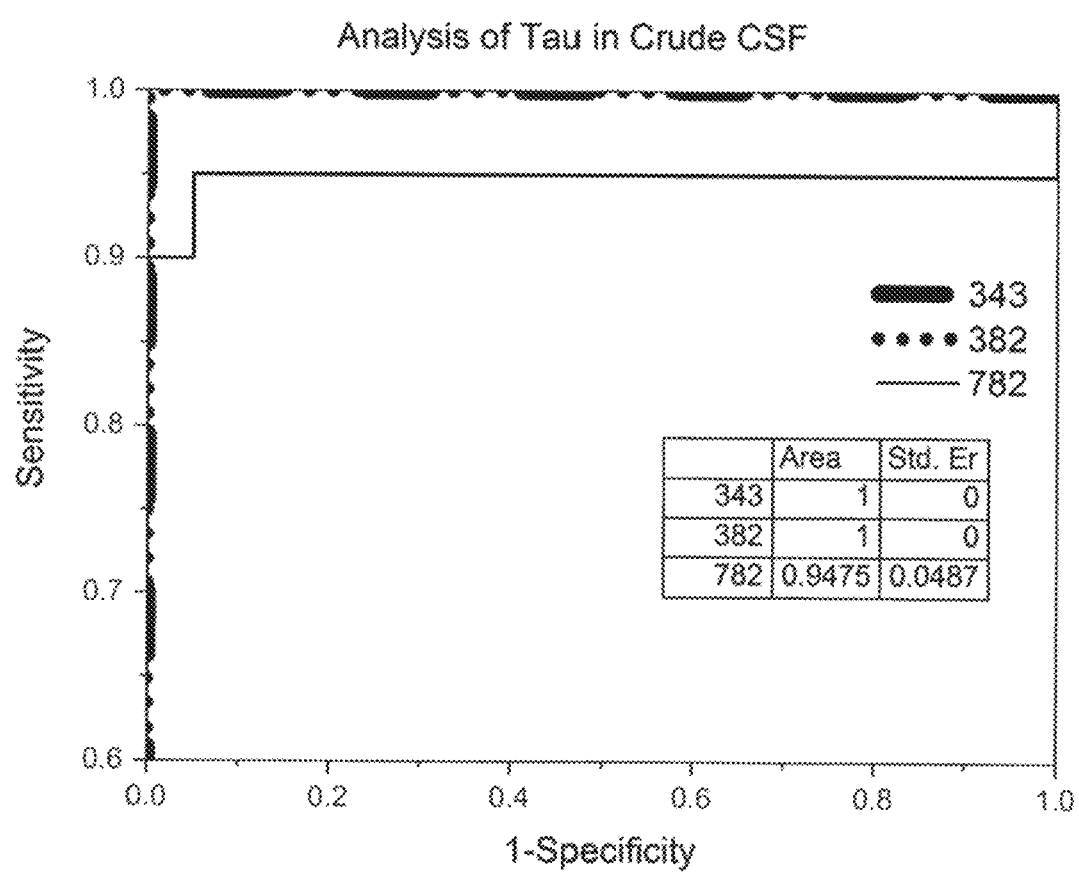
FIG. 13 shows the predictive power of the pT3xhT43 ("343"), pT3xpT82 ("382"), and hT7xpT82 ("782") assays in differentiating AD from HV subjects.
Figure 14A:
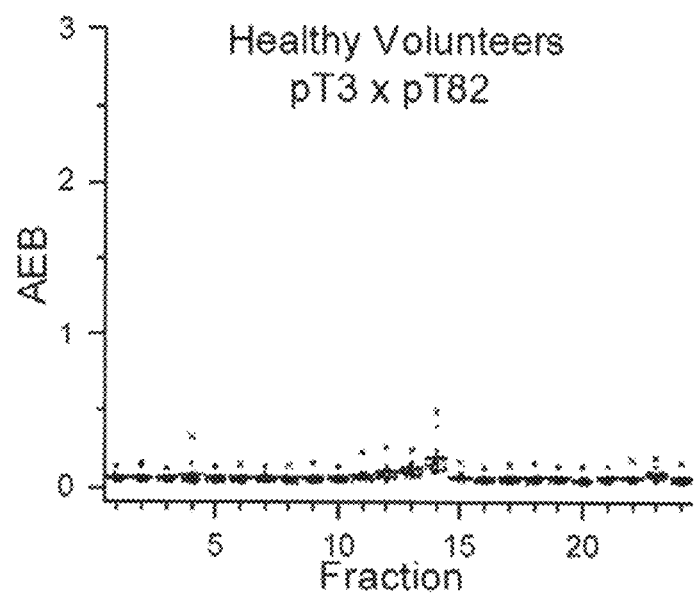
FIGS. 14A-14F show the signal from (A, B) pT3xhT43 ("343"), (C, D) pT3xpT82 ("382"), and (E, F) hT7xpT82 ("782") assays carried out on rp-HPLC fractions of CSF from (A, C, E) AD and (B, D, F) HV subjects.
Figure 14B:
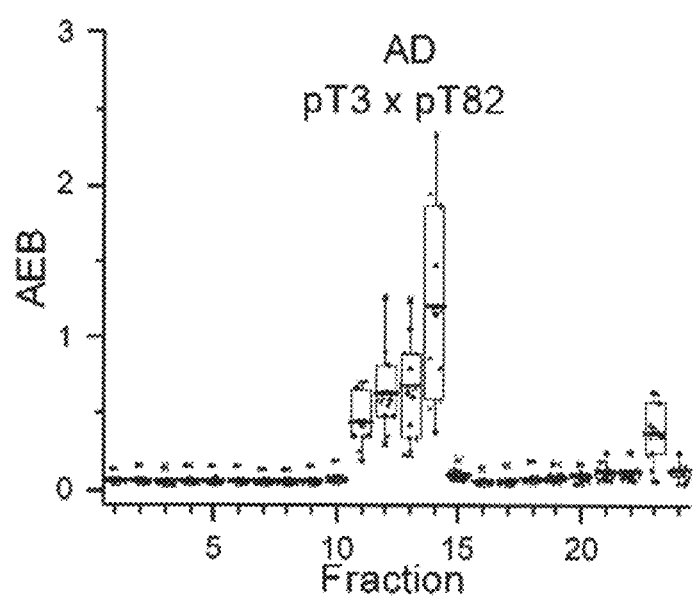
Figure 14C:
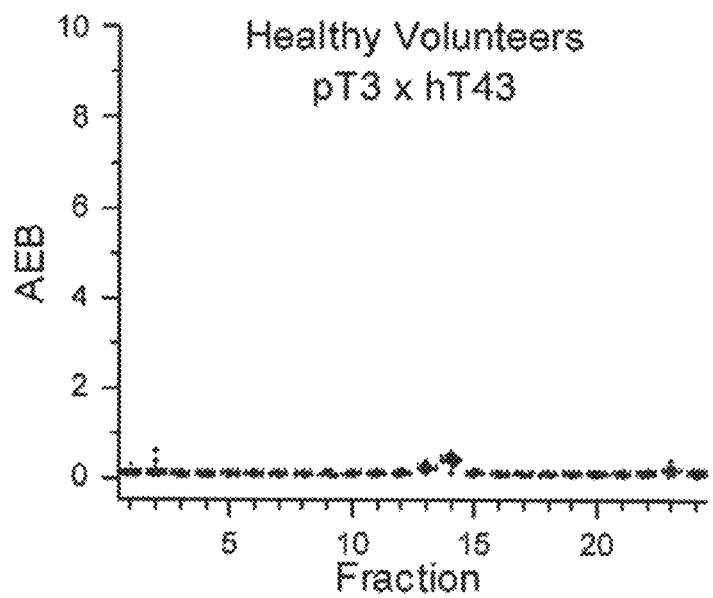
Figure 14D:
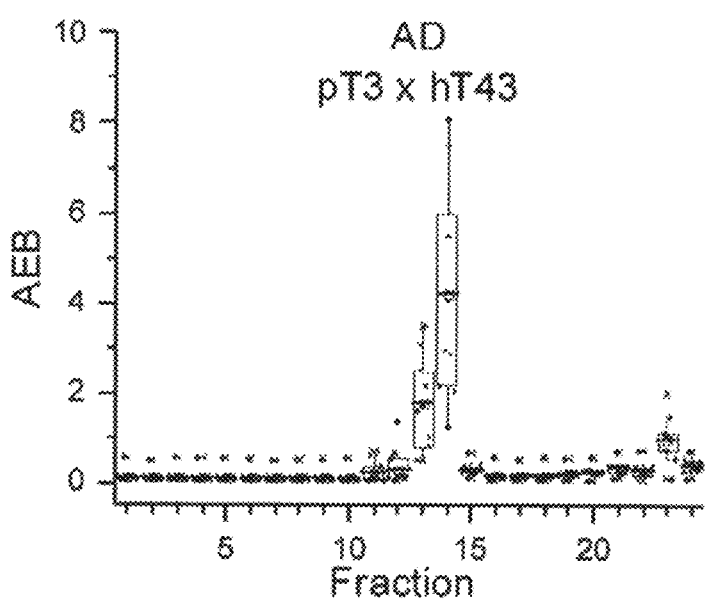
Figure 14E:
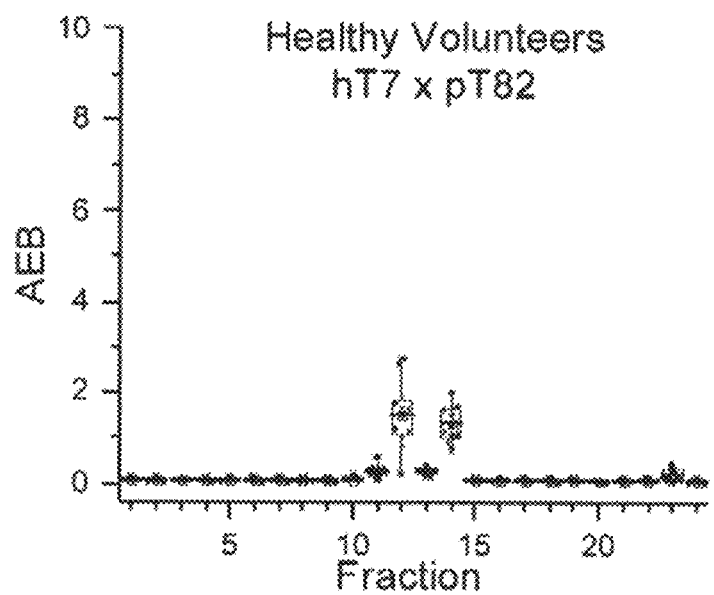
Figure 14F:
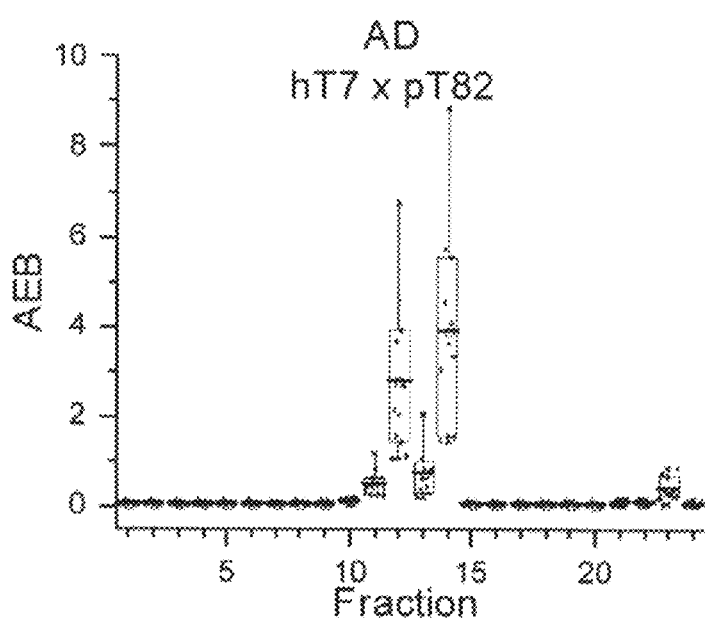

The data from FIG. 11 was used to create ROC curves for the ability of the pT3xhT43, pT3xpT82, and hT7xpT82 assays to differentiate the AD from HV samples. All three assays showed excellent specificity and sensitivity. However, the two pT3-based assays (pT3xhT43, pT3xpT82, which detect p217+ tau) had improved diagnostic power over the hT7-based assay (FIG. 13).

A subset of the same CSF samples measured in FIG. 12 (n=11 per group) were fractionated by rpHPLC and then measured with pT3xhT43, pT3xpT82, and hT7xpT82 assays (the latter was measure of the same tau fragments in a phosphorylation-independent manner) (FIG. 14). The profile of tau fragments observed was similar to that seen in Example 7 and FIG. 7. That is, two major species were seen with both pT82-based assays, pT3xpT82 and hT7xpT82, while only one of the peaks was seen with the pT3xhT43 assay. Both major species were present at higher concentrations in the AD group than the HV group. Further, the pT3-based assays (p217+ tau) showed a greater differential between the groups than the hT7-based assay (total tau), as detected in the crude CSF analysis. The larger p217+ tau species (Fractions 13-14) provided the largest AD vs. HV differential (FIG. 14).

The sum of all major tau fragments in FIG. 14 (fractions 11-14) was calculated, then compared between the AD and HV subgroups. The percent increase of pT3-epitope-containing tau (pT3xhT43 or pT3xpT82) in AD was greater than twice that seen with non-pT3-epitope containing tau (hT7xpT82) (Table 5).

TABLE 5

Total tau signal in pT3 vs. non-pT3 assays

| Assay | Mean AEB in AD | Standard Deviation in AD | Mean AEB in HV | Standard Deviation in HV | % Increase in AD |
|---|---|---|---|---|---|
| pT3/pT82 | 0.74 | 0.32 | 0.12 | 0.05 | 620 |
| pT3/hT43 | 1.65 | 1.88 | 0.22 | 0.14 | 750 |
| hT7/pT82 | 2.00 | 1.66 | 0.84 | 0.66 | 250 |

Analysis of the signal in each FIG. 14 fraction independently, vs. as a sum as done in Table 5, was performed to reveal which fraction yielded the greatest AD vs. HV signal. The most informative fragment pool was detected using the pT3 antibody on fragment pools 13 and 14 (Table 6).

TABLE 6

Tau signal in different tau fragment pools in pT3 vs. non-pT3 assays
pT3 Assay Identifies AD patients better than a Non-pT3 Assay:
Differences per Fragment Pool

| Assay | Fragment Pool | Mean AEB in AD | Mean AEB in HV | % AD over HV |
|---|---|---|---|---|
| pT3xhT43 | 11 | 0.22 | 0.105 | 210 |
|  | 12 | 0.333 | 0.113 | 295 |
|  | 13 | 1.78 | 0.235 | 757 |
|  | 14 | 4.25 | 0.407 | 1044 |
| pT3xpT82 | 11 | 0.447 | 0.079 | 566 |
|  | 12 | 0.631 | 0.098 | 644 |
|  | 13 | 0.681 | 0.121 | 563 |
|  | 14 | 1.2 | 0.193 | 622 |
| hT7xpT82 | 11 | 0.51 | 0.29 | 176 |
|  | 12 | 2.8 | 1.51 | 185 |
|  | 13 | 0.73 | 0.26 | 281 |
|  | 14 | 3.94 | 1.31 | 301 |

Cohort 3: "HV Vs. ARAD Vs. Early Stage AD Cohort"

CSF samples (LF) from clinically defined normal (CDR 0) vs. mild memory complaint (CDR 0.5) subjects (n=20 per group) were obtained from Janssen study ALZ1005/2002. Levels of Aβ42, tTau, and pTau181 were determined by Innotest ELISA. Based on the CDR and CSF Aβ42 scores, the subjects were classified into (a) HV=CDR 0 and Aβ42>600 pg/ml, (b) ARAD=CDR 0 and Aβ42<600 pg/ml, (c) potentially non-AD dementia=CDR 0.5 and Aβ42>600 pg/ml, and (d) early stage AD=CDR 0.5 and Aβ42<600 pg/ml.

Figure 15F:
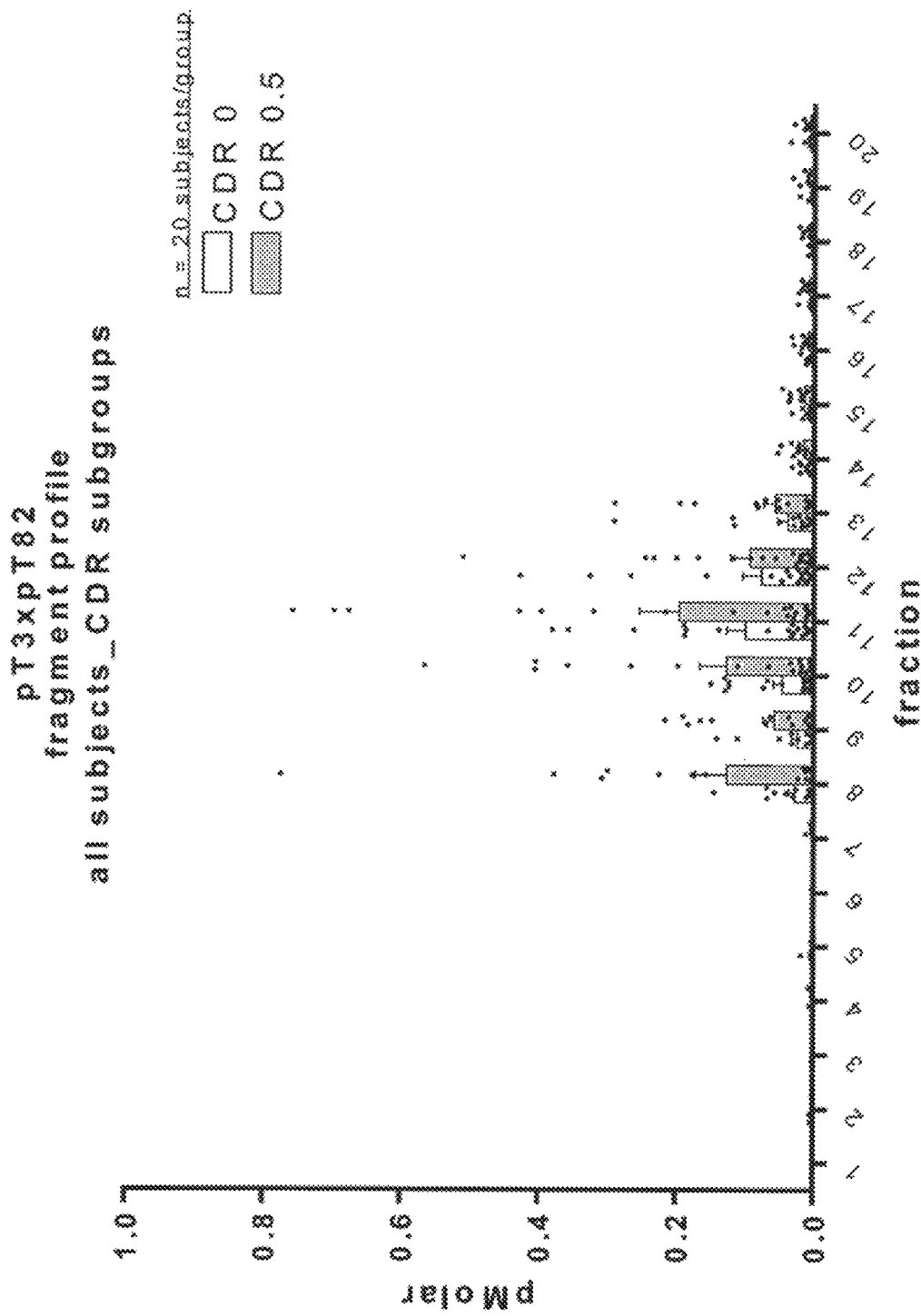
FIGS. 15A-15O show the signal from (A-E) pT3xhT43, (F-J) pT3xpT82, and (K-O) hT7xpT82 assays carried out on rp-HPLC fractions of CSF from CDR 0 and CDR 0.5 subjects.
Figure 15I:
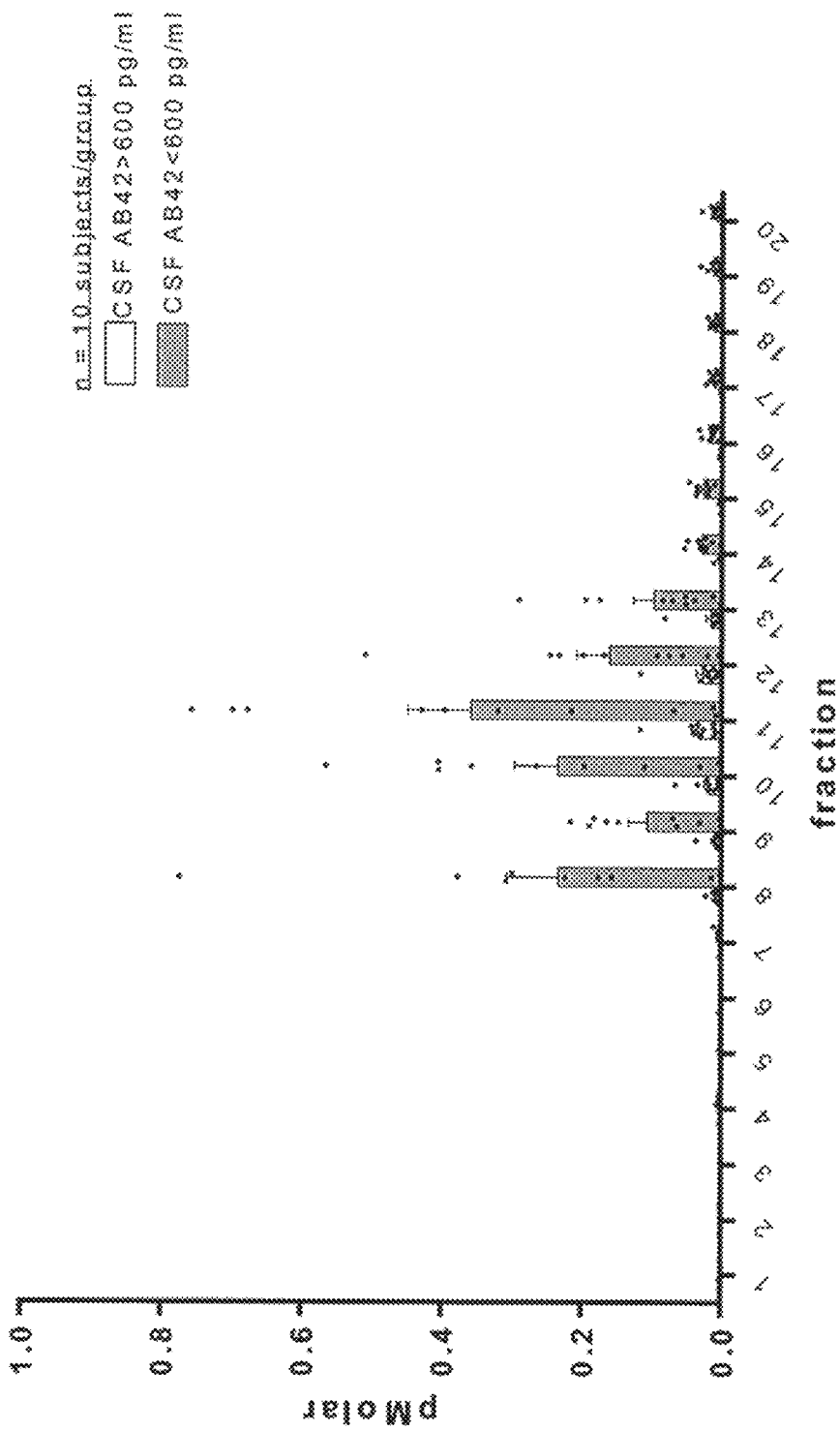
Figure 15N:
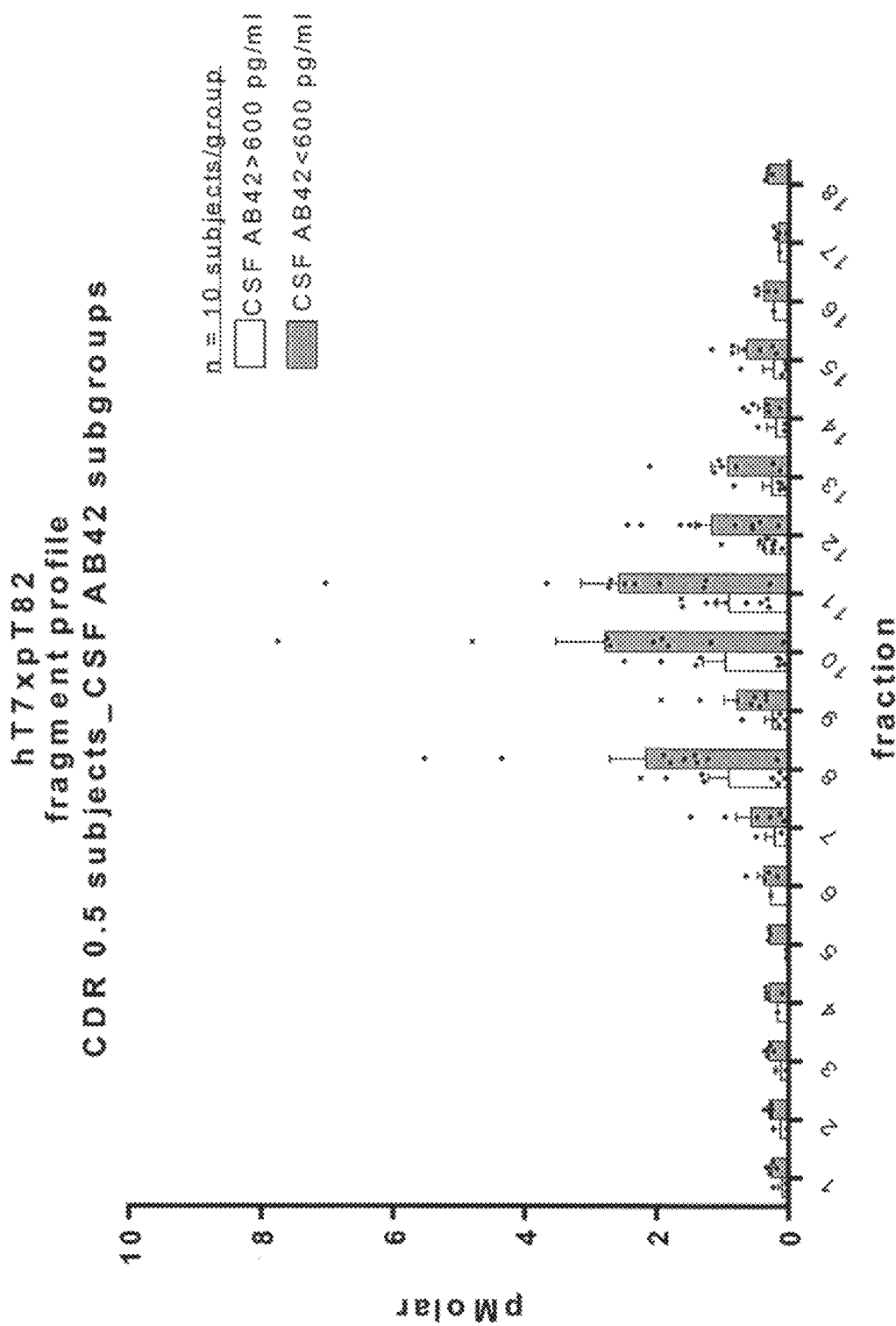

CSF samples were also fractionated by rpHPLC and measured with pT3-based (pT3xhT43, FIGS. 15A-15E and pT3xpT82, FIGS. 15F-15J) and total tau (hT7xpT82, FIGS. 15K-15O) assays. All the pT3-based and hT7-based assays showed elevated signal in CDR 0 vs. 0.5 (FIGS. 15A, 15F and 15K), and in samples with Aβ42<600 pg/ml vs. >600 pg/ml (FIGS. 15B, 15G and 15L). Breakdown by CDR× Aβ42 level is shown in FIGS. 15C, 15D, 15H, 15I, 15M and 15N, and summed signal across all fractions is illustrated in FIGS. 15E, 15J and 15O. The signal levels were highest in the Aβ42<600 pg/ml+CDR 0.5 subgroup, consistent with elevated p217+ tau signal in early stage AD vs. HV or ARAD. The separation between subgroups was superior in pT3-based assays vs. hT7-based assay, indicating that hyperphosphorylation of the pT3 epitope is particularly enriched (above simple total tau elevation) in disease.

Cohort 4 ("CDR 0 vs CDR1 Cohort")

LF CSF samples from clinically defined normal (Clinical Dementia Rating 0; CDR 0) vs. mild memory complaint (CDR 1) subjects (n=5 per group) were obtained from Washington University. CDR & MMSE, as well as CSF Aβ42, tTau, and pTau181 measurements by Innotest assays were obtained at Washington University. Prior to shipment, samples were coded so that Janssen was blind to sample identity or characterization. rpHPLC and Simoa tTau & p217+ tau measurements were performed at Janssen Neuroscience Biomarkers, La Jolla and sent to Washington University for analysis.

Figure 16A:
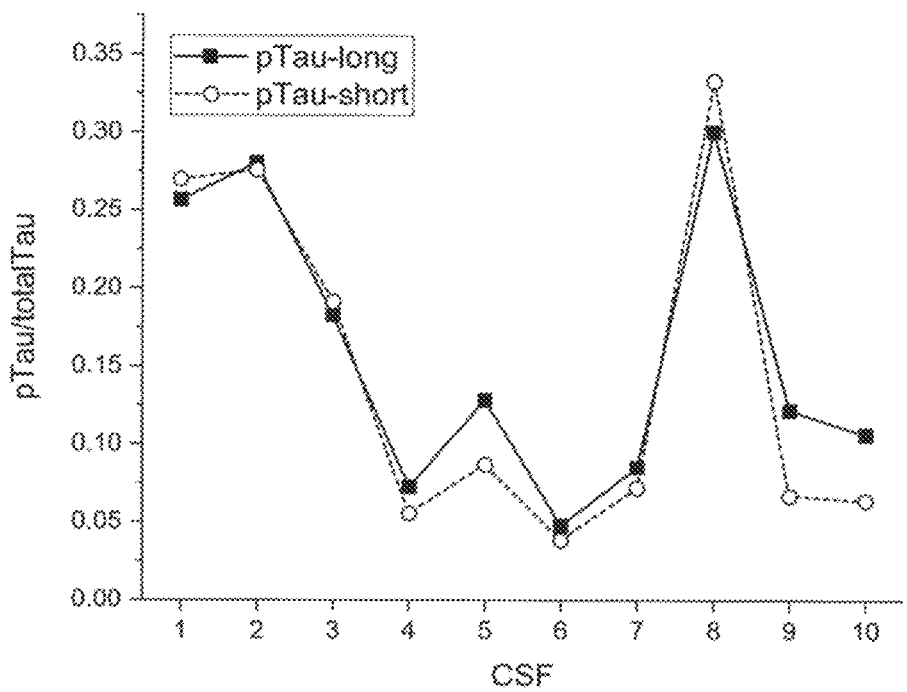
FIGS. 16A-16B show the results of (A) ratio of pT3xpT82 vs hT7xpT82 analysis (pTau short) or ratio of pT3xhT43 vs hT7xpT82 analysis (pTau long) on crude CSF and (B) ratio of pT3xpT82 vs. hT7xpT82 analysis of rp-HPLC fractions of CSF, compared to MMSE score; all from a blinded cohort of CDR 0 and CDR1 subjects.

CSF samples were measured crude or after rpHPLC fractionation, using both pT3-based assays (pT3xhT43 & pT3xpT82) and tTau (hT7xpT82). The data was expressed as a ratio between the two pT3 assays (Table 7), to assess relative impact of the short tau species, or as (FIGS. 16A-16B) a ratio between either pT3 assay and tTau, to assess relative impact of this phosphorylation event. In both cases the result accurately predicted CDR status for 9 of the 10 subjects. The 1 outlier subject was determined to also have abnormally low Tau by Innotest, and so may represent dementia from a non-tauopathy. Intriguingly a correlation between p217+ Tau/tTau ratio and MMSE was observed, suggesting the signal detected by the pT3-assays may track with cognition.

TABLE 7

Ratio of pT3xpT82 (p217 + short) vs pT3xhT43 (p217 + long) analysis on crude CSF

| | | | | | Innotest Aβ, tTau, pTau | | | P217 + tau |
|---|---|---|---|---|---|---|---|---|
| ID | CDR | MMSE | Gender | age_at_LP | Innotest Aβ | Inno_Tau | Inno-pTau | P217 + short/P217 + long |
| 24064* | 1 | 28 | M | 77 | + | 119.44 | 30.154 | low |
| 24593 | 1 | 23 | F | 55 | + | 816.427 | 104.47 | 1.25 |
| 25711 | 1 | 28 | M | 79 | + | 450.005 | 65.486 | 1.78 |
| 62496 | 1 | 24 | M | 85 | + | 1126.919 | 153.024 | 1.34 |
| 64397 | 0 | 30 | F | 72 | − | 261.846 | 44.805 | 0.81 |
| 64722 | 0 | 30 | F | 77 | − | 247.99 | 55.951 | 0.99 |
| 64996 | 0 | 30 | M | 80 | − | 427.871 | 96.301 | 0.82 |
| 65839 | 0 | 30 | F | 68 | − | 180.452 | 39.263 | 0.99 |
| 65922 | 0 | 28 | M | 58 | − | 539.75 | 96.29 | low |
| 68031 | 1 | 27 | M | 68 | + | 1080.048 | 120.47 | 1.22 |

*CDR 1 & Aβ positive but has low Tau & pTau on Innotest and Simoa

Cohort 5 ("HV Vs. MCI Vs. AD Cohort")

LF CSF samples from clinically and biochemically (Innotest AB42>600 pg/ml) defined HV (n=7) were obtained from Precision Medicine (San Diego, Calif.). LF CSF samples from clinically and biochemically (Innotest AB42<600 pg/ml) defined MCI (n=28) and AD (n=12) were obtained from University of Antwerp. rpHPLC and Simoa p217+ tau measurements were performed at Janssen Neuroscience Biomarkers, La Jolla.

Figure 17A:
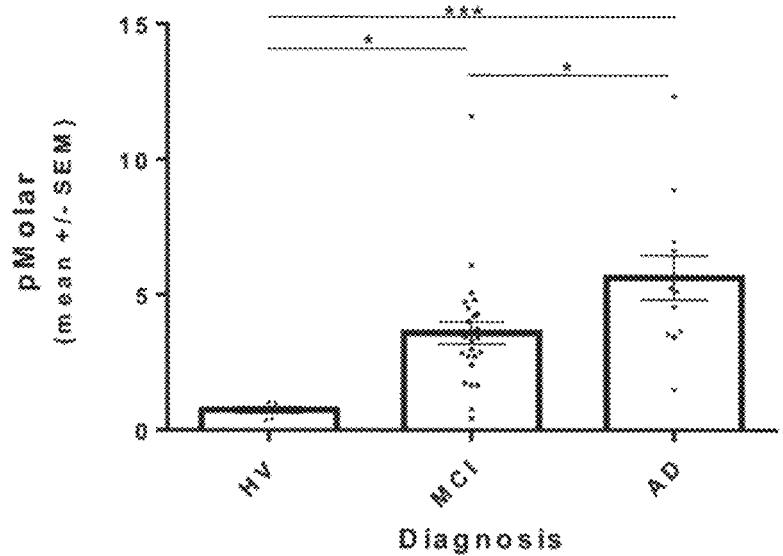
FIGS. 17A-17T show the results of (A) pT3xhT43, (B) pT3xpT82, and (C) hT7xpT82 analysis on crude CSF, (D) correlation of the two pT3 assays on crude CSF, (E) correlation of pT3xpT82 vs hT7xpT82 on crude CSF, (F) correlation of pT3xhT43 vs Innotest tTau on crude CSF, (G) correlation of pT3xhT43 vs Innotest pTau181 on crude CSF, (H) correlation of pT3xhT43 vs Innotest AB42 on crude CSF, (I) correlation of pT3xhT43 vs Innotest AB42/40 ratio on crude CSF; pT3xhT43 signal, (M-P) pT3xpT82 signal, or (Q-T) hT7xpT82 signal in (J,M,Q) all rp-HPLC fractions as well as (K, N, R) sums of all fractions, (O,S) sums of early peak fractions (short tau fragments), or (L,P,T) sums of late peak fractions (larger tau fragments); all from a cohort of HV, MCI, and AD subjects.
Figure 17B:
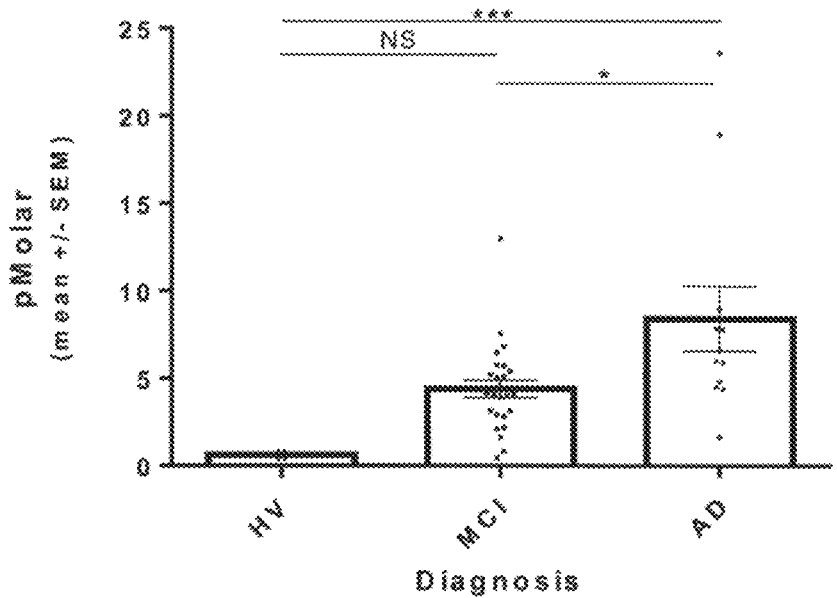
Figure 17C:
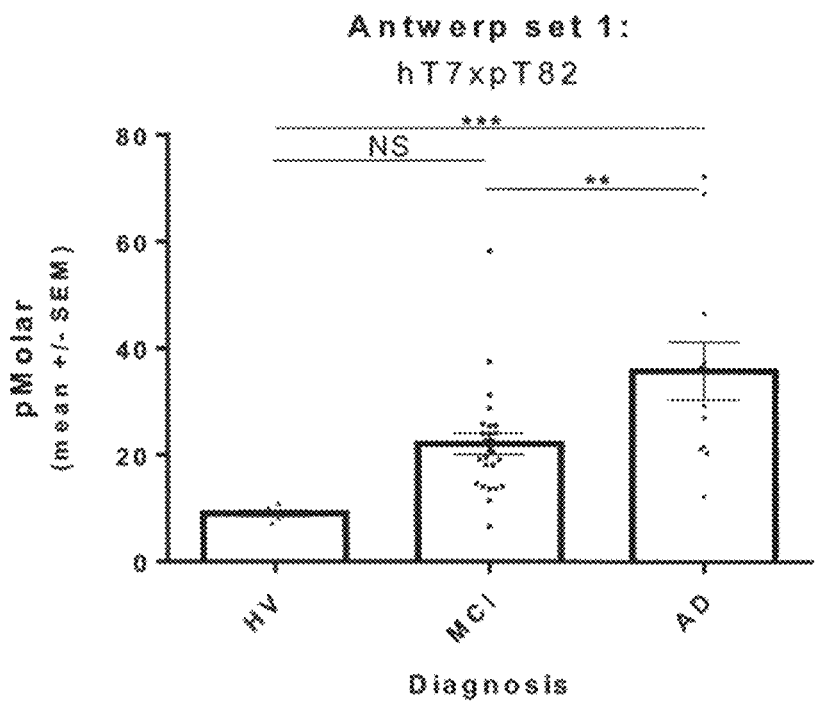
Figure 17D:
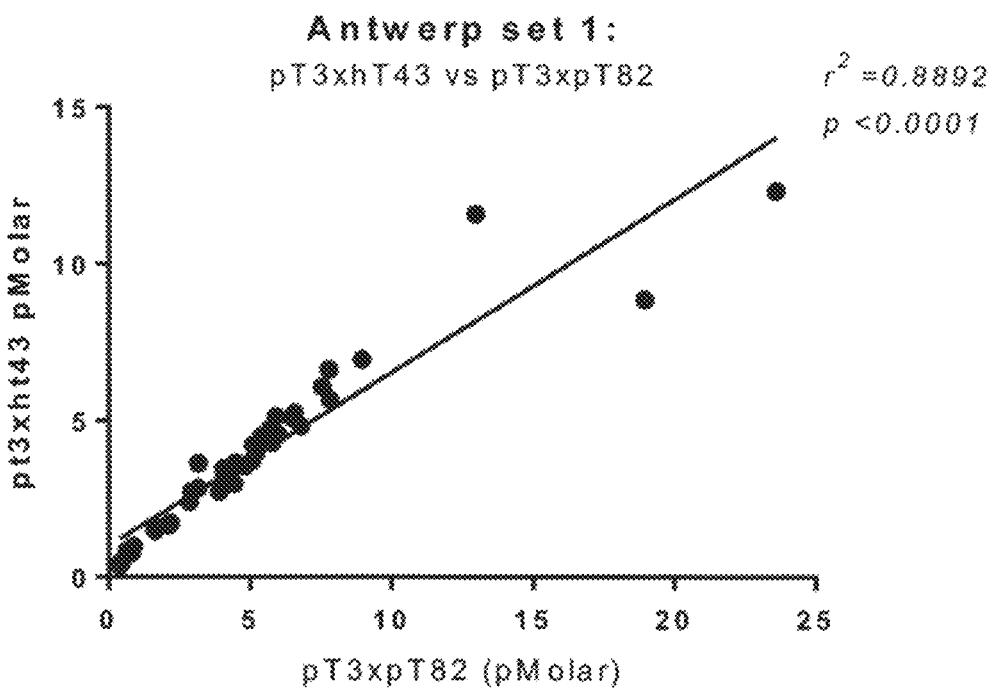
Figure 17E:
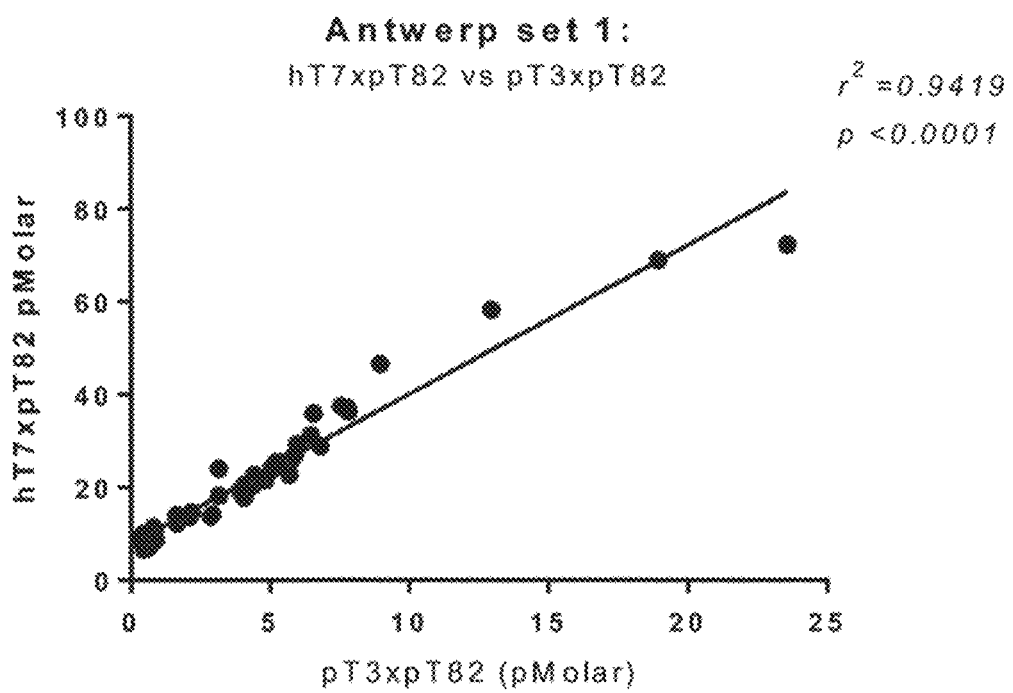
Figure 17F:
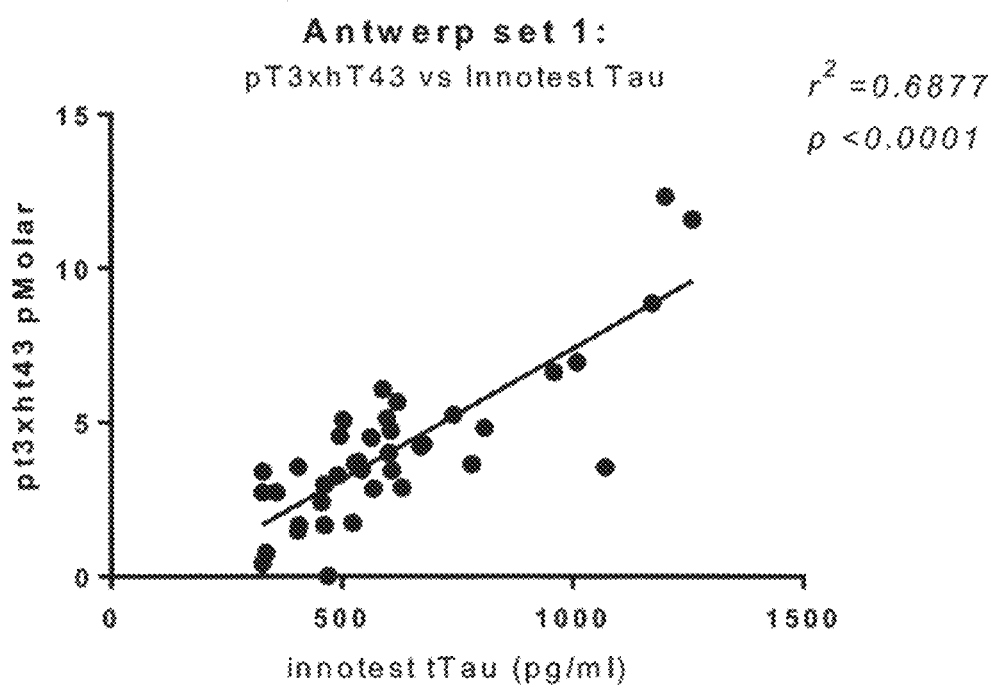
Figure 17G:
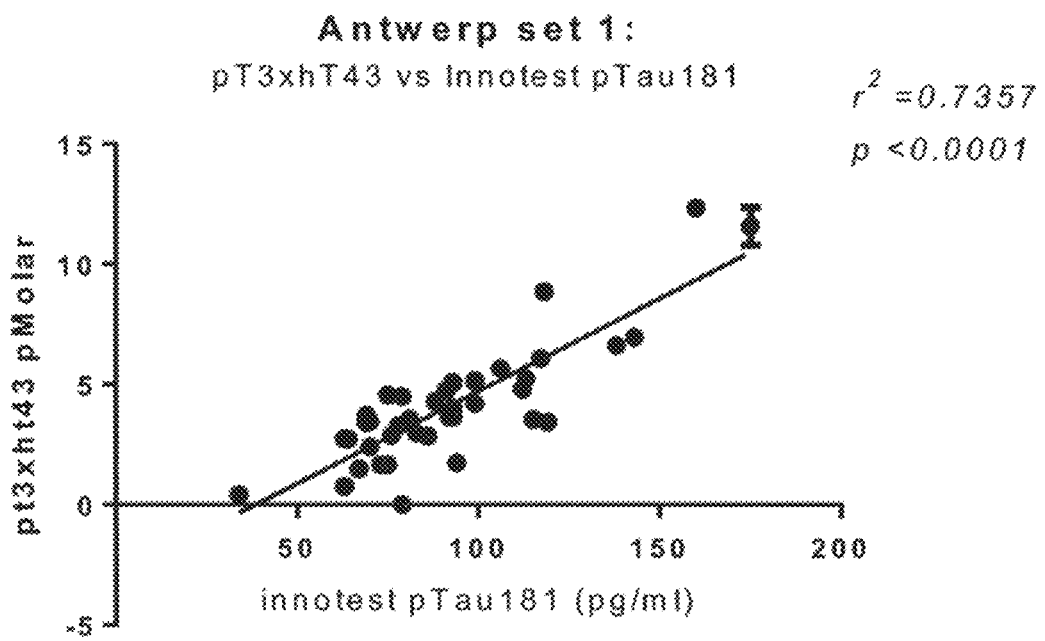
Figure 17H:
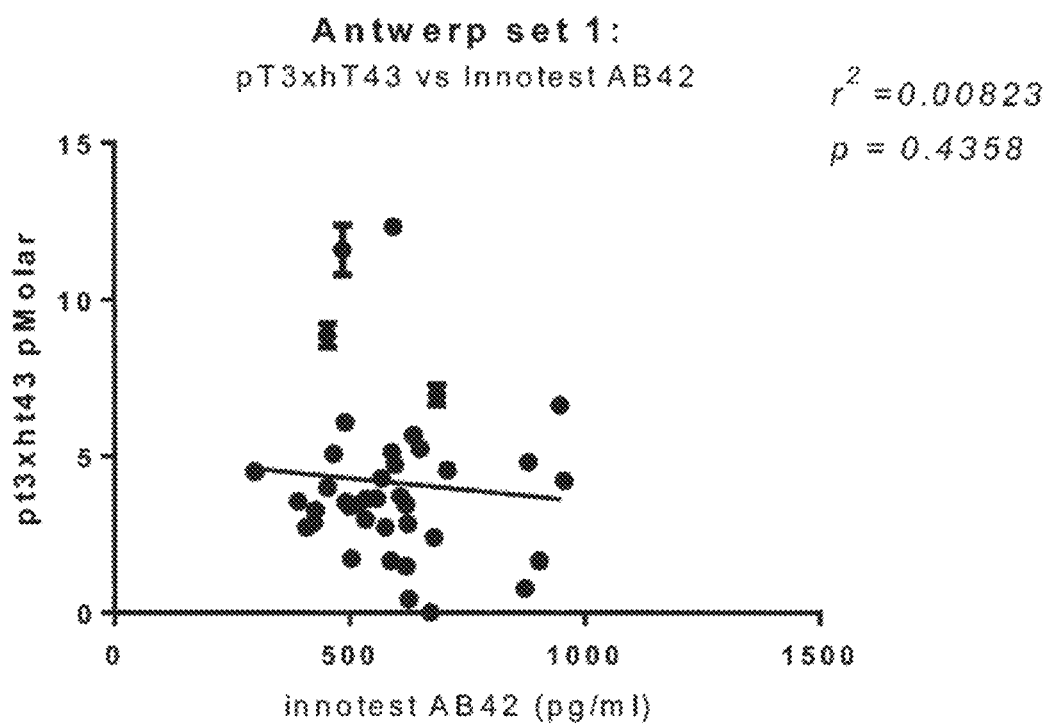
Figures 17I, 17J:
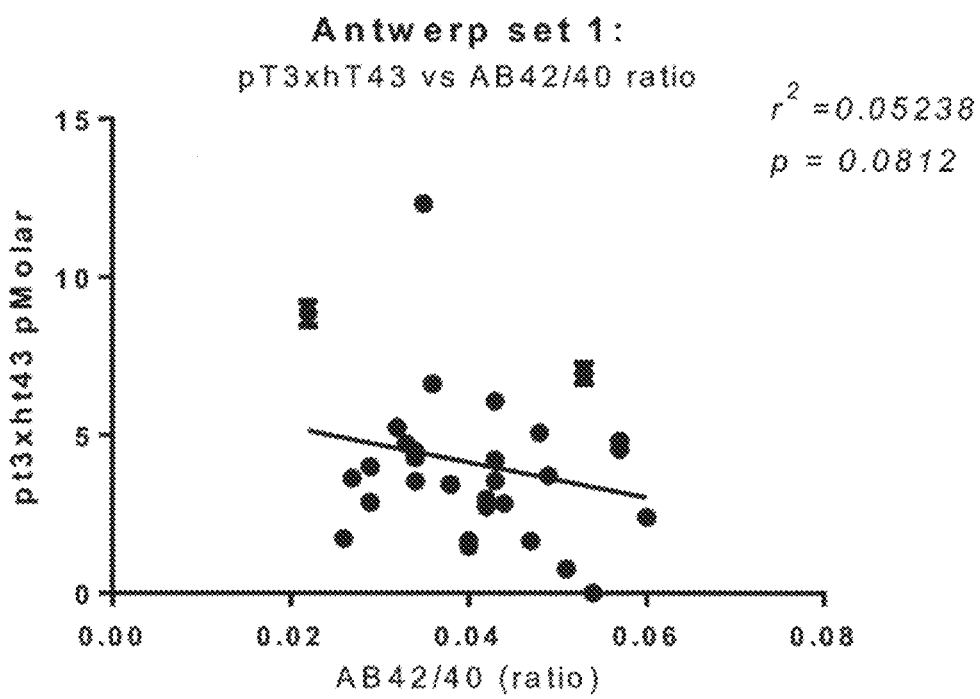
Figure 17K:
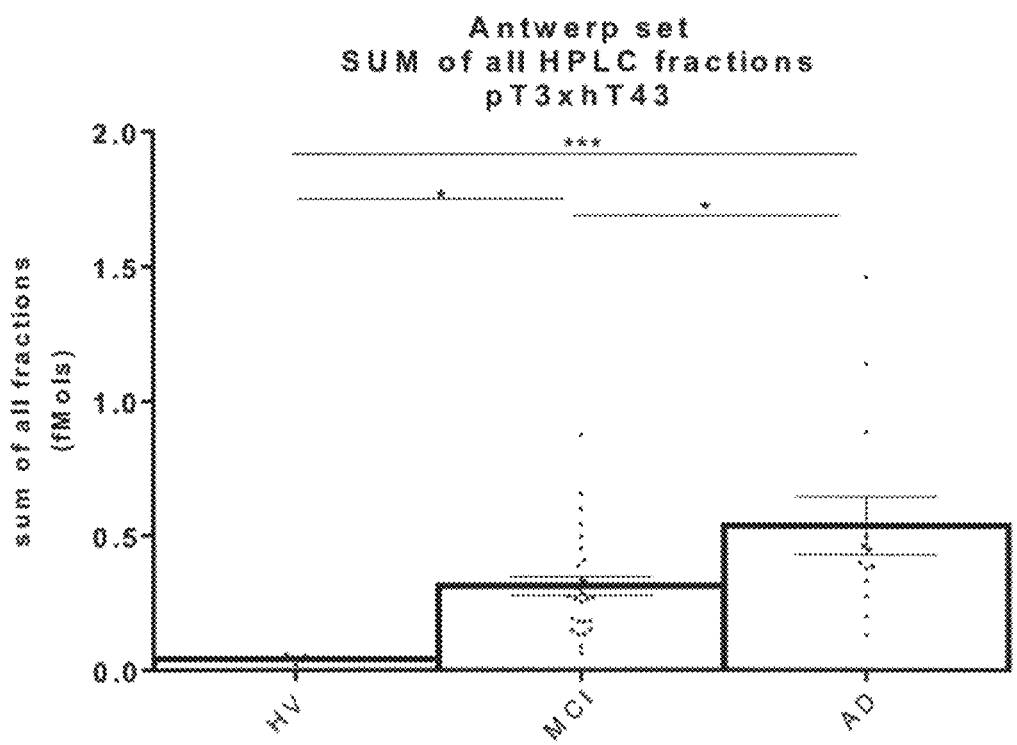
Figure 17L:
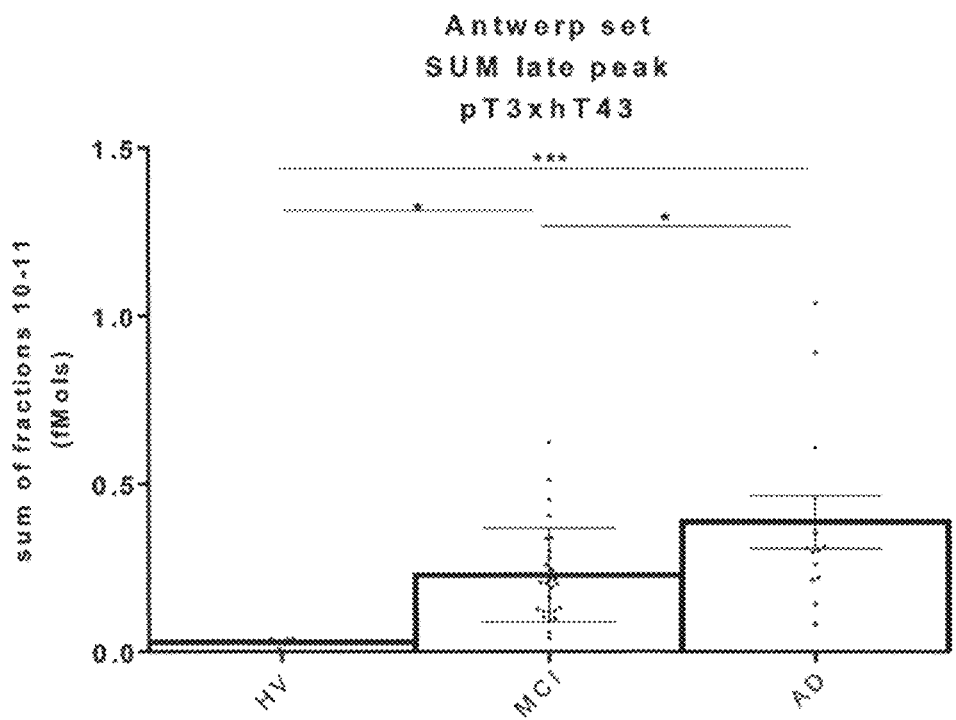
Figure 17M:
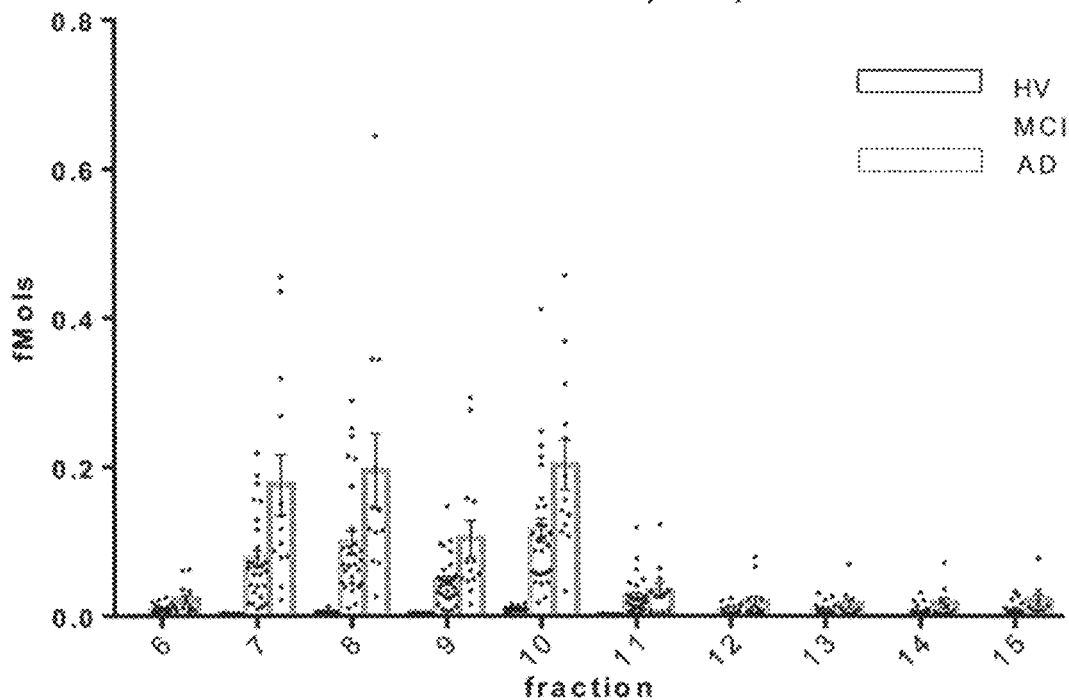
Figure 17N:
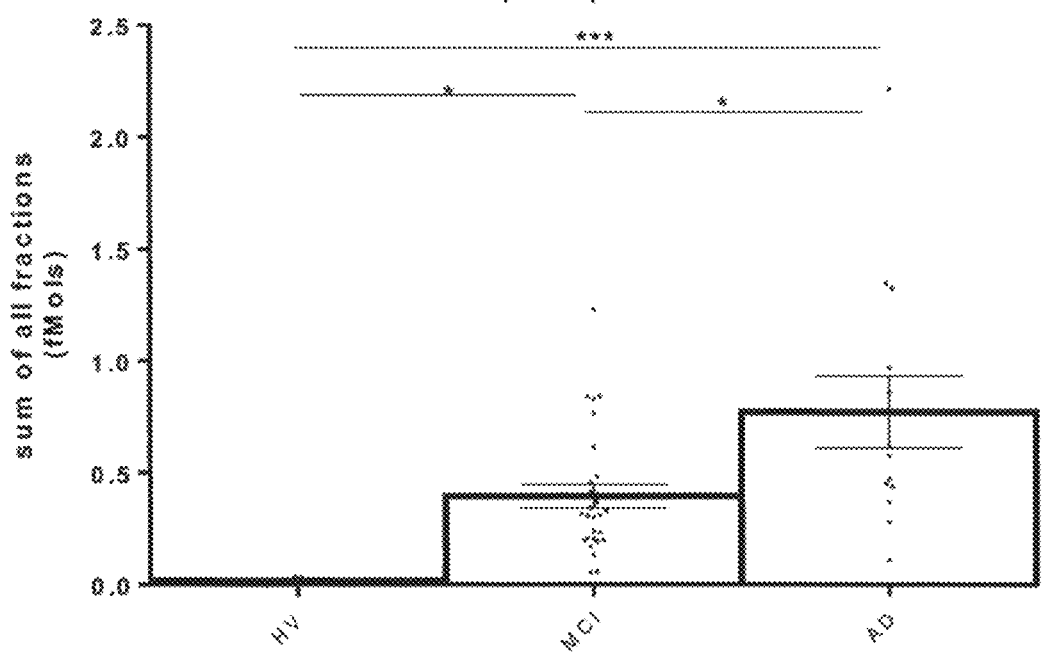
Figure 17O:
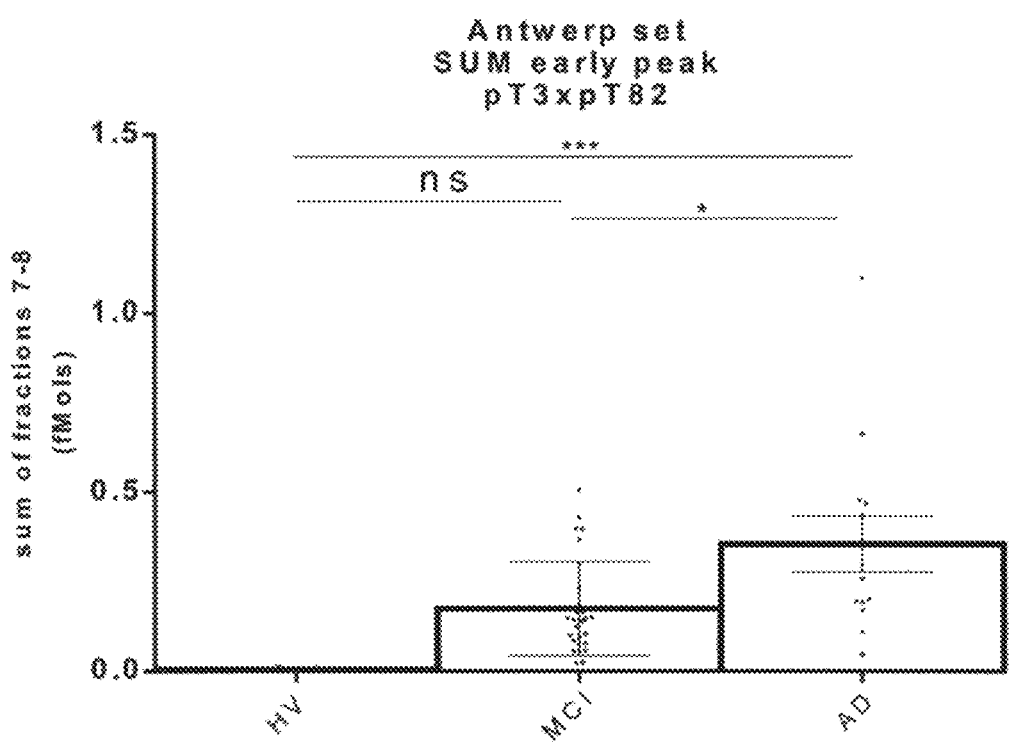
Figure 17P:
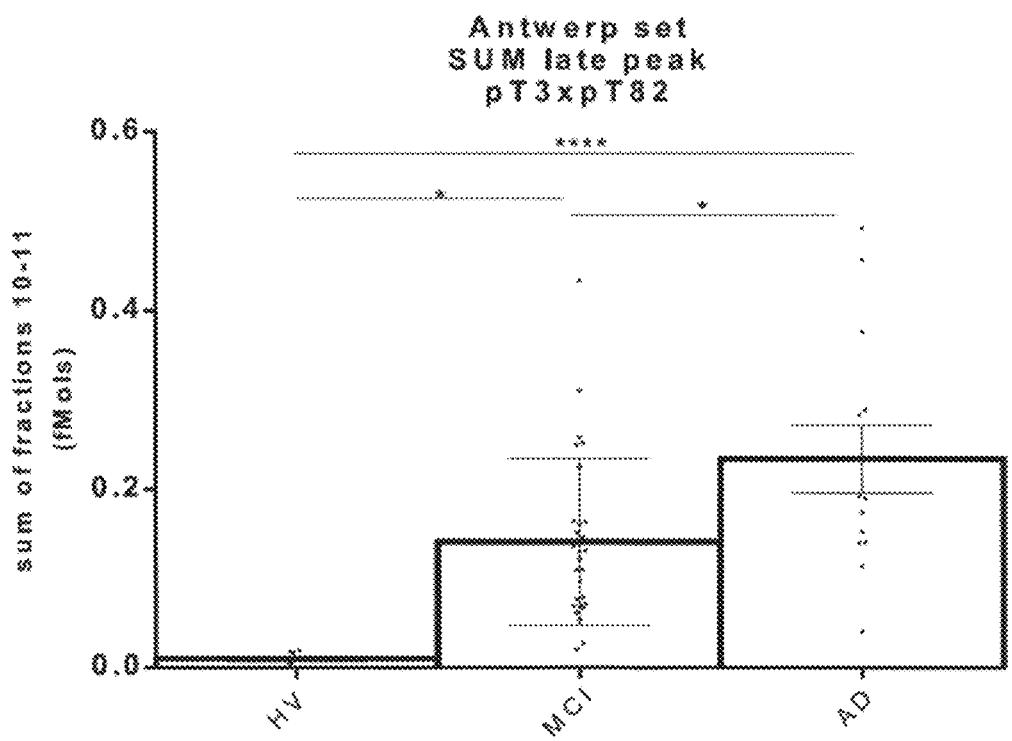
Figure 17Q:
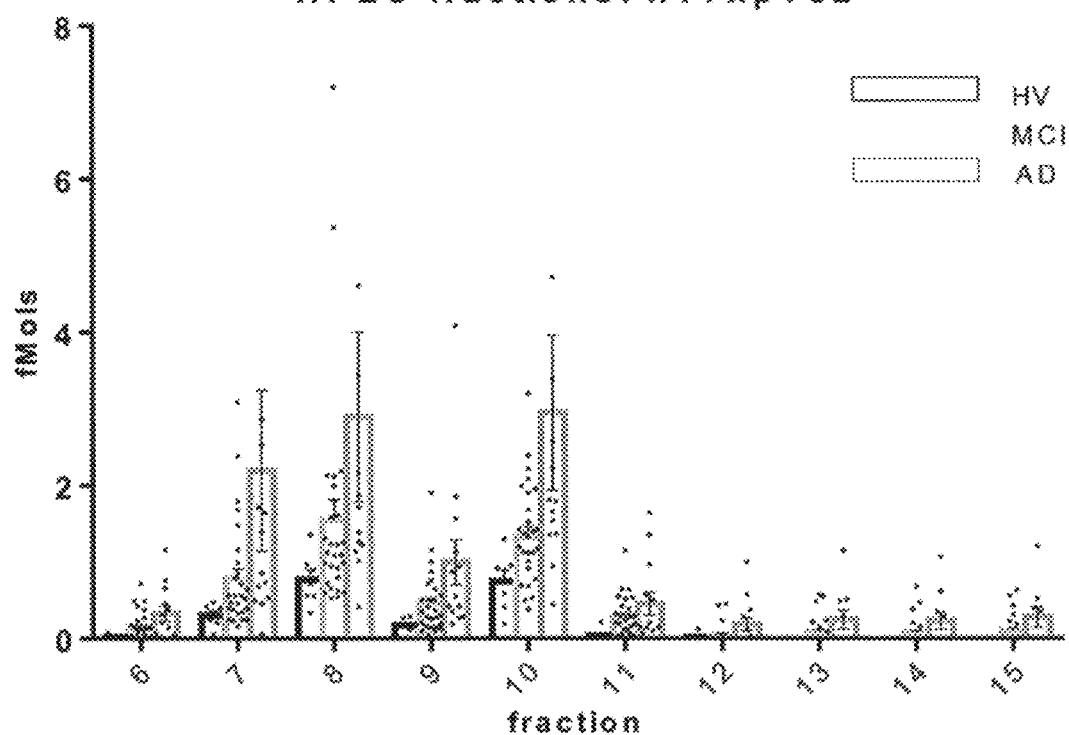
Figure 17R:
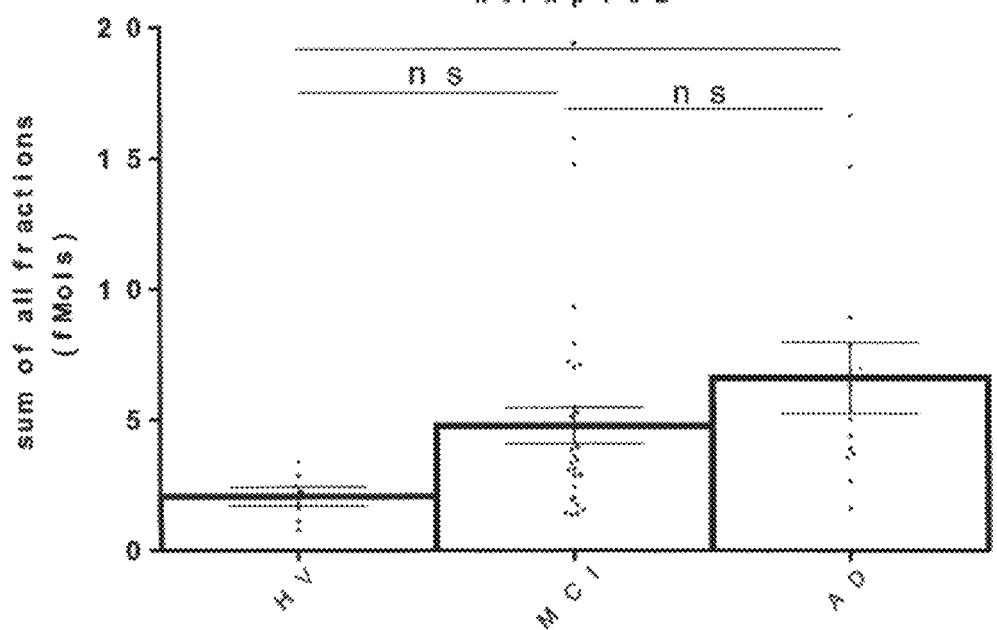
Figure 17S:
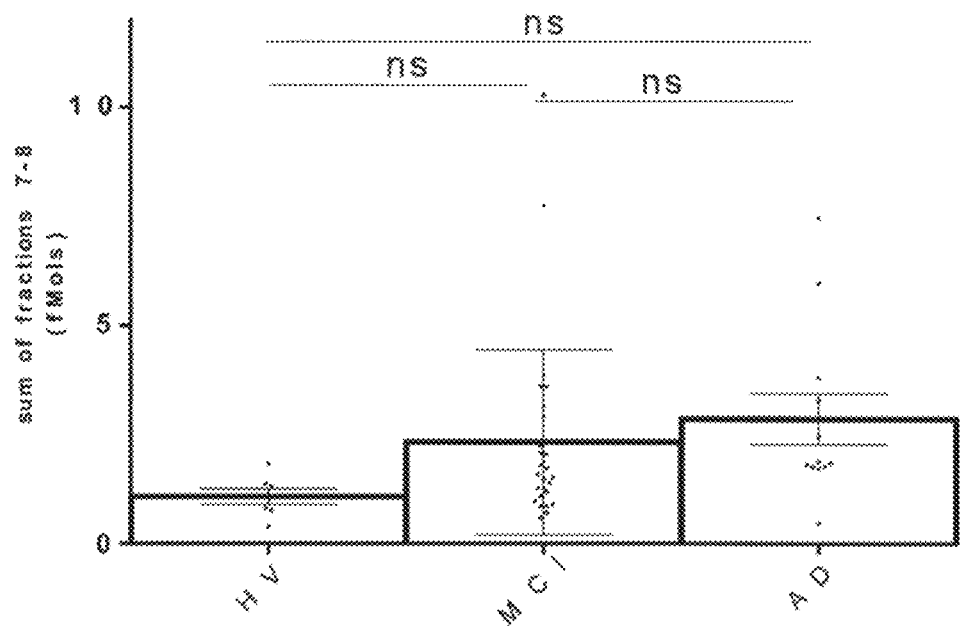
Figure 17T:
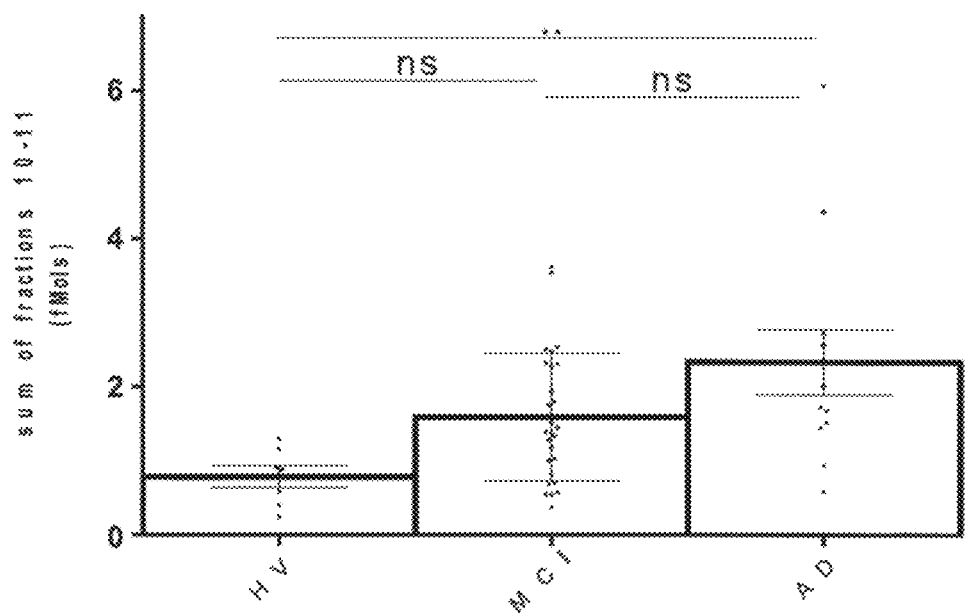

CSF samples were measured crude or after rpHPLC fractionation, using both pT3-based assays (pT3xhT43 & pT3xpT82) and tTau (hT7xpT82). All the pT3-based and hT7-based assays showed elevated signal progressively increasing signal in the HV vs MCI vs. AD groups (FIGS. 17A-C) and correlated well with each other (as seen Cohort 1, FIG. 9) (FIGS. 17D and 17E). The pT3 assays also correlated to some extent with Innotest tTau and pTau181 (FIGS. 17F and 17G), but not with Innotest AB42 or AB42/40 ration (FIGS. 17H and 17I). Similar results for diagnostic staging were observed in crude CSF measurements (FIGS. 17A-17C) or rpHPLC fractionated material (FIGS. 17J-17T). As seen in Cohort 3, the separation of HV vs MCI vs AD was more pronounced (greater statistically significance) using the pT3-based assays than the tTau assay, highlighting the pathological relevance of this pT3-assay measurement.

Cohort 6 ("Disease Severity and Progression Cohort")

CSF samples (LF) from clinically defined AD (Clinical Dementia Rating 1+) subjects (n=235) were obtained from Janssen study ELN115727301/302. These samples were baseline (pre-dose) samples from all subjects in the trial. In addition, CSF samples from 78 week follow up on the placebo subjects (n=90) was included to evaluate biomarkers of disease progression. Cognitive assessment (ADAS-COG, MMSE, NTB, and CDR.SOB), ApoE genotype, gender, & age were obtained from the trial. Innotest AB42, Innotest AB40, Simoa neurofilament light (NFL), pT3xpT82, pT3xhT43, and hT7xpT82 assays were performed at Janssen Neuroscience Biomarkers, La Jolla. Subjects were confirmed amyloid positive or negative based on the AB42/40 ratio cutoff of 0.09 (e.g. subjects with ratio <0.09=amyloid positive=AD, while those >0.09=amyloid negative=dementia from non-AD cause). 27 of the 235 subjects were determined to be amyloid negative thus each group was analyzed separately.

Figure 18A:
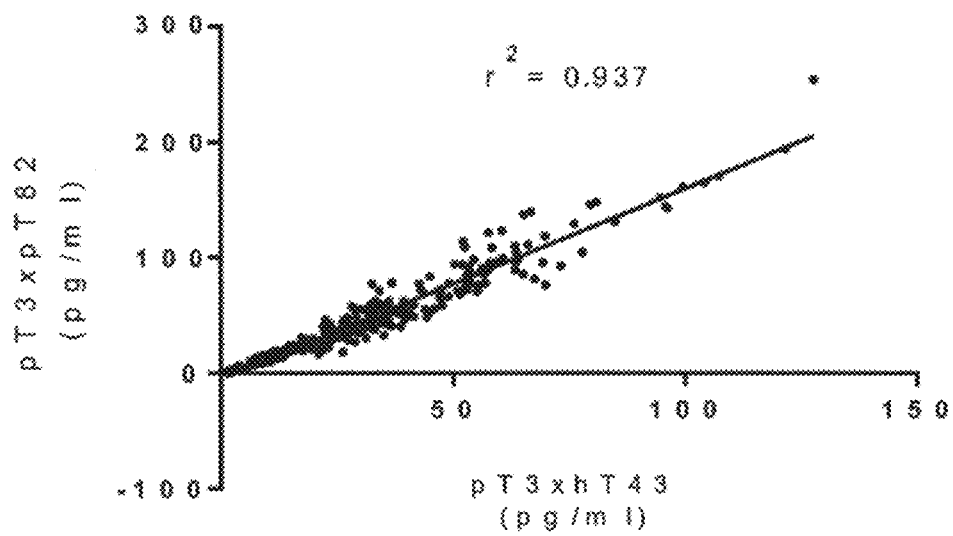
FIGS. 18A-18P show the results of (A) pT3xpT82 (p217+ short) vs pT3xhT43 (p217+ long), (B) pT3xpT82 vs hT7xpT82 (tTau short), (C) pT3xpT82 vs. NFL, and (D) pT3xhT43 or (E) pT3xpT82 vs amyloid status, as well as (F-I, N-P) pT3xhT43 or (J-M) pT3xpT82 correlation with (F-M) various cognition scores or (N-P) change in these scores over 78 weeks; all from cohort of 235 subjects (90 of which had the 78 week follow up) from Janssen study ELN115727301/302 on mild-moderate AD subjects. The subjects were initially enrolled (and classified as AD) based on cognition, however upon biochemical evaluation (AB40 and AB42) it was determined that 27 of the subjects were amyloid negative, and thus likely represent dementia of non-AD causes. These subjects are analyzed as a separate cohort in the figures above and designated as amyloid negative=0, while the amyloid positive subjects=1.
Figure 18B:
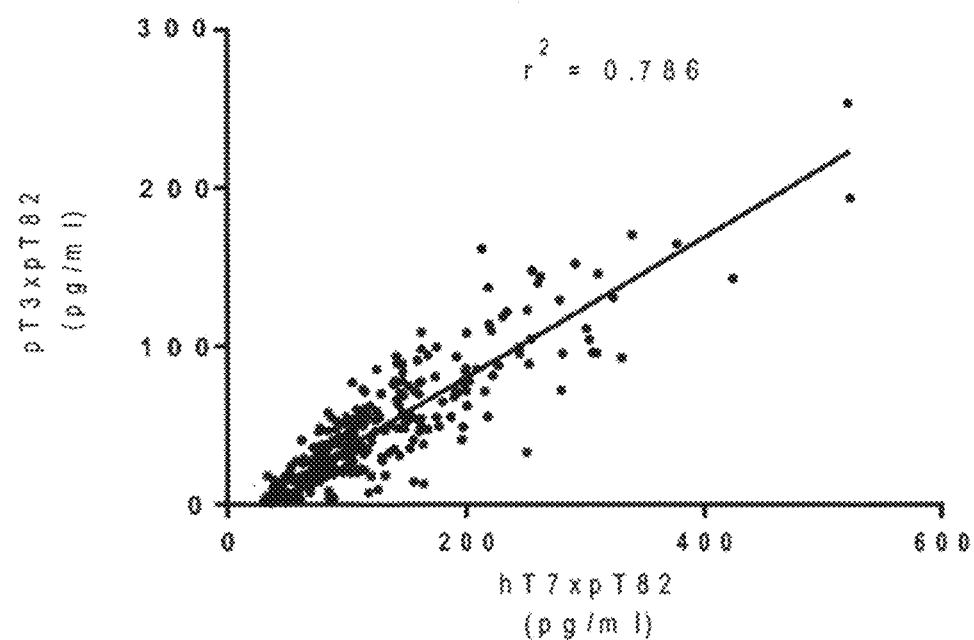
Figure 18C:
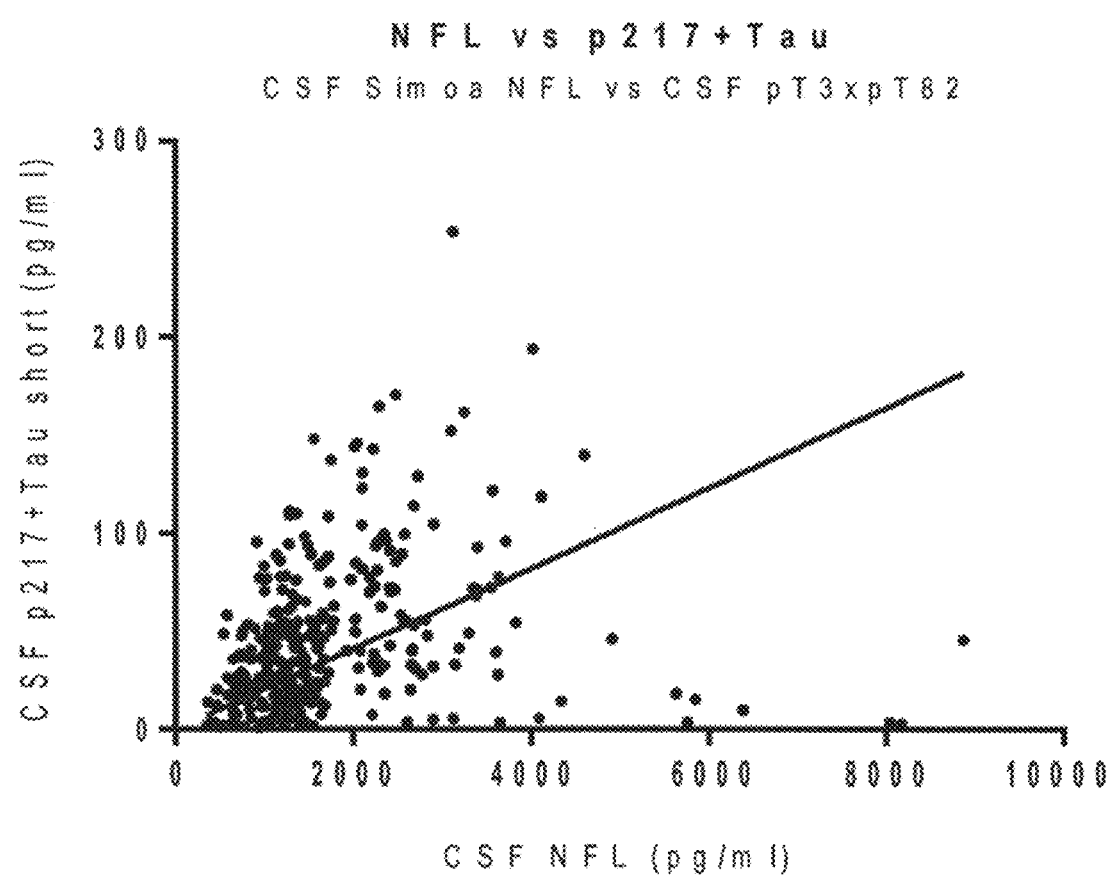

Signal from crude CSF measurements again revealed good correlation between the two pT3 assays and with the tTau assay (FIGS. 18A and 18B), but not with NFL (FIG. 18C), a suspected marker of general neurodegeneration, suggesting that the pT3-assay may recognize a specific form or stage of neurodegeneration.

Figure 18D:
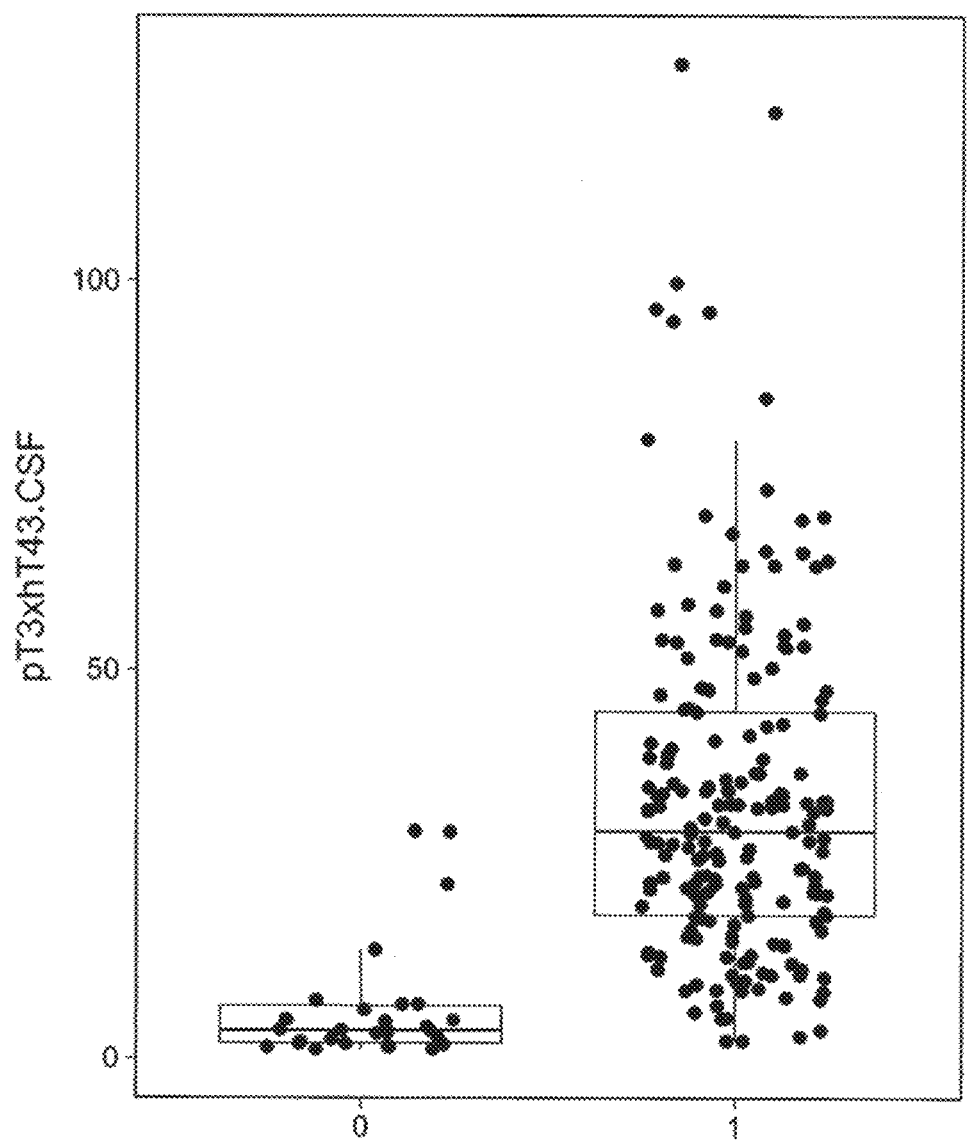
Figure 18E:
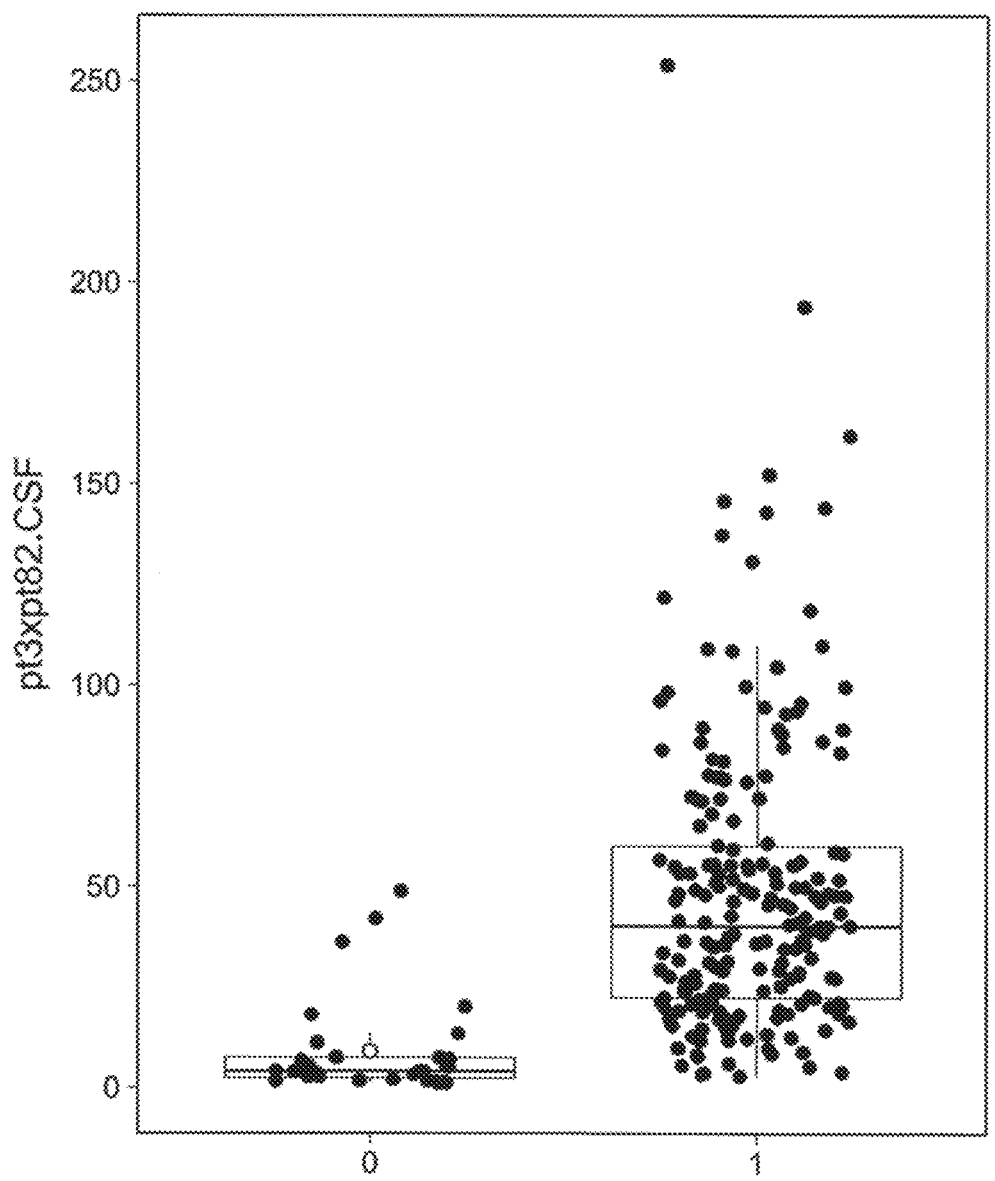
Figure 18F:
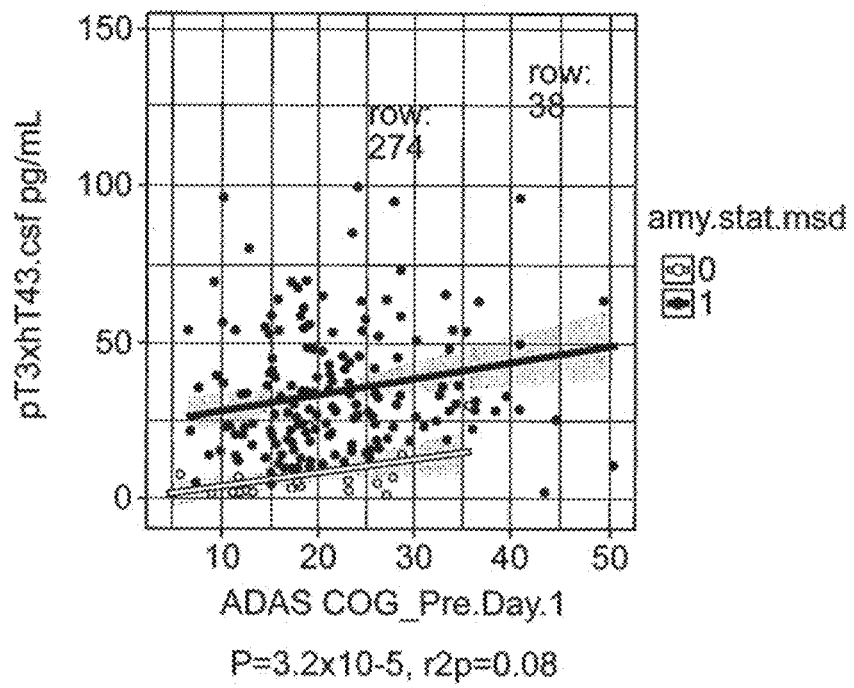
Figure 18G:
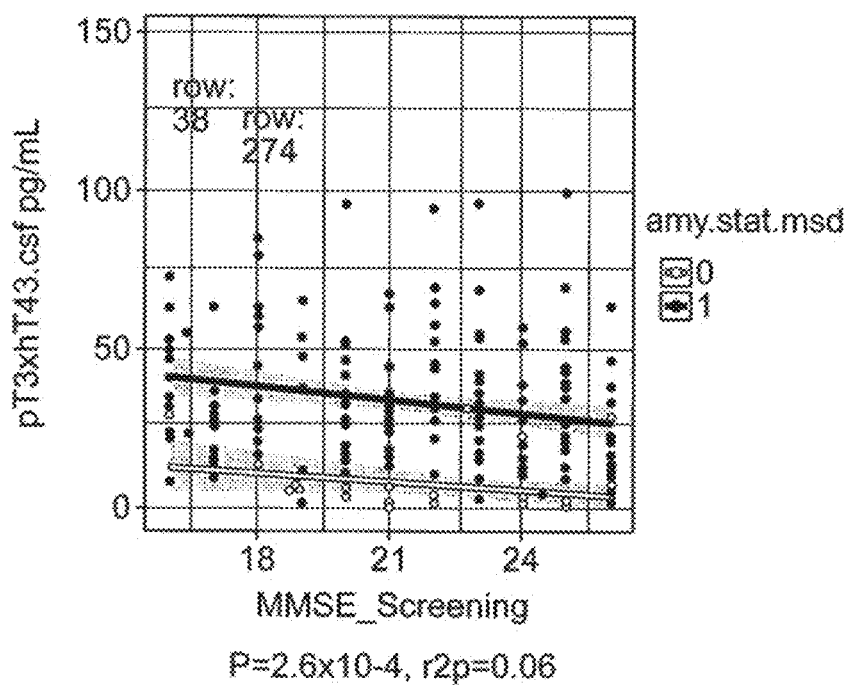
Figure 18H:
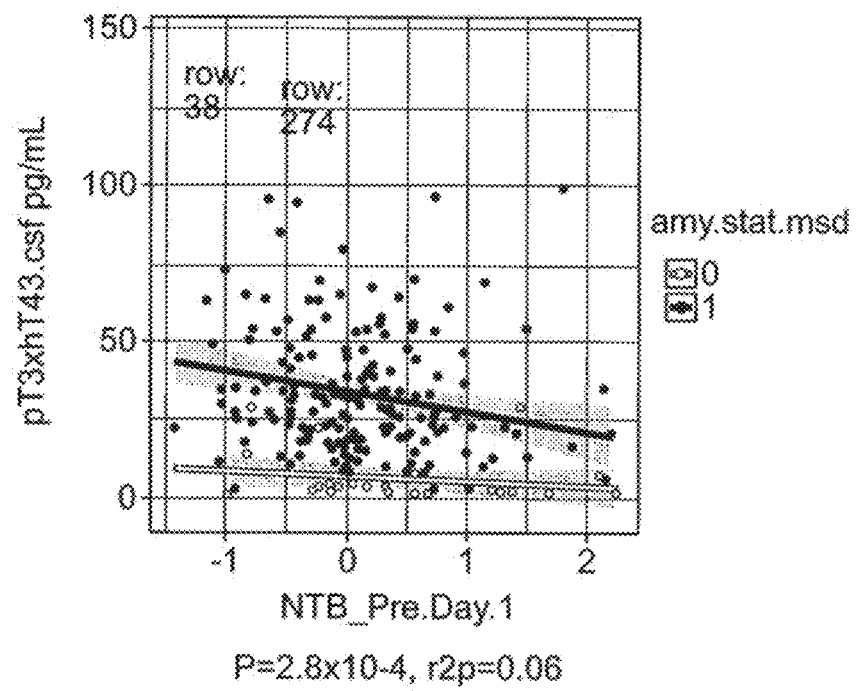
Figure 18I:
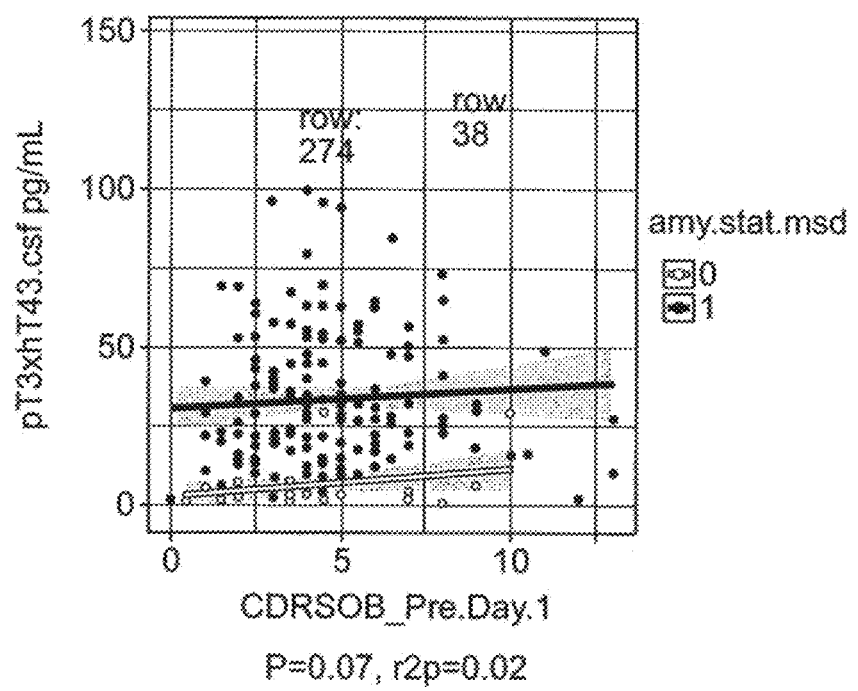
Figure 18J:
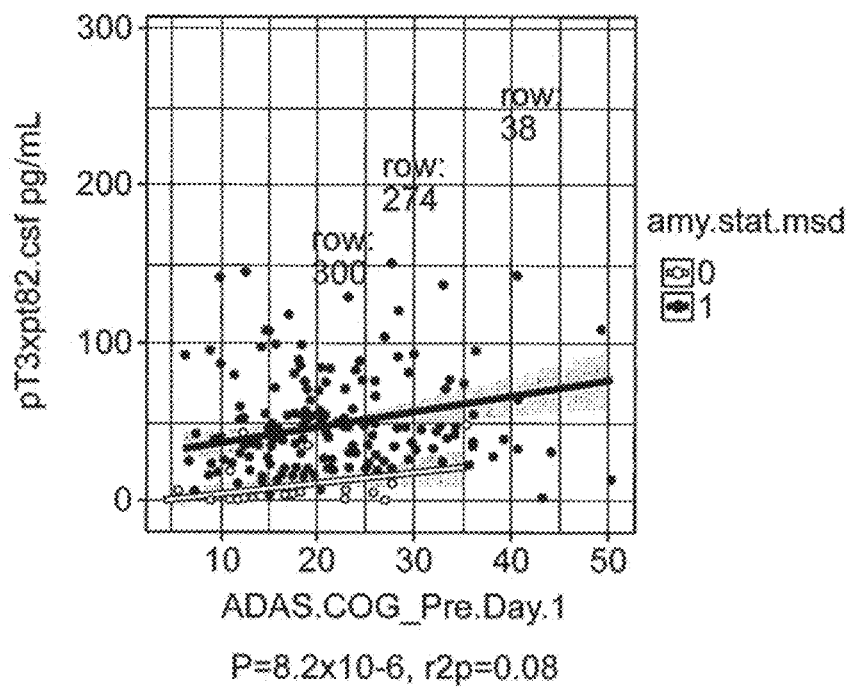
Figure 18K:
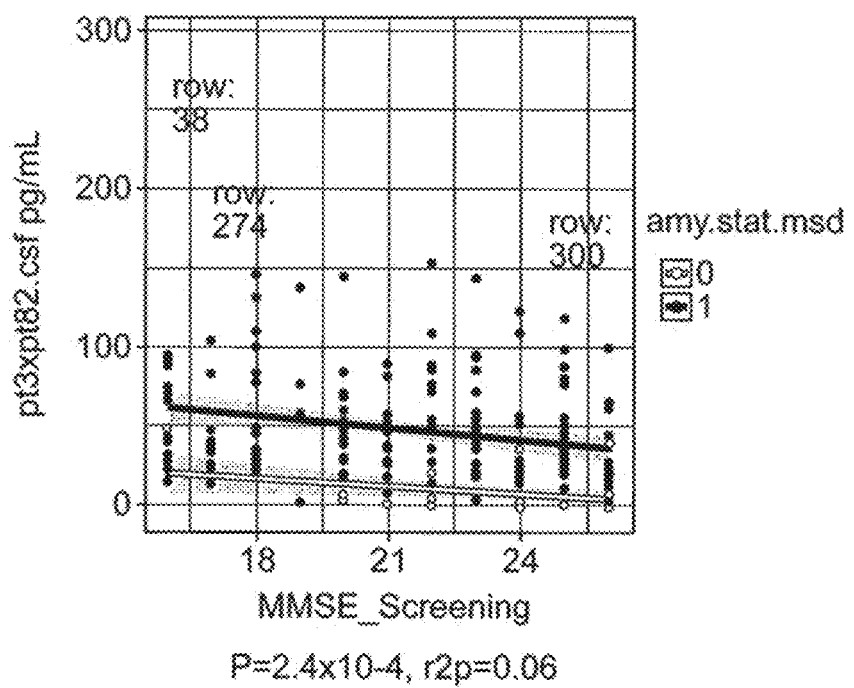
Figure 18L:
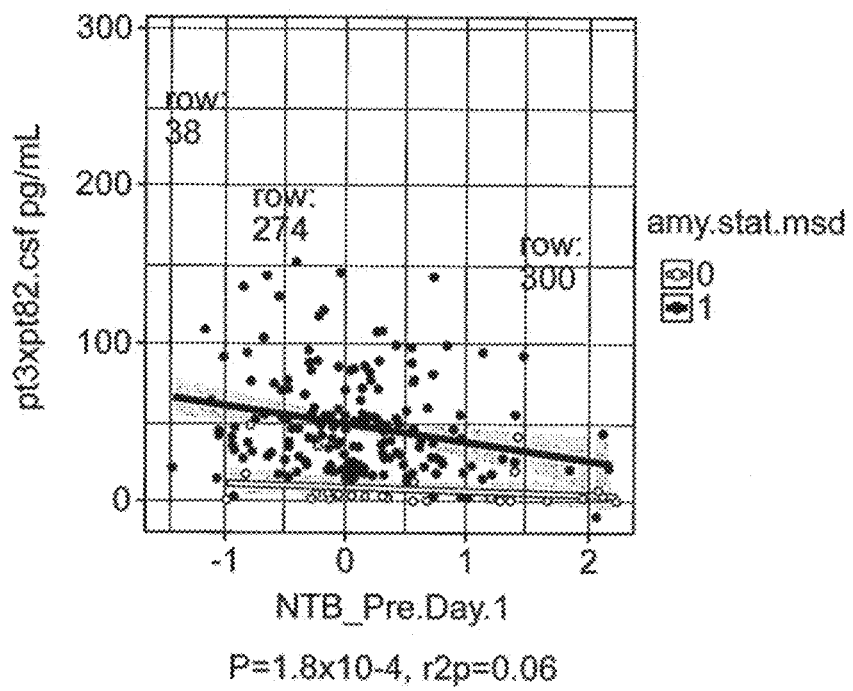
Figure 18M:
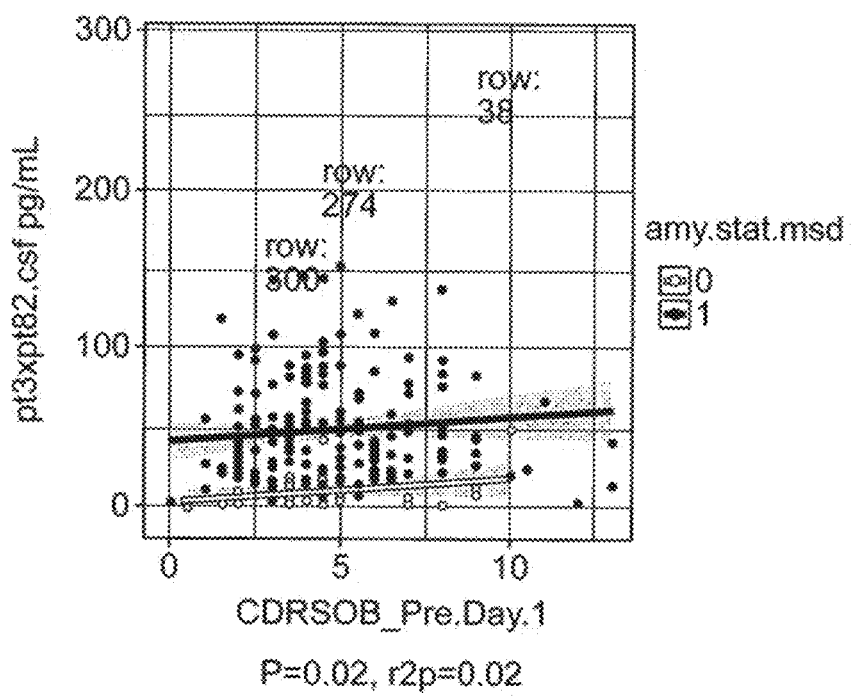

The pT3-based assays again revealed higher signal in the amyloid positive vs negative subjects (FIGS. 18D-18E).

Figure 16B:
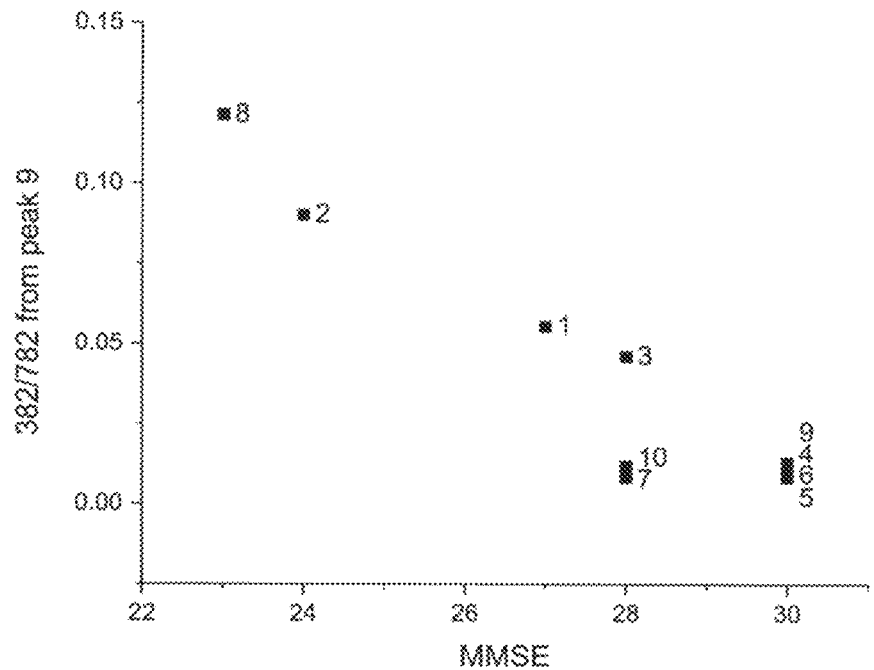
Figure 18N:
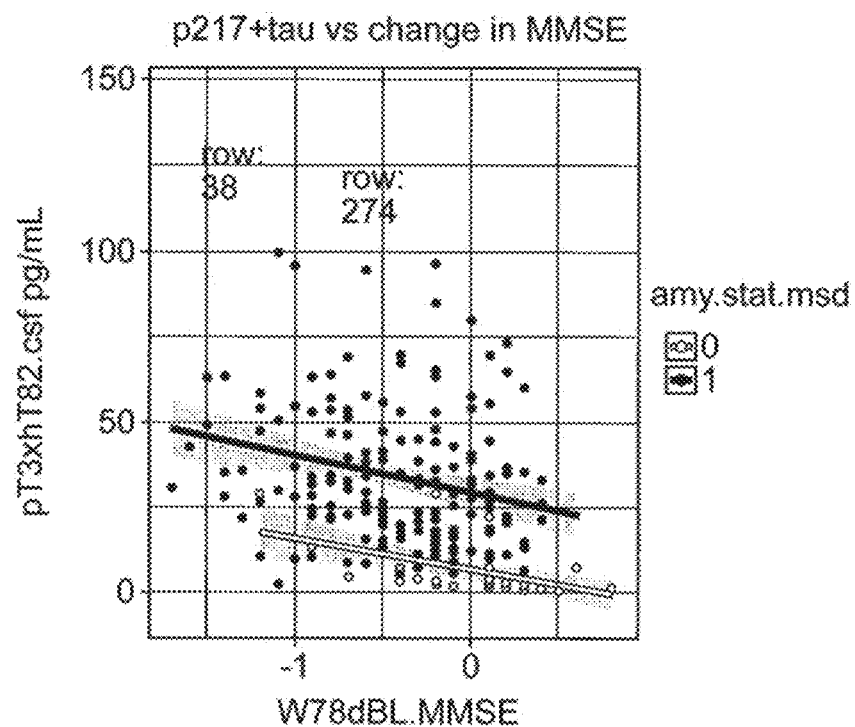
Figure 18O:
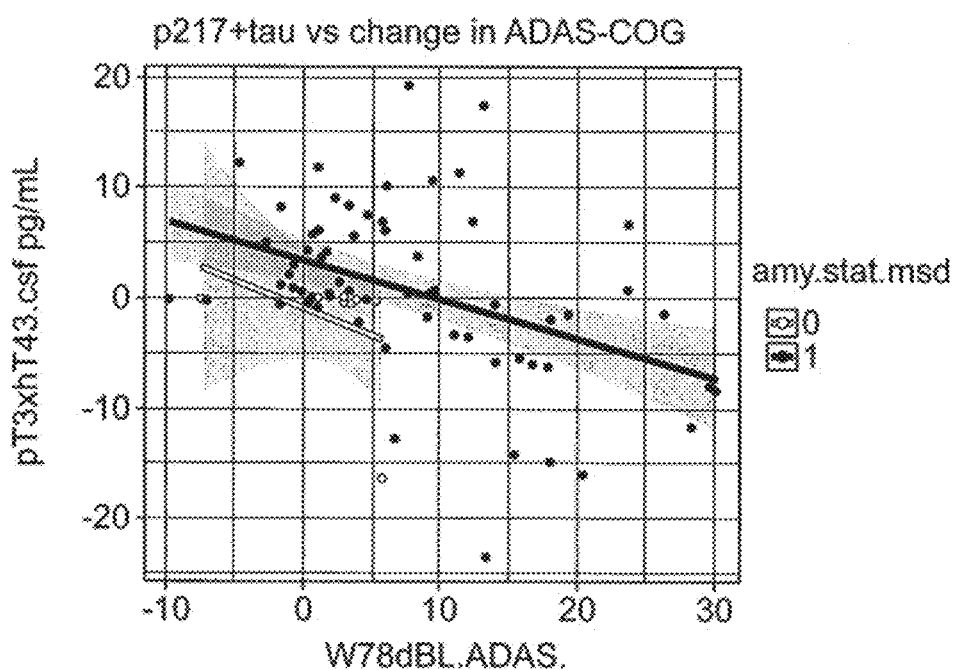
Figure 18P:
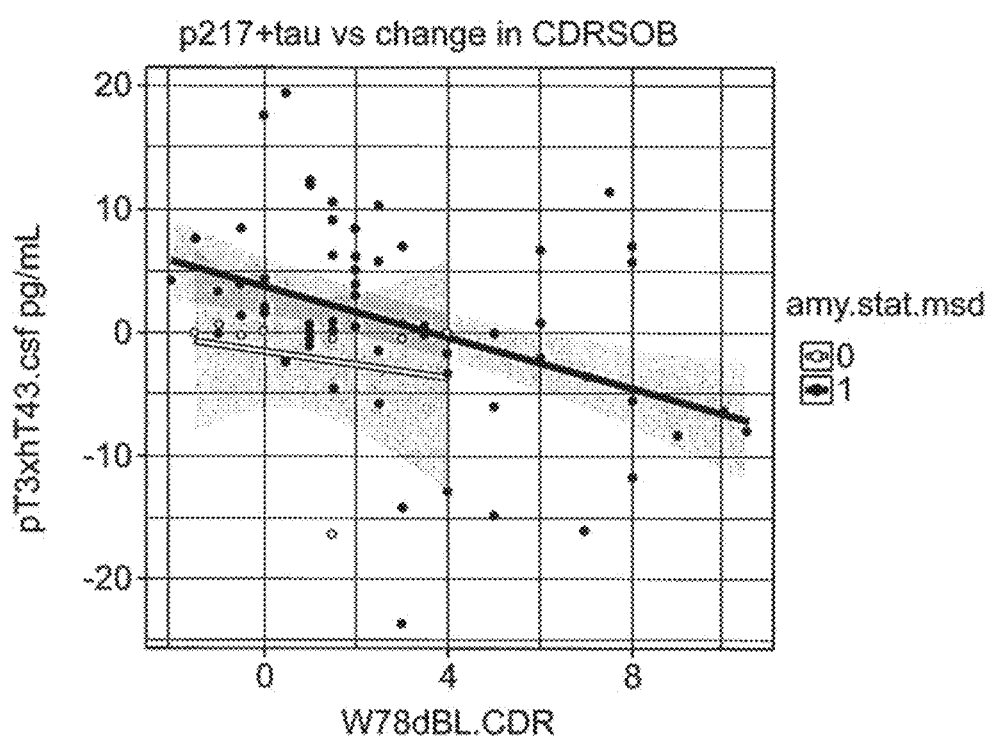

The pT3-based assays revealed modest correlation with several cognition scores (ADAS-COG, MMSE, NTB, CDR-.SOB, FIGS. 18F-18M), corroborating the finding in Cohort 4 (FIG. 16B). Intriguingly the baseline pT3-based assay signal correlated modestly with change in cognition scores over the 18 month follow up period as well, suggesting ability to predict cognitive decline (FIGS. 18N-18P). The ratio of pT3-based signal to tTau signal (p217 tau/tTau) yielded similar results, data not shown.

The correlations with cognition and change in cognition were seen in both the amyloid positive and negative groups, however the latter group was a small sample set. If confirmed this suggests the p217+ vs cognition connection may not be AD-specific.

Example 9. Quantification of p217+ Tau that is Free Vs. Bound by Antibody

The assays described in Example 3 were carried out as follows.

Figure 19:
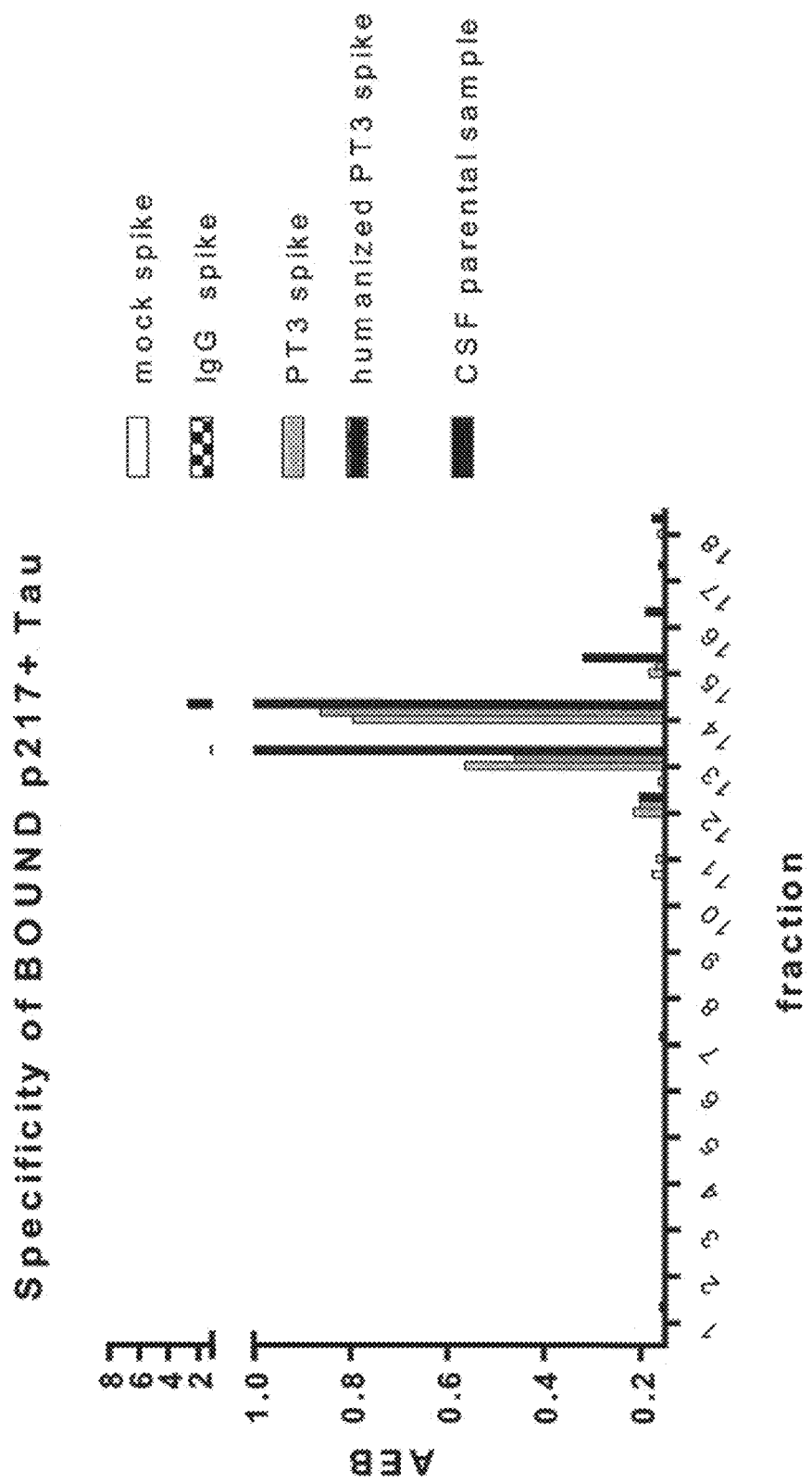
FIG. 19 shows the signal from a pT3xhT43 assay carried out on rp-HPLC fractions of AD CSF samples spiked with IgG, pT3 mAb, humanized pT3 mAb or mock control, followed by immunoprecipitation to collect antibody-bound p217+ tau.

Assay 1: Quantification of Free Vs. Bound p217+ Tau in Biological Fluid Via Immunocapture/Depletion Followed by rpHPLC The assay was tested by spiking antibody into CSF samples. Pooled AD CSF was spiked with 10 ug of pT3 mAb, humanized pT3 mAb, msIgG or comparable volume of PBS (mock) and incubated at 4° C. for 24 hr followed by immunocapture. The samples, as well as parental CSF not subjected to immunocapture, were fractionated on rpHPLC, and each fraction was measured using the pT3xhT43 assay to assess the amount of total and bound p217+ tau. Substantial signal was observed in one major peak, similar to that seen in Example 7 and FIG. 7, in the parental sample (total p217+ tau) and the pT3 mAb or humanized pT3 mAb immunocaptures (bound p217+ tau), but not in the mock or IgG immunocaptures (FIG. 19).

Figure 20A:
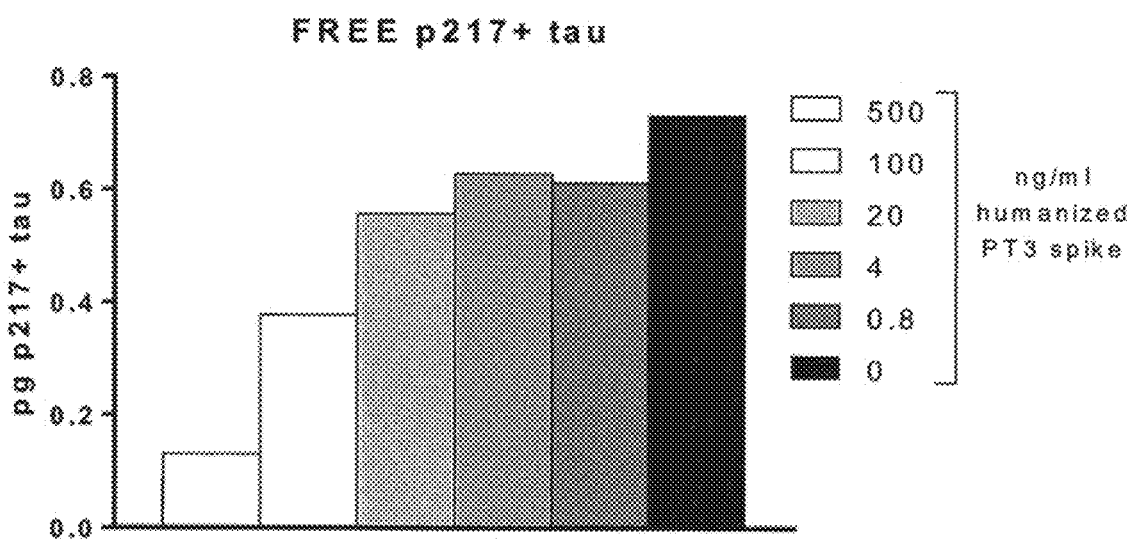
FIGS. 20A-20B show the antibody dose dependency of the immunocapture/rpHPLC method for quantifying (A) antibody-free and (B) antibody-bound p217+ tau, with data graphed as the sum of signal in rpHPLC fractions 12-16.
Figure 20B:
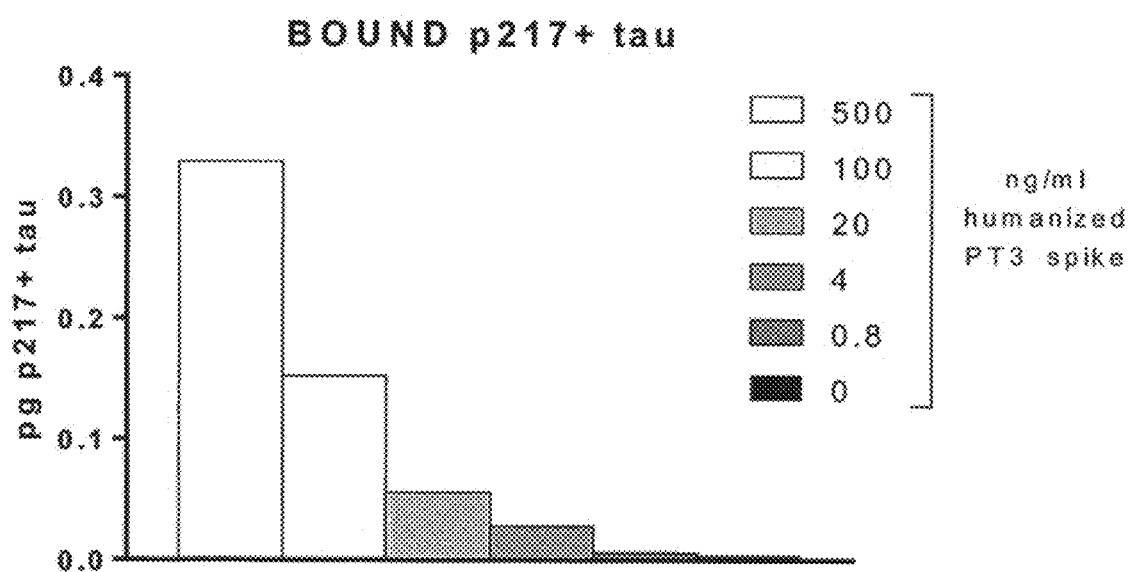

Pooled AD CSF was spiked with titrations of humanized pT3 mAb, incubated at 22° C. for 2 hr, followed by immunocapture, rpHPLC, and pT3xhT43 assay to assess bound p217+ tau (FIG. 20A). The IgG depleted supernatant was also fractionated and measured to assess free p217+ tau (FIG. 20B). Spiking with humanized pT3 mAb increased the amount of measured bound p217+ tau, and decreased the amount of free p217+ tau, in a dose dependent manner.

Taken together, the results show that this method, which is a direct measurement of target engagement, is specific for antibodies that are targeted to the p217+ tau epitope (FIG. 19) and is targeted-antibody dose dependent (FIG. 20).

Assay 2: Quantification of Free Vs. Bound p217+ Tau in Biological Fluid Via Selective Denaturing of Antibody Biological samples (e.g. CSF) were heated at near boiling for 4 minutes, followed by a chilling on ice and subsequent measurement with the pT3xhT43 and/or pT3xpT82 assays. The precise time of this process were determined to irreversibly damage antibodies in the sample such that they cannot interfere with the assay (FIG. 21), but do not impact the p217+ tau signal itself (FIG. 21). It is believed that this is due to the particular lack of tertiary structure in tau protein, allowing it to be particularly stable at high temperature. This sample was termed total p217+ tau, while parallel measurement of a sample that had not been subjected to the heat treatment was termed free p217+ tau. Subtracting free from total concentration yielded bound p217+ tau measurement.

The impact of heat on the assay was determined, as follows.

Figure 21A:
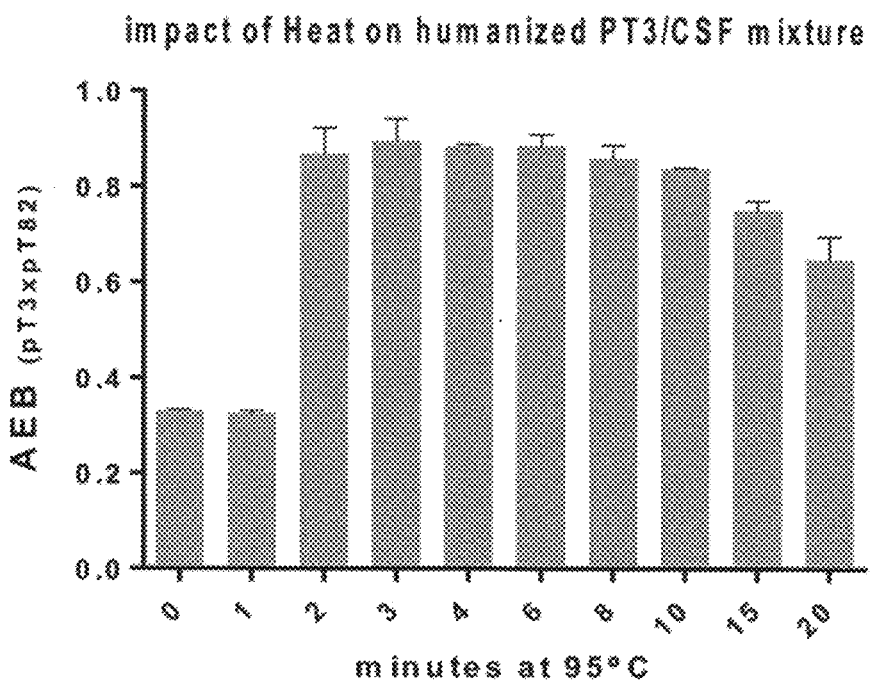

Impact of heat on a CSF/humanized pT3 mAb mixture: Aliquots of pooled AD CSF were spiked with humanized pT3 mAb to 1 µg/ml, incubated for 2 hrs at 22° C., heated for 0-20 minutes at 95° C., chilled to 4° C., then measured using the pT3xpT82 assay at a 1:10 dilution (FIG. 21A). The p217+ tau signal was low through ~2 minutes of heat treatment, then returned to levels seen in unspiked CSF and was stable through ~10 minutes of heat before dropping.

Figure 21B:
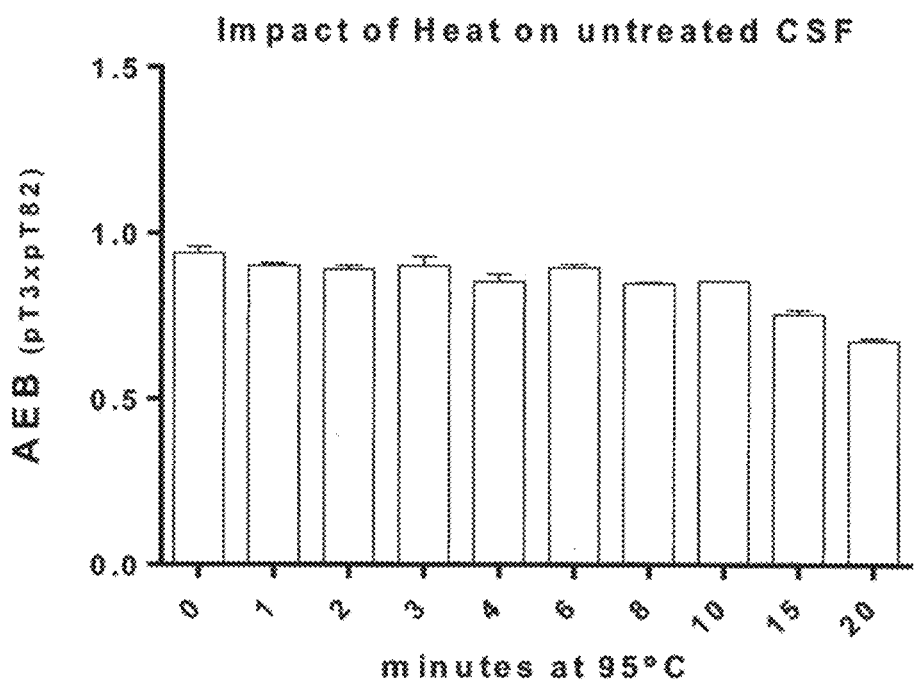

Impact of heat of naïve CSF: Aliquots of pooled AD CSF were heated for 0-20 minutes at 95° C., then chilled to 4° C., before measuring using the pT3xpT82 assay at a 1:10 dilution (FIG. 21B). The p217+ tau signal was stable through ~10 minutes of heat before dropping.

Impact of heat on ability of humanized pT3 mAb to interfere with the pT3xpT82 assay: Aliquots of humanized pT3 mAb at 10 µg/ml in PBS were heated for 0-20 minutes at 95° C., then chilled to 4° C. These samples were then mixed with pooled AD CSF (to 1 µg/ml final concentration of humanized pT3 mAb) and incubated for 2 hrs at 22° C. before measuring using the pT3xpT82 assay at a 1:10 dilution (FIG. 21C). The p217+ tau signal was low through ~2 minutes of JNJ heat treatment, then returned to levels seen in unspiked CSF (see FIG. 21B) and was stable through at least 20 minutes of heat.

Figure 22A:
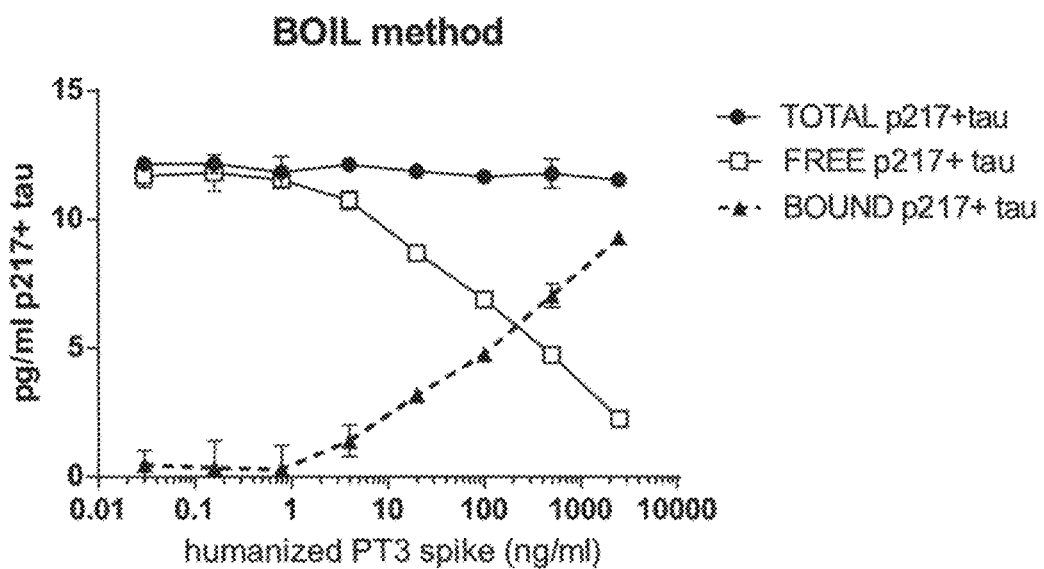
FIGS. 22A-22C show (A) heat-mediated denaturation and (B) immunocapture/rpHPLC methods for quantifying antibody-free vs. antibody-bound p217+ tau.; (C) shows a comparison of the methods.
Figure 22B:
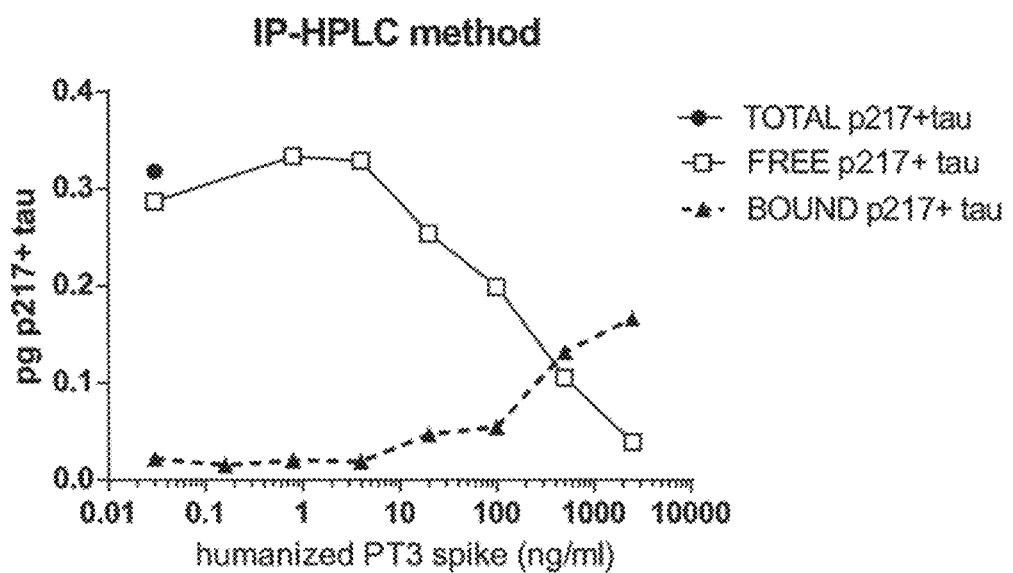
Figure 22C:
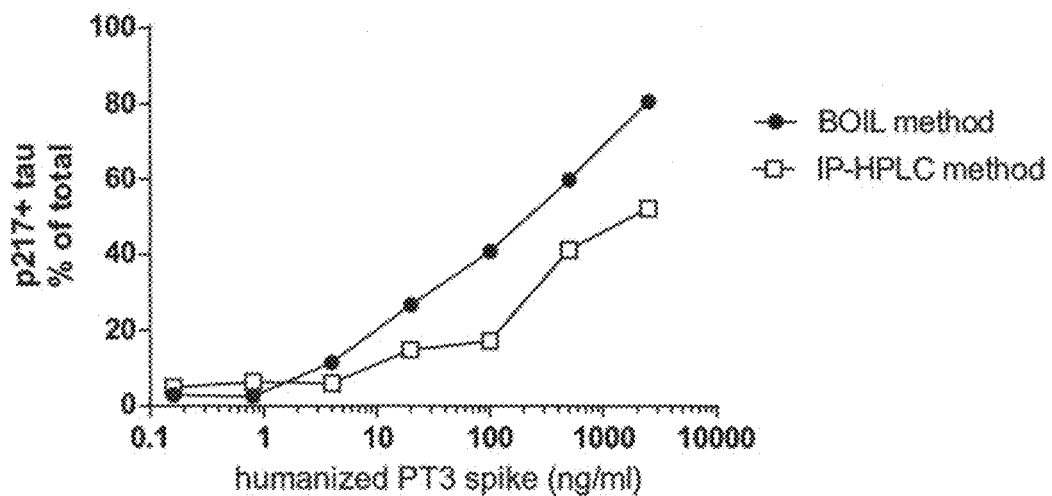

Parallel aliquots of pooled AD CSF were titrated with humanized pT3 mAb, incubated for 2 hr at 22° C., then subjected to either the heat denaturing process (with 4 minutes of heat) (FIG. 22A) or immunocapture/rpHPLC (FIG. 22B) before measurement using the pT3xpT82 assay. Both methods showed a humanized pT3 mAb dose dependent increase in bound, decrease in free, and no change in total p217+ tau signal. Further, the heat-mediated denaturing method yielded comparable humanized pT3 mAb dose dependency, and relative free vs. bound vs. total p217+ measurements, to that obtained using the more laborious immunocapture/rpHPLC method of Assay 1 (FIG. 22C). Therefore, the heat method is recommended for standard sample analysis.

Example 10. p217+ Tau Signal in Preclinical Animal Models

To support preclinical studies, naïve samples from various common lab animals were evaluated using the pT3-based assays and/or sequence-aligned to predict cross reactivity.

Cynomolgus Macaque

Figure 23:
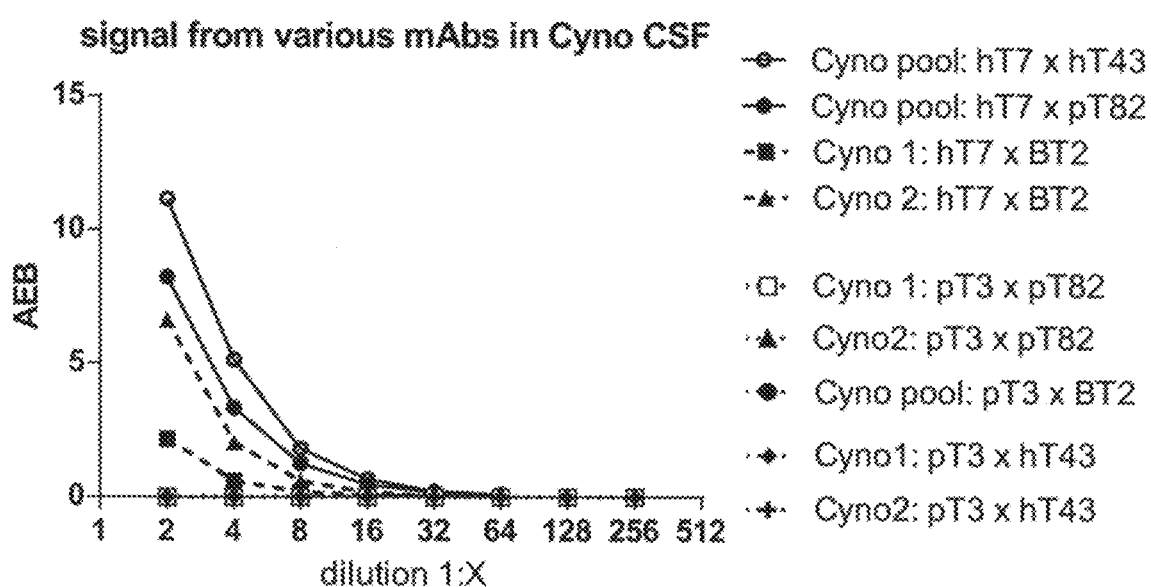
FIG. 23 shows a lack of pT3-based assay recognition of p217+ tau in Cynomolgus Macaque CSF.

CSF from two Cynomolgus Macaques was measured at various dilutions using pT3-based and hT7-based assays (FIG. 23). For comparability, the same detection antibodies were paired with each of the two capture antibodies. In some cases, the two individual CSFs were tested separately (Cyno 1 or Cyno 2), and in other cases, the CSF samples were pooled to save volume. Substantial signal (AEB) was seen in all assays using hT7 as the capture antibody, regardless of the detection antibody, but no signal was detected in any of the assays using pT3 as the capture antibody. Additionally, plate based assays with pT3 have shown that even in homogenates of Cynomolgus Macaque brain, there is very little or no pT3-based signal, despite the large signal in AD human brain (data not shown). This suggests that despite high levels of tau, the pT3 epitope is not preserved in this species. Indeed, analysis of published protein sequences suggests one amino acid is different between human and Cynomolgus Macaque in the pT3 core epitope, and structural modeling, based on crystal structure of humanized pT3 mAb with tau, suggests this change could abolish binding of pT3 (data not shown).

Common Marmoset

Figure 24A:
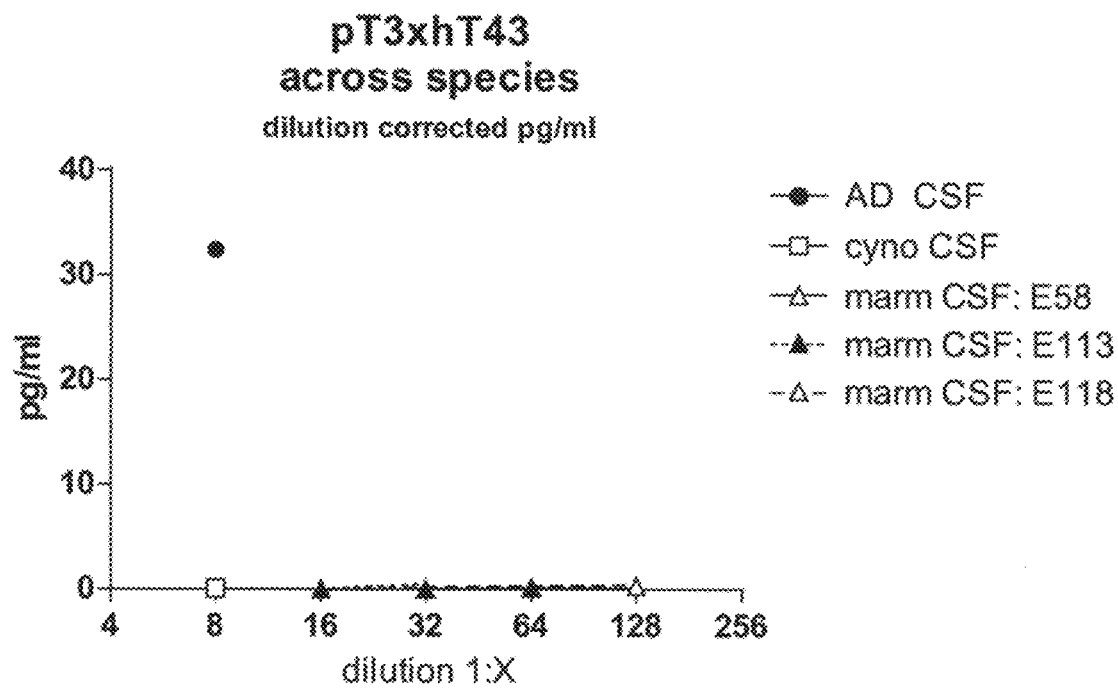
FIGS. 24A-24C show measurements of p217+ tau in Marmoset CSF as determined using the (A) pT3xhT43, (B) pT3xpT82 and (C) hT7xpT82 assays.
Figure 24B:
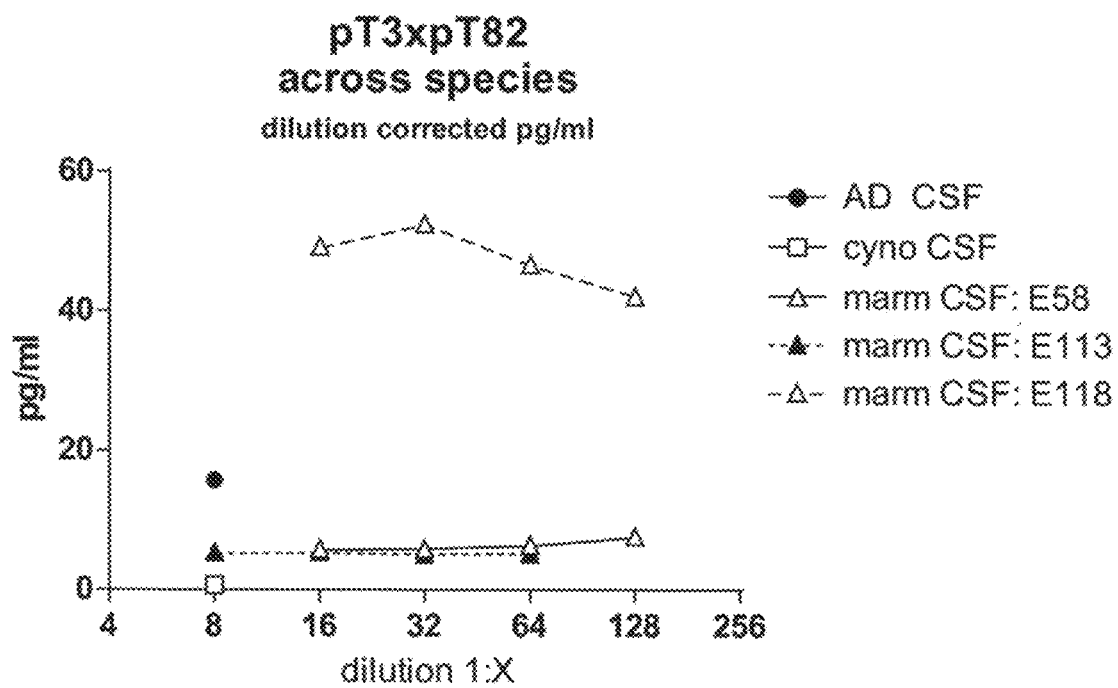
Figure 24C:
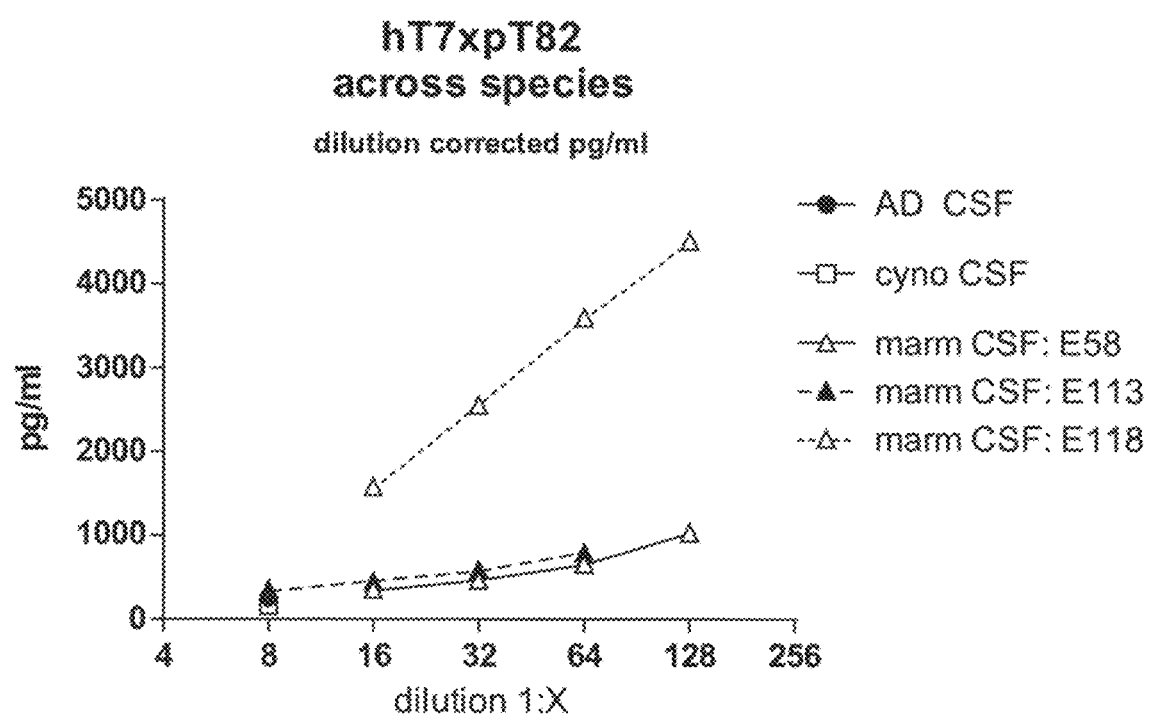
Figure 25A:
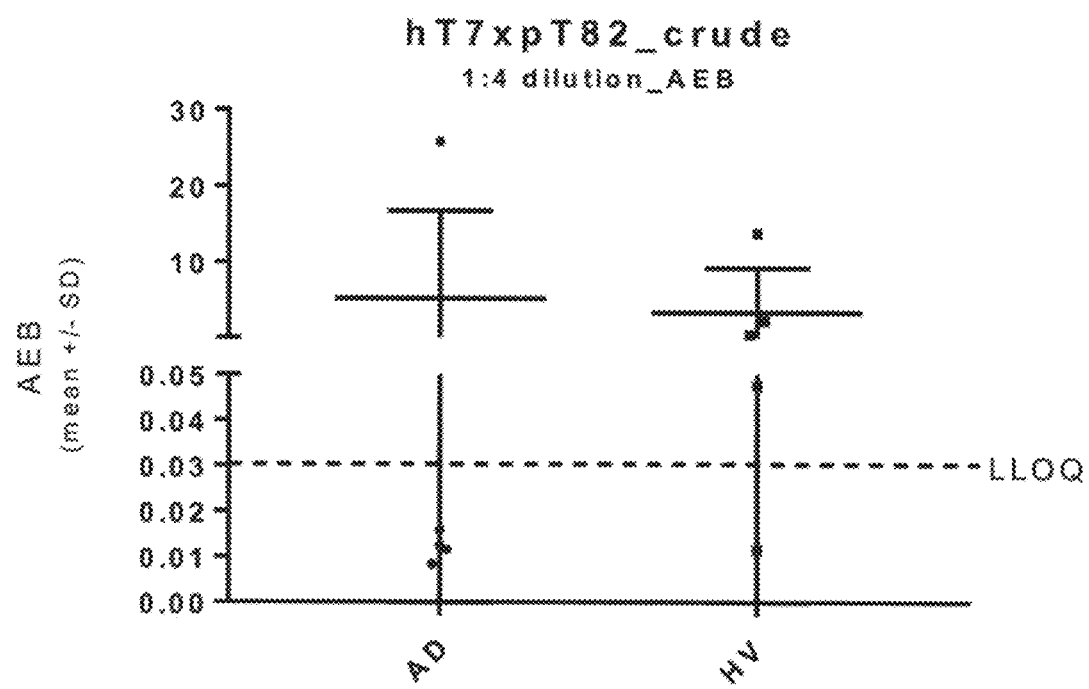
FIGS. 25A-25D show measurements of (A,B) hT7xpT82 (tTau) or (C,D) pT3xpT82 (p217+ tau short) in crude serum from 4 AD and 4HV subjects. Measurements were performed at (A,C) 1:4 or (B,D) 1:16 dilution, note lack of dilution linearity and sensitivity
Figure 25B:
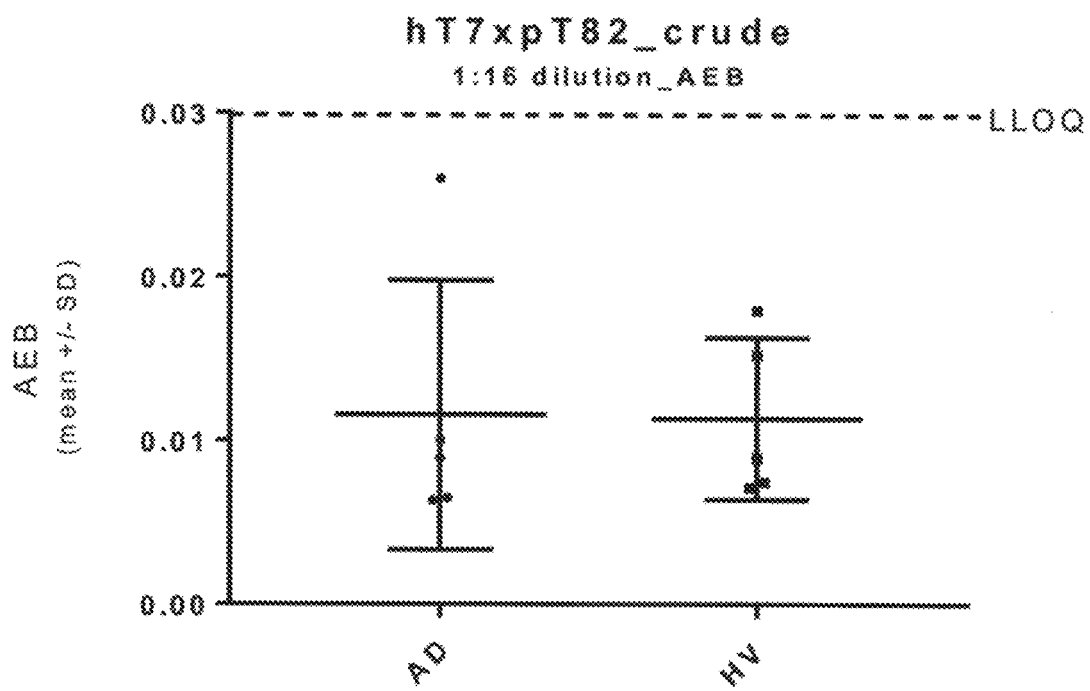
Figure 25C:
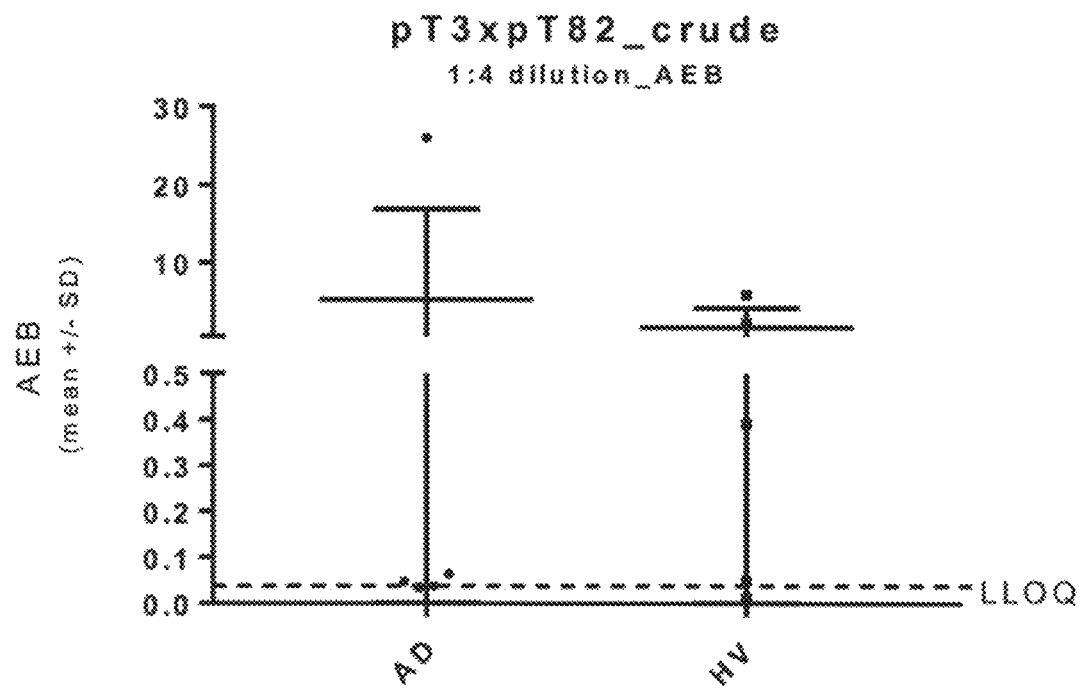
Figure 25D:
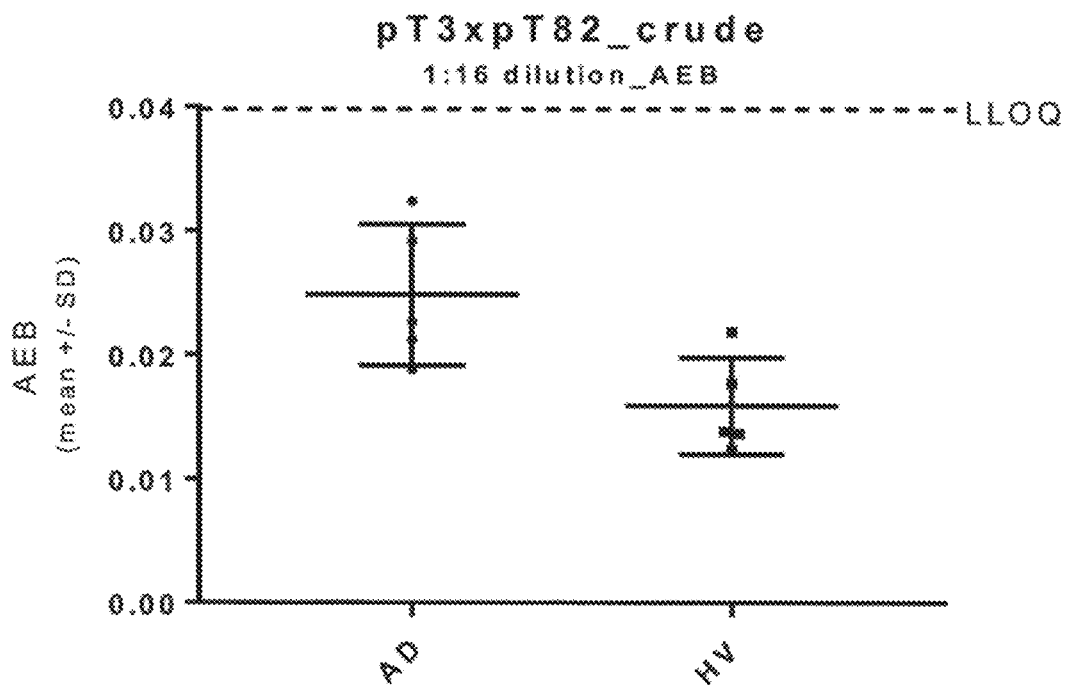

CSF from Common Marmoset was tested using pT3-based and hT7-based assays (FIG. 24). CSF from three Common Marmosets was measured at various dilutions using pT3xhT43, pT3xpT82, and hT7xpT82 assays. For comparability, a pooled Cynomolgus Macaque CSF (negative control) and pooled AD human CSF (positive control) were tested simultaneously. Substantial signal (AEB) was seen in Marmoset CSF using the pT3xpT82 (FIG. 24B) and hT7xpT82 (FIG. 24C) assays, but not with the pT3xhT43 assay (FIG. 24A).

This suggested that the hT43 epitope was lacking in this species, and indeed, a protein sequence alignment does indicate that one amino acid is different between human and Common Marmoset in the hT43 epitope, while the pT3, hT7, and pT82 epitopes are preserved. Measurement of Marmoset brain homogenate with same assays confirmed that there was substantial signal with the pT3xpT82 and hT7xpT82 assays, but very little with the pT3xhT43 assay (data not shown). Thus, analysis of p217+ tau signal in Marmoset was achieved using the pT3xpT82 assay.

Mouse, Rat, Dog, Pig

Alignment of predicted tau protein sequences in mouse, rat, dog, or pig (NCBI Accession numbers: NP_001033698.1, NP_058908.2, NP_001104271.1, and AGJ26517.1, respectively) with human sequence suggests that pT3 is 100% conserved in these species. However, the hT43 and pT82 sequences of mouse, rat, dog and pig are not identical with those of human, and thus, samples from these would need to be evaluated using the pT3xhT43 and pT3xpT82 assays.

Taken together, the data presented here indicates that the pT3xhT43 and pT3xpT82 assays developed on the Simoa platform for CSF measurement are highly sensitive, having femtogram sensitivity, are precise, accurate, dilution linear, and analyte stable. The assays appear to correlate well with classical AD biomarkers and dementia scores and may be superior to those measures in identifying and staging AD subjects.

The assays can be used to measure the level of total p217+ tau in CSF, or to evaluate the fragment profile of p217+ in rpHPLC-fractionated CSF. The assays can also be combined with preanalytical manipulation to measure the levels of p217+ tau that is bound by endogenous or exogenously administered antibodies, vs. p217+ tau that is free of antibody. Thus, the assays can be used as predictive biomarkers to identify subjects for whom anti-p217+ tau antibody therapy will be suitable, by identifying subjects with high levels of the p217+ tau target. By measuring levels of total, free, and therapeutic antibody-bound p217+ tau, the assays can also be used as pharmacodynamics markers.

Example 11. p217+ Tau Signal in Blood

While measurement of Tau in CSF has shown great utility in diagnosis and staging of neurodegenerative disorders, collection of CSF has limitations (e.g., patient burden, clinical site experience, collection volume and frequency constraints). As such, there is great interest in adapting Tau measurements to use on blood products (e.g. serum, plasma). Recent literature has however indicated that tau measurements in crude serum or plasma do not exhibit ideal diagnostic performance and may be plagued by sensitivity and matrix interference hurdles. The pT3-based assays may represent a new opportunity however due to its high sensitivity and specificity.

Figure 26A:
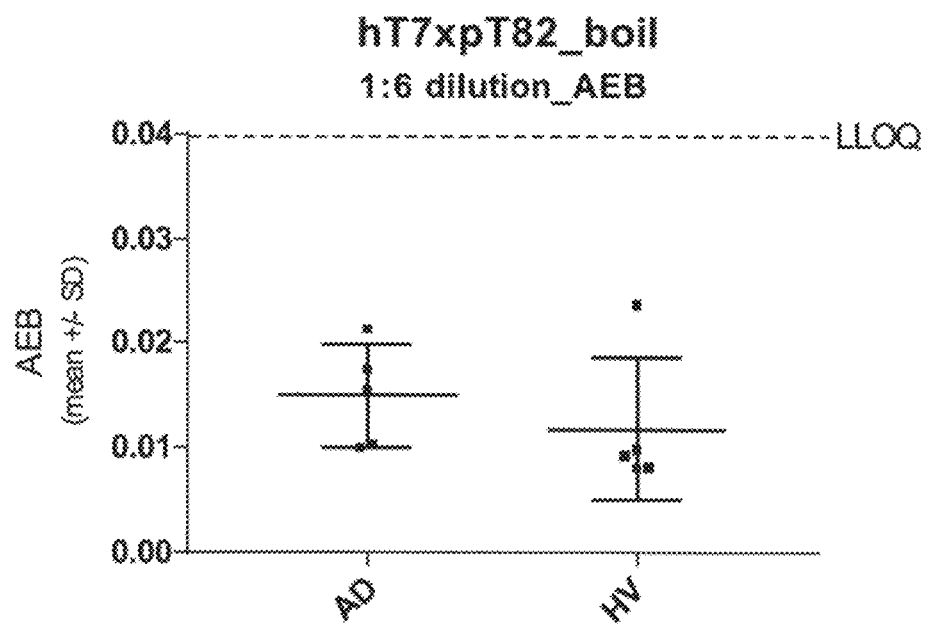
FIGS. 26A-26B show measurements of (A) hT7xpT82 (tTau) or (B) pT3xpT82 (p217+ tau short) in serums pretreated with NaOAc and heat denaturation, from the same 4 AD and 4HV subjects evaluated in FIGS. 25A-25D.
Figure 26B:
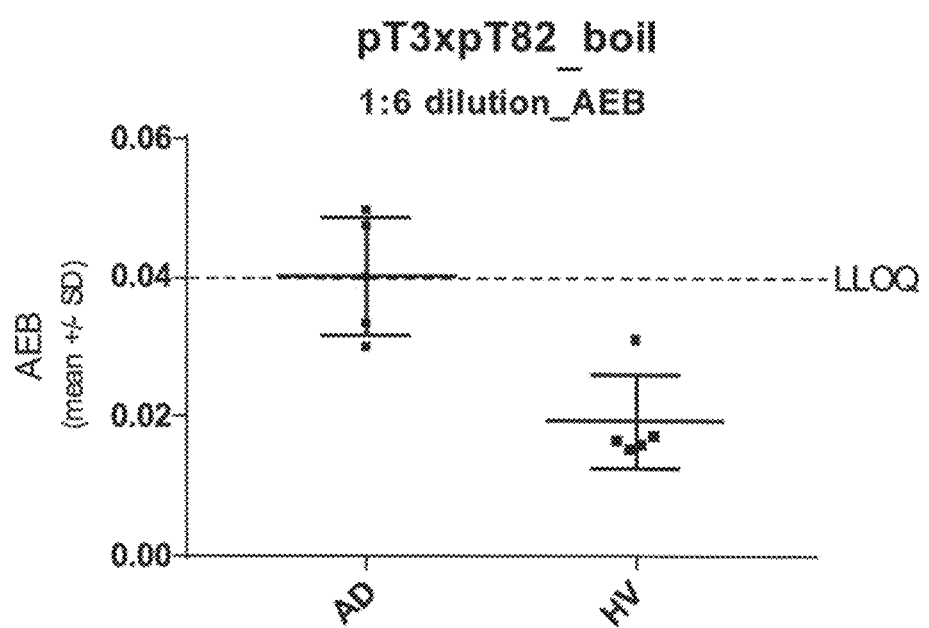
Figure 27:
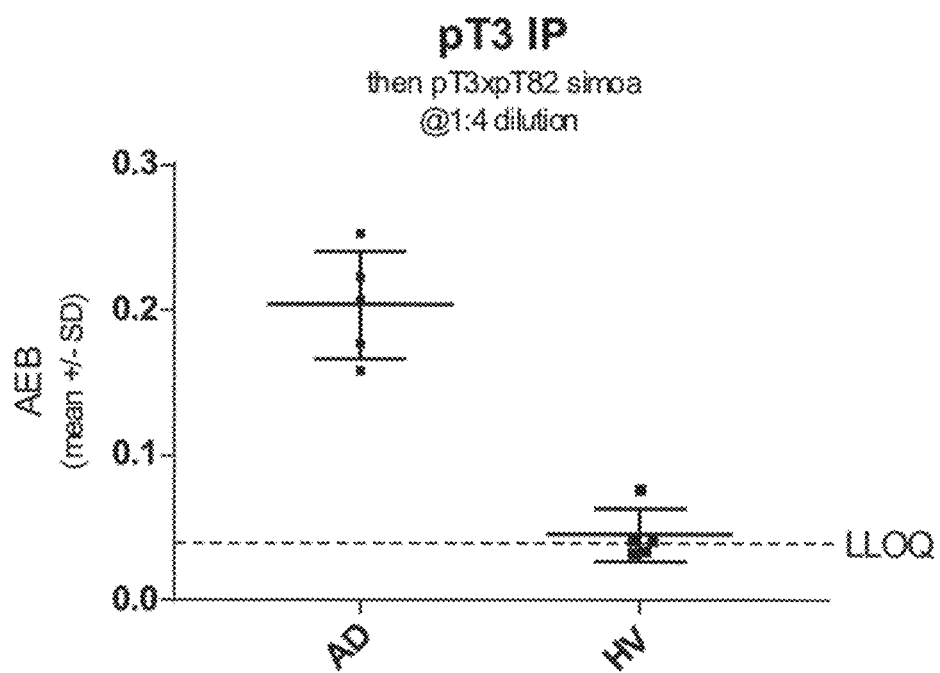
FIG. 27 shows measurements of pT3xpT82 (p217+ tau short) in pT3-immunoprecipitations (IP) of serums from the same 4 AD and 4HV subjects evaluated in FIGS. 25A-25D and FIGS. 26A-26B.

Serum from clinically defined AD & HV subjects (n=4 each) was measured with the pT3xpT82 and hT7xpT82 assays, either in crude sample at various dilutions ("crude", FIGS. 25A-25D), in acid (NaOAc pH5) treated and denatured sample ("boil", FIGS. 26A-26B) as in D'Abramo et al. 2016 to remove most matrix interference, and after immunoprecipitation (IP) with pT3 beads followed by heat denaturing of the elute ("pT3 IP", FIG. 27).

Measurement in crude serum revealed most samples were below the limit of quantification (LOQ), with few outlier samples reporting much higher levels. However, the signal did not survive modest dilution and was deemed to thus be an interference artifact. Evaluation of the highest dilution tested (FIGS. 25B and 25D), and thus the least impacted by interference, suggested that the pT3xpT82 assay may detect slightly more signal in AD samples, but all are below LOQ so may not be accurate and/or precise.

Measurement in serum after acid treatment (to dissociate protein-protein interactions) and heat (to denature most non-tau proteins) reduced all pT3xpT82 and hT7xpT82 signal to near or below LOQ (FIGS. 26A-26B). Again, the pT3xpT82 assay may detect slightly more signal in AD samples but all are near LOQ so may not be accurate and/or precise.

Measurement in serum after pT3-IP and denaturing, to remove most interfering substances and concentrate the p217+ tau, revealed much higher levels in the AD samples than in the HV samples (FIG. 27). The p217+ levels were ~4× higher than in the crude or boil measurements and as such the HV samples were now at LOQ and the AD samples were now all in linear range.

These results indicated that the pT3-based assays described herein may have utility as a blood-based measurement of pathological tau, particularly when paired with and enrichment strategy such as IP.

While the invention has been described in detail, and with reference to specific embodiments thereof, it will be apparent to one of ordinary skill in the art that various changes and modifications can be made therein without departing from the spirit and scope of the invention.

REFERENCES

Abhinandan and Martin, *Mol Immunol.* 45:3832-9, 2008
Almagro, *Mol Recognit.* 17:132-43, 2004
Barthelemy et al., *J Alzheimers Dis.* 51(4):1033-43, 2016
Butner and Kirschner, *J Cell Biol.* 115(3):717-30, 1991
Chothia and Lesk, *J Mol Biol.* 196:901-17, 1987
Chothia et al., *J Mol. Biol.* 227: 799-817, 1992
Clavaguera et al., *Nat Cell Biol.* 11:909-13, 2009
D'Abramo et al *Neurobiol Aging.* 37:58-65, 2016
Epitope Mapping Protocols in Methods in Molecular Biology, Vol. 66, G. E. Morris, Ed. (1996)
Fishwild et al., *Nat Biotechnol.* 14:845-51, 1996
Frost et al., *J Biol Chem.* 284:12845-52, 2009
Hanger et al. *J Biol Chem.* 282(32):23645-54, 2007
Hanger et al., *Trends Mol Med.* 15:112-9, 2009
Iqbal et al., *Curr Alzheimer Res.* 7(8): 656-664, 2010
Knappik et al., *J Mol Biol.* 296:57-86, 2000 Kohler and Milstein, *Nature.* 256:495-7, 1975
Krebs et al., *J Immunol Methods.* 254:67-84, 2001
Lefranc et al., *Dev Comp Immunol.* 27:55-77, 2003
Lonberg et al., *Nature.* 368:856-9, 1994
Mendez et al., *Nat Genet.* 15:146-56, 1997
Meredith et al. *PLoS One.* 8(10):e76523, 2013
Morris et al., *Neuron,* 70:410-26, 2011
Russell et al., *J Alzheimers Dis.* 55(1):303-313, 2017
Shi et al., *J Mol Biol.* 397:385-96, 2010
Tramontano et al., *J. Mol. Biol.* 215:175-182, 1990
Wu and Kabat, *J Exp Med.* 132:211-50, 1970

We claim:

1. An isolated antibody or antigen binding fragment thereof that binds tau comprising:
   (a) an immunoglobulin heavy chain comprising a heavy chain complementarity determining region (HCDR) 1, HCDR2 and HCDR3 comprising amino acid sequences of SEQ ID NOs: 12, 13 and 14, respectively; and
   (b) an immunoglobulin light chain comprising a light chain complementarity determining region (LCDR) 1, LCDR2 and LCDR3 comprising amino acid sequences of SEQ ID NOs: 15, 16 and 17, respectively.

2. The isolated antibody or antigen binding fragment thereof of claim 1 wherein the antibody or antigen binding fragment thereof comprises a heavy chain variable region that is at least 95% identical to SEQ ID NO: 18 and a light chain variable region that is at least 95% identical to SEQ ID NO: 19.

3. The isolated antibody or antigen binding fragment thereof of claim 1 wherein the antibody or antigen binding fragment thereof comprises:
   (a) an immunoglobulin heavy chain comprising a HCDR1, HCDR2 and HCDR3 consisting of amino acid sequences of SEQ ID NOs: 12, 13 and 14, respectively; and
   (b) an immunoglobulin light chain comprising LCDR1, LCDR2 and LCDR3 consisting of amino acid sequences of SEQ ID NOs: 15, 16 and 17, respectively.

4. The isolated antibody or antigen binding fragment thereof of claim 3 wherein the antibody or antigen binding fragment thereof comprises a heavy chain variable region that is at least 95% identical to SEQ ID NO: 18-and a light chain variable region that is at least 95% identical to SEQ ID NO: 19.

5. The isolated antibody or antigen binding fragment thereof of claim 1 wherein the antibody or antigen binding fragment thereof comprises a heavy chain variable region comprising amino acid sequence of SEQ ID NO: 18 and a light chain variable region comprising amino acid sequence of SEQ ID NO: 19.

6. The isolated antibody or antigen binding fragment thereof of claim 5 wherein the antibody or antigen binding fragment thereof comprises a heavy chain variable region consisting of amino acid sequence of SEQ ID NO: 18 and a light chain variable region consisting of amino acid sequence of SEQ ID NO: 19.

* * * * *

SEQUENCE LISTING

```
<160> NUMBER OF SEQ ID NOS: 37

<210> SEQ ID NO 1
<211> LENGTH: 441
<212> TYPE: PRT
<213> ORGANISM: Artificial Sequence
<220> FEATURE:
<223> OTHER INFORMATION: tau protein 2N4R

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190
```

-continued

```
Asp Arg Ser Gly Tyr Ser Ser Pro Gly Ser Pro Gly Thr Pro Gly Ser
    195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 10
<212> TYPE: PRT
<213> ORGANISM: Artificial Sequence
<220> FEATURE:
<223> OTHER INFORMATION: CDR-H1 Sequence of PT82 mAb

<400> SEQUENCE: 2

Gly Phe Thr Phe Ser Asn Tyr Trp Met Asn
1               5                   10

<210> SEQ ID NO 3
<211> LENGTH: 19
<212> TYPE: PRT
<213> ORGANISM: Artificial Sequence
<220> FEATURE:
<223> OTHER INFORMATION: CDR-H2 Sequence of PT82 mAb

<400> SEQUENCE: 3

Gln Ile Arg Leu Gln Ser Asp Asn Tyr Ala Thr Arg Tyr Ala Glu Ser
1               5                   10                  15

Val Lys Gly

<210> SEQ ID NO 4
```

```
<211> LENGTH: 4
<212> TYPE: PRT
<213> ORGANISM: Artificial Sequence
<220> FEATURE:
<223> OTHER INFORMATION: CDR-H3 sequence of PT82 mAb

<400> SEQUENCE: 4

Gly Ile Thr Tyr
1

<210> SEQ ID NO 5
<211> LENGTH: 11
<212> TYPE: PRT
<213> ORGANISM: Artificial Sequence
<220> FEATURE:
<223> OTHER INFORMATION: CDR-L1 Sequence of PT82 mAb

<400> SEQUENCE: 5

Lys Ala Ser Gln Asn Val Gly Thr Ala Val Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDR-L2 Sequence of PT82 mAb

<400> SEQUENCE: 6

Ser Ala Ser Ile Arg Tyr Thr
1               5

<210> SEQ ID NO 7
<211> LENGTH: 9
<212> TYPE: PRT
<213> ORGANISM: Artificial Sequence
<220> FEATURE:
<223> OTHER INFORMATION: CDR-L3 Sequence of PT82 mAb

<400> SEQUENCE: 7

Gln Gln Phe Ser Ser Tyr Pro Tyr Thr
1               5

<210> SEQ ID NO 8
<211> LENGTH: 115
<212> TYPE: PRT
<213> ORGANISM: Artificial Sequence
<220> FEATURE:
<223> OTHER INFORMATION: VH sequence of PT82 mAb

<400> SEQUENCE: 8

Glu Val Lys Leu Glu Glu Ser Gly Gly Leu Val Gln Pro Gly Gly
1               5                   10                  15

Ser Met Lys Leu Ser Cys Val Ala Ser Gly Phe Thr Phe Ser Asn Tyr
                20                  25                  30

Trp Met Asn Trp Ile Arg Gln Ser Pro Glu Lys Gly Leu Glu Trp Val
            35                  40                  45

Ala Gln Ile Arg Leu Gln Ser Asp Asn Tyr Ala Thr Arg Tyr Ala Glu
        50                  55                  60

Ser Val Lys Gly Arg Phe Thr Ile Ser Arg Asp Glu Ser Lys Thr Ser
65                  70                  75                  80

Val Tyr Leu Gln Met Asn Asn Leu Arg Thr Glu Asp Thr Gly Ile Tyr
                85                  90                  95

Tyr Cys Thr Gly Gly Thr Thr Tyr Trp Gly Gln Gly Thr Leu Val Thr
```

Val Ser Ala
        115

<210> SEQ ID NO 9
<211> LENGTH: 107
<212> TYPE: PRT
<213> ORGANISM: Artificial Sequence
<220> FEATURE:
<223> OTHER INFORMATION: VL sequence of PT82 mAb

<400> SEQUENCE: 9

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Ile Arg Tyr Thr Gly Val Pro Asp Arg Phe Thr Gly
    50                  55                  60

Ser Gly Ser Gly Thr Asp Phe Thr Leu Thr Ile Asn Tyr Met Gln Ser
65                  70                  75                  80

Glu Asp Leu Ala Asp Tyr Phe Cys Gln Gln Phe Ser Ser Tyr Pro Tyr
                85                  90                  95

Thr Phe Gly Gly Gly Thr Lys Leu Glu Ile Lys
            100                 105

<210> SEQ ID NO 10
<211> LENGTH: 8
<212> TYPE: PRT
<213> ORGANISM: Artificial Sequence
<220> FEATURE:
<223> OTHER INFORMATION: PT82 mAb epitope, aa119-126 of SEQ ID NO:1

<400> SEQUENCE: 10

Ala Gly His Val Thr Gln Ala Arg
1               5

<210> SEQ ID NO 11
<211> LENGTH: 11
<212> TYPE: PRT
<213> ORGANISM: Artificial Sequence
<220> FEATURE:
<223> OTHER INFORMATION: PT82 mAb epitope, aa117 to 127 of SEQ ID NO:1

<400> SEQUENCE: 11

Glu Ala Ala Gly His Val Thr Gln Ala Arg Met
1               5                   10

<210> SEQ ID NO 12
<211> LENGTH: 10
<212> TYPE: PRT
<213> ORGANISM: Artificial Sequence
<220> FEATURE:
<223> OTHER INFORMATION: HCDR1 of HT43 mAb

<400> SEQUENCE: 12

Gly Phe Thr Phe Arg Ser Tyr Gly Met Ser
1               5                   10

<210> SEQ ID NO 13
<211> LENGTH: 17
<212> TYPE: PRT

```
<213> ORGANISM: Artificial Sequence
<220> FEATURE:
<223> OTHER INFORMATION: HCDR2 of HT43 mAb

<400> SEQUENCE: 13

Thr Ile Asn Ser Asp Gly Ser Tyr Thr Tyr Tyr Pro Asp Ser Val Lys
1               5                   10                  15

Gly

<210> SEQ ID NO 14
<211> LENGTH: 8
<212> TYPE: PRT
<213> ORGANISM: Artificial Sequence
<220> FEATURE:
<223> OTHER INFORMATION: HCDR3 of HT43 mAb

<400> SEQUENCE: 14

Ser Trp Asp Gly Ala Met Asp Tyr
1               5

<210> SEQ ID NO 15
<211> LENGTH: 16
<212> TYPE: PRT
<213> ORGANISM: Artificial Sequence
<220> FEATURE:
<223> OTHER INFORMATION: LCDR1 of HT43 mAb

<400> SEQUENCE: 15

Arg Ser Ser Gln Ser Ile Leu His Ser Asn Gly Asn Thr Tyr Phe Glu
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: LCDR2 of HT43 mAb

<400> SEQUENCE: 16

Lys Val Ser Asn Arg Phe Ser
1               5

<210> SEQ ID NO 17
<211> LENGTH: 9
<212> TYPE: PRT
<213> ORGANISM: Artificial Sequence
<220> FEATURE:
<223> OTHER INFORMATION: LCDR3 of HT43 mAb

<400> SEQUENCE: 17

Phe Gln Gly Ser Leu Val Pro Trp Thr
1               5

<210> SEQ ID NO 18
<211> LENGTH: 117
<212> TYPE: PRT
<213> ORGANISM: Artificial Sequence
<220> FEATURE:
<223> OTHER INFORMATION: Heavy chain variable region of HT43 mAb

<400> SEQUENCE: 18

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Arg Ser Tyr
            20                  25                  30
```

```
Gly Met Ser Trp Val Arg Gln Thr Pro Asp Lys Arg Leu Glu Trp Val
            35                  40                  45

Thr Thr Ile Asn Ser Asp Gly Ser Tyr Thr Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Val Ser Trp Asp Gly Ala Met Asp Tyr Trp Gly Gln Gly Thr Ser
            100                 105                 110

Val Thr Val Ser Ser
        115

<210> SEQ ID NO 19
<211> LENGTH: 112
<212> TYPE: PRT
<213> ORGANISM: Artificial Sequence
<220> FEATURE:
<223> OTHER INFORMATION: Light chain variable region of HT43 mAb

<400> SEQUENCE: 19

Asp Val Leu Val Thr Gln Thr Pro Leu Ser Leu Pro Val Ser Leu Gly
 1               5                  10                  15

Asp Gln Ala Ser Ile Ser Cys Arg Ser Ser Gln Ser Ile Leu His Ser
            20                  25                  30

Asn Gly Asn Thr Tyr Phe Glu Trp Tyr Leu Gln Arg Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Leu Val Pro Trp Thr Phe Gly Gly Gly Thr Lys Leu Glu Ile Lys
            100                 105                 110

<210> SEQ ID NO 20
<211> LENGTH: 14
<212> TYPE: PRT
<213> ORGANISM: Artificial Sequence
<220> FEATURE:
<223> OTHER INFORMATION: HT43 mAb epitope, aa7 to 20 of SEQ ID NO:1

<400> SEQUENCE: 20

Glu Phe Glu Val Met Glu Asp His Ala Gly Thr Tyr Gly Leu
 1               5                  10

<210> SEQ ID NO 21
<211> LENGTH: 5
<212> TYPE: PRT
<213> ORGANISM: Artificial Sequence
<220> FEATURE:
<223> OTHER INFORMATION: hT7 mAb epitope, aa 159-163 of SEQ ID NO: 1

<400> SEQUENCE: 21

Pro Pro Gly Gln Lys
 1               5

<210> SEQ ID NO 22
<211> LENGTH: 58
<212> TYPE: PRT
```

```
<213> ORGANISM: Artificial Sequence
<220> FEATURE:
<223> OTHER INFORMATION: calibrant peptide pT3xhT43
<220> FEATURE:
<221> NAME/KEY: dPEG4 linker
<222> LOCATION: (20)..(21)
<220> FEATURE:
<221> NAME/KEY: dPEG4 linker
<222> LOCATION: (38)..(39)
<220> FEATURE:
<221> NAME/KEY: phosphorylated threonine
<222> LOCATION: (44)..(44)
<220> FEATURE:
<221> NAME/KEY: phosphorylated threonine
<222> LOCATION: (49)..(49)
<220> FEATURE:
<221> NAME/KEY: C-terminal amide
<222> LOCATION: (58)..(58)

<400> SEQUENCE: 22

Pro Arg Gln Glu Phe Glu Val Met Glu Asp His Ala Gly Thr Tyr Gly
1               5                   10                  15

Leu Gly Asp Arg Gly Lys Thr Lys Ile Ala Thr Pro Arg Gly Ala Ala
            20                  25                  30

Pro Pro Gly Gln Lys Gly Gly Ser Arg Ser Arg Thr Pro Ser Leu Pro
        35                  40                  45

Thr Pro Pro Thr Arg Glu Pro Lys Lys Val
    50                  55

<210> SEQ ID NO 23
<211> LENGTH: 38
<212> TYPE: PRT
<213> ORGANISM: Artificial Sequence
<220> FEATURE:
<223> OTHER INFORMATION: calibrant peptide pT3xpT82
<220> FEATURE:
<221> NAME/KEY: N-terminal acetyl group
<222> LOCATION: (1)..(1)
<220> FEATURE:
<221> NAME/KEY: dPEG4 linker
<222> LOCATION: (18)..(19)
<220> FEATURE:
<221> NAME/KEY: phosphorylated threonine
<222> LOCATION: (24)..(24)
<220> FEATURE:
<221> NAME/KEY: phosphorylated threonine
<222> LOCATION: (29)..(29)
<220> FEATURE:
<221> NAME/KEY: C-terminal amide
<222> LOCATION: (38)..(38)

<400> SEQUENCE: 23

Ser Leu Glu Asp Glu Ala Ala Gly His Val Thr Gln Ala Arg Met Val
1               5                   10                  15

Ser Lys Gly Ser Arg Ser Arg Thr Pro Ser Leu Pro Thr Pro Pro Thr
            20                  25                  30

Arg Glu Pro Lys Lys Val
        35

<210> SEQ ID NO 24
<211> LENGTH: 34
<212> TYPE: PRT
<213> ORGANISM: Artificial Sequence
<220> FEATURE:
<223> OTHER INFORMATION: calibrant peptide hT7xpT82
<220> FEATURE:
<221> NAME/KEY: N-terminal acetyl group
<222> LOCATION: (1)..(1)
<220> FEATURE:
<221> NAME/KEY: dPEG4 linker
```

-continued

```
<222> LOCATION: (20)..(21)
<220> FEATURE:
<221> NAME/KEY: C-terminal amide
<222> LOCATION: (34)..(34)

<400> SEQUENCE: 24

Ala Ser Leu Glu Asp Glu Ala Ala Gly His Val Thr Gln Ala Arg Met
1               5                   10                  15

Val Ser Lys Pro Arg Gly Ala Ala Pro Pro Gly Gln Lys Gly Gln Ala
            20                  25                  30

Asn Ala

<210> SEQ ID NO 25
<211> LENGTH: 11
<212> TYPE: PRT
<213> ORGANISM: Artificial Sequence
<220> FEATURE:
<223> OTHER INFORMATION: p217+ tau epitope
<220> FEATURE:
<221> NAME/KEY: phosphorylated threonine
<222> LOCATION: (2)..(2)

<400> SEQUENCE: 25

Arg Thr Pro Ser Leu Pro Thr Pro Pro Thr Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: p217+ tau epitope
<220> FEATURE:
<221> NAME/KEY: phosphorylated threonine
<222> LOCATION: (7)..(7)

<400> SEQUENCE: 26

Arg Thr Pro Ser Leu Pro Thr Pro Pro Thr Arg
1               5                   10

<210> SEQ ID NO 27
<211> LENGTH: 11
<212> TYPE: PRT
<213> ORGANISM: Artificial Sequence
<220> FEATURE:
<223> OTHER INFORMATION: p217+ tau epitope
<220> FEATURE:
<221> NAME/KEY: phosphorylated threonine
<222> LOCATION: (2)..(2)
<220> FEATURE:
<221> NAME/KEY: phosphorylated threonine
<222> LOCATION: (7)..(7)

<400> SEQUENCE: 27

Arg Thr Pro Ser Leu Pro Thr Pro Pro Thr Arg
1               5                   10

<210> SEQ ID NO 28
<211> LENGTH: 118
<212> TYPE: PRT
<213> ORGANISM: Artificial Sequence
<220> FEATURE:
<223> OTHER INFORMATION: PT3 mouse mAb VH

<400> SEQUENCE: 28

Glu Val Lys Leu Val Glu Ser Gly Gly Asp Leu Val Lys Pro Gly Gly
1               5                   10                  15
```

```
Ser Leu Lys Leu Ser Cys Ala Ala Ser Gly Phe Thr Phe Ser Ser Tyr
            20                  25                  30

Ala Met Ser Trp Val Arg Gln Asn Pro Glu Lys Arg Leu Glu Trp Val
        35                  40                  45

Ala Ser Ile Ser Lys Gly Gly Asn Thr Tyr Tyr Pro Asn Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Leu Tyr Tyr Cys Ala
                85                  90                  95

Arg Gly Trp Gly Asp Tyr Gly Trp Phe Ala Tyr Trp Gly Gln Val Thr
            100                 105                 110

Leu Val Thr Val Ser Ala
            115
```

```
<210> SEQ ID NO 29
<211> LENGTH: 107
<212> TYPE: PRT
<213> ORGANISM: Artificial Sequence
<220> FEATURE:
<223> OTHER INFORMATION: PT3 mouse mAb VL

<400> SEQUENCE: 29

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Arg Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Leu Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Leu
                85                  90                  95

Thr Phe Gly Asp Gly Thr Lys Leu Glu Leu Lys
            100                 105
```

```
<210> SEQ ID NO 30
<211> LENGTH: 118
<212> TYPE: PRT
<213> ORGANISM: Artificial Sequence
<220> FEATURE:
<223> OTHER INFORMATION: PT3 humanized mAb VH

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ser Ile Ser Lys Gly Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Gly Trp Gly Asp Tyr Gly Trp Phe Ala Tyr Trp Gly Gln Val Thr
            100                 105                 110

Leu Val Thr Val Ser Ser
        115

<210> SEQ ID NO 31
<211> LENGTH: 107
<212> TYPE: PRT
<213> ORGANISM: Artificial Sequence
<220> FEATURE:
<223> OTHER INFORMATION: PT3 humanized mAb VL

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Arg Tyr
            20                  25                  30

Leu Asn Trp Phe Gln Gln Lys Pro Gly Lys Ala Pro Lys Ser Leu Ile
        35                  40                  45

Tyr Arg Ala Asn Arg Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gln Gly Thr Lys Leu Glu Ile Lys
            100                 105

<210> SEQ ID NO 32
<211> LENGTH: 5
<212> TYPE: PRT
<213> ORGANISM: Artificial Sequence
<220> FEATURE:
<223> OTHER INFORMATION: PT3 mouse mAb HCDR1, Kabat numbering

<400> SEQUENCE: 32

Ser Tyr Ala Met Ser
1               5

<210> SEQ ID NO 33
<211> LENGTH: 16
<212> TYPE: PRT
<213> ORGANISM: Artificial Sequence
<220> FEATURE:
<223> OTHER INFORMATION: PT3 mouse mAb HCDR2, Kabat numbering

<400> SEQUENCE: 33

Ser Ile Ser Lys Gly Gly Asn Thr Tyr Tyr Pro Asn Ser Val Lys Gly
1               5                   10                  15

<210> SEQ ID NO 34
<211> LENGTH: 10
<212> TYPE: PRT
<213> ORGANISM: Artificial Sequence
<220> FEATURE:
<223> OTHER INFORMATION: PT3 mouse mAb HCDR3, Kabat numbering

<400> SEQUENCE: 34

Gly Trp Gly Asp Tyr Gly Trp Phe Ala Tyr
1               5                   10

<210> SEQ ID NO 35

```
<211> LENGTH: 11
<212> TYPE: PRT
<213> ORGANISM: Artificial Sequence
<220> FEATURE:
<223> OTHER INFORMATION: PT3 mouse mAb LCDR1, Kabat numbering

<400> SEQUENCE: 35

Lys Ala Ser Gln Asp Ile Asn Arg Tyr Leu Asn
1               5                   10

<210> SEQ ID NO 36
<211> LENGTH: 7
<212> TYPE: PRT
<213> ORGANISM: Artificial Sequence
<220> FEATURE:
<223> OTHER INFORMATION: PT3 mouse mAb LCDR2, Kabat numbering

<400> SEQUENCE: 36

Arg Ala Asn Arg Leu Leu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: PT3 mouse mAb LCDR3, Kabat numbering

<400> SEQUENCE: 37

Leu Gln Tyr Asp Glu Phe Pro Leu Thr
1               5
```